United States Patent
Jakob et al.

(10) Patent No.: US 10,265,310 B2
(45) Date of Patent: Apr. 23, 2019

(54) 6-MEMBERED CYCLIC AMINES OR LACTAMES SUBSTITUTED WITH UREA AND PHENYL

(71) Applicant: GRÜNENTHAL GMBH, Aachen (DE)

(72) Inventors: Florian Jakob, Aachen (DE); Sonja Nordhoff, Aachen (DE); David Rider, Aachen (DE); Markus Wagener, Aachen (DE); Gregor Bahrenberg, Monschau-Kozen (DE); Torsten Dunkern, Jüchen (DE)

(73) Assignee: GrÜNENTHAL GMBH, Aachen (DE)

( * ) Notice: Subject to any disclaimer, the term of this patent is extended or adjusted under 35 U.S.C. 154(b) by 0 days.

(21) Appl. No.: 15/710,249

(22) Filed: Sep. 20, 2017

(65) Prior Publication Data
US 2018/0078541 A1 Mar. 22, 2018

(30) Foreign Application Priority Data

Sep. 21, 2016 (EP) ................................. 16020340

(51) Int. Cl.
| | | |
|---|---|---|
| A61K 31/451 | (2006.01) | |
| A61K 31/17 | (2006.01) | |
| A61K 31/085 | (2006.01) | |
| A61K 31/03 | (2006.01) | |
| A61K 31/445 | (2006.01) | |
| A61K 31/45 | (2006.01) | |
| A61K 31/4545 | (2006.01) | |
| C07D 401/12 | (2006.01) | |
| C07D 211/16 | (2006.01) | |
| C07D 211/56 | (2006.01) | |
| C07D 211/94 | (2006.01) | |

(52) U.S. Cl.
CPC ............ *A61K 31/451* (2013.01); *A61K 31/03* (2013.01); *A61K 31/085* (2013.01); *A61K 31/17* (2013.01); *A61K 31/445* (2013.01); *A61K 31/45* (2013.01); *A61K 31/4545* (2013.01); *C07D 211/16* (2013.01); *C07D 211/56* (2013.01); *C07D 211/94* (2013.01); *C07D 401/12* (2013.01)

(58) Field of Classification Search
CPC ...... A61K 31/03; A61K 31/085; A61K 31/17; A61K 31/445; A61K 31/45; A61K 31/451; A61K 31/4545; C07D 211/16; C07D 211/56; C07D 211/94; C07D 401/12
See application file for complete search history.

(56) References Cited

U.S. PATENT DOCUMENTS 8,592,454 B2 11/2013 Shirai et al.
2005/0009815 A1 1/2005 DeVita et al.

2011/0178060 A1 7/2011 Shirai et al.
2017/0066718 A1 3/2017 Takahashi et al.
2017/0240512 A1 8/2017 Yukimasa et al.

FOREIGN PATENT DOCUMENTS

| EP | 2 336 105 A1 | 6/2011 | |
|---|---|---|---|
| FR | 2 338 043 | * 12/1977 | ........... A61K 31/445 |
| WO | 03 045920 A1 | 6/2003 | |
| WO | 2015/079692 A1 | 6/2015 | |
| WO | 2016/021629 A1 | 2/2016 | |

OTHER PUBLICATIONS

Maddox et al., J. Biol. Chem., 1997, 272, 6972-6978.
Chiang et al., Pharmacol. Rev., 2006, 58, 463-487.
Fredman and Serhan, Biochem. J., 2011, 437, 185-197.
Migeotte et al., Cytokine Growth Factor Rev., 2006, 17, 501-519.
Romano et al., Eur J Pharmacol. 2015, 760, 49-63.
Yatomi et al., Physiol. Rep., 2015, 3, pii, e12628.
Norling et al., JCI Insight, 2016, 1, e85922.
Zhang et al., Inflamm. Res., 2008, 57, 157-162.
Barnig et al., Sci. Transl. Med., 2013, 5, 174ra26.
Levy et al., Nat Med. 2002, 8, 1018-23.
Celik et al., Clin Exp Allergy, 2007, 37, 1494-1501.
Vachier I et al,. J. Allergy Clin. Immunol., 2005, 115, 55-60.
Karp et al., Nat. Immunol. 2004, 5, 388-392.
Kim et al., Int. J. Chron. Obstruct. Pulmon. Dis., 2016, 11 1119-1128.
Hu et al., J. Neuroinflammation. 2012, 9, 278.
Ji et al., Trends Neurosci. 2011, 34, 599-609.
Clark, et al., "LP99: Discovery and synthesis of the first selective BRD7/9 bromodomain inhibitor"; Angew. Chem. Int. Ed. 2015, 54, 6217-6221.
XP-002775814 "2-Thiazolecarboxylic acid, 5-[[[6-oxo-2-phenyl-3-pipendinyl)amino]carbonyl]amino]-, ethyl ester, Jul. 8, 2015.

* cited by examiner

*Primary Examiner* — Erich A Leeser
(74) *Attorney, Agent, or Firm* — Norris McLaughlin P.A.

(57) ABSTRACT

The present invention relates to a compound according to general formula (I)

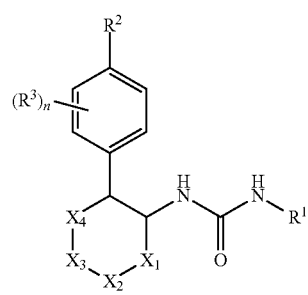

which acts as a modulator of FPR2 and can be used in the treatment and/or prophylaxis of disorders which are at least partially mediated by FPR2.

15 Claims, No Drawings

6-MEMBERED CYCLIC AMINES OR LACTAMES SUBSTITUTED WITH UREA AND PHENYL

This application claims foreign priority benefit under 35 U.S.C. § 119 of the European Patent Application No. 16 020 340.2, filed Sep. 21, 2016, the disclosure of which patent application is incorporated herein by reference.

The present invention relates to a compound according to general formula (I)

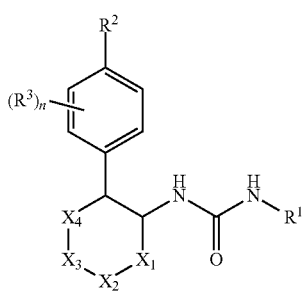

which acts as a modulator of FPR2 and can be used in the treatment and/or prophylaxis of disorders which are at least partially mediated by FPR2.

FPR2 (alias lipoxin A4 receptor, FPRL1, LXA4R, ALXR) is a G-protein coupled receptor family member that has been shown to mediate calcium mobilization in response to the eicosanoid family member lipoxin A4 (LXA4) and its analogues (Maddox et al., J. Biol. Chem., 1997, 272, 6972-6978). The receptor is widely expressed and has been shown to bind to a large number of different ligands, including endogenous proteins (serum amyloid A) bacterial products (the formyl peptide N-formyl-methionine-leucyl-phenylalanine), other lipid-derivatives (resolvin D1 (RvD1) and its analogues) and peptides, including neuropeptides ($A_\beta 42$) and HIV (gp41 and gp120-derived peptides), amongst many others (Chiang et al., Pharmacol. Rev., 2006, 58, 463-487; Fredman and Serhan, Biochem. J., 2011, 437, 185-197; Migeotte et al., Cytokine Growth Factor Rev., 2006, 17, 501-519).

Wide ranging anti-inflammatory and pro-resolving effects of FPR2 ligands have been shown in pre-clinical models. For example, in vivo activities for LXA4, or derivatives, or stable analogues, and RvD1, or derivatives, or stable analogues have been demonstrated in arthritis, asthma, cardiovascular diseases, chronic obstructive pulmonary disease (COPD) colitis, corneal injury, cystic fibrosis, dermal inflammation, fibrosis of the lung and kidney, glomerulonephritis, graft versus host disease (GvHD), inflammatory pain, ischemia/reperfusion injury, periodontitis, peritonitis, post-operative pain, pancreatitis, retinopathy and sepsis (Fredman and Serhan, Biochem. J., 2011, 437, 185-197; Romano et al., Eur J Pharmacol. 2015, 760, 49-63; Yatomi et al., Physiol. Rep., 2015, 3, pii, e12628). It has been demonstrated that the FPR2 agonist 17-R-RvD1 is able to reduce the severity of arthritis in the K/BxN serum transfer model of arthritis (Norling et al., JCI Insight, 2016, 1, e85922) and the stable agonist BML-111 has similar actions in the collagen-induced arthritis model (Zhang et al., Inflamm. Res., 2008, 57, 157-162). The potential use of FPR2 modulators in lung diseases has been well documented. In terms of asthma, it has been demonstrated that the addition of LXA4 or RvD1, or their stable analogues, are able to improve asthmatic symptoms in animal models (Barnig et al., Sci. Transl. Med., 2013, 5, 174ra26; Levy et al., Nat Med. 2002, 8, 1018-23). It has also been demonstrated that in severe asthma patients there are reduced levels of LXA4 (Celik et al., Clin Exp Allergy, 2007, 37, 1494-1501). Similar reductions in pulmonary LXA4 levels were seen in patients with COPD (Vachier I et al., J. Allergy Clin. Immunol., 2005, 115, 55-60) and cystic fibrosis (Karp et al., Nat. Immunol. 2004, 5, 388-392). RvD1 attenuated smoking-induced emphysema in vivo (Kim et al., Int. J. Chron. Obstruct. Pulmon. Dis., 2016, 11 1119-1128) and 17-R-RvD1 attenuates pulmonary fibrosis by inhibiting neutrophilic inflammation and promoting pulmonary restoration (Yatomi et al., Physiol. Rep., 2015, 3, pii, e12628).

In addition to anti-inflammatory and pro-resolution effects of FPR2-ligands, they have also been demonstrated to have effects on pain mechanisms. LXA4 has been directly shown to alleviate hyperalgesia and bone-cancer-related pain in animal models (Fredman and Serhan, Biochem. J., 2011, 437, 185-197; Hu et al., J. Neuroinflammation. 2012, 9, 278). Furthermore, the FPR2 agonist RvD1 has been shown to reduce inflammatory pain, spontaneous pain and post-operative pain and post-surgical pain (Ji et al., Trends Neurosci. 2011, 34, 599-609).

The biological properties of FPR2 agonists include, but are not limited to, regulation of inflammation, regulation of hyperalgesia, regulation of proinflammatory mediator production and/or release, regulation of migration and activation of monocytes/macrophages/microglia/astrocytes/dendritic cells and neutrophils, regulation of lymphocyte activation, regulate innalte lymphoid cell activation, proliferation and differentiation, regulation of cytokine production and/or release, regulation of immune reactions, regulation of phagocytosis/efferocytosis, regulation of apoptosis. Further, FPR2 is believed to be involved in the modulation of immune responses, such as those elicited through Graft versus Host Disease (GvHD).

Compounds which are active as modulators of FPR2 are also known from WO 2015/079692.

It was an object of the present invention to provide novel compounds which are modulators, preferably activators of FPR2, and which preferably have advantages over the compounds of the prior art. The novel compounds should in particular be suitable for use in the treatment and/or prophylaxis of disorders or diseases which are at least partially mediated by FPR2.

This object has been achieved by the subject-matter of the patent claims.

It was surprisingly found that the compounds according to the present invention are highly potent modulators of the FPR2 receptor.

The present invention relates to a compound according to general formula (I)

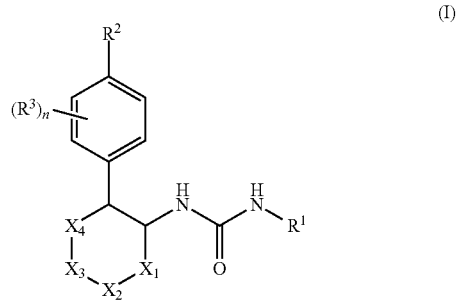

wherein
- $X_2$ represents $N(L-R^4)$ and $X_1$, $X_3$ and $X_4$ represent $CH_2$; or
- $X_2$ represents $N(L-R^4)$ and $X_3$ represents $C(O)$ and $X_1$ and $X_4$ represent $CH_2$; or
- $X_4$ represents $N(L-R^4)$, and $X_3$ represents $CH_2$ or $C(O)$ and $X_1$ and $X_2$ represent $CH_2$;

and n represents 0, 1 or 2

$R^1$ represents phenyl or 5 or 6-membered heteroaryl, $R^2$ represents H, F, Cl, Br, CN, $C_{1-6}$-alkyl, $C_{3-6}$-cycloalkyl, $CHF_2$, $CH_2F$, $CF_3$, OH, $OCHF_2$, $OCH_2F$, $OCF_3$, O—$C_{1-6}$-alkyl, S—$C_{1-6}$-alkyl, S(O)—$C_{1-6}$-alkyl, $S(O)_2$—$C_{1-6}$-alkyl, O—$C_{3-6}$-cycloalkyl, S—$C_{3-6}$-cycloalkyl, S(O)—$C_{3-6}$-cycloalkyl, $S(O)_2$—$C_{3-6}$-cycloalkyl, $NH_2$, $N(H)(C_{1-6}$-alkyl), $N(C_{1-6}$-alkyl$)_2$, $N(H)(C_{3-6}$-cycloalkyl), $N(C_{1-6}$-alkyl$)(C_{3-6}$-cycloalkyl), $NC(O)(C_{1-6}$-alkyl), $NC(O)(C_{3-6}$-cycloalkyl), NC(O)(3 to 6-membered heterocycloalkyl);

$R^3$ represents F, Cl, Br, $CHF_2$, $CH_2F$, $CF_3$, $C_{1-6}$-alkyl, $C_{3-6}$-cycloalkyl, O—$C_{1-6}$-alkyl, $OCHF_2$, $OCH_2F$, $OCF_3$, S(O)—$C_{1-6}$-alkyl, S(O)—$C_{3-6}$-cycloalkyl, $S(O)_2$—$C_{1-6}$-alkyl, $S(O)_2$—$C_{3-6}$-cycloalkyl;

L represents bond, $C_{1-6}$-alkylene, C(O), $S(O)_2$, $C(CH_3)_2$; and $R^4$ represents H, $C_{1-6}$-alkyl, $C_{3-6}$-cycloalkyl, 3 to 6-membered heterocycloalkyl, aryl, 5 or 6-membered heteroaryl, $C(O)NH_2$, $C(O)N(H)(C_{1-6}$-alkyl), $C(O)N(C_{1-6}$-alkyl$)_2$, $C(O)N(H)(C_{3-6}$-cycloalkyl), $C(O)N(H)(3$ to 6-membered heterocycloalkyl), $C(O)N(H)(aryl)$, $C(O)N(H)(5$ or 6-membered heteroaryl), $C(O)N(C_{1-6}$-alkyl$)(C_{3-6}$-cycloalkyl), $C(O)N(C_{1-6}$-alkyl$)(3$ to 6-membered heterocycloalkyl), $C(O)N(C_{1-6}$-alkyl$)(aryl)$, $C(O)N(C_{1-6}$-alkyl$)(5$ or 6-membered heteroaryl), $C(O)N(C_{3-6}$-cycloalkyl$)(C_{3-6}$-cycloalkyl), $C(O)N(C_{3-6}$-cycloalkyl$)(3$ to 6-membered heterocycloalkyl), $C(O)N(C_{3-6}$-cycloalkyl$)(aryl)$, $C(O)N(C_{3-6}$-cycloalkyl$)(5$ or 6-membered heteroaryl), $C(O)O$—$(C_{1-6}$-alkyl), $C(O)O$—$(C_{3-6}$-cycloalkyl), C(O)O-(3 to 6-membered heterocycloalkyl), C(O)O-(aryl), C(O)O-(5 or 6-membered heteroaryl), S(O)—$C_{1-6}$-alkyl, $S(O)_2$—$C_{1-6}$-alkyl, S(O)—$C_{3-6}$-cycloalkyl, $S(O)_2$—$C_{3-6}$-cycloalkyl, $C_{1-6}$-alkylene-OH, $C_{1-6}$-alkylene-O—$C_{1-6}$-alkyl, $C_{1-6}$-alkylene-$C_{3-6}$-cycloalkyl, $C_{1-6}$-alkylene-3 to 6-membered heterocycloalkyl, $C_{1-6}$-alkylene-aryl, $C_{1-6}$-alkylene-5 or 6-membered heteroaryl;

wherein $C_{1-6}$-alkyl in each case independently from one another is linear or branched, saturated or unsaturated;

wherein $C_{1-6}$-alkylene is linear and saturated or unsaturated;

wherein $C_{1-6}$-alkyl, $C_{1-6}$-alkylene, $C_{3-6}$-cycloalkyl and 3 to 6-membered heterocycloalkyl in each case independently from one another are unsubstituted or mono- or polysubstituted with one or more substituents selected from F, Cl, CN, $C_{1-6}$-alkyl, $CF_3$, $CF_2H$, $CFH_2$, $CF_2Cl$, $CFCl_2$, C(O)—$C_{1-6}$-alkyl, C(O)—OH, C(O)—$OC_{1-6}$-alkyl, C(O)—$NH_2$, C(O)—$N(H)(C_{1-6}$-alkyl), C(O)—$N(C_{1-6}$-alkyl$)_2$, OH, =O, $OCF_3$, $OCF_2H$, $OCFH_2$, $OCF_2Cl$, $OCFCl_2$, O—$C_{1-6}$-alkyl, O—C(O)—$C_{1-6}$-alkyl, O—C(O)—O—$C_{1-6}$-alkyl, O—(CO)—$N(H)(C_{1-6}$-alkyl), O—C(O)—$N(C_{1-6}$-alkyl$)_2$, O—$S(O)_2$—$NH_2$, O—$S(O)_2$—$N(H)(C_{1-6}$-alkyl), O—$S(O)_2$—$N(C_{1-6}$-alkyl$)_2$, $NH_2$, $N(H)(C_{1-6}$-alkyl), $N(C_{1-6}$-alkyl$)_2$, N(H)—C(O)—$C_{1-6}$-alkyl, N(H)—C(O)—O—$C_{1-6}$-alkyl, N(H)—C(O)—$NH_2$, N(H)—C(O)—$N(H)(C_{1-6}$-alkyl), N(H)—C(O)—$N(C_{1-6}$-alkyl$)_2$, $N(C_{1-6}$-alkyl$)$-C(O)—$C_{1-6}$-alkyl, $N(C_{1-6}$-alkyl$)$-C(O)—O—$C_{1-6}$-alkyl, $N(C_{1-6}$-alkyl$)$-C(O)—$NH_2$, $N(C_{1-6}$-alkyl$)$-C(O)—$N(H)(C_{1-6}$-alkyl), $N(C_{1-6}$-alkyl$)$-C(O)—$N(C_{1-6}$-alkyl$)_2$, N(H)—$S(O)_2$—$C_{1-6}$-alkyl, N(H)—$S(O)_2$—$C_{1-6}$-alkyl, N(H)—$S(O)_2$—O—$C_{1-6}$-alkyl, N(H)—$S(O)_2$—$NH_2$, N(H)—$S(O)_2$—$N(H)(C_{1-6}$-alkyl), N(H)—$S(O)_2N(C_{1-6}$-alkyl$)_2$, $N(C_{1-6}$-alkyl$)$-$S(O)_2$—OH, $N(C_{1-6}$-alkyl$)$-$S(O)_2$—$C_{1-6}$-alkyl, $N(C_{1-6}$-alkyl$)$-$S(O)_2$—O—$C_{1-6}$-alkyl, $N(C_{1-6}$-alkyl$)$-$S(O)_2$—$NH_2$, $N(C_{1-6}$-alkyl$)$-$S(O)_2$—$N(H)(C_{1-6}$-alkyl), $N(C_{1-6}$-alkyl$)$-$S(O)_2$—$N(C_{1-6}$-alkyl$)_2$, $SCF_3$, $SCF_2H$, $SCFH_2$, S—$C_{1-6}$-alkyl, S(O)—$C_{1-6}$-alkyl, $S(O)_2$—$C_{1-6}$-alkyl, $S(O)_2$—OH, $S(O)_2$—O—$C_{1-6}$-alkyl, $S(O)_2$—$NH_2$, $S(O)_2$—$N(H)(C_{1-6}$-alkyl), $S(O)_2$—$N(C_{1-6}$-alkyl$)_2$, $C_{3-6}$-cycloalkyl, 3 to 6-membered heterocycloalkyl, phenyl, 5 or 6-membered heteroaryl, O—$C_{3-6}$-cycloalkyl, O-(3 to 6-membered heterocycloalkyl), O-phenyl, O-(5 or 6-membered heteroaryl), C(O)—$C_{3-6}$-cycloalkyl, C(O)-(3 to 6-membered heterocycloalkyl), C(O)-phenyl, C(O)-(5 or 6-membered heteroaryl), $S(O)_2$—$(C_{3-6}$-cycloalkyl), $S(O)_2$-(3 to 6-membered heterocycloalkyl), $S(O)_2$-phenyl or $S(O)_2$-(5 or 6-membered heteroaryl);

wherein aryl, phenyl and 5 or 6-membered heteroaryl in each case independently from one another are unsubstituted or mono- or disubstituted with one or two substituents selected from F, Cl, Br, CN, $C_{1-6}$-alkyl, $CF_3$, $CF_2H$, $CFH_2$, $C_{1-4}$-alkylene-$CF_3$, $C_{1-4}$-alkylene-$CF_2H$, $C_{1-4}$-alkylene-$CFH_2$, C(O)—$C_{1-6}$-alkyl, C(O)—OH, C(O)—$OC_{1-6}$-alkyl, C(O)—N(H)(OH), C(O)—$NH_2$, C(O)—$N(H)(C_{1-6}$-alkyl), C(O)—$N(C_{1-6}$-alkyl$)_2$, OH, $OCF_3$, $OCF_2H$, $OCFH_2$, $OCF_2Cl$, $OCFCl_2$, O—$C_{1-6}$-alkyl, O—$C_{3-6}$-cycloalkyl, O-(3 to 6-membered heterocycloalkyl), $NH_2$, $N(H)(C_{1-6}$-alkyl), $N(C_{1-6}$-alkyl$)_2$, N(H)—C(O)—$C_{1-6}$-alkyl, $N(C_{1-6}$-alkyl$)$-C(O)—$C_{1-6}$-alkyl, N(H)—C(O)—$NH_2$, N(H)—C(O)—$N(H)(C_{1-6}$-alkyl), N(H)—C(O)—$N(C_{1-6}$-alkyl$)_2$, $N(C_{1-6}$-alkyl$)$-C(O)—$N(H)(C_{1-6}$-alkyl), $N(C_{1-6}$-alkyl$)$-C(O)—$N(C_{1-6}$-alkyl$)_2$, N(H)—$S(O)_2$—$C_{1-6}$-alkyl, $SCF_3$, S—$C_{1-6}$-alkyl, S(O)—$C_{1-6}$-alkyl, $S(O)_2$—$C_{1-6}$-alkyl, $S(O)_2$—$NH_2$, $S(O)_2$—$N(H)(C_{1-6}$-alkyl), $S(O)_2$—$N(C_{1-6}$-alkyl$)_2$, $C_{3-6}$-cycloalkyl, $C_{1-4}$-alkylene-$C_{3-6}$-cycloalkyl, 3 to 6-membered heterocycloalkyl, $C_{1-4}$-alkylene-(3 to 6-membered heterocycloalkyl), phenyl or 5 or 6-membered heteroaryl;

in the form of the free compound or a physiologically acceptable salt thereof.

In a preferred embodiment, the compound according to the present invention is present in form of the free compound. For the purpose of specification, "free compound" preferably means that the compound according to the present invention is not present in form of a salt. Methods to determine whether a chemical substance is present as the free compound or as a salt are known to the skilled artisan such as $^{14}N$ or $^{15}N$ solid state NMR, x-ray diffraction, x-ray powder diffraction, IR, Raman, XPS. $^1H$-NMR recorded in solution may also be used to consider the presence of protonation.

In another preferred embodiment, the compound according to the present invention is present in form of a physiologically acceptable salt. For the purposes of this specification, the term "physiologically acceptable salt" preferably refers to a salt obtained from a compound according to the present invention and a physiologically acceptable acid or base.

According to the present invention, the compound according to the present invention may be present in any possible form including solvates, cocrystals and polymorphs. For the purposes of this specification, the term "solvate" preferably refers to an adduct of (i) a compound according to the present invention and/or a physiologically acceptable salt thereof with (ii) distinct molecular equivalents of one or more solvents.

Further, the compound according to the present invention may be present in form of the racemate, enantiomers, diastereomers, tautomers or any mixtures thereof.

The compounds according to general formula (I) possess at least two stereogenic carbon atoms and may be stereochemically differentiated according to the relative structural orientation of the phenyl moiety and the urea moiety which are bound to the central nitrogen-containing 6-membered heterocycloalkyl.

In the sense of the present invention, the term "diastereomer" refers to a compound preferably having a diastereomeric ratio of >90:10, more preferably >92:8, even more preferably >95:5, most preferably >98:2 and in particular >99:1 or >99.9:1. Diastereomers differ from each other with respect to their physical and chemical properties. Methods to determine the diastereomeric ratio (dr) are well known to the person skilled in the art and include, but are not limited to, NMR-methods.

In the sense of the present invention, the term "enantiomerically pure compound" or "enantiomer" preferably refers to a compound having an enantiomeric excess of >90% ee, more preferably >92% ee, still more preferably >95% ee, most preferably >98% ee and in particular >98% ee. Methods to determine the enantiomeric excess are well known to the person skilled in the art and include, but are not limited to, optical rotary dispersion, circular dichroism, NMR-methods using chiral auxiliaries ("shift reagents") or separation via chiral HPLC (high performance liquid chromatography, using a chiral stationary phase), chiral GLC (gas-liquid chromatography, using a chiral stationary phase phase) or chiral SFC (supercritical fluid chromatography using a chiral stationary phase).

Further in the sense of the present invention, the term "racemic mixture" or "racemate" refers to a mixture (identified by the prefix "rac-trans" or "rac-cis" in the chemical name) of two corresponding enantiomers wherein said corresponding enantiomers are preferably contained in the mixture in a ratio of from 30:70 to 70:30, more preferably 40:60 to 60:40, most preferably 45:55 to 55:45 and in particular 50:50.

Further in the sense of the present invention, the term "iso-mix" refers to a mixture (identified by the prefix "iso-mix" in the chemical name) of two corresponding diastereomers, wherein said corresponding diastereomers are preferably contained in the mixture in a ratio of from 30:70 to 70:30, more preferably 40:60 to 60:40, most preferably 45:55 to 55:45 and in particular 50:50.

Determination of the absolute stereochemical structure is well known to the person skilled in the art and includes, but are not limited to, x-ray diffractometry.

In the sense of the present invention, the compounds wherein the phenyl and urea moieties which are connected to the central nitrogen-containing 6-membered heterocycloalkyl have a different relative orientation, for instance phenyl moiety up ("bold bond") and urea moiety down ("hashed bond") or vice versa, are referred to as the "trans" diastereomer and are identified hereinafter by the prefix "rac-trans" in the chemical name.

The trans diastereomer is a racemic mixture of two corresponding enantiomers which are identified via the prefix "trans-ent1" and "trans-ent2" in the chemical name, and which are according to general formulae (Ia) and (Ib) shown below:

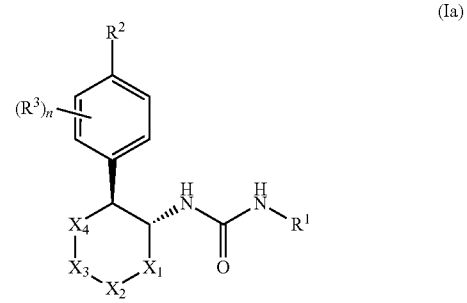

(Ia)

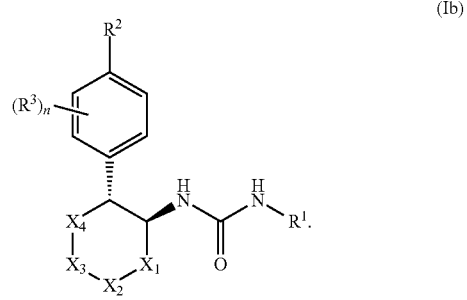

(Ib)

In the following, either one of two corresponding enantiomers "trans-ent1" (identified by the prefix "trans-ent1" in the chemical name) and "trans-ent2" (identified by the prefix "trans-ent2" in the chemical name) is according to general formula (Ia) while the other is according to general formula (Ib). For the purpose of clarification, one of trans-ent1 and trans-ent2 has to be according to general formula (Ia) and the other one has to be according to general formula (Ib).

Further in the sense of the present invention, the compounds wherein the phenyl and urea moieties which are connected to the central nitrogen-containing 6-membered heterocycloalkyl have the same relative orientation, for instance both, the phenyl moiety and the urea moiety, up ("bold bond") or both, the phenyl moiety and the urea moiety, down ("hashed bond") are referred to as the "cis" diastereomer and are identified hereinafter by the prefix "rac-cis" in the chemical name.

The cis diastereomer is a racemic mixture of two enantiomers which are identified via the prefix "cis-ent1" and "cis-ent2" in the chemical name, and which are according to general formulae (Ic) and (Id) shown below:

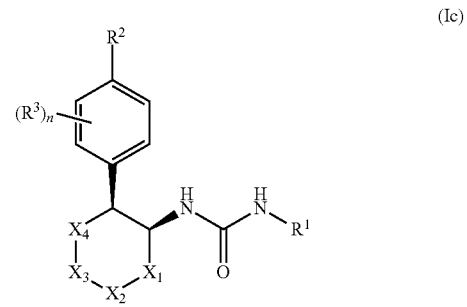

(Ic)

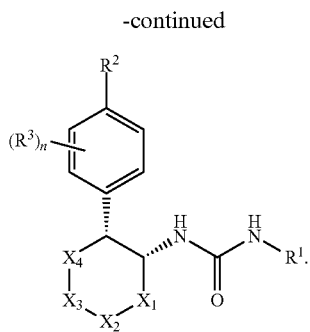

(Id)

In the following, either one of two corresponding enantiomers "cis-ent1" (identified by the prefix "cis-ent1" in the chemical name) and "cis-ent2" (identified by the prefix "cis-ent2" in the chemical name) is according to general formula (Ic) while the other is according to general formula (Id). For the purpose of clarification, one of cis-ent1 and cis-ent2 has to be according to general formula (Ic) and the other one has to be according to general formula (Id).

In the following, either one of the terms "diastereomer 1" (identified by the prefix "dia1" in the chemical name) and "diastereomer 2" (identified by the prefix "dia1" in the chemical name) refers to the cis diastereomer while the other, corresponding diastereomer refers to the trans diastereomer. For the purpose of clarification, one of the corresponding diastereomers 1 and 2 has to be cis and the other one has to be trans.

Hereinafter, a mixture of the trans diastereomer and the cis disastereoisomer, i.e. a mixture of diastereomer 1 and diastereomer 2, is identified by the prefix "iso-mix" in the chemical name.

The present invention also includes isotopic isomers of a compound of the invention, wherein at least one atom of the compound is replaced by an isotope of the respective atom which is different from the naturally predominantly occurring isotope, as well as any mixtures of isotopic isomers of such a compound. Preferred isotopes are $^2$H (deuterium), $^3$H (tritium), $^{13}$C and $^{14}$C. Isotopic isomers of a compound of the invention can generally be prepared by conventional procedures known to a person skilled in the art.

According to the present invention, the terms "$C_{1-6}$-alkyl" and "$C_{1-4}$-alkyl" preferably mean acyclic saturated or unsaturated aliphatic (i.e. non-aromatic) hydrocarbon residues, which can be linear (i.e. unbranched) or branched and which can be unsubstituted or mono- or polysubstituted (e.g. di- or trisubstituted), and which contain 1 to 6 (i.e. 1, 2, 3, 4, 5 or 6) and 1 to 4 (i.e. 1, 2, 3 or 4) carbon atoms, respectively. Preferably, $C_{1-6}$-alkyl and $C_{1-4}$-alkyl are saturated. Preferred $C_{1-6}$-alkyl groups are selected from methyl, ethyl, n-propyl, 2-propyl, n-butyl, isobutyl, sec-butyl, tert-butyl, n-pentyl, 2-pentyl, 3-pentyl, 2-methylbutyl, 3-methylbutyl, 3-methylbut-2-yl, 2-methylbut-2-yl, 2,2-dimethylpropyl, n-hexyl, 2-hexyl, 3-hexyl, 2-methylpentyl, 4-methylpentyl, 4-methylpent-2-yl, 2-methylpent-2-yl, 3,3-dimethylbutyl, 3,3-dimethylbut-2-yl, 3-methylpentyl, 3-methylpent-2-yl and 3-methylpent-3-yl; more preferably methyl, ethyl, n-propyl, 2-propyl, n-butyl, isobutyl, sec-butyl, tert-butyl, n-pentyl, 2-pentyl, 3-pentyl, 2-methylbutyl, 3-methylbutyl, 3-methylbut-2-yl, 2-methylbut-2-yl, 2,2-dimethylpropyl, n-hexyl. Particularly preferred $C_{1-6}$-alkyl groups are selected from $C_{1-4}$-alkyl groups. Preferred $C_{1-4}$-alkyl groups are selected from methyl, ethyl, n-propyl, 2-propyl, n-butyl, isobutyl, sec-butyl and tert-butyl.

Further according to the present invention, the terms "$C_{1-6}$-alkylene" and "$C_{1-4}$-alkylene" relate to a linear and preferably saturated aliphatic residues which are preferably selected from the group consisting of methylene (—CH$_2$—), ethylene (—CH$_2$CH$_2$—), propylene (—CH$_2$CH$_2$CH$_2$—), butylene (—CH$_2$CH$_2$CH$_2$CH$_2$—), pentylene (—CH$_2$CH$_2$CH$_2$CH$_2$CH$_2$—) and hexylene (—CH$_2$CH$_2$CH$_2$CH$_2$CH$_2$CH$_2$—); more preferably methylene (—CH$_2$—) and ethylene (—CH$_2$CH$_2$—) and most preferably methylene (—CH$_2$—). Preferably, $C_{1-6}$-alkylene is selected from $C_{1-4}$-alkylene.

Still further according to the present invention, the term "$C_{3-6}$-cycloalkyl" preferably means cyclic aliphatic hydrocarbons containing 3, 4, 5 or 6 carbon atoms, wherein the hydrocarbons in each case can be saturated or unsaturated (but not aromatic), unsubstituted or mono- or polysubstituted. The $C_{3-6}$-cycloalkyl group can be bound to the respective superordinate general structure via any desired and possible ring member of the cycloalkyl group. The $C_{3-6}$-cycloalkyl group can also be condensed with further saturated, (partially) unsaturated, (hetero)cyclic, aromatic or heteroaromatic ring systems, i.e. with cycloalkyl, heterocyclyl, aryl or heteroaryl residues, which in each case can in turn be unsubstituted or mono- or polysubstituted. Further, the $C_{3-6}$-cycloalkyl group can be singly or multiply bridged such as, for example, in the case of adamantyl, bicyclo[2.2.1]heptyl or bicyclo[2.2.2]octyl. However, preferably, the $C_{3-6}$-cycloalkyl group is neither condensed with further ring systems nor bridged.

Preferred $C_{3-6}$-cycloalkyl groups are selected from the group consisting of cyclopropyl, cyclobutyl, cyclopentyl, cyclohexyl, cyclopentenyl and cyclohexenyl. Particularly preferred $C_{3-6}$-cycloalkyl groups are selected from the group consisting of cyclopropyl, cyclobutyl, cyclopentyl and cyclohexyl, most preferably cyclopropyl.

According to the present invention, the term "3 to 6-membered heterocycloalkyl" preferably means heterocycloaliphatic saturated or unsaturated (but not aromatic) residues having 3 to 6, i.e. 3, 4, 5 or 6 ring members, wherein in each case at least one, if appropriate also two or three carbon atoms are replaced by a heteroatom or a heteroatom group each selected independently of one another from the group consisting of O, S, S(=O), S(=O)$_2$, N, NH and N($C_{1-4}$-alkyl) such as N(CH$_3$), wherein the carbon atoms of the ring can be unsubstituted or mono- or polysubstituted. The 3 to 6-membered heterocycloalkyl group can also be condensed with further saturated or (partially) unsaturated cycloalkyl or heterocyclyl, aromatic or heteroaromatic ring systems. However, preferably, the 3 to 6-membered heterocycloalkyl group is not condensed with further ring systems. The 3 to 6-membered heterocycloalkyl group can be bound to the superordinate general structure via any desired and possible ring member of the heterocycloaliphatic residue if not indicated otherwise. In a preferred embodiment, the 3 to 6-membered heterocycloalkyl group is bound to the superordinate general structure via a carbon atom.

Preferred 3 to 6-membered heterocycloalkyl groups are selected from the group consisting of tetrahydropyranyl, morpholinyl, pyrrolidinyl, 4-methylpiperazinyl, morpholinonyl, azetidinyl, aziridinyl, dithiolanyl, dihydropyrrolyl, dioxanyl, dioxolanyl, dihydropyridinyl, dihydrofuranyl, dihydroisoxazolyl, dihydrooxazolyl, imidazolidinyl, isoxazolidinyl, oxazolidinyl, oxiranyl, oxetanyl, piperazinyl, piperidinyl, pyrazolidinyl, pyranyl, tetrahydropyrrolyl, more preferably tetrahydropyranyl, morpholinyl and pyrrolidinyl.

According to the present invention, the term "aryl" preferably means aromatic hydrocarbons having 6 to 14, i.e. 6, 7, 8, 9, 10, 11, 12, 13 or 14 ring members, preferably having 6 to 10, i.e. 6, 7, 8, 9 or 10 ring members, including phenyls and naphthyls. Each aryl residue can be unsubstituted or mono- or disubstituted. The aryl can be bound to the superordinate general structure via any desired and possible ring member of the aryl residue. The aryl residues can also be condensed with further saturated or (partially) unsaturated cycloalkyl or heterocycloalkyl, aromatic or heteroaromatic ring systems, which can in turn be unsubstituted or mono- or disubstituted. In a preferred embodiment, aryl is condensed with a further ring system. Examples of condensed aryl residues are 2H-benzo[b][1,4]oxazin-3(4H)-onyl, 1H-benzo[d]imidazolyl, 2,3-dihydro-1H-indenyl, tetrahydronaphthalenyl, isochroman, 1,3-dihydroisobenzofuranyl, benzodioxolanyl and benzodioxanyl. Preferably, aryl is selected from the group consisting of phenyl, 1H-benzo[d]imidazolyl, 2H-benzo[b][1,4]oxazin-3(4H)-onyl, 2,3-dihydro-1H-indenyl, tetrahydronaphthalenyl, isochroman, 1,3-dihydroisobenzofuranyl, 1-naphthyl, 2-naphthyl, fluorenyl and anthracenyl, each of which can be respectively unsubstituted or mono- or disubstituted. In another preferred embodiment, aryl is not condensed with any further ring system. A particularly preferred aryl is phenyl, unsubstituted or mono- or disubstituted.

According to the present invention, the term "5- to 6-membered heteroaryl" preferably means a 5 or 6-membered cyclic aromatic residue containing at least 1, if appropriate also 2, 3, 4 or 5 heteroatoms, wherein the heteroatoms are each selected independently of one another from the group S, N and O and the heteroaryl residue can be unsubstituted or mono- or disubstituted, if not indicated otherwise. In the case of substitution on the heteroaryl, the substituents can be the same or different and be in any desired and possible position of the heteroaryl. The binding to the superordinate general structure can be carried out via any desired and possible ring member of the heteroaryl residue if not indicated otherwise. Preferably, the 5- to 6-membered heteroaryl is bound to the suprordinate general structure via a carbon atom of the heterocycle. The heteroaryl can also be part of a bi- or polycyclic system having up to 14 ring members, wherein the ring system can be formed with further saturated or (partially) unsaturated cycloalkyl or heterocycloalkyl, aromatic or heteroaromatic ring systems, which can in turn be unsubstituted or mono- or disubstituted, if not indicated otherwise. In a preferred embodiment, the 5- to 6-membered heteroaryl is part of a bi- or polycyclic, preferably bicyclic, system. In another preferred embodiment, the 5- to 6-membered heteroaryl is not part of a bi- or polycyclic system. Preferably, the 5- to 6-membered heteroaryl is selected from the group consisting of pyridyl (i.e. 2-pyridyl, 3-pyridyl, 4-pyridyl), pyrimidinyl, pyridazinyl, pyrazinyl, pyrrolyl, imidazolyl, pyrazolyl, oxazolyl, isoxazolyl, thiazolyl, isothiazolyl, furanyl, thienyl (thiophenyl), triazolyl, thiadiazolyl, 4,5,6,7-tetrahydro-2H-indazolyl, 2,4,5,6-tetrahydrocyclopenta[c]pyrazolyl, benzofuranyl, benzoimidazolyl, benzothienyl, benzothiadiazolyl, benzothiazolyl, benzotriazolyl, benzooxazolyl, benzooxadiazolyl, quinazolinyl, quinoxalinyl, carbazolyl, quinolinyl, dibenzofuranyl, dibenzothienyl, imidazothiazolyl, indazolyl, indolizinyl, indolyl, isoquinolinyl, naphthyridinyl, oxazolyl, oxadiazolyl, phenazinyl, phenothiazinyl, phthalazinyl, purinyl, phenazinyl, tetrazolyl and triazinyl. Particularly preferred 5- to 6-membered heteroaryl are selected from the group consisting of pyridyl (i.e. 2-pyridyl, 3-pyridyl, 4-pyridyl), pyrimidinyl, pyridazinyl, thienyl (thiophenyl), oxazolyl, thiazolyl, isothiazolyl and benzothienyl.

In connection with the terms "$C_{1-6}$-alkyl", "$C_{1-4}$-alkyl", "$C_{3-6}$-cycloalkyl", "3 to 6-membered heterocycloalkyl" and "$C_{1-6}$-alkylene", the term "substituted" refers in the sense of the present invention, with respect to the corresponding residues or groups, to the single substitution (monosubstitution) or multiple substitution (polysubstitution), e.g. disubstitution or trisubstitution; more preferably to monosubstitution or disubstitution;

of one or more hydrogen atoms each independently of one another by at least one substituent. In case of a multiple substitution, i.e. in case of polysubstituted residues, such as di- or trisubstituted residues, these residues may be polysubstituted either on different or on the same atoms, for example trisubstituted on the same carbon atom, as in the case of $CF_3$, $CH_2CF_3$ or disubstituted as in the case of 1,1-difluorocyclohexyl, or at various points, as in the case of CH(OH)—CH=CH—$CHCl_2$ or 1-chloro-3-fluorocyclohexyl. The multiple substitution can be carried out using the same or using different substituents.

In relation to the terms "phenyl", "aryl" and "5- to 6-membered heteroaryl", the term "substituted" refers in the sense of this invention to the single substitution (monosubstitution) or disubstitution, of one or two hydrogen atoms each independently of one another by at least one substituent. The disubstitution can be carried out using the same or using different substituents.

If a residue occurs multiply within a molecule, then this residue can have respectively different meanings for various substituents: if, for example, both $R^2$ and $R^4$ denote $C_{1-6}$-alkyl, then $C_{1-6}$-alkyl can e.g. represent ethyl for $R^2$ and can represent methyl for $R^4$.

According to the present invention, $C_{1-6}$-alkyl, $C_{1-6}$-alkylene, $C_{3-6}$-cycloalkyl and 3 to 6-membered heterocycloalkyl in each case independently from one another are unsubstituted or mono- or polysubstituted with one or more substituents selected from F, Cl, CN, $C_{1-6}$-alkyl, $CF_3$, $CF_2H$, $CFH_2$, $CF_2Cl$, $CFCl_2$, C(O)—$C_{1-6}$-alkyl, C(O)—OH, C(O)—O$C_{1-6}$-alkyl, C(O)—$NH_2$, C(O)—N(H)($C_{1-6}$-alkyl), C(O)—N($C_{1-6}$-alkyl)$_2$, OH, =O, $OCF_3$, $OCF_2H$, $OCFH_2$, $OCF_2Cl$, $OCFCl_2$, O—$C_{1-6}$-alkyl, O—C(O)—$C_{1-6}$-alkyl, O—C(O)—O—$C_{1-6}$-alkyl, O—(CO)—N(H)($C_{1-6}$-alkyl), O—C(O)—N($C_{1-6}$-alkyl)$_2$, O—S(O)$_2$—$NH_2$, O—S(O)$_2$—N(H)($C_{1-6}$-alkyl), O—S(O)$_2$—N($C_{1-6}$-alkyl)$_2$, $NH_2$, N(H)($C_{1-6}$-alkyl), N($C_{1-6}$-alkyl)$_2$, N(H)—C(O)—$C_{1-6}$-alkyl, N(H)—C(O)—O—$C_{1-6}$-alkyl, N(H)—C(O)—$NH_2$, N(H)—C(O)—N(H)($C_{1-6}$-alkyl), N(H)—C(O)—N($C_{1-6}$-alkyl)$_2$, N($C_{1-6}$-alkyl)-C(O)—$C_{1-6}$-alkyl, N($C_{1-6}$-alkyl)-C(O)—O—$C_{1-6}$-alkyl, N($C_{1-6}$-alkyl)-C(O)—$NH_2$, N($C_{1-6}$-alkyl)-C(O)—N(H)(C alkyl), N($C_{1-6}$-alkyl)-C(O)—N($C_{1-6}$-alkyl)$_2$, N(H)—S(O)$_2$OH, N(H)—S(O)$_2$—$C_{1-6}$-alkyl, N(H)—S(O)$_2$—O—$C_{1-6}$-alkyl, N(H)—S(O)$_2$—$NH_2$, N(H)—S(O)$_2$—N(H)($C_{1-6}$-alkyl), N(H)—S(O)$_2$N($C_{1-6}$-alkyl)$_2$, N($C_{1-6}$-alkyl)-S(O)$_2$—OH, N($C_{1-6}$-alkyl)-S(O)$_2$—$C_{1-6}$-alkyl, N($C_{1-6}$-alkyl)-S(O)$_2$—O—$C_{1-6}$-alkyl, N($C_{1-6}$-alkyl)-S(O)$_2$—$NH_2$, N($C_{1-6}$-alkyl)-S(O)$_2$—N(H)($C_{1-6}$-alkyl), N($C_{1-6}$-alkyl)-S(O)$_2$—N($C_{1-6}$-alkyl)$_2$, $SCF_3$, $SCF_2H$, $SCFH_2$, S(O)—$C_{1-6}$-alkyl, S(O)$_2$—$C_{1-6}$-alkyl, S(O)$_2$—OH, S(O)$_2$—O—$C_{1-6}$-alkyl, S(O)$_2$—$NH_2$, S(O)$_2$—N(H)($C_{1-6}$-alkyl), S(O)$_2$—N($C_{1-6}$-alkyl)$_2$, $C_{3-6}$-cycloalkyl, 3 to 6-membered heterocycloalkyl, phenyl, 5 or 6-membered heteroaryl, cycloalkyl, O-(3 to 6-membered heterocycloalkyl), O-phenyl, O-(5 or 6-membered heteroaryl), C(O)—$C_{3-6}$-cycloalkyl, C(O)-(3 to 6-membered heterocycloalkyl), C(O)-phenyl, C(O)-(5 or 6-membered heteroaryl), S(O)$_2$—($C_{3-6}$-cycloalkyl), S(O)$_2$-(3 to 6-membered heterocycloalkyl), S(O)$_2$-phenyl or S(O)$_2$-(5 or 6-membered heteroaryl). Preferred substituents of $C_{1-6}$-alkyl, $C_{1-6}$-alkylene, $C_{3-6}$-cycloalkyl and 3 to 6-membered heterocycloalkyl are selected from the group consisting of F, Cl, CN, CF$_3$, CF$_2$H, CFH$_2$ and OCF$_3$; more preferably F, Cl, CN, C$_{1-6}$-alkyl and CF$_3$; most preferably F, CN, CH$_3$, CH$_2$CH$_3$ and CF$_3$; and in particular F. According to this embodiment, C$_{1-6}$-alkyl, C$_{1-6}$-alkylene, C$_{3-6}$-cycloalkyl and 3 to 6-membered heterocycloalkyl are preferably each independently from one another unsubstituted, mono-di- or trisubstituted, more preferably unsubstituted or monosubstituted or disubstituted with a substituent selected from the group consisting of F, CH$_3$, CH$_2$CH$_3$, CN and CF$_3$. Preferably, C$_{1-6}$-alkylene groups are unsubstituted.

According to the present invention, aryl, phenyl and 5 or 6-membered heteroaryl in each case independently from one another are unsubstituted or mono- or disubstituted with one or two substituents selected from F, Cl, Br, CN, C$_{1-6}$-alkyl, CF$_3$, CF$_2$H, CFH$_2$, C$_{1-4}$-alkylene-CF$_3$, C$_{1-4}$-alkylene-CF$_2$H, C$_{1-4}$-alkylene-CFH$_2$, C(O)—C$_{1-6}$-alkyl, C(O)—OH, C(O)—OC$_{1-6}$-alkyl, C(O)—N(H)(OH), C(O)—NH$_2$, C(O)—N(H)(C$_{1-6}$-alkyl), C(O)—N(C$_{1-6}$-alkyl)$_2$, OH, OCF$_3$, OCF$_2$H, OCFH$_2$, OCF$_2$Cl, OCFCl$_2$, O—C$_{1-6}$-alkyl, O—C$_{3-6}$-cycloalkyl, O-(3 to 6-membered heterocycloalkyl), O-phenyl, O-(5 or 6-membered heteroaryl), NH$_2$, N(H)(C$_{1-6}$-alkyl), N(C$_{1-6}$-alkyl)$_2$, N(H)—C(O)—C$_{1-6}$-alkyl, N(C$_{1-6}$-alkyl)-C(O)—C$_{1-6}$-alkyl, N(H)—C(O)—NH$_2$, N(H)—C(O)—N(H)(C$_{1-6}$-alkyl), N(H)—C(O)—N(C$_{1-6}$-alkyl)$_2$, N(C$_{1-6}$-alkyl)-C(O)—N(H)(C$_{1-6}$-alkyl), N(C$_{1-6}$-alkyl)-C(O)—N(C$_{1-6}$-alkyl)$_2$, N(H)—S(O)$_2$—C$_{1-6}$-alkyl, SCF$_3$, S—C$_{1-6}$-alkyl, S(O)—C$_{1-6}$-alkyl, S(O)$_2$—C$_{1-6}$-alkyl, S(O)$_2$—NH$_2$, S(O)$_2$—N(H)(C$_{1-6}$-alkyl), S(O)$_2$—N(C$_{1-6}$-alkyl)$_2$, C$_{3-6}$-cycloalkyl, C$_{1-4}$-alkylene-C$_{3-6}$-cycloalkyl, 3 to 6-membered heterocycloalkyl, C$_{1-4}$-alkylene-(3 to 6-membered heterocycloalkyl), phenyl or 5 or 6-membered heteroaryl. Preferred substituents of aryl, phenyl and 5 or 6-membered heteroaryl are selected from the group consisting of F, Cl, Br, CN, C$_{1-6}$-alkyl, CF$_3$, CF$_2$H, CFH, OH, OCF$_3$, OCF$_2$H, OCFH$_2$ and O—C$_{1-6}$-alkyl; more preferably F, Cl, Br, C$_{1-6}$-alkyl, CF$_3$, OH, OCF$_3$, O—C$_{1-6}$-alkyl and O-phenyl; most preferably F, Cl, Br, C$_{1-6}$-alkyl, CF$_3$, OH and O-phenyl; and in particular F, Cl, Br, CH$_3$, CH$_2$CH$_3$, CF$_3$, OH and O-phenyl. According to this embodiment, aryl, phenyl and 5 or 6-membered heteroaryl are preferably each independently from one another unsubstituted, mono- or disubstituted, more preferably unsubstituted or mono- or disubstituted with a substituent selected from the group consisting of F, Cl, Br, C$_{1-6}$-alkyl, CF$_3$, OH and O-phenyl.

In a preferred embodiment the compound according to the present invention is according to general formula (Ia) or (Ib)

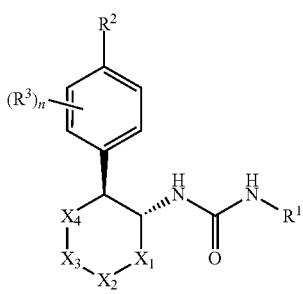

(Ia)

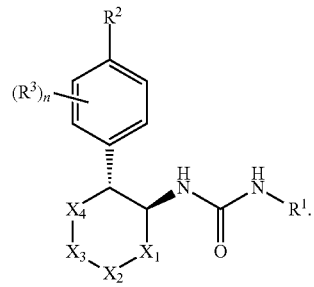

(Ib)

In another preferred embodiment, the compound according to the present invention is according to general formula (Ia). In still another preferred embodiment, the compound according to the present invention is according to general formula (Ib).

In a further preferred embodiment, the compound according to the present invention is according to general formula (Ic) or (Id)

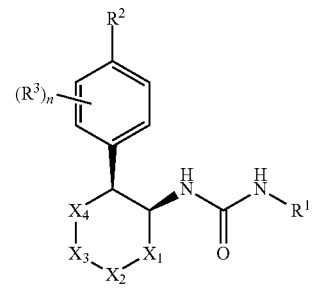

(Ic)

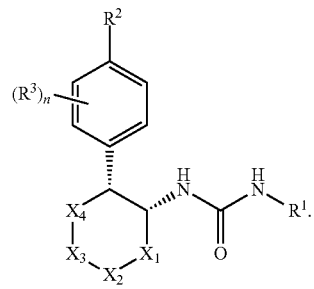

(Id)

In a particularly preferred embodiment, the compound according to the present invention is according to general formula (Ia) or (Ib).

According to the present invention,

X$_2$ represents N(L-R$^4$) and X$_1$, X$_3$ and X$_4$ represent CH$_2$; or

X$_2$ represents N(L-R$^4$) and X$_3$ represents C(O) and X$_1$ and X$_4$ represent CH$_2$; or X$_4$ represents N(L-R$^4$), and X$_3$ represents CH$_2$ or C(O) and X$_1$ and X$_2$ represent CH$_2$.

Preferably, X$_2$ represents N(L-R$^4$) and X$_3$ represents CH$_2$ or C(O) and X$_1$ and X$_4$ represent CH$_2$.

In a preferred embodiment, the compound according to the present invention is according to general formula (II)

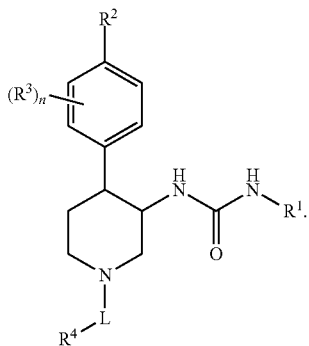

In another preferred embodiment, the compound according to the present invention is according to general formula (III)

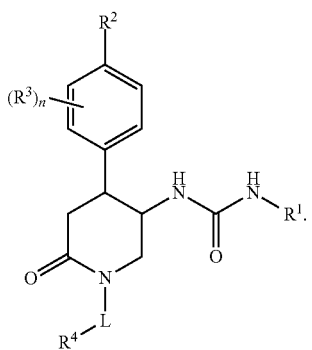

In another preferred embodiment, the compound according to the present invention is according to general formula (IV) or (V):

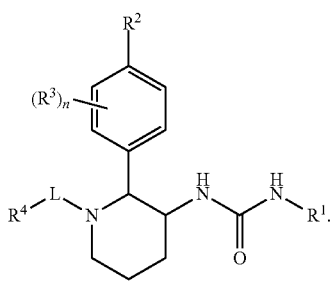

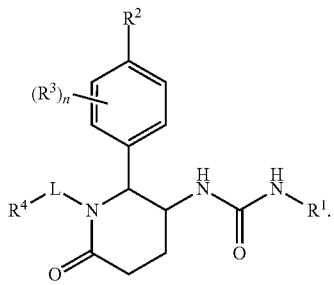

In a preferred embodiment, R$^1$ represents phenyl or 5 or 6-membered heteroaryl, wherein the 5 or 6-membered heteroaryl is selected from the group consisting of pyridyl, pyrimidinyl, pyridazinyl, pyrazinyl, pyrrolyl, imidazolyl, pyrazolyl, oxazolyl, isoxazolyl, thiazolyl, isothiazolyl, furanyl, thienyl (thiophenyl), triazolyl, thiadiazolyl, 4,5,6,7-tetrahydro-2H-indazolyl, 2,4,5,6-tetrahydrocyclopenta[c]pyrazolyl, benzofuranyl, benzoimidazolyl, benzothienyl, benzothiadiazolyl, benzothiazolyl, benzotriazolyl, benzooxazolyl, benzooxadiazolyl, quinazolinyl, quinoxalinyl, carbazolyl, quinolinyl, dibenzofuranyl, dibenzothienyl, imidazothiazolyl, indazolyl, indolizinyl, indolyl, isoquinolinyl, naphthyridinyl, oxazolyl, oxadiazolyl, phenazinyl, phenothiazinyl, phthalazinyl, purinyl, phenazinyl, tetrazolyl and triazinyl. According to this embodiment, preferably phenyl, pyridyl, pyrimidinyl, pyridazinyl, pyrazinyl, pyrrolyl, imidazolyl, pyrazolyl, oxazolyl, isoxazolyl, thiazolyl, isothiazolyl, furanyl, thienyl (thiophenyl), triazolyl, thiadiazolyl, 4,5,6,7-tetrahydro-2H-indazolyl, 2,4,5,6-tetrahydrocyclopenta[c]pyrazolyl, benzofuranyl, benzoimidazolyl, benzothienyl, benzothiadiazolyl, benzothiazolyl, benzotriazolyl, benzooxazolyl, benzooxadiazolyl, quinazolinyl, quinoxalinyl, carbazolyl, quinolinyl, dibenzofuranyl, dibenzothienyl, imidazothiazolyl, indazolyl, indolizinyl, indolyl, isoquinolinyl, naphthyridinyl, oxazolyl, oxadiazolyl, phenazinyl, phenothiazinyl, phthalazinyl, purinyl, phenazinyl, tetrazolyl and triazinyl in each case independently from one another are unsubstituted or mono- or disubstituted more preferably unsubstituted or monosubstituted, with one or two substituents selected from F, Cl, Br, CN, C$_{1-6}$-alkyl, CF$_3$, CF$_2$H, CFH$_2$, C$_{1-4}$-alkylene-CF$_3$, C$_{1-4}$-alkylene-CF$_2$H, C$_{1-4}$-alkylene-CFH$_2$, C(O)—C$_{1-6}$-alkyl, C(O)—OH, C(O)—OC$_{1-6}$-alkyl, C(O)—N(H)(OH), C(O)—NH$_2$, C(O)—N(H)(C$_{1-6}$-alkyl), C(O)—N(C$_{1-6}$-alkyl)$_2$, OH, OCF$_3$, OCF$_2$H, OCFH$_2$, OCF$_2$Cl, OCFCl$_2$, O—C$_{1-6}$-alkyl, O—C$_{3-6}$-cycloalkyl, O-(3 to 6-membered heterocycloalkyl), O-phenyl, O-(5 or 6-membered heterocycloalkyl), NH$_2$, N(H)(C$_{1-6}$-alkyl), N(C$_{1-6}$-alkyl)$_2$, N(H)—C(O)—C$_{1-6}$-alkyl, N(C$_{1-6}$-alkyl)-C(O)—C$_{1-6}$-alkyl, N(H)—C(O)—NH$_2$, N(H)—C(O)—N(H)(C$_{1-6}$-alkyl), N(H)—C(O)—N(C$_{1-6}$-alkyl)$_2$, N(C$_{1-6}$-alkyl)-C(O)—N(H)(C$_{1-6}$-alkyl), N(C$_{1-6}$-alkyl)-C(O)—N(C$_{1-6}$-alkyl)$_2$, N(H)—S(O)$_2$—C$_{1-6}$-alkyl, SCF$_3$, S—C$_{1-6}$-alkyl, S(O)—C$_{1-6}$-alkyl, S(O)$_2$—C$_{1-6}$-alkyl, S(O)$_2$—NH$_2$, S(O)$_2$—N(H)(C$_{1-6}$-alkyl), S(O)$_2$—N(C$_{1-6}$-alkyl)$_2$, C$_{3-6}$-cycloalkyl, C$_{1-4}$-alkylene-C$_{3-6}$-cycloalkyl, 3 to 6-membered heterocycloalkyl, C$_{1-4}$-alkylene-(3 to 6-membered heterocycloalkyl), phenyl or 5 or 6-membered heteroaryl; more preferably F, Cl, Br, CN, unsubstituted C$_{1-6}$-alkyl, CF$_3$, CF$_2$H, CFH$_2$, C$_{1-4}$-alkylene-CF$_3$, C$_{1-4}$-alkylene-CF$_2$H, C$_{1-4}$-alkylene-CFH$_2$, OCF$_3$, OCF$_2$H, OCFH$_2$, OH, O-(unsubstituted C$_{1-6}$-alkyl) and O-(unsubstituted phenyl); still more preferably F, Cl, Br, CN, unsubstituted C$_{1-6}$-alkyl, CF$_3$, CF$_2$H, CFH$_2$, OH, OCF$_3$, OCF$_2$H, OCFH$_2$, O-(unsubstituted C$_{1-6}$-alkyl) and O-(unsubstituted phenyl); most preferably F, Cl, Br, CN, unsubstituted C$_{1-6}$-alkyl, CF$_3$OH and O-(unsubstituted phenyl); and in particular F, Cl, Br, CH$_3$, CF$_3$, OH and O-(unsubstituted phenyl).

Preferably, R$^1$ represents phenyl, pyridyl, pyrimidinyl, thiazolyl, isothiazolyl, thienyl, benzothienyl, pyridazinyl, pyrazinyl, pyrrolyl, imidazolyl or pyrazolyl, wherein preferably phenyl, pyridyl, pyrimidinyl, thiazolyl, isothiazolyl, thienyl, benzothienyl, pyridazinyl, pyrazinyl, pyrrolyl, imidazolyl and pyrazolyl in each case independently from one another are unsubstituted or mono- or disubstituted, more preferably unsubstituted or monosubstituted, with one or more substituents selected from F, Cl, Br, CN, unsubstituted CF$_3$, CF$_2$H, CFH$_2$, C$_{1-4}$-alkylene-CF$_3$, C$_{1-4}$-alkylene-CF$_2$H, C$_{1-4}$-alkylene-CFH$_2$, OH, OCF$_3$, OCF$_2$H, OCFH$_2$, O-(unsubstituted C$_{1-6}$-alkyl) and O-(unsubstituted phenyl);

more preferably $R^1$ represents phenyl, pyridyl, pyrimidinyl, thiazolyl, isothiazolyl, thienyl, benzothienyl, pyridazinyl or pyrazinyl, wherein preferably phenyl, pyridyl, pyrimidinyl, thiazolyl, isothiazolyl, thienyl, benzothienyl, pyridazinyl and pyrazinyl in each case independently from one another are unsubstituted or mono- or disubstituted, more preferably unsubstituted or monosubstituted, with one or more substituents selected from F, Cl, Br, CN, unsubstituted $CF_3$, $CF_2H$, $CFH_2$, $OCF_3$, $OCF_2H$, $OCFH_2$, OH, O-(unsubstituted $C_{1-6}$-alkyl) and O-(unsubstituted phenyl); and most preferably $R^1$ represents phenyl, pyridyl, pyrimidinyl thiazolyl, isothiazolyl, thienyl or benzothienyl, wherein preferably phenyl, pyridyl, pyrimidinyl, thiazolyl, isothiazolyl, thienyl and benzothienyl in each case independently from one another are unsubstituted or mono- or disubstituted, more preferably unsubstituted or monosubstituted, with one or more substituents selected from F, Cl, Br, CN, unsubstituted $CF_3$, OH and O-(unsubstituted phenyl).

In a preferred embodiment, $R^1$ represents phenyl, pyridyl, pyrimidinyl, thiazolyl, isothiazolyl, thienyl or benzothienyl, wherein phenyl, pyridyl, pyrimidinyl, thiazolyl, isothiazolyl, thienyl and benzothienyl independently from one another are unsubstituted, mono- or disubstituted with one or more substituents selected from F, Cl, Br, unsubstituted $CF_3$, OH and O-(unsubstituted phenyl).

According to the present invention, $R^2$ represents H, F, Cl, Br, CN, $C_{3-6}$-cycloalkyl, $CHF_2$, $CH_2F$, $CF_3$, OH, $OCHF_2$, $OCH_2F$, $OCF_3$, O—$C_{1-6}$-alkyl, S—$C_{1-6}$-alkyl, S(O)—$C_{1-6}$-alkyl, $S(O)_2$—$C_{1-6}$-alkyl, O—$C_{3-6}$-cycloalkyl, S—$C_{3-6}$-cycloalkyl, S(O)—$C_{3-6}$-cycloalkyl, $S(O)_2$—$C_{3-6}$-cycloalkyl, $NH_2$, $N(H)(C_{1-6}$-alkyl), $N(C_{1-6}$-alkyl)$_2$, $N(H)(C_{3-6}$-cycloalkyl), $N(C_{1-6}$-alkyl)$(C_{3-6}$-cycloalkyl), $NC(O)(C_{1-6}$-alkyl), $NC(O)(C_{3-6}$-cycloalkyl), NC(O)(3 to 6-membered hetero cyclo alkyl);

preferably H, F, Cl, Br, CN, $C_{1-6}$-alkyl, $C_{3-6}$-cycloalkyl, $CHF_2$, $CH_2F$, $CF_3$, OH, $OCHF_2$, $OCH_2F$, $OCF_3$, O—$C_{1-6}$-alkyl, S—$C_{1-6}$-alkyl, S(O)—$C_{1-6}$-alkyl, $S(O)_2$—$C_{1-6}$-alkyl, O—$C_{3-6}$-cycloalkyl, S—$C_{3-6}$-cycloalkyl, S(O)—$C_{3-6}$-cycloalkyl, $S(O)_2$—$C_{3-6}$-cycloalkyl, $NH_2$, $N(H)(C_{1-6}$-alkyl), $N(C_{1-6}$-alkyl)$_2$, $N(H)(C_{3-6}$-cycloalkyl); more preferably H, F, Cl, Br, CN, $C_{1-6}$-alkyl, $C_{3-6}$-cycloalkyl, $CHF_2$, $CH_2F$, $CF_3$, OH, $OCHF_2$, $OCH_2F$, $OCF_3$, O—$C_{1-6}$-alkyl, S—$C_{1-6}$-alkyl, S(O)—$C_{1-6}$-alkyl or $S(O)_2$—$C_{1-6}$-alkyl; even more preferably H, F, Cl, Br, CN, $C_{1-6}$-alkyl, $C_{3-6}$-cycloalkyl, $CHF_2$, $CH_2F$, $CF_3$, OH, $OCHF_2$, $OCH_2F$, $OCF_3$, O—$C_{1-6}$-alkyl, S—$C_{1-6}$-alkyl or $S(O)_2$—$C_{1-6}$-alkyl; still more preferably H, F, Cl, Br, CN, unsubstituted $C_{1-6}$-alkyl, unsubstituted $C_{3-6}$-cycloalkyl, $CHF_2$, $CH_2F$, $CF_3$, OH, $OCHF_2$, $OCH_2F$, $OCF_3$, O-(unsubstituted $C_{1-6}$-alkyl), S-(unsubstituted $C_{1-6}$-alkyl) or $S(O)_2$-(unsubstituted $C_{1-6}$-alkyl); yet more preferably H, F, Cl, Br, CN, unsubstituted $C_{1-6}$-alkyl, $CF_3$, $OCF_3$, $OCHF_2$, $OCH_2F$, O-(unsubstituted $C_{1-6}$-alkyl), S-(unsubstituted $C_{1-6}$-alkyl) or $S(O)_2$-(unsubstituted $C_{1-6}$-alkyl); most preferably H, F, Cl, Br, $CH_3$, $CH_2CH_3$, $CF_3$, $OCHF_2$, $OCH_2F$, $OCF_3$, O—$CH_3$, S—$CH_3$, $S(O)_2$—$CH_3$, S—$CH_2CH_3$ or $S(O)_2$—$CH_2CH_3$; and in particular H, F, Cl, O—$CH_3$, $CH_2CH_3$, $OCHF_2$, S—$CH_3$ or $S(O)_2$—$CH_3$.

In a particularly preferred embodiment, $R^2$ represents H, F, Cl, Br, $CH_3$, $CH_2CH_3$, OH, O—$CH_3$, O—$CH_2CH_3$, O—$(CH_2)_2CH_3$, O—$CH(CH_3)_2$, $OCHF_2$, $OCH_2F$, $OCF_3$, S—$CH_3$, S—$CH_2CH_3$, S(O)—$CH_3$, S(O)—$CH_2CH_3$, $S(O)_2$—$CH_3$ or $S(O)_2$—$CH_2CH_3$.

According to the present invention, $R^3$ represents F, Cl, Br, $CHF_2$, $CH_2F$, $CF_3$, $C_{1-6}$-alkyl, $C_{3-6}$-cycloalkyl, O—$C_{1-6}$-alkyl, $OCHF_2$, $OCH_2F$, $OCF_3$, S(O)—$C_{1-6}$-alkyl, S(O)—$C_{3-6}$-cycloalkyl, $S(O)_2$—$C_{1-6}$-alkyl or $S(O)_2$—$C_{3-6}$-cycloalkyl; more preferably F, Cl, Br, $CHF_2$, $CH_2F$, $CF_3$, unsubstituted $C_{1-6}$-alkyl, unsubstituted $C_{3-6}$-cycloalkyl, O-(unsubstituted $C_{1-6}$-alkyl), $OCHF_2$, $OCH_2F$ or $OCF_3$; still more preferably F, Cl, Br, $CF_3$, $CH_3$, $CH_2CH_3$, cyclopropyl, $OCH_3$, $OCH_2CH_3$ or $OCF_3$; most preferably F, Cl, Br or $CF_3$; and in particular F.

$R^3$ can be bound to any of the four available carbon atoms of the phenyl ring. Preferably, $R^3$ occupies the meta position(s) relative to $R^2$.

According to the present invention, n represents 0, 1 or 2; preferably 0 or 2. Particularly preferably, n represents 2.

In a preferred embodiment, $R^3$ represents F and/or n represents 2.

Particularly preferably, the compound according to the present invention is according to general formula (X)

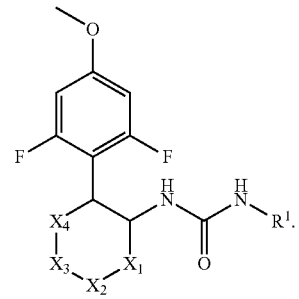

(X)

According to the present invention, L represents bond, $C_{1-6}$-alkylene, C(O), $S(O)_2$ or $C(CH_3)_2$.

Preferably, L represents bond, $CH_2$, $CH_2CH_2$, $CH_2CH_2CH_2$, $CH_2CH_2CH_2CH_2$, $CH_2CH_2CH_2CH_2CH_2$, $CH_2CH_2CH_2CH_2CH_2CH_2$, C(O), $S(O)_2$ or $C(CH_3)_2$; more preferably bond, $CH_2$, C(O), $S(O)_2$ or $C(CH_3)_2$; and most preferably bond, $CH_2$ or C(O).

Further according to the present invention,
$R^4$ represents H, $C_{1-6}$-alkyl, $C_{3-6}$-cycloalkyl, 3 to 6-membered heterocycloalkyl, aryl, 5 or 6-membered heteroaryl, $C(O)NH_2$, $C(O)N(H)(C_{1-6}$-alkyl), $C(O)N(C_{1-6}$-alkyl)$_2$, $C(O)N(H)(C_{3-6}$-cycloalkyl), C(O)N(H)(3 to 6-membered heterocycloalkyl), C(O)N(H)(aryl), C(O)N(H)(5 or 6-membered heteroaryl), $C(O)N(C_{1-6}$-alkyl)$(C_{3-6}$-cycloalkyl), $C(O)N(C_{1-6}$-alkyl)(3 to 6-membered heterocycloalkyl), $C(O)N(C_{1-6}$-alkyl)(aryl), $C(O)N(C_{1-6}$-alkyl)(5 or 6-membered heteroaryl), $C(O)N(C_{3-6}$-cycloalkyl)$(C_{3-6}$-cycloalkyl), $C(O)N(C_{3-6}$-cycloalkyl)(3 to 6-membered heterocycloalkyl), $C(O)N(C_{3-6}$-cycloalkyl)(aryl), $C(O)N(C_{3-6}$-cycloalkyl)(5 or 6-membered heteroaryl), C(O)O—$(C_{1-6}$-alkyl), C(O)O—$(C_{3-6}$-cycloalkyl), C(O)O-(3 to 6-membered heterocycloalkyl), C(O)O-(aryl), C(O)O-(5 or 6-membered heteroaryl), S(O)—$C_{1-6}$-alkyl, $S(O)_2$—$C_{1-6}$-alkyl, S(O)—$C_{3-6}$-cycloalkyl, $S(O)_2$—$C_{3-6}$-cycloalkyl, $C_{1-6}$-alkylene-OH, $C_{1-6}$-alkyl ene-O—$C_{1-6}$-alkyl, $C_{1-6}$-alkyl ene-$C_{3-6}$-cyclo alkyl, $C_{1-6}$-alkylene-3 to 6-membered heterocycloalkyl, $C_{1-6}$-alkylene-aryl, $C_{1-6}$-alkylene-5 or 6-membered heteroaryl;
wherein preferably
$C_{1-6}$-alkyl, $C_{1-6}$-alkylene, $C_{3-6}$-cycloalkyl and 3 to 6-membered heterocycloalkyl in each case independently from one another are unsubstituted or mono- or polysubstituted with one or more substituents selected from F, Cl, CN, $C_{1-6}$-alkyl, $CF_3$, $CF_2H$, $CFH_2$, $CF_2Cl$, $CFCl_2$, C(O)—$C_{1-6}$-alkyl, C(O)—OH, C(O)—$OC_{1-6}$-alkyl, C(O)—$NH_2$, C(O)—$N(H)(C_{1-6}$-alkyl), C(O)—N$(C_{1-6}$-alkyl)$_2$, OH, =O, $OCF_3$, $OCF_2H$, $OCFH_2$, OCF$_2$Cl, OCFCl$_2$, O—C$_{1-6}$-alkyl, O—C(O)—C$_{1-6}$-alkyl, O—C(O)—O—C$_{1-6}$-alkyl, O—(CO)—N(H)(C$_{1-6}$-alkyl), O—C(O)—N(C$_{1-6}$-alkyl)$_2$, O—S(O)$_2$—NH$_2$, O—S(O)$_2$—N(H)(C$_{1-6}$-alkyl), O—S(O)$_2$—N(C$_{1-6}$-alkyl)$_2$, NH$_2$, N(H)(C$_{1-6}$-alkyl), N(C$_{1-6}$-alkyl)$_2$, N(H)—C(O)—C$_{1-6}$-alkyl, N(H)—C(O)—O—C$_{1-6}$-alkyl, N(H)—C(O)—NH$_2$, N(H)—C(O)—N(H)(C$_{1-6}$-alkyl), N(H)—C(O)—N(C$_{1-6}$-alkyl)$_2$, N(C$_{1-6}$-alkyl)-C(O)—C$_{1-6}$-alkyl, N(C$_{1-6}$-alkyl)-C(O)—NH$_2$, N(C$_{1-6}$-alkyl)-C(O)—N(H)(C$_{1-6}$-alkyl), N(C$_{1-6}$-alkyl)-C(O)—N(C$_{1-6}$-alkyl)$_2$, N(H)—S(O)$_2$OH, N(H)—S(O)$_2$—C$_{1-6}$-alkyl, N(H)—S(O)$_2$—O—C$_{1-6}$-alkyl, N(H)—S(O)$_2$—NH$_2$, N(H)—S(O)$_2$—N(H)(C$_{1-6}$-alkyl), N(H)—S(O)$_2$N(C$_{1-6}$-alkyl)$_2$, N(C$_{1-6}$-alkyl)-S(O)$_2$—OH, N(C$_{1-6}$-alkyl)-S(O)$_2$—C$_{1-6}$-alkyl, N(C$_{1-6}$-alkyl)-S(O)$_2$—O—C$_{1-6}$-alkyl, N(C$_{1-6}$-alkyl)-S(O)$_2$—NH$_2$, N(C$_{1-6}$-alkyl)-S(O)$_2$—N(H)(C$_{1-6}$-alkyl), N(C$_{1-6}$-alkyl)-S(O)$_2$—N(C$_{1-6}$-alkyl)$_2$, SCF$_3$, SCF$_2$H, SCFH$_2$, S—C$_{1-6}$-alkyl, S(O)—C$_{1-6}$-alkyl, S(O)$_2$—C$_{1-6}$-alkyl, S(O)$_2$—OH, S(O)$_2$—NH$_2$, S(O)$_2$—N(H)(C$_{1-6}$-alkyl), S(O)$_2$—N(C$_{1-6}$-alkyl)$_2$, C$_{3-6}$-cycloalkyl, 3 to 6-membered heterocycloalkyl, phenyl, 5 or 6-membered heteroaryl, O—C$_{3-6}$-cycloalkyl, O-(3 to 6-membered heterocycloalkyl), O-phenyl, O-(5 or 6-membered heteroaryl), C(O)—C$_{3-6}$-cycloalkyl, C(O)-(3 to 6-membered heterocycloalkyl), C(O)-phenyl, C(O)-(5 or 6-membered heteroaryl), S(O)$_2$—(C$_{3-6}$-cycloalkyl), S(O)$_2$-(3 to 6-membered heterocycloalkyl), S(O)$_2$-phenyl or S(O)$_2$-(5 or 6-membered heteroaryl);

more preferably F, Cl, CN, C$_{1-6}$-alkyl, CF$_3$, CF$_2$H, CFH$_2$ and OCF$_3$; still more preferably F, Cl, CN, C$_{1-6}$-alkyl and CF$_3$; most preferably F, CN, CH$_3$, CH$_2$CH$_3$ and CF$_3$; and in particular F.

Preferably, R$^4$ represents H, C$_{1-6}$-alkyl, C$_{3-6}$-cycloalkyl, 3 to 6-membered heterocycloalkyl, phenyl, 5 or 6-membered heteroaryl, C(O)NH$_2$, C(O)N(H)(C$_{1-6}$-alkyl), C(O)N(C$_{1-6}$-alkyl)$_2$, C(O)N(H)(C$_{3-6}$-cycloalkyl), C(O)N(H)(3 to 6-membered heterocycloalkyl), C(O)N(H)(phenyl), C(O)N(H)(5 or 6-membered heteroaryl), C(O)N(C$_{1-6}$-alkyl)(C$_{3-6}$-cycloalkyl), C(O)N(C$_{1-6}$-alkyl)(3 to 6-membered heterocycloalkyl), C(O)N(C$_{1-6}$-alkyl)(phenyl), C(O)N(C$_{1-6}$-alkyl)(5 or 6-membered heteroaryl), C(O)N(C$_{3-6}$-cycloalkyl)(C$_{3-6}$-cycloalkyl), C(O)N(C$_{3-6}$-cycloalkyl)(3 to 6-membered heterocycloalkyl), C(O)N(C$_{3-6}$-cycloalkyl)(phenyl), C(O)N(C$_{3-6}$-cycloalkyl)(5 or 6-membered heteroaryl), C(O)O—(C$_{1-6}$-alkyl), C(O)O—(C$_{3-6}$-cycloalkyl), C(O)O-(3 to 6-membered heterocycloalkyl), C(O)O-(phenyl), C(O)O-(5 or 6-membered heteroaryl), S(O)—C$_{1-6}$-alkyl, S(O)$_2$—C$_{1-6}$-alkyl, S(O)—C$_{3-6}$-cycloalkyl, S(O)$_2$—C$_{3-6}$-cycloalkyl, C$_{1-6}$-alkylene-OH, C$_{1-6}$-alkylene-O—C$_{1-6}$-alkyl, C$_{1-6}$-alkylene-C$_{3-6}$-cycloalkyl, C$_{1-6}$-alkylene-3 to 6-membered heterocycloalkyl, C$_{1-6}$-alkylene-phenyl, C$_{1-6}$-alkylene-5 or 6-membered heteroaryl;

more preferably H, C$_{1-6}$-alkyl, C$_{3-6}$-cycloalkyl, 3 to 6-membered heterocycloalkyl, phenyl, 5 or 6-membered heteroaryl, C(O)NH$_2$, C(O)N(H)(C$_{1-6}$-alkyl), C(O)N(C$_{1-6}$-alkyl)$_2$, C(O)N(H)(C$_{3-6}$-cycloalkyl), C(O)N(H)(3 to 6-membered heterocycloalkyl), C(O)N(H)(phenyl), C(O)N(H)(5 or 6-membered heteroaryl), C(O)O—(C$_{1-6}$-alkyl), C(O)O—(C$_{3-6}$-cycloalkyl), C(O)O-(3 to 6-membered heterocycloalkyl), S(O)—C$_{1-6}$-alkyl, S(O)$_2$—C$_{1-6}$-alkyl, C$_{1-6}$-alkylene-OH, C$_{1-6}$-alkylene-O—C$_{1-6}$-alkyl, C$_{1-6}$-alkylene-C$_{3-6}$-cycloalkyl, C$_{1-6}$-alkylene-3 to 6-membered heterocycloalkyl, C$_{1-6}$-alkylene-phenyl, C$_{1-6}$-alkylene-5 or 6-membered heteroaryl;

still more preferably H, C$_{1-6}$-alkyl, C$_{3-6}$-cycloalkyl, 3 to 6-membered heterocycloalkyl, phenyl, or 6-membered heteroaryl, C(O)NH$_2$, C(O)N(H)(C$_{1-6}$-alkyl), C(O)N(C$_{1-6}$-alkyl)$_2$, C(O)N(H)(C$_{3-6}$-cycloalkyl), C(O)N(H)(3 to 6-membered heterocycloalkyl), C(O)O—(C$_{1-6}$-alkyl), C(O)O—(C$_{3-6}$-cycloalkyl), C(O)O-(3 to 6-membered heterocycloalkyl), C$_{1-6}$-alkylene-OH, C$_{1-6}$-alkylene-O—C$_{1-6}$-alkyl, C$_{1-6}$-alkylene-C$_{3-6}$-cycloalkyl, C$_{1-6}$-alkylene-3 to 6-membered heterocycloalkyl, C$_{1-6}$-alkylene-phenyl;

most preferably H, C$_{1-6}$-alkyl, C$_{3-6}$-cycloalkyl, 3 to 6-membered heterocycloalkyl, phenyl, C(O)NH$_2$, C(O)N(H)(C$_{1-6}$-alkyl), C(O)N(C$_{1-6}$-alkyl)$_2$, C(O)O—(C$_{1-6}$-alkyl), C$_{1-6}$-alkylene-OH or C$_{1-6}$-alkylene-O—C$_{1-6}$-alkyl; and in particular H, C$_{1-6}$-alkyl, C$_{3-6}$-cycloalkyl, 3 to 6-membered heterocycloalkyl, phenyl, C(O)NH$_2$, C(O)O—(C$_{1-6}$-alkyl), C$_{1-6}$-alkylene-OH or C$_{1-6}$-alkylene-O—C$_{1-6}$-alkyl.

In a preferred embodiment, R$^4$ represents H, C$_{1-6}$-alkyl, C$_{1-6}$-alkylene-OH, C$_{1-6}$-alkylene-O—C$_{1-6}$-alkyl, 3 to 6-membered cycloalkyl, 3 to 6-membered heterocycloalkyl, C(O)NH$_2$, C(O)N(H)(C$_{1-6}$-alkyl), C(O)N(C$_{1-6}$-alkyl)$_2$, C(O)O—(C$_{1-6}$-alkyl) or aryl, preferably phenyl; wherein C$_{1-6}$-alkyl, C$_{1-6}$-alkylene, C$_{3-6}$-cycloalkyl and 3 to 6-membered heterocycloalkyl in each case independently from one another are unsubstituted or mono- or polysubstituted with one or more substituents selected from F, Cl, CN, C$_{1-6}$-alkyl, CF$_3$, CF$_2$H, CFH$_2$ and OCF$_3$.

In another preferred embodiment, R$^4$ represents
H;
C$_{1-6}$-alkyl selected from the group consisting of methyl, ethyl, n-propyl, 2-propyl, n-butyl, isobutyl, sec-butyl, tert-butyl, n-pentyl, 2-pentyl, 3-pentyl, 2-methylbutyl, 3-methylbutyl, 3-methylbut-2-yl, 2-methylbut-2-yl, 2,2-dimethylpropyl and n-hexyl;
  wherein C$_{1-6}$-alkyl is unsubstituted or mono- or polysubstituted with one or more substituents selected from F, Cl, Br, CN, OH, O—CH$_3$, O—CH$_2$CH$_3$, O—(CH$_2$)$_2$CH$_3$ and O—CH(CH$_3$)$_2$;
C$_{1-6}$-alkylene-OH selected from the group consisting of CH$_2$OH, CH$_2$CH$_2$OH, (CH$_2$)$_3$OH, (CH$_2$)$_4$OH, C(H)(OH)—CH$_3$, CH$_2$C(H)(OH)—CH$_3$, C(CH$_3$)$_2$—OH, C(H)(OH)—C(CH$_3$)$_2$, CH$_2$C(CH$_3$)$_2$—OH;
C$_{1-6}$-alkylene-O—C$_{1-6}$-alkyl selected from the group consisting of CH$_2$OCH$_3$, CH$_2$CH$_2$OCH$_3$, (CH$_2$)$_3$OCH$_3$, (CH$_2$)$_4$OCH$_3$, (CH$_2$)$_5$OCH$_3$, (CH$_2$)$_6$OCH$_3$;
3 to 6-membered cycloalkyl selected from the group consisting of cyclopropyl, cyclobutyl, cyclopentyl and cyclohexyl;
3 to 6-membered heterocycloalkyl selected from the group consisting of tetrahydropyranyl, morpholinyl, pyrrolidinyl, 4-methylpiperazinyl, morpholinonyl, azetidinyl, aziridinyl, dithiolanyl, dihydropyrrolyl, dioxanyl, dioxolanyl, dihydropyridinyl, dihydrofuranyl, dihydroisoxazolyl, dihydrooxazolyl, imidazolidinyl, isoxazolidinyl, oxazolidinyl, oxiranyl, oxetanyl, piperazinyl, piperidinyl, pyrazolidinyl, pyranyl and tetrahydropyrrolyl;
C(O)NH$_2$;
C(O)N(H)(C$_{1-6}$-alkyl) selected from the group consisting of C(O)N(H)(CH$_3$) and C(O)N(H)(CH$_2$CH$_3$);
C(O)N(C$_{1-6}$-alkyl)$_2$ selected from the group consisting of C(O)N(CH$_3$)$_2$ and C(O)N(CH$_2$CH$_3$)$_2$;
C(O)O—(C$_{1-6}$-alkyl) selected from the group consisting of C(O)O—CH$_3$, C(O)O—CH$_2$CH$_3$, C(O)O—(CH$_2$)$_2$CH$_3$, C(O)O—CH(CH$_3$)$_2$;
S(O)—C$_{1-6}$-alkyl selected from the group consisting of S(O)—CH$_3$, S(O)—CH$_2$CH$_3$, S(O)—(CH$_2$)$_2$CH$_3$, S(O)—CH(CH$_3$)$_2$;

S(O)$_2$—C$_{1-6}$-alkyl selected from the group consisting of S(O)$_2$—CH$_3$, S(O)$_2$—CH$_2$CH$_3$, S(O)$_2$—(CH$_2$)$_2$CH$_3$, S(O)$_2$—CH(CH$_3$)$_2$;

S(O)—C$_{3-6}$-cycloalkyl selected from the group consisting of S(O)-cyclopropyl, S(O)-cyclobutyl, S(O)-cyclopentyl, S(O)-cyclohexyl;

S(O)$_2$—C$_{3-6}$-cycloalkyl selected from the group consisting of S(O)$_2$-cyclopropyl, S(O)$_2$-cyclobutyl, S(O)$_2$-cyclopentyl, S(O)$_2$-cyclohexyl; or phenyl.

More preferably, R$^4$ represents H; methyl, CF$_3$, CHF$_2$, CH$_2$F, ethyl, CH$_2$CF$_3$, CH$_2$CHF$_2$, CH$_2$CH$_2$F, CF$_2$CH$_3$, CHFCH$_3$, n-propyl, 2-propyl, n-butyl, isobutyl, sec-butyl, tert-butyl, CH$_2$OH, CH$_2$CH$_2$OH, (CH$_2$)$_3$OH, (CH$_2$)$_4$OH, C(H)(OH)—CH$_3$, CH$_2$C(H)(OH)—CH$_3$, CH$_2$OCH$_3$, CH$_2$CH$_2$OCH$_3$, (CH$_2$)$_3$OCH$_3$, cyclopropyl, cyclobutyl, cyclopentyl, cyclohexyl, tetrahydropyranyl, morpholinyl, pyrrolidinyl, dioxanyl, oxiranyl, piperazinyl, piperidinyl, pyrazolidinyl, pyranyl, C(O)NH$_2$, C(O)O—CH$_3$, C(O)O—CH$_2$CH$_3$, C(O)O—(CH$_2$)$_2$CH$_3$, S(O)—CH$_3$, S(O)—CH$_2$CH$_3$, S(O)$_2$—CH$_3$, S(O)$_2$—CH$_2$CH$_3$ or phenyl.

In a preferred embodiment,

L represents bond, CH$_2$ or C(O); and/or

R$^4$ represents H, C$_{1-6}$-alkyl, C$_{1-6}$-alkylene-OH, C$_{1-6}$-alkylene-O—C$_{1-6}$-alkyl, 3 to 6-membered cycloalkyl, 3 to 6-membered heterocycloalkyl, C(O)NH$_2$, C(O)N(H)(C$_{1-6}$-alkyl), C(O)N(C$_{1-6}$-alkyl)$_2$, C(O)O—(C$_{1-6}$-alkyl); S(O)—C$_{1-6}$-alkyl, S(O)$_2$—C$_{1-6}$-alkyl, S(O)—C$_{3-6}$-cycloalkyl, S(O)$_2$—C$_{3-6}$-cycloalkyl, or aryl.

More preferably,

L represents bond, CH$_2$ or C(O); and

R$^4$ represents

H;

C$_{1-6}$-alkyl selected from the group consisting of methyl, ethyl, n-propyl, 2-propyl, n-butyl, isobutyl, sec-butyl, tert-butyl, n-pentyl, 2-pentyl, 3-pentyl, 2-methylbutyl, 3-methylbutyl, 3-methylbut-2-yl, 2-methylbut-2-yl, 2,2-dimethylpropyl and n-hexyl;

wherein C$_{1-6}$-alkyl is unsubstituted or mono- or polysubstituted with one or more substituents selected from F, Cl, Br, CN, OH, O—CH$_3$, O—CH$_2$CH$_3$, O—(CH$_2$)$_2$CH$_3$ and O—CH(CH$_3$)$_2$;

C$_{1-6}$-alkylene-OH selected from the group consisting of CH$_2$OH, CH$_2$CH$_2$OH, (CH$_2$)$_3$OH, (CH$_2$)$_4$OH, C(H)(OH)—CH$_3$, CH$_2$C(H)(OH)—CH$_3$, C(CH$_3$)$_2$—OH, C(H)(OH)—C(CH$_3$)$_2$, CH$_2$C(CH$_3$)$_2$—OH, C$_{1-6}$-alkylene-O—C$_{1-6}$-alkyl selected from the group consisting of CH$_2$OCH$_3$, CH$_2$CH$_2$OCH$_3$, (CH$_2$)$_3$OCH$_3$, (CH$_2$)$_4$OCH$_3$, (CH$_2$)$_5$OCH$_3$, (CH$_2$)$_6$OCH$_3$, 3 to 6-membered cycloalkyl selected from the group consisting of cyclopropyl, cyclobutyl, cyclopentyl and cyclohexyl;

3 to 6-membered heterocycloalkyl selected from the group consisting of tetrahydropyranyl, morpholinyl, pyrrolidinyl, 4-methylpiperazinyl, morpholinonyl, azetidinyl, aziridinyl, dithiolanyl, dihydropyrrolyl, dioxanyl, dioxolanyl, dihydropyridinyl, dihydrofuranyl, dihydroisoxazolyl, dihydrooxazolyl, imidazolidinyl, isoxazolidinyl, oxazolidinyl, oxiranyl, oxetanyl, piperazinyl, piperidinyl, pyrazolidinyl, pyranyl and tetrahydropyrrolyl;

C(O)NH$_2$,

C(O)N(H)(C$_{1-6}$-alkyl) selected from the group consisting of C(O)N(H)(CH$_3$) and C(O)N(H)(CH$_2$CH$_3$);

C(O)N(C$_{1-6}$-alkyl)$_2$ selected from the group consisting of C(O)N(CH$_3$)$_2$ and C(O)N(CH$_2$CH$_3$)$_2$;

C(O)O—(C$_{1-6}$-alkyl) selected from the group consisting of C(O)O—CH$_3$, C(O)O—CH$_2$CH$_3$, C(O)O—(CH$_2$)$_2$CH$_3$, C(O)O—CH(CH$_3$)$_2$;

S(O)—C$_{1-6}$-alkyl selected from the group consisting of S(O)—CH$_3$, S(O)—CH$_2$CH$_3$, S(O)—(CH$_2$)$_2$CH$_3$, S(O)—CH(CH$_3$)$_2$;

S(O)$_2$—C$_{1-6}$-alkyl selected from the group consisting of S(O)$_2$—CH$_3$, S(O)$_2$—CH$_2$CH$_3$, S(O)$_2$—(CH$_2$)$_2$CH$_3$, S(O)$_2$—CH(CH$_3$)$_2$;

S(O)—C$_{3-6}$-cycloalkyl selected from the group consisting of S(O)-cyclopropyl, S(O)-cyclobutyl, S(O)-cyclopentyl, S(O)-cyclohexyl;

S(O)$_2$—C$_{3-6}$-cycloalkyl selected from the group consisting of S(O)$_2$-cyclopropyl, S(O)$_2$-cyclobutyl, S(O)$_2$-cyclopentyl, S(O)$_2$-cyclohexyl; or phenyl.

In a particularly preferred embodiment,

X$_2$ represents N(L-R$^4$) and X$_3$ represents CH$_2$ or C(O) and X$_1$ and X$_4$ represent CH$_2$;

or

X$_4$ represents N(L-R$^4$) and X$_1$, X$_2$ and X$_3$ represent CH$_2$;

and n represents 0, 1 or 2

R$^1$ represents phenyl, pyridyl, pyrimidinyl, thiazolyl, isothiazolyl, thienyl or benzothienyl, wherein phenyl, pyridyl, pyrimidinyl, thiazolyl, isothiazolyl, thienyl and benzothienyl independently from one another are unsubstituted or monosubstituted with one or more substituents selected from F, Cl, Br, unsubstituted CF$_3$, OH and O-(unsubstituted phenyl);

R$^2$ represents Cl, O—CH$_3$, F, H, CH$_3$, CH$_2$CH$_3$, O—CH$_2$F, O—CHF$_2$, O—CF$_3$, S—CH$_2$CH$_3$, S(O)$_2$—CH$_3$ or S(O)$_2$—CH$_2$CH$_3$;

R$^3$ represents F;

L represents bond, CH$_2$ or C(O); and

R$^4$ represents

H;

C$_{1-6}$-alkyl selected from the group consisting of methyl, ethyl, n-propyl, 2-propyl, n-butyl, isobutyl, sec-butyl, tert-butyl, n-pentyl, 2-pentyl, 3-pentyl, 2-methylbutyl, 3-methylbutyl, 3-methylbut-2-yl, 2-methylbut-2-yl, 2,2-dimethylpropyl and n-hexyl;

wherein C$_{1-6}$-alkyl is unsubstituted or mono- or polysubstituted with one or more substituents selected from F, Cl, Br, CN, OH, O—CH$_3$, O—CH$_2$CH$_3$, O—(CH$_2$)$_2$CH$_3$ and O—CH(CH$_3$)$_2$;

C$_{1-6}$-alkylene-OH selected from the group consisting of CH$_2$OH, CH$_2$CH$_2$OH, (CH$_2$)$_3$OH, (CH$_2$)$_4$OH, C(H)(OH)—CH$_3$, CH$_2$C(H)(OH)—CH$_3$, C(CH$_3$)$_2$—OH, C(H)(OH)—C(CH$_3$)$_2$, CH$_2$C(CH$_3$)$_2$—OH, C$_{1-6}$-alkylene-O—C$_{1-6}$-alkyl selected from the group consisting of CH$_2$OCH$_3$, CH$_2$CH$_2$OCH$_3$, (CH$_2$)$_3$OCH$_3$, (CH$_2$)$_4$OCH$_3$, (CH$_2$)$_5$OCH$_3$, (CH$_2$)$_6$OCH$_3$, 3 to 6-membered cycloalkyl selected from the group consisting of cyclopropyl, cyclobutyl, cyclopentyl and cyclohexyl;

3 to 6-membered heterocycloalkyl selected from the group consisting of tetrahydropyranyl, morpholinyl, pyrrolidinyl, 4-methylpiperazinyl, morpholinonyl, azetidinyl, aziridinyl, dithiolanyl, dihydropyrrolyl, dioxanyl, dioxolanyl, dihydropyridinyl, dihydrofuranyl, dihydroisoxazolyl, dihydrooxazolyl, imidazolidinyl, isoxazolidinyl, oxazolidinyl, oxiranyl, oxetanyl, piperazinyl, piperidinyl, pyrazolidinyl, pyranyl and tetrahydropyrrolyl;

C(O)NH₂,
C(O)N(H)(C₁₋₆-alkyl) selected from the group consisting of C(O)N(H)(CH₃) and C(O)N(H)(CH₂CH₃);
C(O)N(C₁₋₆-alkyl)₂ selected from the group consisting of C(O)N(CH₃)₂ and C(O)N(CH₂CH₃)₂;
C(O)O—(C₁₋₆-alkyl) selected from the group consisting of C(O)O—CH₃, C(O)O—CH₂CH₃, C(O)O—(CH₂)₂CH₃, C(O)O—CH(CH₃)₂;
S(O)—C₁₋₆-alkyl selected from the group consisting of S(O)—CH₃, S(O)—CH₂CH₃, S(O)—(CH₂)₂CH₃, S(O)—CH(CH₃)₂;
S(O)₂—C₁₋₆-alkyl selected from the group consisting of S(O)₂—CH₃, S(O)₂—CH₂CH₃, S(O)₂—(CH₂)₂CH₃, S(O)₂—CH(CH₃)₂;
S(O)—C₃₋₆-cycloalkyl selected from the group consisting of S(O)-cyclopropyl, S(O)-cyclobutyl, S(O)-cyclopentyl, S(O)-cyclohexyl;
S(O)₂—C₃₋₆-cycloalkyl selected from the group consisting of S(O)₂-cyclopropyl, S(O)₂-cyclobutyl, S(O)₂-cyclopentyl, S(O)₂-cyclohexyl; or
phenyl;
in the form of the free compound or a physiologically acceptable salt thereof.

In a preferred embodiment, the compound according to the present invention is selected from the group consisting of
1 rac-trans-1-(4-chlorophenyl)-3-(-4-(4-methoxyphenyl)-6-oxopiperidin-3-yl)urea
2 rac-trans-1-(1-acetyl-4-(4-methoxyphenyl)piperidin-3-yl)-3-(4-chlorophenyl)urea
3 rac-trans-1-(4-bromophenyl)-3-(4-(4-methoxyphenyl)-6-oxopiperidin-3-yl)urea
4 rac-trans-1-(4-chlorophenyl)-3-(4-(4-methoxyphenyl)piperidin-3-yl)urea
5 rac-trans-1-(1-acetyl-4-(2,6-difluoro-4-methoxyphenyl)piperidin-3-yl)-3-(4-chlorophenyl)urea
6 rac-trans-1-(4-bromophenyl)-3-(4-(4-methoxyphenyl)piperidin-3-yl)urea
7 rac-trans-1-(4-chlorophenyl)-3-(4-(4-methoxyphenyl)-1-methyl-6-oxopiperidin-3-yl)urea
8 rac-trans-1-(4-bromophenyl)-3-(4-(2,6-difluoro-4-methoxyphenyl)piperidin-3-yl)urea
9 rac-trans-1-(4-chlorophenyl)-3-(4-(2,6-difluoro-4-methoxyphenyl)piperidin-3-yl)urea
10 trans-ent1-1-(4-chlorophenyl)-3-(4-(4-methoxyphenyl)-1-methyl-6-oxopiperidin-3-yl)urea
11 trans-ent2-1-(4-chlorophenyl)-3-(4-(4-methoxyphenyl)-1-methyl-6-oxopiperidin-3-yl)urea
12 rac-trans-1-(4-chlorophenyl)-3-(1-(cyclopropanecarbonyl)-4-(4-methoxyphenyl)piperidin-3-yl)urea
13 rac-trans-1-(4-chlorophenyl)-3-(1-(2-hydroxyacetyl)-4-(4-methoxyphenyl)piperidin-3-yl)urea
14 rac-trans-1-(4-chlorophenyl)-3-(1-(2,2-difluoropropanoyl)-4-(4-methoxyphenyl)piperidin-3-yl)urea
15 rac-trans-1-(4-chlorophenyl)-3-(4-(4-methoxyphenyl)-1-(3-methoxypropanoyl)piperidin-3-yl)urea
16 rac-trans-1-(4-chlorophenyl)-3-(4-(4-methoxyphenyl)-1-(tetrahydro-2H-pyran-4-carbonyl)-piperidin-3-yl)urea
17 rac-trans-1-(4-chlorophenyl)-3-(1-isobutyryl-4-(4-methoxyphenyl)piperidin-3-yl)urea
18 rac-trans-1-(4-chlorophenyl)-3-[4-(4-methoxyphenyl)-1-(3-methyl-butanoyl)-piperidin-3-yl]-urea
19 rac-trans-1-(1-acetyl-4-(4-methoxyphenyl)piperidin-3-yl)-3-(6-chloropyridin-3-yl)urea
20 rac-trans-2-(5-(3-(4-chlorophenyl)ureido)-4-(4-methoxyphenyl)-2-oxopiperidin-1-yl)acetamide
21 rac-trans-methyl 2-(5-(3-(4-chlorophenyl)ureido)-4-(4-methoxyphenyl)-2-oxopiperidin-1-yl)acetate
22 rac-trans-1-(1-acetyl-4-(4-methoxyphenyl)piperidin-3-yl)-3-(4-bromophenyl)urea
23 rac-trans-1-(4-chlorophenyl)-3-(4-(2,6-difluoro-4-methoxyphenyl)-6-oxopiperidin-3-yl)urea
24 rac-trans-1-(4-chlorophenyl)-3-(1-(cyclopropylmethyl)-4-(4-methoxyphenyl)-6-oxopiperidin-3-yl)urea
25 rac-trans-1-(1-acetyl-4-(4-methoxyphenyl)piperidin-3-yl)-3-(pyrimidin-5-yl)urea
26 rac-trans-1-(1-acetyl-4-(4-methoxyphenyl)piperidin-3-yl)-3-(6-methylpyridin-3-yl)urea
27 rac-trans-1-(1-acetyl-4-(4-methoxyphenyl)piperidin-3-yl)-3-(6-(trifluoromethyl)pyridin-3-yl)urea
28 rac-trans-1-(1-acetyl-4-(4-methoxyphenyl)piperidin-3-yl)-3-(6-methylpyridin-3-yl)urea
29 rac-trans-1-(4-chlorophenyl)-3-(1-(cyclopropylmethyl)-4-(2,6-difluoro-4-methoxyphenyl)-6-oxopiperidin-3-yl)urea
30 rac-trans-1-(4-chlorophenyl)-3-(1-(3-hydroxypropanoyl)-4-(4-methoxyphenyl)piperidin-3-yl)urea
31 rac-trans-1-(4-chlorophenyl)-3-(4-(2,6-difluoro-4-methoxyphenyl)-1-(2-hydroxyethyl)-6-oxopiperidin-3-yl)urea
32 rac-trans-1-(4-chlorophenyl)-3-(1-(2-hydroxyethyl)-4-(4-methoxyphenyl)-6-oxopiperidin-3-yl)urea
34 rac-trans-1-(1-acetyl-4-(2,6-difluoro-4-methoxyphenyl)piperidin-3-yl)-3-(4-bromophenyl)urea
35 rac-trans-methyl 2-(5-(3-(4-chlorophenyl)ureido)-4-(2,6-difluoro-4-methoxyphenyl)-2-oxopiperidin-1-yl)acetate
36 trans-ent1-1-(4-chlorophenyl)-3-(4-(2,6-difluoro-4-methoxyphenyl)piperidin-3-yl)urea
37 trans-ent2-1-(4-chlorophenyl)-3-(4-(2,6-difluoro-4-methoxyphenyl)piperidin-3-yl)urea
38 rac-trans-1-(4-chlorophenyl)-3-(1-(cyclopropanecarbonyl)-4-(2,6-difluoro-4-methoxyphenyl)piperidin-3-yl)urea
39 trans-ent1-1-(4-chlorophenyl)-3-(1-(cyclopropanecarbonyl)-4-(2,6-difluoro-4-methoxyphenyl)piperidin-3-yl)urea
40 trans-ent2-1-(4-chlorophenyl)-3-(1-(cyclopropanecarbonyl)-4-(2,6-difluoro-4-methoxyphenyl)piperidin-3-yl)urea
41 rac-trans-1-(4-chlorophenyl)-3-(4-(2-fluoro-4-methoxyphenyl)-6-oxopiperidin-3-yl)urea
42 trans-ent1-1-(4-chlorophenyl)-3-(4-(2-fluoro-4-methoxyphenyl)-6-oxopiperidin-3-yl)urea
43 trans-ent2-1-(4-chlorophenyl)-3-(4-(2-fluoro-4-methoxyphenyl)-6-oxopiperidin-3-yl)urea
44 rac-trans-1-(4-chlorophenyl)-3-(4-(2-fluoro-4-methoxyphenyl)piperidin-3-yl)urea
45 trans-ent1-1-(4-chlorophenyl)-3-(4-(2-fluoro-4-methoxyphenyl)piperidin-3-yl)urea
46 trans-ent2-1-(4-chlorophenyl)-3-(4-(2-fluoro-4-methoxyphenyl)piperidin-3-yl)urea
47 trans-ent1-1-(4-(2,6-difluoro-4-methoxyphenyl)-6-oxopiperidin-3-yl)-3-(pyridin-4-yl)urea
48 trans-ent2-1-(4-(2,6-difluoro-4-methoxyphenyl)-6-oxopiperidin-3-yl)-3-(pyridin-4-yl)urea
49 trans-ent1-1-(4-chlorophenyl)-3-(4-(2,6-difluoro-4-methoxyphenyl)-6-oxopiperidin-3-yl)urea
50 trans-ent2-1-(4-chlorophenyl)-3-(4-(2,6-difluoro-4-methoxyphenyl)-6-oxopiperidin-3-yl)urea
51 rac-trans-1-(5-chlorothiophen-2-yl)-3-(4-(2,6-difluoro-4-methoxyphenyl)-6-oxopiperidin-3-yl)urea
52 rac-trans-1-(5-Chloro-thiophen-3-yl)-3-[4-(2,6-difluoro-4-methoxy-phenyl)-6-oxo-piperidin-3-yl]-urea
53 rac-trans-1-(Benzo[b]thiophen-2-yl)-3-[4-(2,6-difluoro-4-methoxy-phenyl)-6-oxo-piperidin-3-yl]-urea 54 rac-trans-1-[4-(2,6-Difluoro-4-methoxy-phenyl)-6-oxo-piperidin-3-yl]-3-(4-phenoxy-phenyl)-urea
55 rac-trans-1-[4-(2,6-Difluoro-4-methoxy-phenyl)-6-oxo-piperidin-3-yl]-3-(3-methyl-isothiazol-5-yl)-urea
56 rac-trans-1-(5-Chloro-thiazol-2-yl)-3-[4-(2,6-difluoro-4-methoxy-phenyl)-6-oxo-piperidin-3-yl]-urea
57 rac-trans-1-(4-Chloro-3-hydroxy-phenyl)-3-[4-(2,6-difluoro-4-methoxy-phenyl)-6-oxo-piperidin-3-yl]-urea
58 rac-trans-1-(4-Chloro-3-fluoro-phenyl)-3-[4-(2,6-difluoro-4-methoxy-phenyl)-6-oxo-piperidin-3-yl]-urea
59 trans-ent1-1-(4-Chlorophenyl)-3-[4-(2-fluoro-4-methoxy-phenyl)-1-(2-methoxy-ethyl)-6-oxo-piperidin-3-yl]-urea
60 trans-ent2-1-(4-Chlorophenyl)-3-[4-(2-fluoro-4-methoxy-phenyl)-1-(2-methoxy-ethyl)-6-oxo-piperidin-3-yl]-urea
61 trans-ent1-1-(4-Chlorophenyl)-3-[1-(2,2-difluoro-ethyl)-4-(2-fluoro-4-methoxy-phenyl)-6-oxo-piperidin-3-yl]-urea
62 trans-ent2-1-(4-Chlorophenyl)-3-[1-(2,2-difluoro-ethyl)-4-(2-fluoro-4-methoxy-phenyl)-6-oxo-piperidin-3-yl]-urea
63 trans-ent1-1-(4-Chlorophenyl)-3-[4-(2,4-difluoro-phenyl)-1-(2-methoxy-ethyl)-6-oxo-piperidin-3-yl]-urea
64 trans-ent2-1-(4-Chlorophenyl)-3-[4-(2,4-difluoro-phenyl)-1-(2-methoxy-ethyl)-6-oxo-piperidin-3-yl]-urea
65 trans-ent1-1-(4-Chlorophenyl)-3-[1-(2,2-difluoro-ethyl)-4-(2,4-difluoro-phenyl)-6-oxo-piperidin-3-yl]-urea
66 trans-ent2-1-(4-Chlorophenyl)-3-[1-(2,2-difluoro-ethyl)-4-(2,4-difluoro-phenyl)-6-oxo-piperidin-3-yl]-urea
67 trans-ent1-1-(4-Chlorophenyl)-3-[4-(2,4-difluoro-phenyl)-6-oxo-piperidin-3-yl]-urea
68 trans-ent2-1-(4-Chlorophenyl)-3-[4-(2,4-difluoro-phenyl)-6-oxo-piperidin-3-yl]-urea
69 rac-trans-1-(4-chlorophenyl)-3-(4-(4-ethyl-2,6-difluorophenyl)-6-oxopiperidin-3-yl)urea
70 rac-trans-1-(4-chlorophenyl)-3-(4-(4-(difluoromethoxy)-2,6-difluorophenyl)-6-oxopiperidin-3-yl)urea
71 trans-ent2-1-(4-chlorophenyl)-3-(1-(cyclopropanecarbonyl)-4-(2-fluoro-4-methoxyphenyl)piperidin-3-yl)urea
72 rac-trans-1-(4-chlorophenyl)-3-(4-(4-(methylthio)phenyl)-6-oxopiperidin-3-yl)urea
73 rac-trans-1-(4-chlorophenyl)-3-(4-(4-ethylphenyl)-6-oxopiperidin-3-yl)urea
74 rac-trans-1-(4-chlorophenyl)-3-(4-(4-(difluoromethoxy)phenyl)-6-oxopiperidin-3-yl)urea
75 rac-trans-1-(4-chlorophenyl)-3-(4-(4-(methylsulfonyl)phenyl)-6-oxopiperidin-3-yl)urea
76 trans-ent1-1-(4-chlorophenyl)-3-(4-(4-methoxyphenyl)-6-oxopiperidin-3-yl)urea
77 trans-ent2-1-(4-chlorophenyl)-3-(4-(4-methoxyphenyl)-6-oxopiperidin-3-yl)urea
78 rac-trans-1-(4-chlorophenyl)-3-(6-oxo-4-phenylpiperidin-3-yl)urea
79 rac-trans-1-(4-chlorophenyl)-3-(4-phenylpiperidin-3-yl)urea, 1-(4-chlorophenyl)-3-((3S,4S)-4-phenylpiperidin-3-yl)urea
80 trans-ent1-1-(4-chlorophenyl)-3-(4-phenylpiperidin-3-yl)urea, 1-(4-chlorophenyl)-3-((3S,4S)-4-phenylpiperidin-3-yl)urea
81 trans-ent2-1-(4-chlorophenyl)-3-(4-phenylpiperidin-3-yl)urea, 1-(4-chlorophenyl)-3-((3S,4S)-4-phenylpiperidin-3-yl)urea
82 rac-trans-1-(4-chlorophenyl)-3-(1-(cyclopropanecarbonyl)-4-phenylpiperidin-3-yl)urea
83 trans-ent1-1-(4-chlorophenyl)-3-(1-(cyclopropanecarbonyl)-4-phenylpiperidin-3-yl)urea
84 trans-ent2-1-(4-chlorophenyl)-3-(1-(cyclopropanecarbonyl)-4-phenylpiperidin-3-yl)urea
85 rac-trans-1-(4-chlorophenyl)-3-(1-(cyclopropanecarbonyl)-4-(2-fluoro-4-methoxyphenyl)piperidin-3-yl)urea
86 trans-ent1-1-(4-chlorophenyl)-3-(1-(cyclopropanecarbonyl)-4-(2-fluoro-4-methoxyphenyl)piperidin-3-yl)urea
87 dia1-1-(4-chlorophenyl)-3-(2-(2,6-difluoro-4-methoxyphenyl)-1-methylpiperidin-3-yl)urea
88 dia2-1-(4-chlorophenyl)-3-(2-(2,6-difluoro-4-methoxyphenyl)-1-methylpiperidin-3-yl)urea
89 dia1-1-(4-chlorophenyl)-3-(2-(4-methoxyphenyl)-1-methylpiperidin-3-yl)urea
90 dia2-1-(4-chlorophenyl)-3-(2-(4-methoxyphenyl)-1-methylpiperidin-3-yl)urea
91 trans-ent1-1-(4-chlorophenyl)-3-(4-(4-chlorophenyl)-6-oxopiperidin-3-yl)urea
92 trans-ent2-1-(4-chlorophenyl)-3-(4-(4-chlorophenyl)-6-oxopiperidin-3-yl)urea in the form of the free compound or a physiologically acceptable salt thereof.

In a preferred embodiment, the compound according to the present invention is a modulator of FPR2, more preferably an agonist of FPR2. In the sense of the present invention, the term "modulator of FPR2 (FPR2 modulator)" preferably means that the respective compound exhibits in a target engagement assay an EC50 value on FPR2 of at most 10 µM ($10 \cdot 10^{-6}$ mol/L); more preferably at most 1 µM; still more preferably at most 500 nM ($10^{-9}$ mol/L); yet more preferably at most 300 nM; even more preferably at most 100 nM; most preferably at most 10 nM; and in particular at most 1 nM.

A preferred target engagement assay for testing compounds for their potency (EC50) on human FPR2 or FPR1 is described herein below:

Cells (hFPR1-Gα15-CHO or hFPR2-Aq-CHO) are suspended in 10 mL of respective complete medium (F12(1×) HAM media; 10% HI-FBS; 0.1 mg/ml Hygromycin B and 0.2 mg/ml Zeocin [for hFPR1 only]; 0.4 mg/mL Geneticin and 0.25 mg/ml Zeocin [for hFPR2-Aq only]) and viability is checked using Trypan Blue exclusion. After washing, the cells are plated at 10,000 cells per well in 40 µL complete medium in a 384-well sterile clear bottom black plate and incubated in a 5% $CO_2$ incubator at 37° C. for 18 hours. Plating media is removed from each well by decanting and gentle tapping before 30 µL of 0.5× Calcium 5 dye solution (0.5×FLIPR Calcium 5 dye (Molecular devices, R8186)); HBSS; 20 mM HEPES; 2.5 mM Probenecid; 0.025% Pluronic F-127; pH adjusted to 7.4) is added to each well and the plate is then incubated at 37° C. for 30 minutes. For the assay the plate is equilibrated at room temperature for 10 minutes before placing it in the FLIPR. Compounds are dissolved in DMSO and serially diluted over an 11 point half log (3.16 fold) dilution (2 mM to 20 nM). Compounds are then diluted 1:50 in assay buffer (HBSS; 20 mM HEPES; 2.5 mM Probenecid; 0.05% gelatin; 0.1% BSA; pH adjusted to 7.4) just before performing the assay. Compounds are finally added to the respective wells of the cell plate (final assay concentration 10 µM to 100 pM) using the FLIPR (e.g. FLIPR-Tetra, Molecular Devices) and fluorescence readings are captured for 5 minutes. The increase in fluorescence from the basal reading in the presence of the compounds is compared with that of the control wells (wells having no compound) to calculate the activity of the compounds. The $EC_{50}$ values of the compounds can be determined using e.g. Graph pad Prism software.

In a preferred embodiment, the compound according to the present invention exhibits in a target engagement assay an EC50 value on FPR2 of at most 1 µM ($10^{-6}$ mol/L); still more preferably at most 500 nM ($10^{-9}$ mol/L); yet more preferably at most 300 nM; even more preferably at most 100 nM; most preferably at most 10 nM; and in particular at most 1 nM or at most 100 pM ($10^{-12}$ mol/L) or at most 10 pM.

In a preferred embodiment, the compound according to the present invention exhibits in a target engagement assay an EC50 value on FPR2 in the range of from 0.1 nM ($10^{-9}$ mol/L) to 1000 nM; still more preferably 0.1 nM to 800 nM; yet more preferably 0.1 nM to 500 nM; even more preferably 0.1 nM to 300 nM; most preferably 0.1 nM to 100 nM; and in particular 0.1 nM to 10 nM. In another preferred embodiment, the compound according to the present invention exhibits in a target engagement assay an EC50 value on FPR2 in the range of from 1 pM ($10^{-12}$ mol/L) to 1000 nM; still more preferably 1 pM to 800 nM; yet more preferably 1 pM to 500 nM; even more preferably 1 pM to 300 nM; most preferably 1 pM to 100 nM; and in particular 1 pM to 10 nM.

In a preferred embodiment, the compound according to the present invention does not activate FPR1. According to this embodiment, the compound according to the present invention exhibits in a target engagement assay an EC50 value on FPR1 of at least 1 nM ($10^{-9}$ mol/L); still more preferably at least 500 nM; yet more preferably at least 1 µM ($10^{-6}$ mol/L); even more preferably at least 100 µM; most preferably at least 500 µM; and in particular at least 1 mM ($10^{-3}$ mol/L).

Preferably, the compound according to the present invention exhibits a ratio (EC50 on FPR2)/(EC50 on FPR1) in a target engagement assay of >1, more preferably >10, even more preferably >50, still more preferably >100, most preferably >500 and in particular >1000.

Preferably, the compounds according to the present invention are useful as non-peptides modulators of the human FPR2 receptor. More preferably, the compounds according to the present invention are agonists of the human FPR2 receptor.

Therefore, the compounds according to the present invention are preferably useful for the in vivo treatment or prevention of diseases in which participation of FPR2 is implicated.

The present invention therefore further relates to a compound according to the present invention for use in the modulation of FPR2 activity.

Therefore, another aspect of the present invention relates to a compound according to the present invention for use in the treatment and/or prophylaxis of a disorder which is mediated at least in part by FPR2, preferably without the activation of FPR1. Still another aspect of the present invention relates to a method of treatment of a disorder which is mediated at least in part by FPR2, preferably without the activation of FPR1; comprising the administration of a therapeutically effective amount of a compound according to the present invention to a subject in need thereof, preferably a human.

A further aspect of the invention relates to a compound according to the present invention as medicament.

Another aspect of the present invention relates to a pharmaceutical dosage form comprising a compound according to the present invention. Preferably, the pharmaceutical dosage form comprises a compound according to the present invention and one or more pharmaceutical excipients such as physiologically acceptable carriers, additives and/or auxiliary substances; and optionally one or more further pharmacologically active ingredient. Examples of suitable physiologically acceptable carriers, additives and/or auxiliary substances are fillers, solvents, diluents, colorings and/or binders. These substances are known to the person skilled in the art (see H. P. Fiedler, Lexikon der Hilfsstoffe fur Pharmazie, Kosmetik and angrenzende Gebiete, Editio Cantor Aulendoff).

The pharmaceutical dosage form according to the present invention is preferably for systemic, topical or local administration, preferably for oral administration. Therefore, the pharmaceutical dosage form can be in form of a liquid, semisolid or solid, e.g. in the form of injection solutions, drops, juices, syrups, sprays, suspensions, tablets, patches, films, capsules, plasters, suppositories, ointments, creams, lotions, gels, emulsions, aerosols or in multiparticulate form, for example in the form of pellets or granules, if appropriate pressed into tablets, decanted in capsules or suspended in a liquid, and can also be administered as such.

The pharmaceutical dosage form according to the present invention is preferably prepared with the aid of conventional means, devices, methods and processes known in the art. The amount of the compound according to the present invention to be administered to the patient may vary and is e.g. dependent on the patient's weight or age and also on the type of administration, the indication and the severity of the disorder. Preferably 0.001 to 100 mg/kg, more preferably 0.05 to 75 mg/kg, most preferably 0.05 to 50 mg of a compound according to the present invention are administered per kg of the patient's body weight.

FPR2 is believed to have potential to modify a variety of diseases or disorders in mammals such as humans. These include inflammatory diseases, diabetes, obstructive airway diseases, autoimmune diseases, allergic conditions, rheumatological disorders, HIV-mediated retroviral 5 infections, infectious diseases, sepsis, cardiovascular disorders, fibrotic disorders, neuroinflammation, neurological disorders, pain, prion-mediated diseases, amyloid-mediated disorders, chronic obstructive pulmonary disease (COPD), asthma, idiopathic pulmonary fibrosis (IPF), inflammatory bowel disease (IBD), ulcerative colitis (UC), rheumatoid arthritis (RA), psoriatic arthritis (PsA), multiple sclerosis (MS). Further, FPR2 is believed to be involved in the modulation of immune responses, such as those elicited through Graft versus Host Disease (GvHD).

Therefore, another aspect of the present invention relates to a compound according to the present invention for use in the treatment and/or prophylaxis of a disorder selected from the group consisting of inflammatory diseases, diabetes, obstructive airway diseases, autoimmune diseases, allergic conditions, rheumatological disorders, HIV-mediated retroviral 5 infections, infectious diseases, sepsis, cardiovascular disorders, fibrotic disorders, neuroinflammation, neurological disorders, pain, prion-mediated diseases, amyloid-mediated disorders and Graft versus Host Disease (GvHD).

Still another aspect of the present invention relates to a compound according to the present invention for use in the treatment and/or prophylaxis of a disorder selected from the group consisting of chronic obstructive pulmonary disease (COPD), asthma, idiopathic pulmonary fibrosis (IPF), inflammatory bowel disease (IBD), ulcerative colitis (UC), rheumatoid arthritis (RA), psoriatic arthritis (PsA) and multiple sclerosis (MS).

A further aspect of the present invention relates to a method of treatment of a disorder selected from the group consisting of inflammatory diseases, diabetes, obstructive airway diseases, autoimmune diseases, allergic conditions, rheumatological disorders, HIV-mediated retroviral 5 infections, infectious diseases, sepsis, cardiovascular disorders, fibrotic disorders, neuroinflammation, neurological disorders, pain, prion-mediated diseases and amyloid-mediated disorders.

EXAMPLES

The compounds according to the present invention were produced in the manner described below.

Abbreviations

AcOH=acetic acid; Boc=tert-butyloxycarbonyl; Bu=butyl; Tf=triflate; DCM=dichloromethane; DIPEA=N,N-diisopropylethylamine; DMF=N,N-dimethylformamid; DMAP=4-(dimethylamino)-pyridine; DMS=dimethylsulfide; DMSO=dimethylsulfoxid; DPPA=diphenyl phosphorazidate; Et=ethyl; Et$_2$O=diethyl ether; EtOAc=ethylacetate; EtOH=ethanol; h=hour; HATU=[O-(7-Azabenzotriazol-1-yl)-N,N,N,N-tetramethyluronium-hexafluorphosphate]; HFIP=hexafluoroisopropanol; MeOH=methanol; min=minute; Rt=retention time; RT=room temperature; TEA=triethylamine; tert=tertiary; THF=tetrahydrofuran.

The following analytical LC/MS methods were used:
Method 1:
Instrument Name: LCMS/MS API 2000; Instrument manufacturer: Applied Biosystem; HPLC: Shimadzu Prominence; Column (Name, Size, type): Zorbax Extend (C18 4.6×50 mm, 5 micron),
Eluent (solvent): A channel: 10 mM Ammonium Acetate in water; B channel: Acetonitrile (Organic phase);
Dual Wavelength: At 220 and 260 nm; Detector: UV;
Gradient condition: A: Buffer 10 mM Ammonium Acetate in water; B: Acetonitrile;
Flow rate: 1.2 ml/min; Column Temperature: 25° C.; Injection Volume: 2 μL;
LC-MS gradient: mobile phase: from 90% [buffer] and 10% [CH$_3$CN] to 70% [buffer] and 30% [CH$_3$CN] in 1.5 min, further to 10% [buffer] and 90% [CH$_3$CN] in 3.0 min, held this mobile phase composition to 4 min and finally back to initial condition in 5 min).

| TIME | MODULE | % A (Buffer) | % B (CH$_3$CN) |
|---|---|---|---|
| 0.01 | Pumps | 90 | 10 |
| 1.50 | Pumps | 70 | 30 |
| 3.00 | Pumps | 10 | 90 |
| 4.00 | Pumps | 10 | 90 |
| 5.00 | Pumps | 90 | 10 |
| 5.10 | System Controller | Stop | |

Mass conditions: Ionization technique: ESI (Electron Spray Ionization) using API (Atmospheric pressure Ionization) source; Declustering Potential: 10-70 V depending on the ionization of compound; Mass range: 100-800 amu; Scan type: Q1; Polarity: +Ve; Ion Source: Turbo spray; Ion spray voltage: +5500 for +ve mode; Mass Source temperature: 200° C.
Method 2:
Column: Acquity UPLC HSS T3 1.8 μm (Part No. 186003538) 2.1×50 mm; Detection: 190-400 nm; Column temperature: 80° C.; Eluent A: Water+0.1% formic acid, Eluent B: Acetonitrile+0.1% formic acid, Gradient: Start 2% B, 1 min 100% B, 1.09 min 100% B, 1.11 min 2% B, 1.2 min 2% B Stop, Flow: 2.5 ml/min, Run time: 1.2 min.

In the following, when entantiomers are depicted sometimes the phenyl moiety and the urea moiety are connected to the central nitrogen-containing 6-membered heterocycloalkyl by a wavy bond ($\xi$) which shall indicate that the absolute stereochemistry is not known. In such cases, the relative orientation of the phenyl moiety to the urea moiety is specified by the prefix, i.e. "trans" or "cis" which is given below the formula and/or in the chemical name. For example, in the formulae below, the prefix "trans" is used to indicate that the relative orientation of the phenyl moiety to the urea moiety is trans:

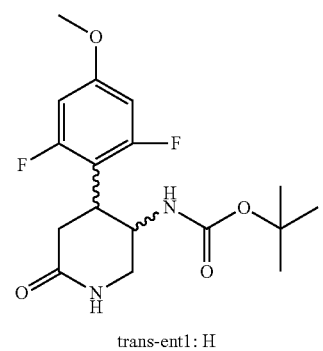

trans-ent1: H

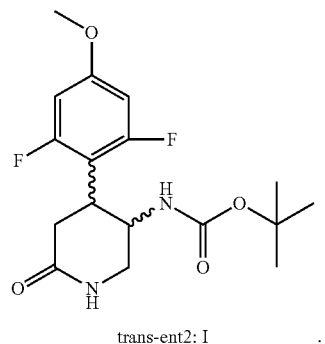

trans-ent2: I

Synthesis of Key Intermediate A: Preparation of rac-trans-tert-butyl (4-(2,6-difluoro-4-methoxyphenyl)piperidin-3-yl)carbamate

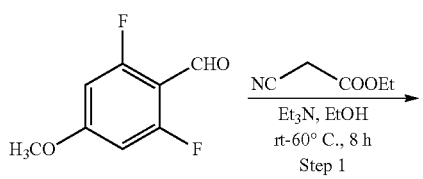

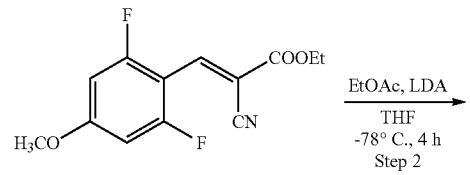

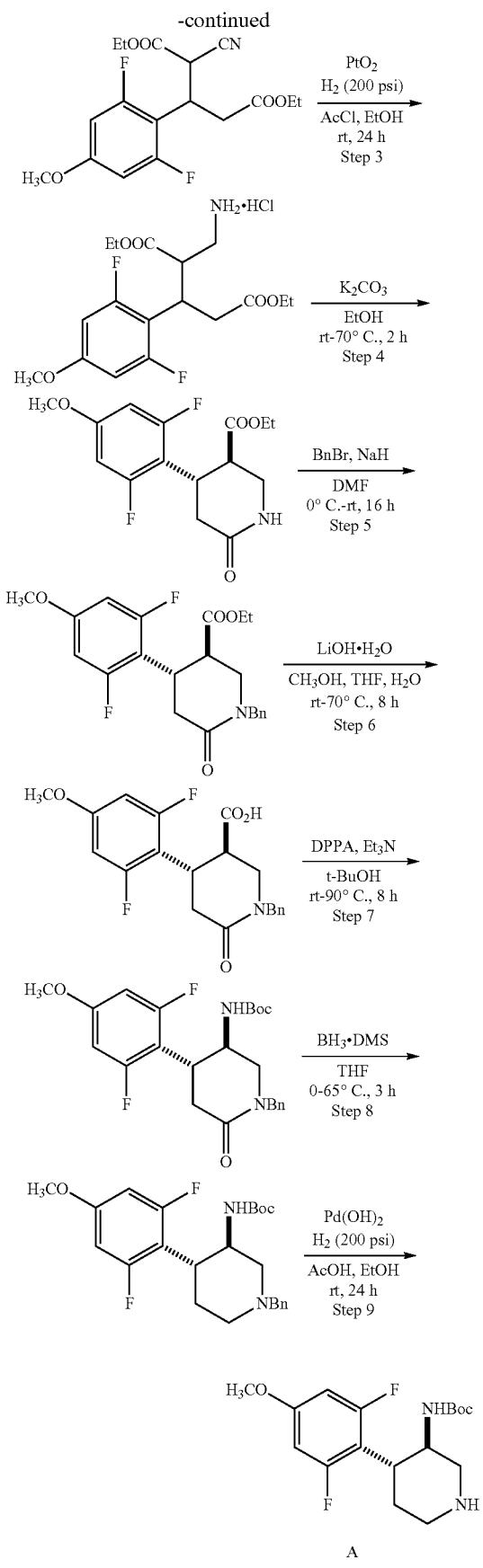

1a): rac-trans-ethyl 1-benzyl-4-(2,6-difluoro-4-methoxyphenyl)-6-oxopiperidine-3-carboxylate Step1:

A stirred solution of 2,6-difluoro-4-methoxybenzaldehyde (50.0 g, 0.290 mol) in EtOH (500 mL) was charged with ethyl 2-cyanoacetate (39.4 g, 0.348 mol) and TEA (48.4 mL, 0.348 mol) at RT. The resulting solution was heated at 60° C. for 8 h. Upon reaction completion, the reaction mixture was cooled to RT and concentrated under reduced pressure. The crude product was dissolved in EtOAc (250 mL) and washed with water (2×150 mL). The organic layer was separated, dried over anhydrous $Na_2SO_4$ and concentrated under reduced pressure to afford (E)-ethyl 2-cyano-3-(2,6-difluoro-4-methoxyphenyl)acrylate (50.0 g, 64%) as a yellow solid (TLC system: 30% EtOAc in pet ether; $R_f$: 0.5).

Step2:

A stirred solution of EtOAc (25 mL) in THF (250 mL) was charged with LDA (2M) in THF solution (135 mL, 1.88 mol) at 78° C. for over 1 h. The reaction mixture was stirred for 30 min at same temperature. (E)-ethyl 2-cyano-3-(2,6-difluoro-4-methoxyphenyl)acrylate (25.0 g, 0.649 mol) in THF (250 mL) was added to the reaction mixture at 78° C. dropwise over 1 h. The resulting reaction mixture was stirred at 0° C. for 4 h. Upon reaction completion, the reaction mixture was quenched with aqueous $NH_4Cl$ solution (250 mL) and was extracted with EtOAc (3×100 mL). The organic layer was separated, dried over anhydrous $Na_2SO_4$ and concentrated under reduced pressure. The crude product was purified by flash chromatography (10% EtOAc:hexane). All pure fractions were collected and concentrated under reduced pressure to afford diethyl 2-cyano-3-(2,6-difluoro-4-methoxyphenyl)pentanedioate (24.0 g, 72%) as yellow oil (TLC System: 30% EtOAc in pet-ether, $R_f$: 0.4).

Step3:

A stirred solution of acetyl chloride (25 mL, 0.004 mol) in EtOH (240 mL) was charged with diethyl 2-cyano-3-(2,6-difluoro-4-methoxyphenyl)pentanedioate (24.0 g, 0.067 mol) and $PtO_2$ (2.40 g) at RT. The resulting reaction mixture was stirred at RT in presence of hydrogen atmosphere (200 psi) for 24 h. Upon reaction completion, the reaction mixture was filtered through a celited plug and washed with EtOH (100 mL). The organic layer was concentrated under reduced pressure to afford diethyl 2-(aminomethyl)-3-(2,6-difluoro-4-methoxyphenyl)pentanedioate hydrochloride [28.0 g (crude)] as pale black liquid (TLC System: 50% EtOAc in pet ether, $R_f$: 0.2). The crude product was preceded to next step without purification.

Step4:

A stirred solution of diethyl 2-(aminomethyl)-3-(2,6-difluoro-4-methoxyphenyl)pentanedioate hydrochloride (21.0 g, 0.053 mol) in EtOH (1200 mL) was charged with $K_2CO_3$ (18.3 g, 0.132 mol) at RT. The resulting solution was heated at 70° C. for 2 h. Upon reaction completion, the reaction mixture was cooled to RT and EtOH was evaporated. The crude product was dissolved in $CH_2Cl_2$ (500 mL), filtered through a celite plug and washed with $CH_2Cl_2$ (100 mL). The organic layer was dried over anhydrous $Na_2SO_4$ and concentrated under reduced pressure to afford rac-trans-ethyl 4-(2,6-difluoro-4-methoxyphenyl)-6-oxopiperidine-3-carboxylate (15.0 g, 83%) as brown oil (TLC system: 100% EtOH; $R_f$: 0.4).

Step5:

A stirred solution of rac-trans-ethyl 4-(2,6-difluoro-4-methoxyphenyl)-6-oxopiperidine-3-carboxylate (15.0 g, 0.047 mol) in DMF (75 mL) was charged with 60% NaH dispersion in oil (1.50 g, 0.062 mol) slowly over 30 min at 0° C. The reaction mixture was stirred at same temperature for 30 min. Benzyl bromide (9.00 g, 0.052 mol) was added to the reaction mixture at 0° C. dropwise over 30 min. The resulting solution was stirred at RT for 16 h. Upon reaction completion, the reaction mixture was poured into ice water (500 mL) and extracted with EtOAc (3×100 mL). The organic layer was separated, washed with water (3×100 mL) and brine (1×100 mL). The organic layer was dried over anhydrous $Na_2SO_4$ and concentrated under reduced pressure. The crude product was purified by flash chromatography (40% EtOAc:hexane). All pure fractions were collected and concentrated under reduced pressure to afford rac-trans-ethyl 1-benzyl-4-(2,6-difluoro-4-methoxyphenyl)-6-oxopiperidine-3-carboxylate (15.0 g, 78%) as yellow oil (TLC System: 50% EtOAc in pet-ether, $R_f$: 0.5).

$^1$H NMR (400 MHz, DMSO-$d_6$): δ 7.37-7.26 (m, 5H), 6.44-6.41 (m, 2H), 4.80-4.77 (d, J=14.4 Hz, 1H), 4.56-4.50 (m, 1H), 3.96-3.89 (m, 2H), 3.76 (s, 3H), 3.73-3.66 (m, 1H), 3.55-3.46 (m, 2H), 3.45-3.26 (m, 1H), 2.91-2.84 (m, 1H), 2.74-2.70 (m, 1H), 0.98-0.94 (t, J=7.2 Hz, 3H).

1b): Key Intermediate A

Step6:
A stirred solution of rac-trans-ethyl 1-benzyl-4-(2,6-difluoro-4-methoxyphenyl)-6-oxopiperidine-3-carboxylate (2.80 g, 0.0069 mol) in THF (15 mL) and EtOH (15 mL) was charged with LiOH.$H_2O$ (0.58 g, 0.013 mol) in water (3.0 mL) at RT. The resulting solution was heated at 70° C. for 8 h. Upon reaction completion, the reaction mixture was cooled to RT and concentrated under reduced pressure. Water (100 mL) was added to the reaction mixture and acidified with HCl (1M, pH adjusted to 2) and extracted with 10%-THF in EtOAc (3×100 mL). The organic layer was separated and dried over anhydrous $Na_2SO_4$ and concentrated under reduced pressure to afford rac-trans-1-benzyl-4-(2,6-difluoro-4-methoxyphenyl)-6-oxopiperidine-3-carboxylic acid (2.00 g, 77%) as an off-white solid.

Step7:
A stirred solution of rac-trans-1-benzyl-4-(2,6-difluoro-4-methoxyphenyl)-6-oxopiperidine-3-carboxylic acid (1.50 g, 0.04 mol) and $Et_3N$ (1.1 mL, 0.008 mol) in t-BuOH (15 mL) was charged with diphenylphosphorylazide (1.65 g, 0.006 mol) at RT. The resulting solution was heated at 90° C. for 8 h. Upon reaction completion, the reaction mixture was cooled to RT and t-BuOH was removed under reduced pressure The crude product was purified by flash chromatography (50% EtOAc:hexane). All pure fractions were collected and concentrated under reduced pressure to afford rac-trans-tert-butyl (1-benzyl-4-(2,6-difluoro-4-methoxyphenyl)-6-oxopiperidin-3-yl)carbamate (0.50 g, 28%) as an off-white solid (TLC System: 60% EtOAc in pet-ether, $R_f$: 0.5).

Step8:
A stirred solution of rac-trans-tert-butyl (1-benzyl-4-(2,6-difluoro-4-methoxyphenyl)-6-oxopiperidin-3-yl)carbamate (4.70 g, 0.010 mol) in THF (47 mL) was charged with $BH_3$.DMS (2M) in THF solution (10.6 mL, 0.021 mol) at 0° C. The resulting solution was heated at 65° C. for 3 h. Upon reaction completion, the reaction mixture was quenched with aqueous $NH_4Cl$ solution (50 mL) and was extracted with EtOAc (3×100 mL). The organic layer was separated, dried over anhydrous $Na_2SO_4$ and concentrated under reduced pressure. The crude product was purified by flash chromatography (30% EtOAc:hexane). All pure fractions were collected and concentrated under reduced pressure to afford rac-trans-tert-butyl (1-benzyl-4-(2,6-difluoro-4-methoxyphenyl)piperidin-3-yl)carbamate (2.60 g, 57%) as a pale yellow liquid.

Step9:
A stirred solution of rac-trans-tert-butyl (1-benzyl-4-(2,6-difluoro-4-methoxyphenyl)piperidin-3-yl)carbamate (2.50 g, 0.005 mol) in EtOH (240 mL) and catalytic amount of AcOH was charged with Pd(OH)$_2$ (0.25 g, 0.001 mol) in the autoclave at RT. The resulting mixture was stirred at RT in presence of hydrogen atmosphere (200 psi) for 24 h. Upon reaction completion, the reaction mixture was filtered through a celited plug and washed with EtOH (50 mL). The organic layer was concentrated under reduced pressure to afford 1.50 g of crude product as an off-white solid which was purified by flash chromatography (5% MeOH:DCM). All pure fractions were collected and concentrated under reduced pressure to afford key intermediate A (958 mg, 56%) as an off-white solid.

$^1$H NMR (400 MHz, DMSO-$d_6$): δ 6.61-6.28 (m, 3H), 3.73-3.71 (m, 4H), 2.92-2.82 (d, J=10.0 Hz, 2H), 2.80-2.77 (m, 1H), 2.42-2.31 (m, 2H), 1.90-1.82 (m, 1H), 1.59-1.56 (s, J=10.8 Hz, 1H), 1.16 (s, 9H).

Synthesis of Key Intermediate B: Preparation of rac-trans-tert-butyl (4-(2,6-difluoro-4-methoxyphenyl)-6-oxopiperidin-3-yl)carbamate

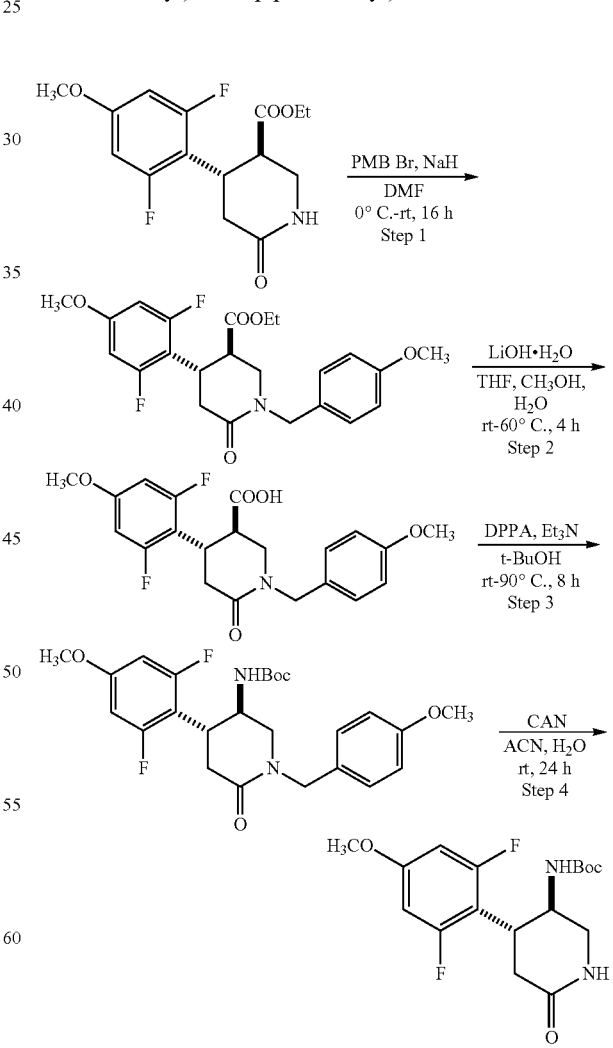

B

Step1:

A stirred solution of rac-trans-ethyl 4-(2,6-difluoro-4-methoxyphenyl)-6-oxopiperidine-3-carboxylate (20.0 g, 0.063 mol) [synthesis described in synthesis of key intermediate A] in DMF (100 mL) was charged with 60% NaH dispersion in oil (3.30 g, 0.137 mol) slowly over 30 min at 0° C. The reaction mixture was stirred for 30 min at same temperature. p-Methoxy benzyl bromide (10 mL, 0.069 mol) was added to the reaction mixture at 0° C. dropwise over 30 min. The resulting solution was stirred at RT for 16 h. Upon reaction completion, the reaction mixture was poured into ice water (1000 mL) and extracted with EtOAc (3×500 mL). The organic layer was separated, washed with water (3×200 mL) and brine (1×100 mL). The organic layer was dried over anhydrous $Na_2SO_4$ and concentrated under reduced pressure. The crude product was purified by flash chromatography (40% EtOAc:hexanes). All pure fractions were collected and concentrated under reduced pressure to afford rac-trans-ethyl 4-(2,6-difluoro-4-methoxyphenyl)-1-(4-methoxybenzyl)-6-oxopiperidine-3-carboxylate (14.0 g, 51%) as yellow oil (TLC System: 50% EtOAc in pet-ether, $R_f$: 0.5).

Step2:

A stirred solution of rac-trans-ethyl 4-(2,6-difluoro-4-methoxyphenyl)-1-(4-methoxybenzyl)-6-oxopiperidine-3-carboxylate (14.0 g, 0.032 mol) in THF (50 mL) and MeOH (50 mL) was charged with aqueous $LiOH \cdot H_2O$ (2.71 g, 0.064 mol) in water (90 mL) at RT. The resulting solution was heated at 60° C. for 4 h. Upon reaction completion, the reaction mixture was cooled to RT, MeOH and THF were evaporated. Water (100 mL) was added to the reaction mixture, acidified with HCl (1M, pH adjusted to 2) and was extracted with 10% THF in EtOAc (3×500 mL). The organic layer was separated, dried over anhydrous $Na_2SO_4$ and concentrated under reduced pressure to afford rac-trans-4-(2,6-difluoro-4-methoxyphenyl)-1-(4-methoxybenzyl)-6-oxopiperidine-3-carboxylic acid (6.00 g, 46%) as an off-white solid.

Step3:

A stirred solution of rac-trans-4-(2,6-difluoro-4-methoxyphenyl)-1-(4-methoxybenzyl)-6-oxopiperidine-3-carboxylic acid (6.00 g, 0.016 mol) and TEA (5.65 mL, 0.040 mol) in t-BuOH (72 mL) was charged with diphenylphosphorylazide (5.24 mL, 0.024 mol) at RT. The resulting solution was heated at 90° C. for 8 h. Upon reaction completion, the reaction mixture was cooled to RT, t-BuOH was removed under reduced pressure and the crude product was purified by flash chromatography (50% EtOAc:hexanes). All pure fractions were collected and concentrated under reduced pressure to afford rac-trans-tert-butyl (4-(2,6-difluoro-4-methoxyphenyl)-1-(4-methoxybenzyl)-6-oxopiperidin-3-yl) carbamate (4.00 g, 52%) as a pale yellow solid (TLC System: 50% EtOAc in pet-ether, $R_f$: 0.5).

Step4:

A stirred solution of rac-trans-tert-butyl (4-(2,6-difluoro-4-methoxyphenyl)-1-(4-methoxybenzyl)-6-oxopiperidin-3-yl)carbamate (5.00 g, 0.104 mol) in acetonitrile (130 mL) was charged with a solution of ceric ammonium nitrate (6.90 g, 0.012 mol) in water (65 mL) at RT. The resulting solution was stirred at RT for 16 h. After 16 h, TLC shows starting material. Again, a solution of ceric ammonium nitrate (6.90 g, 0.012 mol) in water (65 mL) was added to the reaction mixture at RT and stirred for another 8 h at same temperature. Upon reaction completion, acetonitrile was concentrated, diluted with water (50 mL) and extracted with EtOAc (3×100 mL). The organic layer was separated, washed with saturated $NH_4Cl$ solution (13×100 mL) and brine (1×100 mL). The organic layer was dried over anhydrous $Na_2SO_4$, concentrated under reduced pressure and the crude product was purified by flash chromatography (4% MeOH:$CH_2Cl_2$). All pure fractions were collected, concentrated and triturated with n-heptane:$CH_2Cl_2$ (2:1, 10 mL) to afford key intermediate B (0.30 g, 10%) as an off-white solid (TLC System: 10% MeOH:$CH_2Cl_2$, $R_f$: 0.5).

$^1$H NMR (300 MHz, $CDCl_3$): δ 6.47-6.44 (d, J=10.5 Hz, 2H), 5.91 (bs, 1H), 4.35 (bs, 2H), 3.77 (s, 3H), 3.67-3.64 (d, J=10.5 Hz, 1H), 3.45-3.36 (m, 1H), 3.20-3.13 (m, 1H), 2.98-2.88 (t, J=17.4 Hz, 1H), 2.68-2.60 (dd, J=17.7, 5.6 Hz, 1H), 1.29 (s, 9H).

Synthesis of Key Intermediate C: Preparation of rac-trans-tert-butyl (4-(4-methoxyphenyl)piperidin-3-yl)carbamate

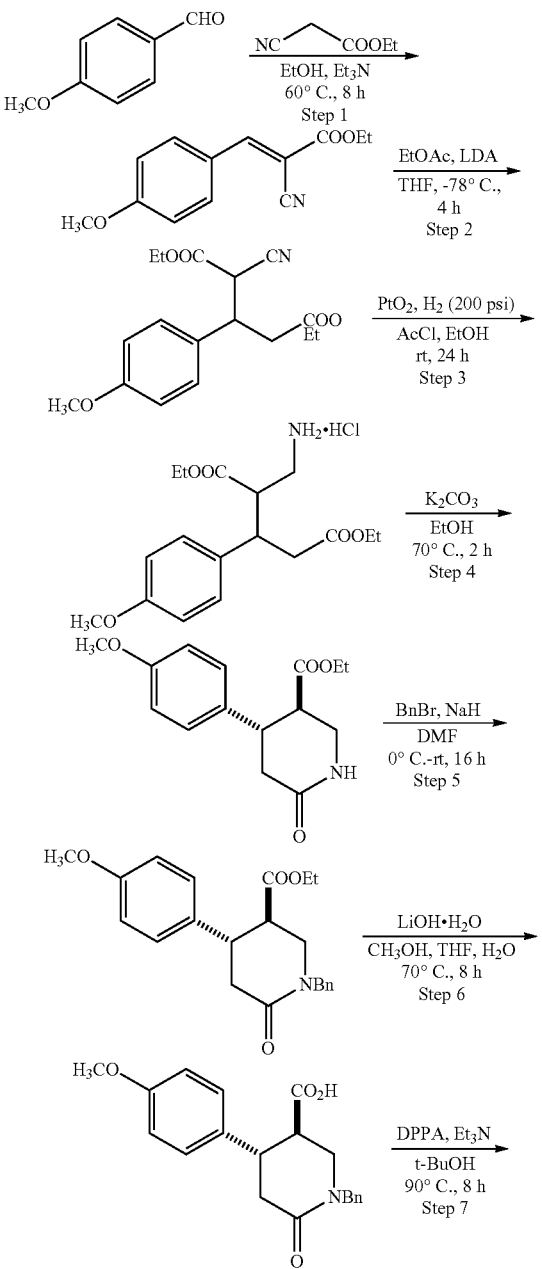

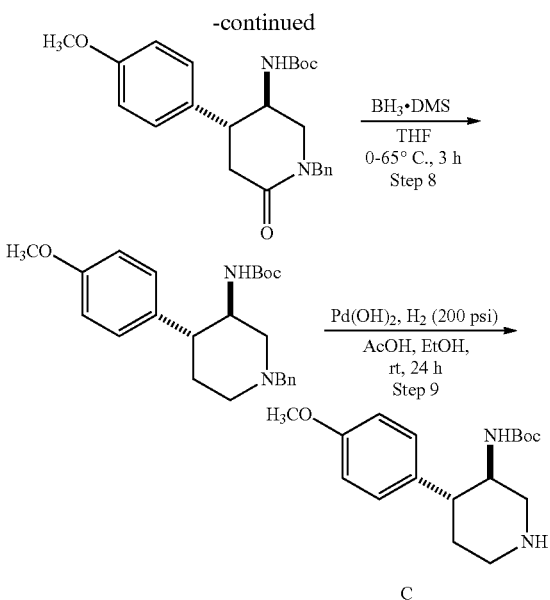

3a): rac-trans-ethyl 1-benzyl-4-(4-methoxyphenyl)-6-oxopiperidine-3-carboxylate

Step1:

A stirred solution of 4-methoxybenzaldehyde (200 g, 1.469 mol) in EtOH (2000 mL) was charged with ethyl 2-cyanoacetate (164 g, 1.543 mol) and TEA (409 mL, 2.840 mol) at RT. The resulting solution was heated at 60° C. for 8 h. Upon reaction completion, the reaction mixture was cooled to RT and concentrated under reduced pressure. The crude product was dissolved in EtOAc (2.5 L) and washed with water (2×300 mL). The organic layer was separated, dried over anhydrous $Na_2SO_4$ and concentrated under reduced pressure to afford (E)-ethyl 2-cyano-3-(4-methoxyphenyl)acrylate (305 g, 96%) as a yellow solid (TLC system: 30% EtOAc in Hexanes; $R_f$: 0.5).

Step2:

A stirred solution of EtOAc (190 mL, 1.948 mol) in THF (750 mL) was charged with LDA (2M) in THF solution (942 mL, 1.883 mol) at 78° C. for over 1 h. The reaction mixture was stirred for another 30 min at same temperature. (E)-ethyl 2-cyano-3-(4-methoxyphenyl)acrylate (150 g, 0.649 mol) in THF (750 mL) was added to the reaction mixture at 78° C. dropwise over 1 h. The reaction mixture was stirred at 0° C. for 4 h. Upon reaction completion, the reaction mixture was quenched with aqueous $NH_4Cl$ solution (1.0 L) and was extracted with EtOAc (3×1000 mL). The organic layer was separated, dried over anhydrous $Na_2SO_4$ and concentrated under reduced pressure. The crude product was purified by flash chromatography (10% EtOAc:hexanes). All pure fractions were collected and concentrated under reduced pressure to afford diethyl 2-cyano-3-(4-methoxyphenyl)pentanedioate (155 g, 74%) as yellow oil (TLC System: 30% EtOAc in pet-ether, $R_f$: 0.4).

Step3:

A stirred solution of acetyl chloride (173 mL, 2.42 mol) in EtOH (1.55 L) were charged with diethyl 2-cyano-3-(4-methoxyphenyl)pentanedioate (155 g, 0.485 mol) and $PtO_2$ (5.00 g) at RT. The reaction mixture was stirred in presence of hydrogen atmosphere (200 psi) for 24 h. Upon reaction completion, the reaction mixture was filtered through a celite plug and washed with EtOAc (200 mL). The organic layer was concentrated under reduced pressure to afford diethyl 2-(aminomethyl)-3-(4-methoxyphenyl)pentanedioate hydrochloride [170 g (crude)] as a pale black liquid (TLC System: 50% EtOAc in pet ether, $R_f$: 0.2).

Step4:

A stirred solution of diethyl 2-(aminomethyl)-3-(4-methoxyphenyl)pentanedioate hydrochloride (120 g, 0.363 mol) in EtOH (1200 mL) was charged with $K_2CO_3$ (125 g, 0.906 mol) at RT. The resulting solution was heated at 70° C. for 2 h. Upon reaction completion, the reaction mixture was cooled to RT and EtOH was evaporated. The crude product was dissolved in $CH_2Cl_2$ (1000 mL), filtered through a celite plug and was washed with $CH_2Cl_2$ (200 mL). The organic layer was dried over anhydrous $Na_2SO_4$ and concentrated under reduced pressure to afford rac-trans-ethyl 4-(4-methoxyphenyl)-6-oxopiperidine-3-carboxylate (54.0 g, 57%) as a brown oil (TLC system: 100% EtOAc; $R_f$: 0.4).

Step5:

A stirred solution of rac-trans-ethyl 4-(4-methoxyphenyl)-6-oxopiperidine-3-carboxylate (34.0 g, 0.129 mol) in DMF (340 mL) was charged with 60% NaH dispersion in oil (6.20 g, 0.155 mol) slowly over 30 min at 0° C. The reaction mixture was stirred at same temperature for 30 min. Benzyl bromide (28.7 g, 0.168 mol) was added to the reaction mixture at 0° C. dropwise over 30 min. The resulting solution was stirred at RT for 16 h. Upon reaction completion, the reaction mixture was poured into ice water (1000 mL) and extracted with EtOAc (3×500 mL). The organic layer was separated, washed with water (3×200 mL) and brine (1×100 mL). The organic layer was dried over anhydrous $Na_2SO_4$ and concentrated under reduced pressure. The crude product was purified by flash chromatography (40% EtOAc:hexanes). All pure fractions were collected and concentrated under reduced pressure to afford rac-trans-ethyl 1-benzyl-4-(4-methoxyphenyl)-6-oxopiperidine-3-carboxylate (13.0 g, 31%) as yellow oil (TLC System: 50% EtOAc in pet-ether, $R_f$: 0.5).

$^1$H NMR (400 MHz, $CDCl_3$): δ 7.36-7.26 (m, 5H), 7.11-7.09 (d, J=8.8 Hz, 2H), 6.84-6.82 (d, J=8.4 Hz, 2H), 4.78-4.75 (d, J=14.4 Hz, 1H), 4.54-4.51 (d, J=14.4 Hz, 1H), 3.95-3.84 (m, 2H), 3.78 (s, 3H), 3.60-3.44 (m, 1H), 3.37-3.30 (m, 2H), 2.93-2.90 (m, 1H), 2.84-2.79 (m, 1H), 2.71-2.32 (m, 1H), 0.96-0.92 (t, J=7.2 Hz, 3H).

3b): rac-trans-tert-butyl (1-benzyl-4-(4-methoxyphenyl)-6-oxopiperidin-3-yl)carbamate Step6:

A stirred solution of rac-trans-ethyl 1-benzyl-4-(4-methoxyphenyl)-6-oxopiperidine-3-carboxylate (19.0 g, 0.054 mol) in THF (50 mL) and MeOH (50 mL) was charged with aqueous $LiOH.H_2O$ (5.64 g, 0.135 mol) in water (90 mL) at RT. The resulting solution was heated at 70° C. for 8 h. Upon reaction completion, the reaction mixture was cooled to RT and EtOH and THF were removed under reduced pressure. Water (100 mL) was added to the reaction mixture, acidified with HCl (1M, pH adjusted to 2) and extracted with 10% THF in EtOAc (3×500 mL). The organic layer was separated, dried over anhydrous $Na_2SO_4$ and concentrated under reduced pressure to afford 7 (15.0 g, 82%) as an off-white solid.

Step7:

A stirred solution of rac-trans-1-benzyl-4-(4-methoxyphenyl)-6-oxopiperidine-3-carboxylic acid (15.0 g, 0.044 mol) and $Et_3N$ (18.4 mL, 0.133 mol) in t-BuOH (180 mL) was charged with diphenylphosphorylazide (14.4 mL, 0.066 mol) at RT. The resulting solution was heated at 90° C. for 8 h. Upon reaction completion, the reaction mixture was cooled to RT and t-BuOH was removed under reduced pressure. The crude product was purified by flash chromatography (50% EtOAc:hexanes). All pure fractions were collected and concentrated under reduced pressure to afford rac-trans-tert-butyl (1-benzyl-4-(4-methoxyphenyl)-6-oxopiperidin-3-yl)carbamate (12.0 g, 56%) as an off-white solid (TLC System: 60% EtOAc in pet-ether, $R_f$: 0.5).

$^1$H NMR (300 MHz, CDCl$_3$): δ 736-7.26 (m, 5H), 7.11-7.08 (d, J=8.7 Hz, 2H), 6.86-6.83 (d, J=9.6 Hz, 2H), 4.71 (bs, 1H), 4.50-4.02 (m, 2H), 4.02 (bs, 1H), 3.79 (s, 3H), 3.52-3.46 (dd, J=12, 7.5 Hz, 1H), 3.06-3.00 (d, J=4.8 Hz, 2H), 2.87-2.62 (9 m, 2H), 1.30 (s, 9H).

3c): Key Intermediate C

Step8:
A solution of rac-trans-tert-butyl (1-benzyl-4-(4-methoxyphenyl)-6-oxopiperidin-3-yl)carbamate (5.00 g, 0.0122 mol) in THF (50 mL) was charged with BH$_3$.DMS (2M) in THF solution (12.2 mL, 0.024 mol) dropwise at 0° C. for over 10 min. The reaction mixture was stirred at 65° C. for 3 h. Upon completion of the reaction, the reaction mixture was poured into aqueous NH$_4$Cl solution (100 mL) and was extracted with EtOAc (3×50 mL). The combined organic layers were dried over anhydrous Na$_2$SO$_4$ and concentrated under reduced pressure. The crude product was purified by flash chromatography (30% EtOAc:Hexanes). All pure fractions were collected and concentrated under reduced pressure to afford rac-trans-tert-butyl (1-benzyl-4-(4-methoxyphenyl)piperidin-3-yl)carbamate (3.82 g, 79%) as an off-white solid.

Step9:
A solution of rac-trans-tert-butyl (1-benzyl-4-(4-methoxyphenyl)piperidin-3-yl)carbamate (3.82 g, 0.01 mol) in EtOH (40 mL) was charged with 20% Pd(OH)$_2$ (1.00 g) and catalytic amount of acetic acid (0.30 mL) in the autoclave. The reaction mixture was stirred at RT for 24 h under H$_2$ atmosphere (200 psi). Upon completion of the reaction, the reaction mixture was filtered through a celite plug and washed with EtOH (50 mL). The combined organic layer was concentrated under reduced pressure. The crude product was purified by flash chromatography (8% MeOH:CH$_2$Cl$_2$). All pure fractions were collected and concentrated under reduced pressure to afford key intermediate C (2.60 g, 88%) as a pale brown solid.

$^1$H NMR (300 MHz, DMSO-d$_6$): δ 7.12-7.09 (d, J=8.7 Hz, 2H), 6.83-6.80 (d, J=8.7 Hz, 2H), 6.52-6.49 (d, J=9.3 Hz, 1H), 3.69 (s, 3H), 3.46-3.40 (m, 1H), 3.02-2.83 (m, 2H), 2.44-2.41 (m, 3H), 2.30-2.23 (t, J=11.1 Hz, 1H), 1.66-1.43 (m, 2H), 1.22 (s, 9H).

Synthesis of Key Intermediate D: Preparation of rac-trans-tert-butyl (4-(4-methoxyphenyl)-6-oxopiperidin-3-yl)carbamate

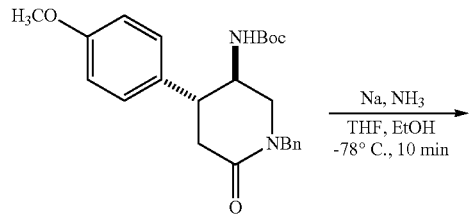

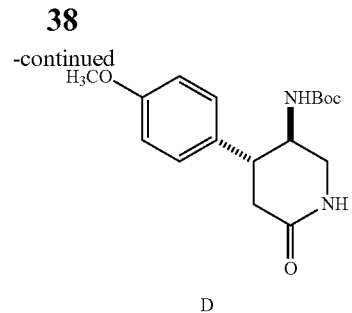

D

Ammonia gas (800 mL) was condensed at −78° C. by using Dewar condenser. Sodium metal (~6.00 g) was charged to the solution portionwise until blue colour is stable. A solution of rac-trans-tert-butyl (1-benzyl-4-(4-methoxyphenyl)-6-oxopiperidin-3-yl)carbamate (6.00 g, 0.014 mol) [synthesis described in synthesis of key intermediate C] in THF (60 mL) was added dropwise to the reaction mixture at −78° C. and stirred for 10 min at same temperature. EtOH (6.0 mL) was added to the mixture at −78° C. and stirred for another 10 min. Solid NH$_4$Cl (10.0 g) was added to the reaction mixture and slowly warmed to RT. Saturated NH$_4$Cl solution (50 mL) was added to the reaction mixture and extracted with EtOAc (2×50 mL). The combined organic layer was dried over anhydrous Na$_2$SO$_4$ and concentrated under reduced pressure. The crude product was purified by flash chromatography (10% MeOH:CH$_2$Cl$_2$). All pure fractions were collected and concentrated under reduced pressure to afford key intermediate D (2.56 g, 55%) as a white solid.

$^1$H NMR-VT at 348.2 K (400 MHz, DMSO-d$_6$): δ 7.25 (bs, 1H), 7.18-7.15 (d, J=9.0 Hz, 2H), 6.87-6.84 (d, J=8.4 Hz, 2H), 6.45 (bs, 1H), 3.90-3.82 (m, 1H), 3.74 (s, 3H), 3.27-3.23 (m, 1H), 3.08-2.99 (m, 2H), 2.42-2.39 (d, J=9.0 Hz, 2H), 1.23 (s, 9H).

Synthesis of Key Intermediate E: Preparation of rac-trans-4-(2-fluoro-4-methoxyphenyl)-6-oxopiperidine-3-carboxylic acid

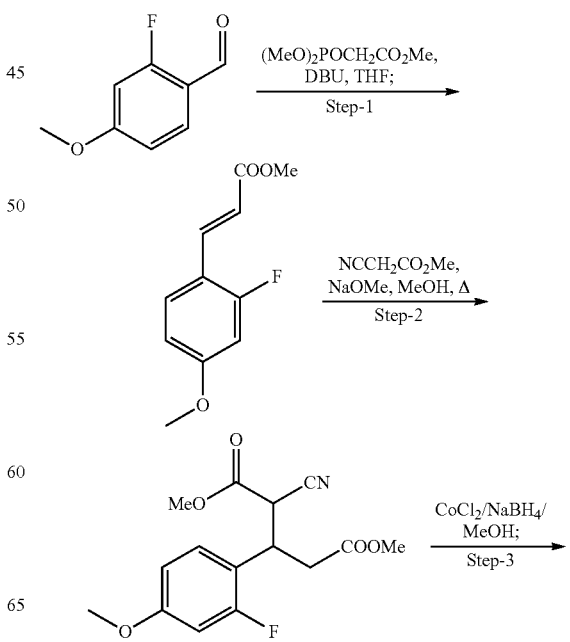

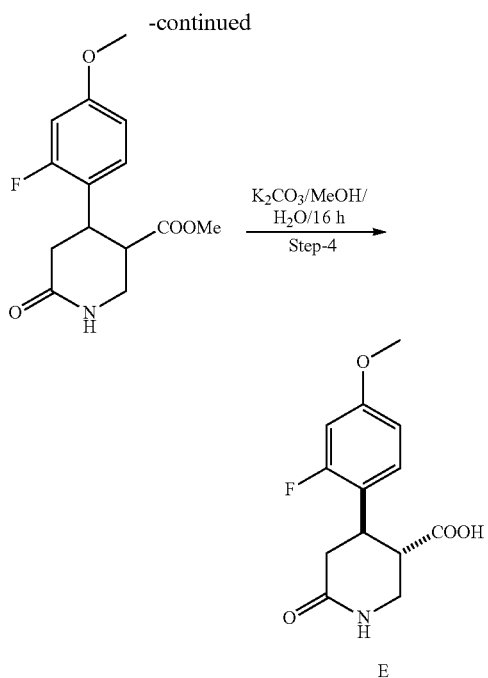

Step1:

To a stirred solution of 2-fluoro-4-methoxybenzaldehyde (5 g, 32.47 mmol, 1 eq) and trimethylphosphonoacetate (5.62 mL, 38.96 mmol, 1.2 eq) in THF (100 mL) was added DBU (6.3 mL, 42.21 mmol, 1.3 eq). The solution was stirred at ambient temperature for 24 h and concentrated under vacuum. Crude obtained was dissolved in 1:4 EtOAc/Hexane (250 mL), washed sequentially with water (150 mL) and brine (100 mL). The organic phase was then dried over sodium sulfate, filtered and evaporated under reduced pressure to yield a crude solid. Purification over silica gel (100-200 mesh) using 0 to 20% EtOAc/hexane gradient rendered 3-(2-fluoro-4-Methoxy-phenyl)-acrylic acid methyl ester (6 g, 88%) as off white solid.

Step2:

To a stirred solution of sodium methoxide (25% in methanol, 15 mL, 71.42 mmol, 2.5 eq) in methanol (120 mL) was added methyl cyanoacetate (3 mL, 34.28 mmol, 1.2 eq) and the mixture was stirred at ice cooled condition for 30 min. To this solution was added 3-(2-fluoro-4-methoxy-phenyl)-acrylic acid methyl ester (6.0 g, 28.57 mmol, 1 eq) and the resulting yellowish mixture was stirred for 18 h at RT. The mixture was quenched with aqueous 1N HCl solution (150 mL) at ice cooled condition until acidification and extracted with EtOAc (2×300 mL). Combined organic phase was washed by brine (100 mL) and dried over sodium sulfate, filtered and evaporated under reduced pressure to furnish the crude as reddish viscous oil. It was then purified over 100-200 silica gel using 0 to 40% EtOAc/hexane gradient to produce the diastereomeric mixture of 2-cyano-3-(2-fluoro-4-methoxy-phenyl)-pentanedioic acid dimethyl ester (6.0 g, 68%) as yellowish viscous liquid.

Step3:

To a stirred solution of 2-cyano-3-(2-fluoro-4-methoxy-phenyl)-pentanedioic acid dimethyl ester (8.0 g, 25.89 mmol, 1 eq) in MeOH (300 mL) was added cobalt(II) chloride hexahydrate (15.6 g, 64.7 mmol, 2.5 eq) followed by portion wise addition of $NaBH_4$ (6.54 g, 170.87 mmol, 6.6 eq) at 0° C. and stirred for 16 h at RT. The reaction was quenched with aqueous 1N HCl, acidified and evaporated under reduced pressure for removing the volatiles. The resulting crude was dissolved in EtOAc (300 mL) and washed sequentially by water (100 mL) and brine (100 mL). Organic phase was dried over sodium sulfate, filtered and evaporated under reduced pressure to furnish the crude as off white solid. It was then purified over 100-200 silica gel using 40 to 100% EtOAc/hexane gradient to produce diastereomeric mixture of 4-(2-fluoro-4-methoxy-phenyl)-6-oxo-piperidine-3-carboxylic acid methyl ester (4.5 m, 62%) as off white solid.

Step4:

To a stirred solution of 4-(2-fluoro-4-methoxy-phenyl)-6-oxo-piperidine-3-carboxylic acid methyl ester (4.5 g, 16.01 mmol, 1 eq) in $MeOH/H_2O$ (60 mL, 5:1) was added $K_2CO_3$ (5 g, 36.23 mmol, 2.2 eq) and heated to reflux for 16 h. MeOH was then evaporated under reduced pressure followed by acidification with 1N HCl at 0° C. to render a precipitation. Precipitate was then filtered under suction and the filter cake was repeatedly washed with EtOAc (2×50 mL). The residue was transferred to a round bottle flask and washed with $Et_2O$ to furnish the compound 4-(2-fluoro-4-methoxy-phenyl)-6-oxo-piperidine-3-carboxylic acid as off white solid (2.8 g, 65%).

Synthesis of Key Intermediate F: Preparation of rac-trans-4-(2,6-difluoro-4-methoxyphenyl)-6-oxopiperidine-3-carboxylic acid

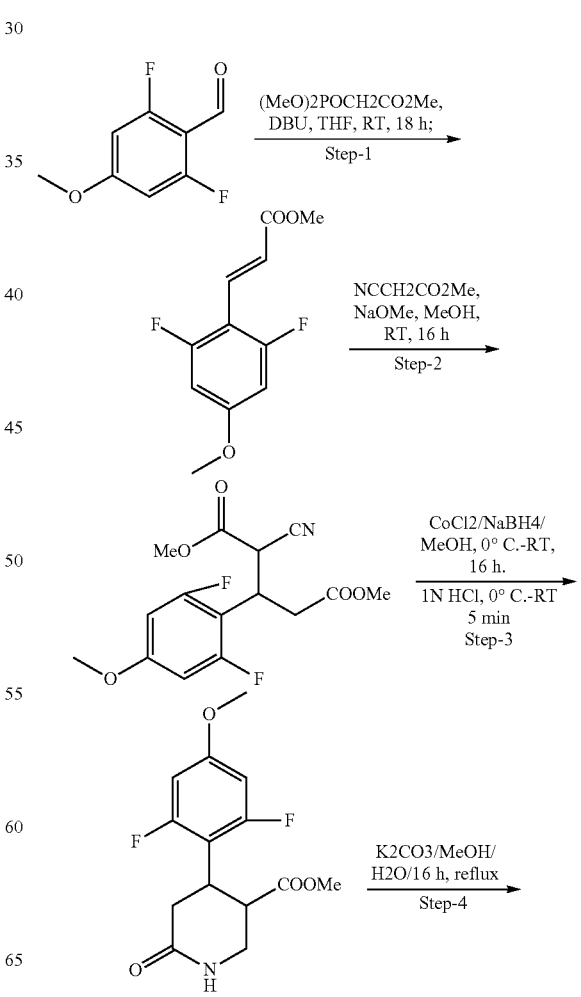

-continued

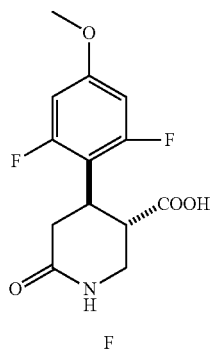

Step 1:
To a stirred solution of 2,6-difluoro-4-methoxybenzaldehyde (5 g, 29.05 mmol, 1 eq) in THF (100 mL) was added trimethylphosphonoacetate (5.03 mL, 34.86 mmol, 1.2 eq) and DBU (5.65 mL, 37.76 mmol, 1.3 eq). The solution was stirred at RT for 24 h. It was then concentrated in vacuo and dissolved in 1:2 EtOAc/Hexane (250 mL). The resulting solution was washed sequentially with 1N aq. HCl (100 mL), saturated aqueous NaHCO₃ (100 mL) and finally with brine (100 mL). The organic phase was then dried over sodium sulfate, filtered and evaporated under reduced pressure to yield the crude (E)-methyl 3-(2,6-difluoro-4-methoxyphenyl)acrylate as off white solid (5.8 g, 87%). It was used for the next step without further purification.

Step 2:
To a stirred solution of sodium methoxide (25% in MeOH, 28.4 ml, 131.57 mmol, 5 eq) in MeOH (120 mL) was added methyl cyanoacetate (2.78 mL, 31.58 mmol, 1.2 eq) and the mixture was stirred at ice cooled condition for 30 min. To this solution was added (E)-methyl 3-(2,6-difluoro-4-methoxyphenyl)acrylate (6.0 g, 23.31 mmol, 1 eq) and the resulting yellowish mixture was stirred for 18 h at RT. The mixture was quenched with 1N HCl solution (100 mL) at ice cooled condition for acidification. The resulting mixture was then extracted with EtOAc (2×300 mL) and the combined organic phase was washed by saturated aqueous brine (100 mL). The organic phase was dried over sodium sulfate, filtered and evaporated under reduced pressure to furnish the crude as reddish viscous oil. It was then purified over 100-200 mesh silica gel using hexane to 40% EtOAc/hexane gradient to get dimethyl 2-cyano-3-(2-fluoro-4-methoxyphenyl)pentanedioate (6.0 g, 69%) as diastereomeric mixture.

Step 3:
To a stirred solution of dimethyl 2-cyano-3-(2-fluoro-4-methoxyphenyl)pentanedioate (6.0 g, 18.34 mmoL, 1 eq) in MeOH (150 mL) was added cobalt(II) chloride hexahydrate (11.0 g, 45.87 mmol, 2.5 eq) followed by portion wise addition of NaBH₄ (6.0 g, 128.38 mmol, 7.0 eq) at 0° C. and stirred for 16 h at RT. The reaction was quenched with 1N aqueous HCl (~150 mL), acidified and then evaporated under reduced pressure for removing the volatiles. The resulting crude was then extracted with EtOAc (2×250 mL) and the combined organic phase was washed sequentially by water (100 mL) and brine (100 mL). The organic phase was then dried over sodium sulfate, filtered and evaporated under reduced pressure to furnish the crude as colorless solid. It was then purified over 100-200 mesh silica gel using 40 to 100% EtOAc/hexane gradient to produce methyl 4-(2,6-difluoro-4-methoxyphenyl)-6-oxopiperidine-3-carboxylate (2.5 g, 45%) as diastereomeric mixture.

Step 4:
To a stirred solution of methyl 4-(2,6-difluoro-4-methoxyphenyl)-6-oxopiperidine-3-carboxylate (8.7 g, 29.09 mmol, 1 eq) in MeOH/H₂O (60 mL, 5:1) was added K₂CO₃ (14.0 g, 101.45 mmol, 3.50 eq) and heated to reflux for 16 h. MeOH was then evaporated under reduced pressure followed by acidification with 1N HCl at 0° C. to render a precipitation. It was then filtered under suction and the filter cake was repeatedly washed with EtOAc (2×50 mL). The residue was transferred to a round bottle flask and washed with Et₂O to furnish (3S,4R)-4-(2,6-difluoro-4-methoxyphenyl)-6-oxopiperidine-3-carboxylic acid as off white solid (7.0 g, 84%).

Synthesis of Key Intermediate G: Preparation of rac-trans-5-amino-4-(2,6-difluoro-4-methoxyphenyl)piperidin-2-one

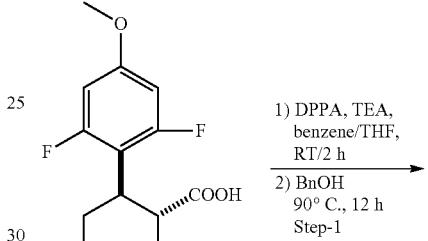

G

Step 1:
To a stirred solution of intermediate F (500 mg, 1.75 mmol, 1 eq) in benzene-THF mixture (20 mL, 3:1) was added Et₃N (0.5 mL, 3.5 mmol, 2.0 eq) followed by DPPA (0.5 mL, 2.27 mmol, 1.3 eq) at RT and the resulting mixture was allowed stir for 2 h at the same condition. Benzyl alcohol (250 mg, 2.275 mmol, 1.3 eq) was then added and the resulting mixture was again stirred for another 16 h at 70° C. Volatiles were removed under reduced pressure to yield a reddish crude gum. It was extracted with EtOAc (2×60 mL) and the combined organic phase was washed sequentially by water and brine. The organic phase was dried over sodium sulfate, filtered and evaporated under reduced pressure to furnish the crude as yellowish gummy solid. It was purified over 100-200 silica gel using DCM to 10% MeOH/DCM gradient to produce rac-trans-benzyl (4-(2,6-difluoro-4-methoxyphenyl)-6-oxopiperidin-3-yl)carbamate (150 mg, 22% yield) as off white solid.

Step2:

To a stirred solution of rac-trans-benzyl (4-(2,6-difluoro-4-methoxyphenyl)-6-oxopiperidin-3-yl)carbamate (400 mg, 1.02 mmol, 1 eq) in MeOH (30 mL) was added Pd/C (10%, 100 mg) under degassed (argon, 30 min) condition at RT. Resulting mixture was allowed stir for 4 h under hydrogen atmosphere using a balloon filled with the same. Reaction mixture was filtered through celite bed and was repeatedly washed with MeOH (3×10 mL). Collected organic filtrate was concentrated under reduced pressure to yield yellowish crude rac-trans-5-amino-4-(2,6-difluoro-4-methoxyphenyl)piperidin-2-one (380 mg), which was used as such for the next step without further purification.

Synthesis of Key Intermediate H and I: Preparation of trans-ent1-tert-butyl (4-(2,6-difluoro-4-methoxyphenyl)-6-oxopiperidin-3-yl)carbamate (H) and trans-ent2-tert-butyl (4-(2,6-difluoro-4-methoxyphenyl)-6-oxopiperidin-3-yl)carbamate (I)

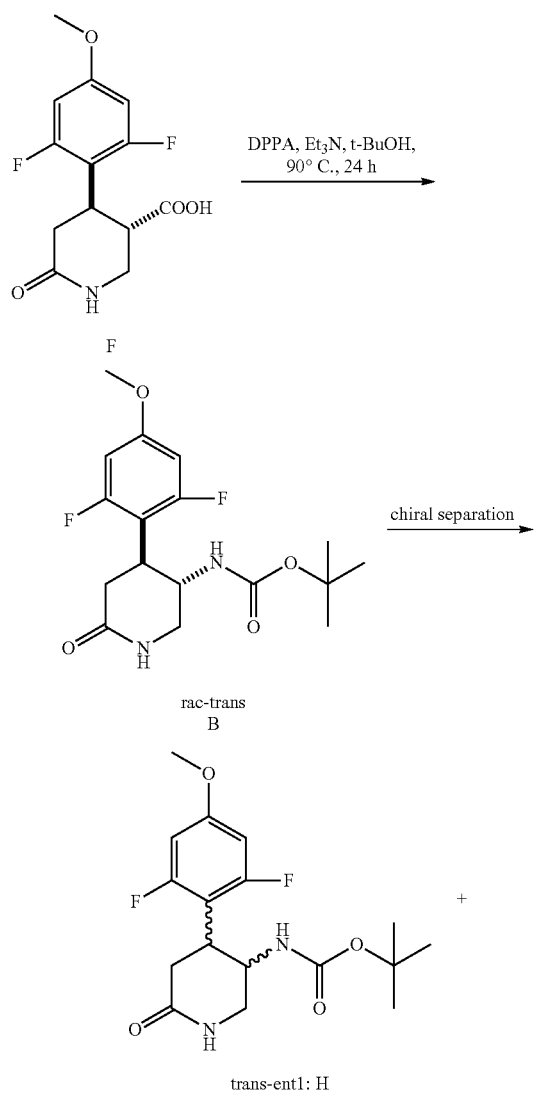

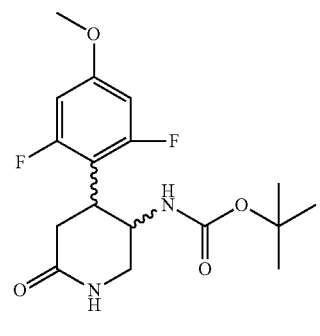

trans-ent2: I

To a stirred solution of intermediate F (trans racemic) (4.3 g, 14.3 mmol, 1.0 eq) in t-BuOH (100 mL) was added Et$_3$N (6.2 mL, 42.9 mmol, 3.0 eq), DPPA (4.28 mL, 18.6 mmol, 1.3 eq) and the reaction mixture was heated up to 90° C. for 24 h. The volatiles were evaporated and the residue was diluted with sat.NaHCO$_3$ (40 mL), extracted with EtOAC (2×50 mL). The organic layer was dried over anhydrous Na$_2$SO$_4$, evaporated under reduced pressure. The crude was purified by purified by column chromatography on silica gel (230-400 mesh) using 5-10% MeOH in DCM as eluent to get intermediate B (trans racemic) (1.05 g, ~20%) as a white solid, TLC system: 100% EtOAc, R$_f$: 0.45.

$^1$H NMR (400 MHz, DMSO-d$_6$): δ 7.60-7.59 (d, J=3.2 Hz, 1H), 6.87-6.84 (d, J=8.8 Hz, 1H), 6.67-6.64 (d, J=11.2 Hz, 1H), 4.10-4.01 (m, 1H), 3.73 (s, 3H), 3.21-3.05 (m, 3H), 2.44-2.38 (m, 2H), 1.23-1.19 (m, 9H).

The racemic intermediate B was subjected to chiral separation by chiral SFC (Column/dimensions: Lux Cellulose-2 (250×4.6) mm, 5μ) to render both the enantiomers as intermediate H (first eluting enantiomer; specific rotation: [−5.0°; C=0.25% solution in CHCl$_3$] at ≅25° C.) and intermediate I (second eluting enantiomer; specific rotation: [+5.1°; C=0.25% solution in CHCl$_3$] at ≅25° C.).

Synthesis of Key Intermediate J, K and L: Preparation of rac-trans-tert-butyl (4-(2-fluoro-4-methoxyphenyl)-6-oxopiperidin-3-yl)carbamate (J), trans-ent1-tert-butyl (4-(2-fluoro-4-methoxyphenyl)-6-oxopiperidin-3-yl)carbamate (K) and trans-ent2-tert-butyl (4-(2-fluoro-4-methoxyphenyl)-6-oxopiperidin-3-yl)carbamate (L)

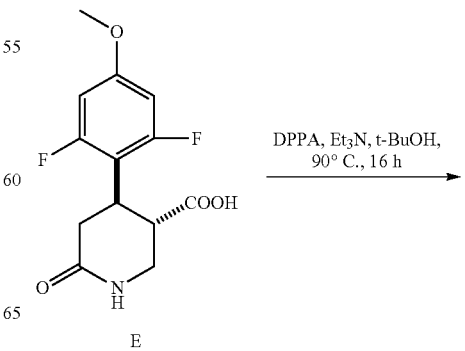

E

-continued

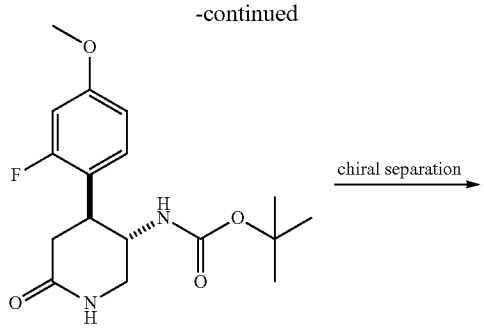

J

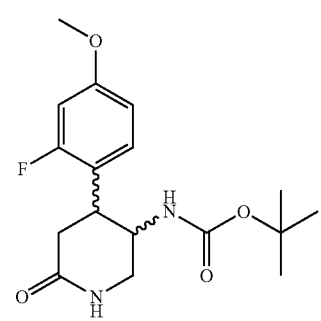

trans-ent1: K

+

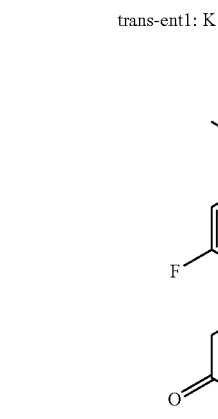

trans-ent2: L

To a stirred solution of intermediate E (12.0 g, 44.94 mmol, 1.0 eq) in t-BuOH (100 ml) was added Et₃N (18.7 mL, 134.83 mmol, 3.0 eq), DPPA (12.3 mL, 53.92 mmol, 1.2 eq) and the reaction mixture was heated 90° C. for 16 hours. After 16 h, volatiles were evaporated to get crude compound, was purified by purified by column chromatography on silica gel (60-120 mesh) using 5% MeOH in DCM as eluent to get intermediate J (5.2 g, 34%) as an off white solid. TLC system: (1:4) EtOAc/Pet ether, $R_f$: 0.15.

$^1$H NMR (300 MHz, DMSO-d₆): δ 7.58 (d, J=2.4 Hz, 1H), 7.23-7.17 (m, 1H), 6.83-6.70 (m, 3H), 3.99-3.96 (m, 1H), 3.72 (s, 3H), 3.24-3.16 (m, 2H), 3.07-3.00 (m, 1H), 2.40-2.38 (m, 2H), 1.23 (s, 9H).

The racemic intermediate J was subjected to chiral separation by chiral SFC (Column/dimensions: Chiralpak IC (250×30) mm, 5μ) to render both the enantiomers as intermediate K (first eluting enantiomer) and intermediate L (second eluting enantiomer).

Synthesis of Key Intermediate M and N: Preparation of trans-ent1-tert-butyl (4-(2,4-difluorophenyl)-6-oxopiperidin-3-yl)carbamate (M) and trans-ent2-tert-butyl (4-(2,4-difluorophenyl)-6-oxopiperidin-3-yl)carbamate (N)

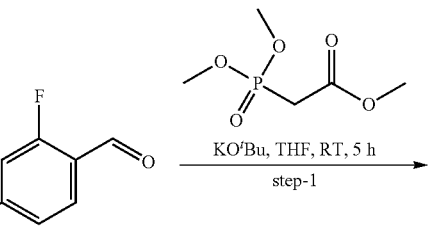

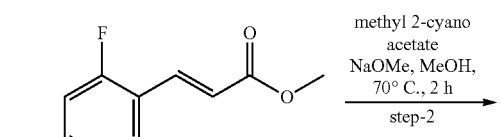

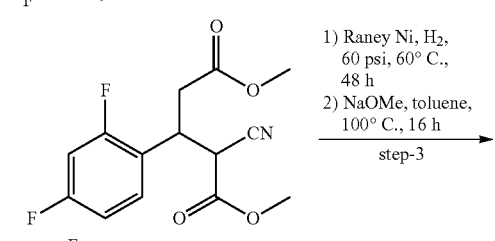

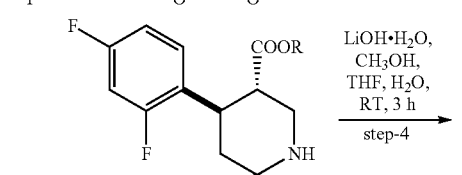

R = Me, Et

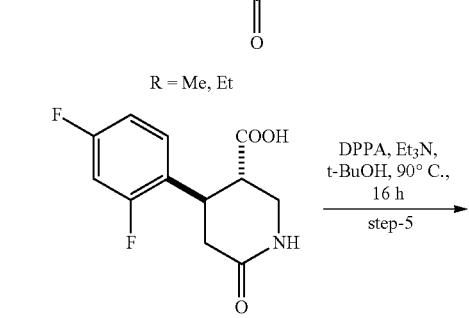

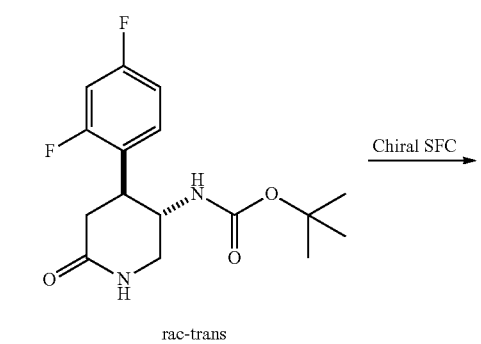

rac-trans

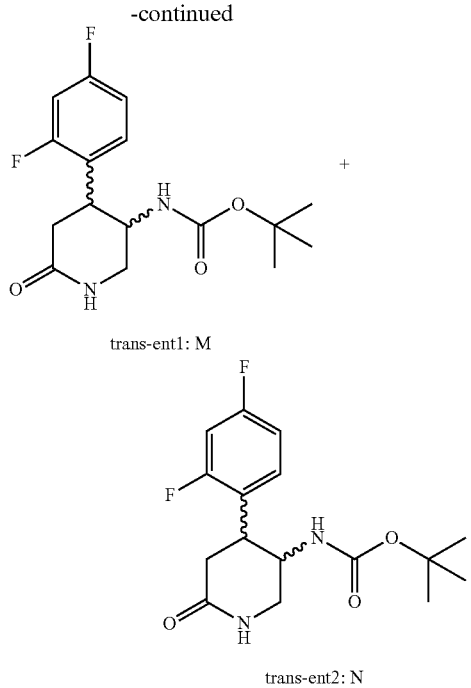

trans-ent1: M trans-ent2: N

Step1:

To a stirred solution of methyl (dimethoxyphosphoryl) acetate (12.8 mL, 77.46 mmol, 1.1 eq) in THF (70.0 mL)) was added KO'Bu (8.69 g, 77.46 mmol, 1.1 eq) at RT and the reaction mixture was stirred for 10 min. Then 2,4-difluorobenzaldehyde (10.0 g, 70.42 mmol, 1.0 eq) in THF (20 mL) was added drop wise stirred at RT for 2 h. Methyl (dimethoxyphosphoryl) acetate (5.8 mL, 35.21 mmol, 0.5) and KO'Bu (3.95 g, 35.21 mmol, and 0.5 eq) was added as lot-2 and stirred for 30 minutes. After 3 h, reaction mixture was diluted with water (200 mL) extracted with EtOAc (2×100 mL), organic layer was dried over anhydrous $Na_2SO_4$, and evaporated under reduced pressure gave crude compound, which was purified by column chromatography on silica gel (100-200 mesh) using EtOAc/pet ether (1:9) as eluent to get (E)-methyl 3-(2,4-difluorophenyl)acrylate (12.0 g, 86%) as a white solid. TLC system: EtOAc: Pet ether (1:9), $R_f$: 0.5.

Step2:

To a stirred suspension of (E)-methyl 3-(2,4-difluorophenyl)acrylate (10 g, 50.5 mmol, 1.0 eq) in MeOH (100 mL) was added methyl cyanoacetate (5.9 g, 60.6 mmol, 1.2 eq), followed by drop wise addition of NaOMe 30% in MeOH (13.6 mL, 75.75 mmol, 1.5 eq) at RT. After addition was completed, resulting reaction mixture was heated to reflux for 2 h. The volatiles were evaporated under reduced pressure, diluted with toluene (100 mL) and washed with 1N HCl (50 mL), aq. NaHCO₃ (50 mL). Organic layer was dried over anhydrous $Na_2SO_4$, and evaporated under reduced pressure gave crude compound, which was purified by column chromatography on silica gel (100-200 mesh) using EtOAc/pet ether (2:8) as eluent to get dimethyl 2-cyano-3-(2,4-difluorophenyl)pentanedioate (10.0 g, 68%). TLC system: EtOAc/Pet ether (1:4); $R_f$: 0.3.

Step3:

To suspension of Raney Ni (15.0 g) in ethanol (700 mL) was added dimethyl 2-cyano-3-(2,4-difluorophenyl)pentanedioate (70.0 g, 185.18 mmol, 1.0 eq). Resulting reaction mixture was stirred in par shaker under 60 psi at 50° C. for 24 h. After 24 h, reaction mixture was passed through celite bed washed with ethanol (500 mL), filtrate was evaporated, washed with Et₂O to get solid. Obtained solid (mixture of cis and trans) (40.0 g, 149.25 mmol, 1.0 eq) was taken in toluene (500 mL), NaOMe (30% in MeOH) (26.8 mL, 149.25 mmol, 1.0 eq) was added and the reaction mixture was heated to 100° C. for 2 h. The reaction mixture was diluted with cold water, extracted with EtOAc (2×500 mL). Aqueous layer washed with water (2×500 mL), brine (500 mL), dried over anhydrous $Na_2SO_4$, and evaporated under reduced pressure gave crude compound, which was washed with Et₂O (500 mL) to give a mixture of (3S,4R)-methyl 4-(2,4-difluorophenyl)-6-oxopiperidine-3-carboxylate and (3S,4R)-ethyl 4-(2,4-difluorophenyl)-6-oxopiperidine-3-carboxylate (trans racemic) (36.0 g, 55%). TLC system: EtOAc/Pet ether (7:3); $R_f$: 0.2.

Step4:

A stirred solution of rac-trans-methyl 4-(2,4-difluorophenyl)-6-oxopiperidine-3-carboxylate and (3S,4R)-ethyl 4-(2,4-difluorophenyl)-6-oxopiperidine-3-carboxylate (36.0 g, 134.3 mmol, 1.0 eq) in THF/MeOH/H₂O (300 mL, 2:1:1) was added LiOH (16.92 g, 402.9 mmol, 3.0 eq) and the reaction mixture was stirred at RT for 3 h. The volatiles were evaporated diluted with water (50 mL), extracted with EtOAC (2×50 mL) to remove impurities, then the aqueous layer was acidified with 1N HCl (pH-6), solid was precipitated, was filtered, washed with Et₂O (50 mL) and dried to get to get rac-trans-4-(2,4-difluorophenyl)-6-oxopiperidine-3-carboxylic acid (30.0 g, 87%) TLC system MeOH/DCM (1:9), $R_f$: 0.1.

Step5:

To a stirred solution of rac-trans-4-(2,4-difluorophenyl)-6-oxopiperidine-3-carboxylic acid (2×10.0 g, 39.37 mmol, 1.0 eq) in t-BuOH (100 mL) was added Et₃N (16.38 mL, 118.11 mmol, 3.0 eq), DPPA (10.8 mL, 47.24 mmol, 1.2 eq) and the reaction mixture was heated 90° C. for 16 h. After 16 h, volatiles were evaporated to get crude compound, which was purified by purified by column chromatography on silica gel (60-120 mesh) using 5% MeOH in DCM as eluent to get tert-butyl ((3S,4S)-4-(2,4-difluorophenyl)-6-oxopiperidin-3-yl)carbamate (trans racemic) (10.0 g, 40%) as a white solid. TLC system: (1:4) EtOAc/Pet ether, $R_f$: 0.15.

¹H NMR (300 MHz, DMSO-d₆): δ 12.8-11.5 (br s, 1H), 7.73 (s, 1H), 7.49-7.40 (m, 1H), 7.21-7.14 (m, 1H), 7.09-7.04 (m, 1H), 3.58-3.23 (m, 3H), 3.07-3.01 (m, 1H), 2.39-2.36 (m, 2H).

The racemic compound was subjected to chiral separation by chiral SFC (Column/dimensions: Chiralpak IC (250×30) mm, 5μ) to render both the enantiomers as intermediate M (first eluting enantiomer) and intermediate N (second eluting enantiomer).

Synthesis of Key Intermediates O and P: Preparation of trans-ent1-tert-butyl (4-(4-chlorophenyl)-6-oxopiperidin-3-yl)carbamate (O) and trans-ent2-tert-butyl (4-(4-chlorophenyl)-6-oxopiperidin-3-yl) carbamate (P)

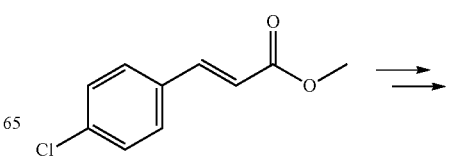

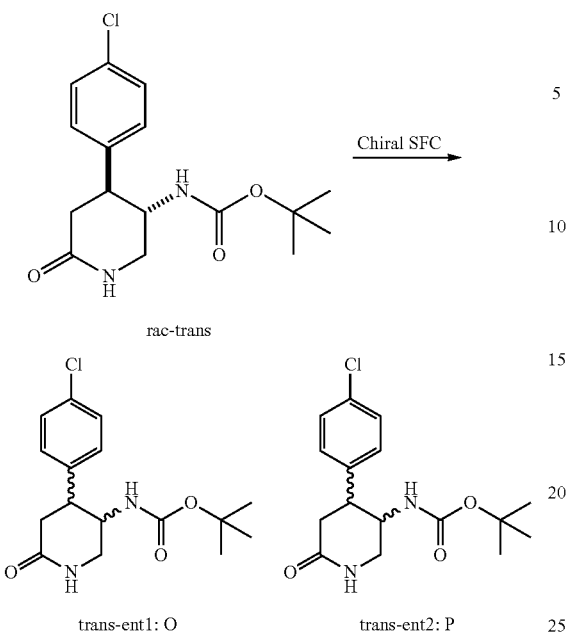

Starting from (E)-3-(4-chlorophenyl)acrylic acid, rac-trans-tert-butyl (4-(4-chlorophenyl)-6-oxopiperidin-3-yl)carbamate was synthesized in analogy to synthesis described for intermediate M, N.

$^1$H NMR (300 MHz, DMSO-$d_6$): δ 7.54 (d, J=2.7 Hz, 1H), 7.35-7.26 (m, 4H), 6.79 (d, J=9.0 Hz, 1H), 3.92-2.87 (m, 1H), 3.22-3.19 (m, 1H), 3.08-2.97 (m, 2H), 2.46-2.32 (m, 2H), 1.21 (s, 9H).

The racemic compound was subjected to chiral separation by chiral SFC (Column/dimensions: Chiralpak IC (250×30) mm, 5μ) to render intermediate O (first eluting enantiomer) and intermediate P (second eluting enantiomer).

Synthesis of Key Intermediate Q and R: Preparation of iso-mix-tert-butyl (2-(4-methoxyphenyl)piperidin-3-yl)carbamate (Q(dia1) and R (dia1))

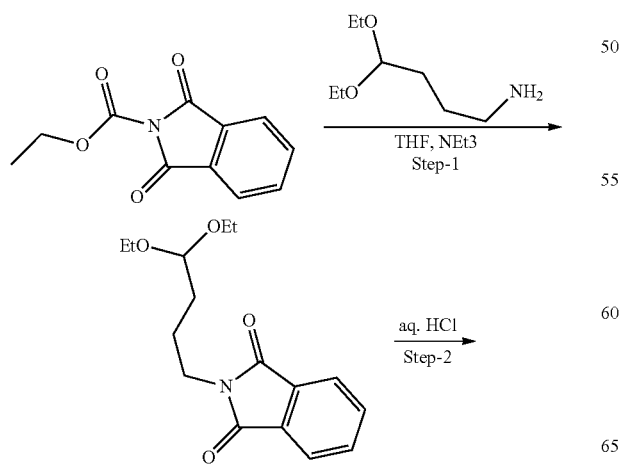

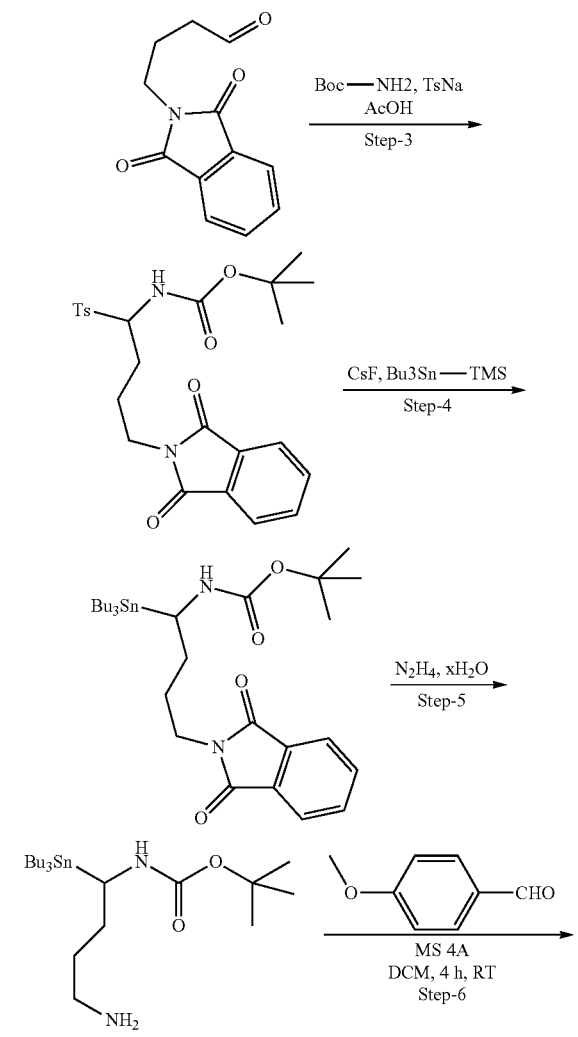

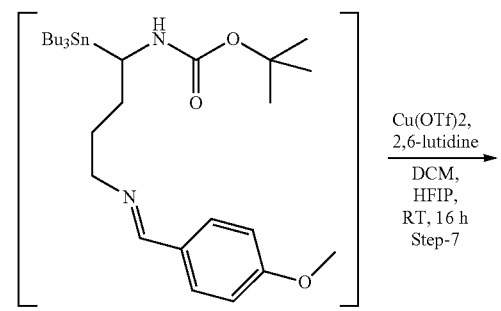

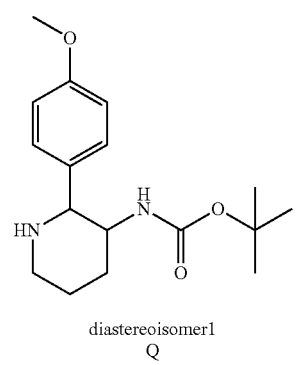

diastereoisomer1
Q

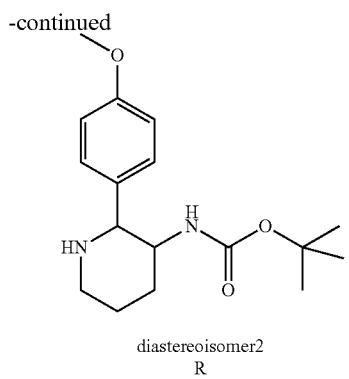

diastereoisomer2
R

Step 1:

To the stirred solution of 1,3-dioxo-1,3-dihydro-isoindole-2-carboxylic acid ethyl ester (10 g, 62 mmol, 1 eq) in dry THF (200 mL) were added 4,4-diethoxy-butylamine (13.6 g, 62 mmol, 1 eq) and TEA (8.6 mL, 62 mmol, 1 eq) under ice cooled condition and stirred at RT for 16 h. After completion of the reaction, it was concentrated under reduced pressure to obtain crude product which was purified by silica gel (100-200 mesh) column chromatography (5% EA/Hexane) to afford 2-(4,4-diethoxy-butyl)-isoindole-1,3-dione (17 g, 94% yield) as light yellowish liquid.

Step 2:

To the stirred solution of 2-(4,4-diethoxy-butyl)-isoindole-1,3-dione (22 g, 75.6 mmol, 1 eq) in acetone (160 mL) was added 1N aqueous HCl (145 mL) and the reaction mixture was heated under reflux for 2 h. After completion of the reaction, it was concentrated under reduced pressure and diluted with EtOAc and washed with water and brine. The combined organic layer was dried over Na2SO4, filtered to get the desired 4-(1,3-dioxo-1,3-dihydro-isoindol-2-yl)-butyraldehyde (13 g, 96% yield) as white solid.

Step 3:

To a stirred solution of 4-(1,3-dioxo-1,3-dihydro-isoindol-2-yl)-butyraldehyde (18 g, 83 mmol, 1 eq) in water:MeOH:HCOOH (260 mL: 138 mL: 35 mL) were added Nap-toluene sulfinate (14.8 g, 83 mmol, 1 eq) and tert butyl carbamate (9.7 g, 83 mmol, 1 eq) and the reaction mixture was stirred at RT for 48 h. After completion of the reaction, the solid was filtered through sintered funnel and washed thoroughly with water and dried under reduced pressure to obtain the desired [4-(1,3-dioxo-1,3-dihydro-isoindol-2-yl)-1-(toluene-4-sulfonyl)-butyl]-carbamic acid tert-butyl ester (28 g, 71% yield) as white solid.

Step 4:

To a stirred solution of dry CsF (4.8 g, 31.8 mmol, 1 eq) in DMF (65 mL) was added [4-(1,3-dioxo-1,3-dihydro-isoindol-2-yl)-1-(toluene-4-sulfonyl)-butyl]-carbamic acid tert-butyl ester (5 g, 10.6 mmol, 1 eq) in DMF (18 mL) and stirred for a period of 15 min followed by the addition of TMS-SnBu3 (7.7 g, 21.2 mmol, 2 eq) and the reaction mixture was stirred vigorously for a period of 4 h. Then the reaction was quenched with MeOH (50 mL) and water (50 mL). The organic layer was separated and the aqueous layer was re-extracted with EtOAc (3×100 mL). The organic layer was dried over anhyd. Na2SO4 and concentrated under reduced pressure to obtain crude product which was purified by silica gel (100-200 mesh) column chromatography (10% EA/Hexane) to afford desired [4-(1,3-dioxo-1,3-dihydro-isoindol-2-yl)-1-tributylstannanyl-butyl]-carbamic acid tert-butyl ester (2.5 g, 39% yield) as colorless oil.

Step 5:

To a stirred solution of [4-(1,3-dioxo-1,3-dihydro-isoindol-2-yl)-1-tributylstannanyl-butyl]-carbamic acid tert-butyl ester (5 g, 8.2 mmol, 1 eq) in EtOH (70 mL) was added hydrazine hydrate (4.1 g, 82 mmol, 10 eq) and stirred under reflux for a period of 45 min. After completion of the reaction, the reaction mixture was diluted with EtOAc and washed with water and brine. The combined organic layer was dried over anhyd. Na2SO4 and concentrated under reduced pressure to obtain (4-amino-1-tributylstannanyl-butyl)-carbamic acid tert-butyl ester (3.9 g, 99% yield) as off white sticky solid.

Step 6:

To a stirred solution of 4-amino-1-tributylstannanyl-butyl)-carbamic acid tert-butyl ester (1 eq) in DCM (8 mL/mmol) was added 4-methoxybenzaldehyde (1 eq) followed by the addition of MS 4 powder (120 mg/mmol) and the reaction mixture was stirred at RT for a period of 16 h. After completion of the reaction the reaction mass was filtered through a short layer of celite pad and concentrated under reduced pressure to get the corresponding tert-butyl (4-((4-methoxybenzylidene)amino)-1-(tributylstannyl)butyl)carbamate as a colorless sticky solid (quantitative yield).

Step 7:

To a stirred solution of Cu(OTf)2 (1 eq) in HFIP (12 mL/mmol) was added 2,6 lutidine (1 eq) and the reaction mixture was stirred at RT for 1 h. The resulting bluish colored solution turned into green. To this solution was added corresponding tert-butyl (4-((4-methoxybenzylidene)amino)-1-(tributylstannyl)butyl)carbamate (1 eq) in DCM (2 mL/mmol) and the reaction mixture was stirred at RT for a period of 24 h. After completion of the reaction, the reaction mixture was diluted with CH2Cl2 (20 mL), treated with a solution of 12% aq NH4OH and brine (1:1, 5 mL/mmol), and stirred vigorously for 15 min at RT. The layers were separated and the aqueous layer was extracted with CH2Cl2 (2 times). The combined organic layers were washed with H2O and brine, dried over anhydrous Na2SO4, filtered, and concentrated in vacuo. Purification was done by silica gel (100-200 mesh) column chromatography (10% EA/Hexane) to afford two different diastereoisomers (cis and trans) of tert-butyl (2-(4-methoxyphenyl)piperidin-3-yl)carbamate.

Intermediate Q (diasteroisomer1, polar, 290 mg): LC-MS (method 1): m/z [M+H]+=307.3 (exact mass calc.=306.19); R$_t$=3.07 min.

Intermediate P (diastereoisomer2, less polar, 395 mg): LC-MS (method 1): m/z [M+H]+=307.3 (exact mass calc.=306.19); R$_t$=2.73 min.

Synthesis of Key Intermediate S and T: Preparation of iso-mix-tert-butyl (2-(2,6-difluoro-4-methoxyphenyl)piperidin-3-yl)carbamate (S(dia1) and T (dia2))

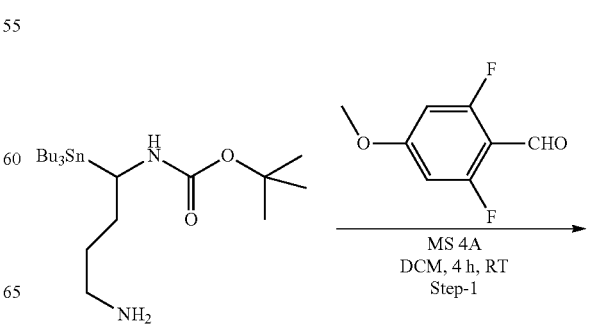

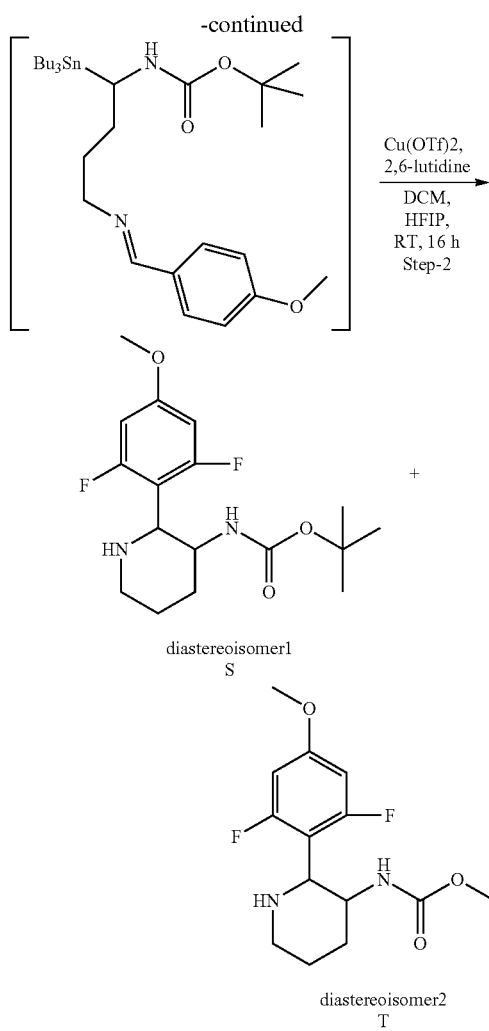

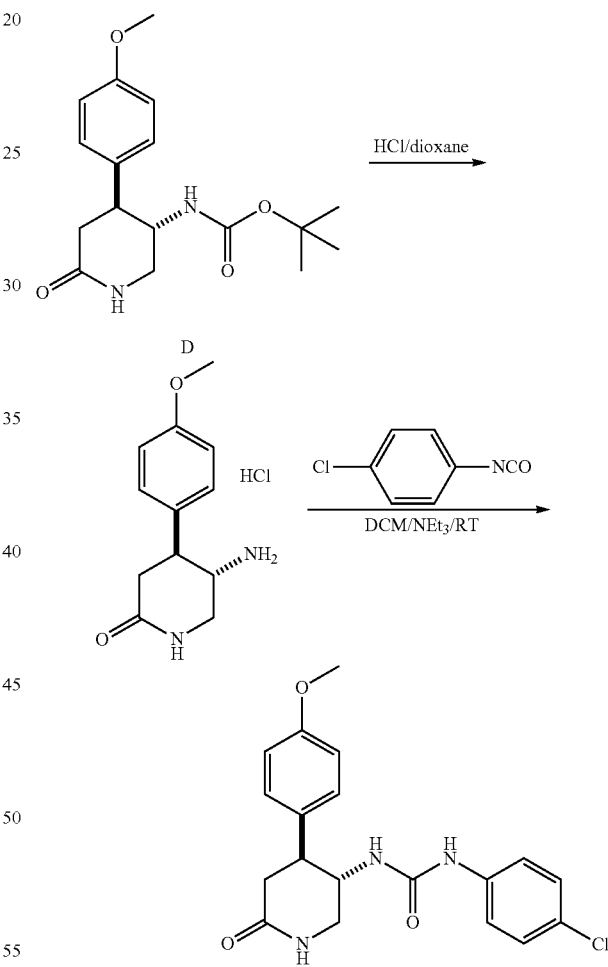

organic layers were washed with H₂O and brine, dried over anhydrous Na₂SO₄, filtered, and concentrated in vacuo. Purification was done by silica gel (100-200 mesh) column chromatography (10% EA/Hexane) to afford two different diastereoisomers (cis and trans) of tert-butyl (2-(2,6-difluoro-4-methoxyphenyl)piperidin-3-yl)carbamate.

Intermediate S (diastereoisomer1, polar): LC-MS (Method 1): m/z [M+H]⁺=343.2 (exact mass calc.=342.18); $R_t$=3.10 min.

Intermediate T (diastereoisomer2, less polar): LC-MS (Method 1): m/z [M+H]⁺=343.2 (exact mass calc.=342.18); $R_t$=2.88 min.

Preparation of: rac-trans-1-(4-chlorophenyl)-3-(4-(4-methoxyphenyl)-6-oxopiperidin-3-yl)urea (Example 1)

Step1:
To a stirred solution of 4-amino-1-tributylstannanyl-butyl)-carbamic acid tert-butyl ester (1 eq) in DCM (8 mL/mmol) was added 4-methoxybenzaldehyde (1 eq) followed by the addition of MS 4 powder (120 mg/mmol) and the reaction mixture was stirred at RT for a period of 16 h. After completion of the reaction the reaction mass was filtered through a short layer of celite pad and concentrated under reduced pressure to get the corresponding tert-butyl (4-((2,6-difluoro-4-methoxybenzylidene)amino)-1-(tributylstarmyl)butyl)carbamate as a colorless sticky solid (quantitative yield).

Step2:
To a stirred solution of Cu(OTf)₂ (1 eq) in HFIP (12 mL/mmol) was added 2,6 lutidine (1 eq) and the reaction mixture was stirred at RT for 1 h. The resulting bluish colored solution turned into green. To this solution was added corresponding (E)-tert-butyl (4-((2,6-difluoro-4-methoxybenzylidene)amino)-1-(tributylstannyl)butyl)carbamate (1 eq) in DCM (2 mL/mmol) and the reaction mixture was stirred at RT for a period of 24 h. After completion of the reaction, the reaction mixture was diluted with CH₂Cl₂ (20 mL), treated with a solution of 12% aq NH₄OH and brine (1:1, 5 mL/mmol), and stirred vigorously for 15 min at RT. The layers were separated and the aqueous layer was extracted with CH₂Cl₂ (2 times). The combined To a stirred solution of key intermediate D (0.1 g, 0.31 mmol, 1 eq) in dioxane (8 mL) was added HCl (4M) in dioxane (2 mL) at 0° C. and stirred for 1 h at RT. The reaction mass was concentrated under reduced pressure and triturated with Et₂O to afford rac-trans-5-amino-4-(4-methoxyphenyl)piperidin-2-one (0.07 g, crude) as HCl salt.

To a stirred solution of rac-trans-5-amino-4-(4-methoxyphenyl)piperidin-2-one hydrochloride (0.18 g, 0.7 mmol, 1 eq) in DCM (12 mL) was added Et₃N (0.15 mL, 1.05 mmol, 1.5 eq) followed by 4-chlorophenylisocyanate (0.107 g, 0.7 mmol, 1 eq) at 0° C. and stirred for 2 h at RT. The reaction was quenched with H₂O and the organics were extracted with DCM (2×20 mL), washed with brine (10 mL), dried over Na₂SO₄ and concentrated in vacuo. The crude product was purified by column chromatography (Neutral Alumina, 3% MeOH in DCM) followed by trituration with EtOAc to afford Example 1 (0.1 g, 38%) as white solid. LCMS: calculated for [M+H]⁺: 374, found: 374 (Method 2).

¹H NMR (400 MHz, DMSO-d₆) δ 8.47 (s, 1H), 7.58 (m, 1H), 7.33 (d, J=9 Hz, 2H), 7.24-7.17 (m, 4H), 6.88 (d, J=8 Hz, 2H), 6.16 (d, J=8 Hz, 1H), 4.10-4.00 (m, 1H), 3.71 (s, 3H), 3.30 (m, 1H), 3.16-3.05 (m, 1H), 3.02-2.95 (m, 1H), 2.43-2.40 (m, 2H).

Preparation of: rac-trans-1-(1-acetyl-4-(4-methoxyphenyl)piperidin-3-yl)-3-(4-chlorophenyl)urea (Example 2)

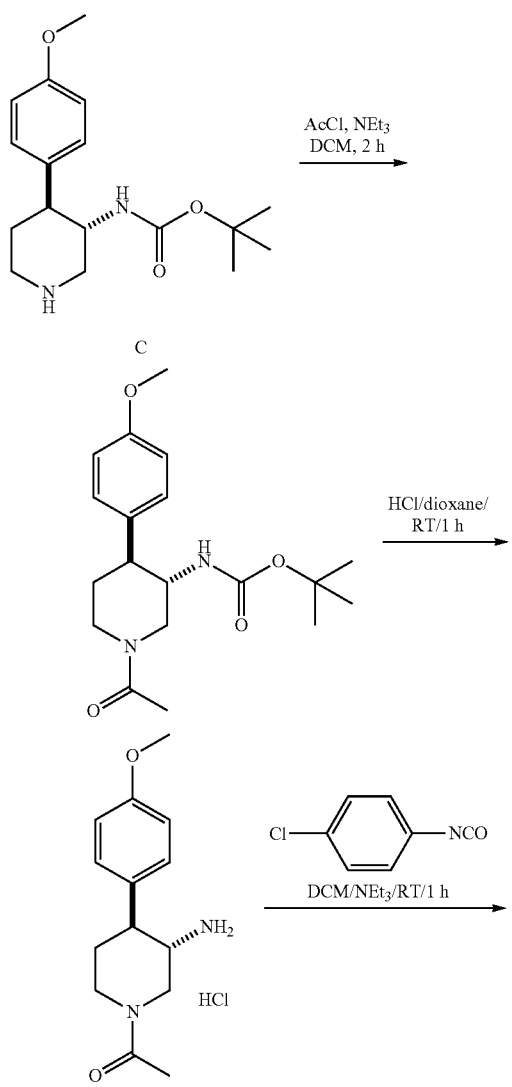

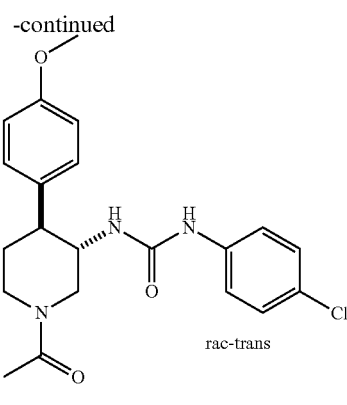

2

To a stirred solution of key intermediate C (0.2 g, 0.65 mmol, 1 eq) in DCM (10 mL) was added Et₃N (0.23 mL, 1.63 mmol, 2.5 eq) followed by acetylchloride (0.056 mL, 0.78 mmol, 1.2 eq) at 0° C. and stirred for 2 h at RT. The reaction mixture was quenched with sat. aqueous NaHCO₃ solution. The organic layer was separated, washed with brine (10 mL), dried over Na₂SO₄ and concentrated under reduced pressure. The crude product was purified by column chromatography (silica gel, 100:200 mesh, 50% EtOAc in hexane) to afford rac-trans-tert-butyl (1-acetyl-4-(4-methoxyphenyl)piperidin-3-yl)carbamate (0.17 g, 75%) as yellow gum.

To a stirred solution of rac-trans-tert-butyl (1-acetyl-4-(4-methoxyphenyl)piperidin-3-yl)carbamate (0.17 g, 0.48 mmol, 1 eq) in dioxane (10 mL) was added HCl (4M) in dioxane (4 mL) at 0° C. and stirred for 1 h at RT. The reaction mass was concentrated in vacuo and triturated with Et₂O to afford rac-trans-1-(3-amino-4-(4-methoxyphenyl)piperidin-1-yl)ethanone (0.14 g, crude) as HCl salt.

To a stirred solution of rac-trans-1-(3-amino-4-(4-methoxyphenyl)piperidin-1-yl)ethanone hydrochloride (0.15 g, 0.527 mmol, 1 eq) in DCM (10 mL) was added Et₃N (0.11 mL, 0.79 mmol, 1.5 eq) followed by 4-chlorophenylisocyanate (0.081 g, 0.527 mmol, 1 eq) at 0° C. and stirred for 2 h at RT. The reaction mixture was quenched with H₂O and the organic components were extracted with DCM (2×15 ml), washed with brine (10 mL), dried over Na₂SO₄ and concentrated in vacuo. The crude product was purified by column chromatography (silica gel, 100:200 mesh, 80% EtOAc in hexane) to afford Example 2 as white solid. LCMS: calculated for [M+H]⁺: 402, found: 402 (Method 2).

¹H NMR (100° C., 400 MHz, DMSO-d₆) δ 8.19 (s, 1H), 7.31 (d, J=8.7 Hz, 2H), 7.19 (d, J=8.8 Hz, 4H), 6.86 (d, J=8.12 Hz, 2H), 5.82 (d, J=7.52 Hz, 1H), 4.25 (m, 4H), 3.72 (m, 4H), 2.27 (m, 2H), 2.06 (s, 3H), 1.28 (d, J=14.28 Hz, 1H), 1.60 (m, 1H).

Preparation of: rac-trans-1-(4-bromophenyl)-3-(4-(4-methoxyphenyl)-6-oxopiperidin-3-yl)urea (Example 3)

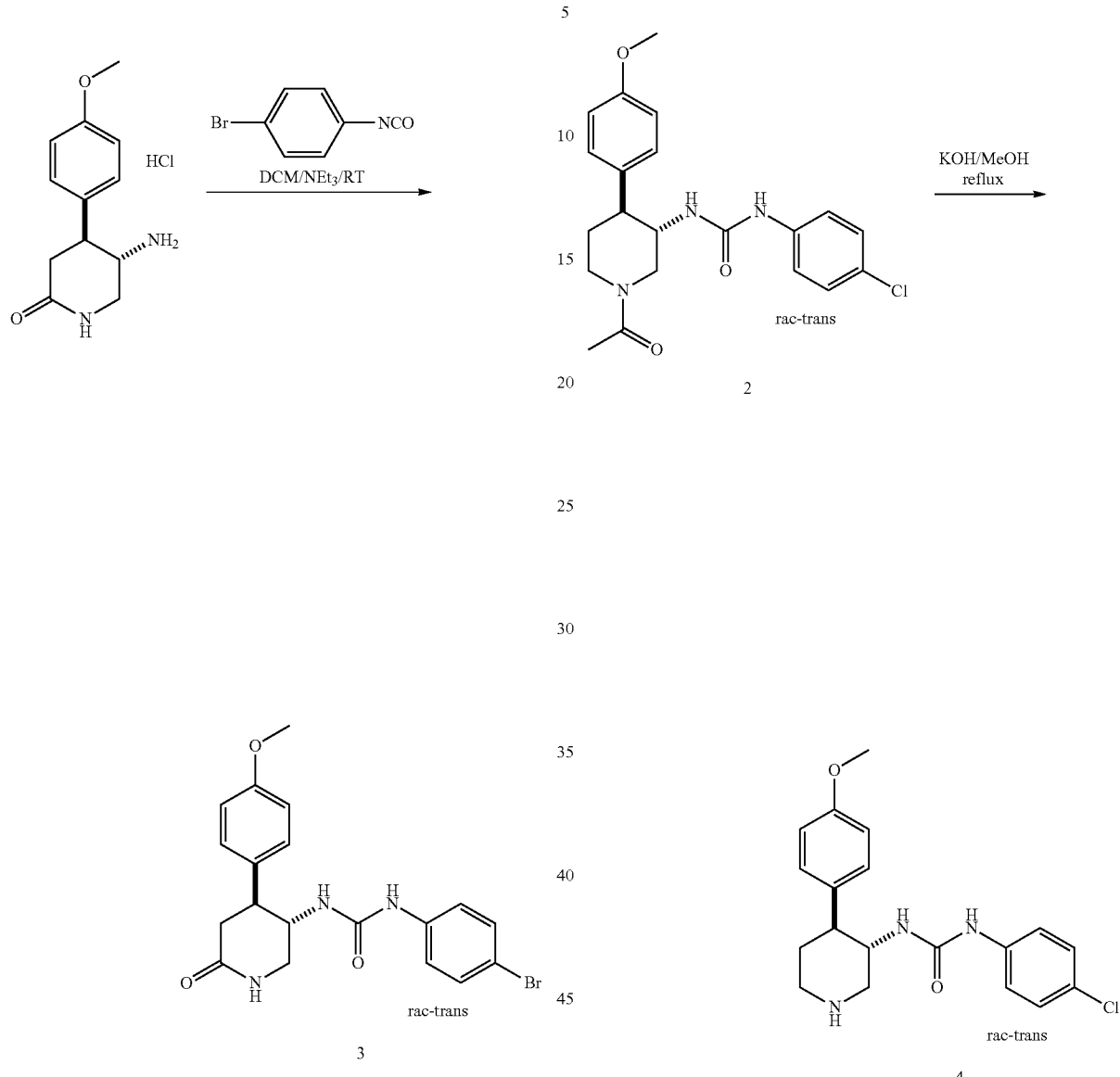

Preparation of: rac-trans-1-(4-chlorophenyl)-3-(4-(4-methoxyphenyl)piperidin-3-yl)urea (Example 4)

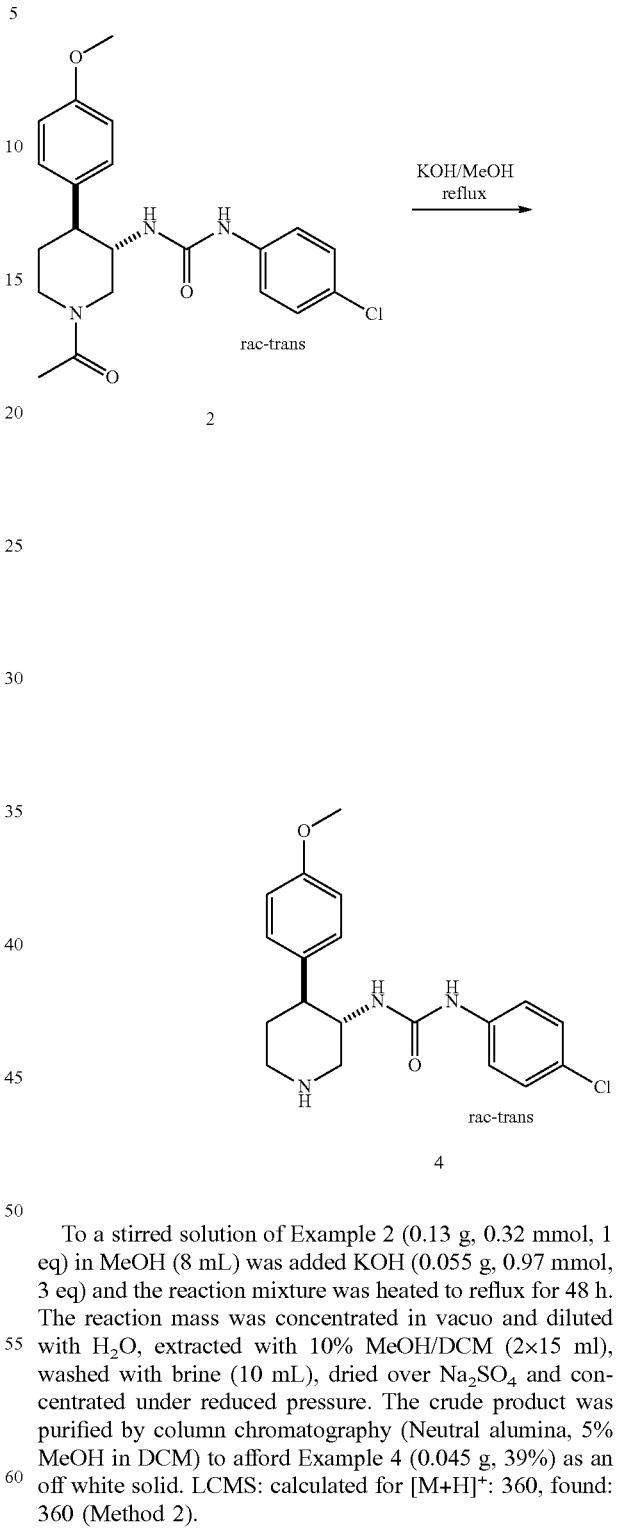

To a stirred solution of rac-trans-5-amino-4-(4-methoxyphenyl)piperidin-2-one hydrochloride (0.15 g, 0.58 mmol, 1 eq) in DCM (10 mL) was added Et$_3$N (0.13 mL, 0.87 mmol, 1.5 eq) followed by 4-bromophenylisocyanate (0.114 g, 0.58 mmol, 1 eq) at 0° C. and stirred for 2 h at RT. The reaction was quenched with H$_2$O and the organics were extracted with DCM (2×15 ml), washed with brine (10 mL), dried over Na$_2$SO$_4$ and concentrated in vacuo. The crude product was purified by column chromatography (Neutral Alumina, 3% MeOH in DCM) followed by trituration with EtOAc to afford Example 3 (0.1 g, 24%) as white solid. LCMS: calculated for [M+H]$^+$: 418, found: 418 (Method 2).

$^1$H NMR (400 MHz, DMSO-d$_6$) δ 8.47 (s, 1H), 7.57 (m, 1H), 7.35 (d, J=9 Hz, 2H), 7.28 (d, J=9 Hz, 2H), 7.19 (d, J=9 Hz, 2H), 6.88 (d, J=9 Hz, 2H), 6.16 (d, J=8 Hz, 1H), 4.10-4.00 (m, 1H), 3.71 (s, 3H), 3.34 (m, 1H), 3.14-3.08 (m, 1H), 3.02-2.96 (m, 1H), 2.43-2.40 (m, 2H).

To a stirred solution of Example 2 (0.13 g, 0.32 mmol, 1 eq) in MeOH (8 mL) was added KOH (0.055 g, 0.97 mmol, 3 eq) and the reaction mixture was heated to reflux for 48 h. The reaction mass was concentrated in vacuo and diluted with H$_2$O, extracted with 10% MeOH/DCM (2×15 ml), washed with brine (10 mL), dried over Na$_2$SO$_4$ and concentrated under reduced pressure. The crude product was purified by column chromatography (Neutral alumina, 5% MeOH in DCM) to afford Example 4 (0.045 g, 39%) as an off white solid. LCMS: calculated for [M+H]$^+$: 360, found: 360 (Method 2).

$^1$H NMR (400 MHz, DMSO-d$_6$) δ 8.31 (s, 1H), 7.29 (d, J=9 Hz, 2H), 7.21-7.13 (m, 4H), 6.83 (d, J=8 Hz, 2H), 5.82 (d, J=8 Hz, 1H), 3.69 (m, 4H), 3.18-3.16 (m, 1H), 2.93-2.88 (m, 1H), 2.27-2.20 (m, 1H), 1.70-1.66 (m, 1H), 1.54-1.50 (m, 1H).

Preparation of: rac-trans-1-(1-acetyl-4-(2,6-difluoro-4-methoxyphenyl)piperidin-3-yl)-3-(4-chlorophenyl)urea (Example 5)

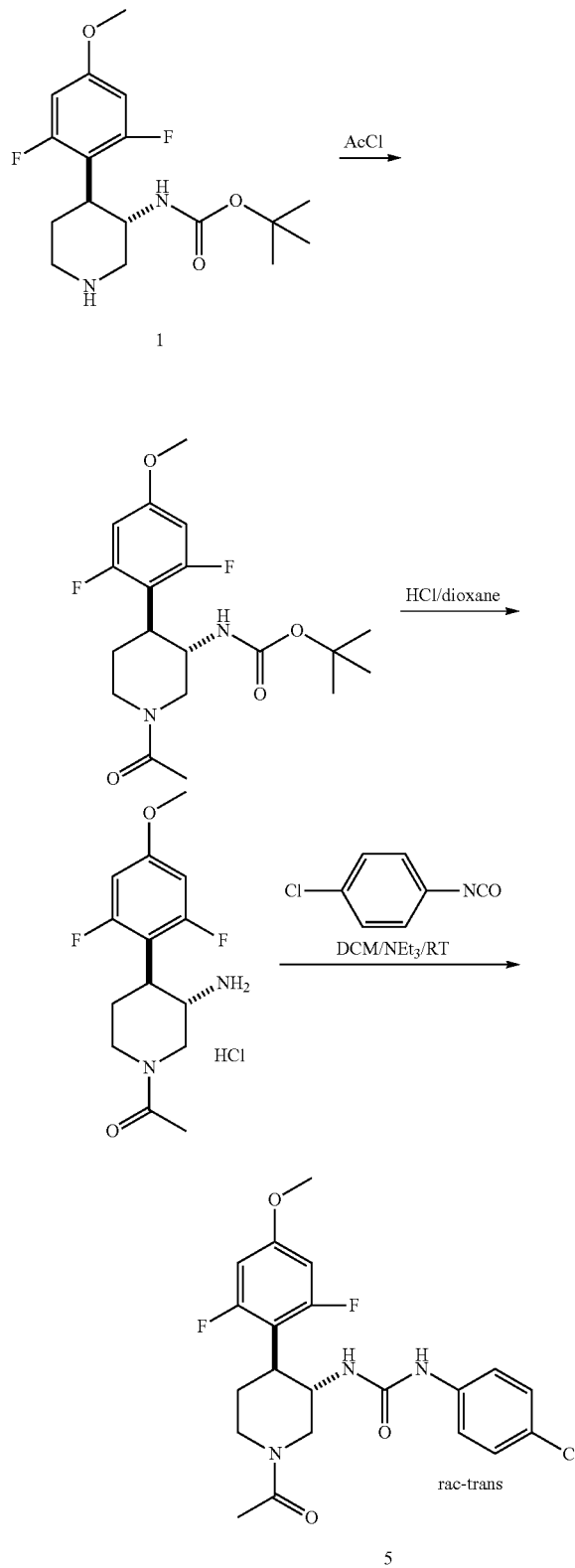

To a stirred solution of key intermediate A (0.7 g, 2.04 mmol, 1 eq) in DCM (25 mL) was added Et$_3$N (0.72 mL, 5.11 mmol, 2.5 eq) followed by acetyl chloride (0.18 mL, 0.245 mmol, 1.2 eq) at 0° C. and stirred for 2 h at RT. The reaction mixture was quenched with sat. aqueous NaHCO$_3$ solution. The organic layer was separated, washed with brine (10 mL), dried over Na$_2$SO$_4$ and concentrated under reduced pressure. The crude product was purified by column chromatography (silica gel, 100-200 mesh, 70% EtOAc in hexane) to afford rac-trans-tert-butyl (1-acetyl-4-(2,6-difluoro-4-methoxyphenyl)piperidin-3-yl) carbamate (0.65 g, 83% yield) as yellow gum.

To a stirred solution of rac-trans-tert-butyl (1-acetyl-4-(2,6-difluoro-4-methoxyphenyl)piperidin-3-yl)carbamate (0.65 g, 1.69 mmol, 1 eq) in dioxane was added HCl (4M) in dioxane (8 mL) at 0° C. and stirred for 1 h at RT. The reaction mass was concentrated in vacuo and triturated with Et$_2$O to afford rac-trans-1-(3-amino-4-(2,6-difluoro-4-methoxyphenyl)piperidin-1-yl)ethanone (0.53 g, crude) as HCl salt.

To a stirred solution of rac-trans-1-(3-amino-4-(2,6-difluoro-4-methoxyphenyl)piperidin-1-yl)ethanone hydrochloride (0.3 g, 0.93 mmol, 1 eq) in DCM (15 mL) was added Et$_3$N (0.2 mL, 1.4 mmol, 1.5 eq) followed by 4-chlorophenylisocyanate (0.144 g, 0.94 mmol, 1 eq) at 0° C. and stirred for 2 h at RT. The reaction mixture was quenched with H$_2$O and the organic components were extracted with DCM (2×20 mL), washed with brine (10 mL), dried over Na$_2$SO$_4$ and concentrated in vacuo. The crude product was purified by column chromatography (Neutral alumina, 4% MeOH in DCM) to afford Example 5 (0.27 g, 66%) as white solid. LCMS: calculated for [M+H]$^+$: 438, found: 438 (Method 2).

$^1$H NMR (100° C., 400 MHz, DMSO-d$_6$) δ 8.25 (s, 1H), 7.28 (d, J=9 Hz, 2H), 7.18 (d, J=9 Hz, 2H), 6.61 (d, J=11 Hz, 2H), 5.84 (d, J=9 Hz, 1H), 4.50-4.10 (m, 2H), 4.00-3.90 (m, 2H), 3.75 (s, 3H), 3.15-3.05 (m, 2H), 2.06 (s, 3H), 1.90-1.75 (m, 2H).

Preparation of: rac-trans-1-(4-bromophenyl)-3-(4-(4-methoxyphenyl)piperidin-3-yl)urea (Example 6) and rac-trans-1-(1-acetyl-4-(4-methoxyphenyl)piperidin-3-yl)-3-(4-bromophenyl)urea (Example 22)

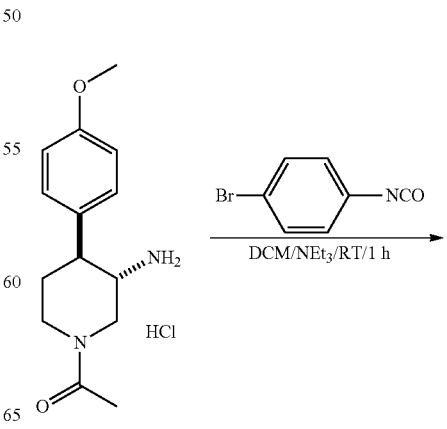

-continued

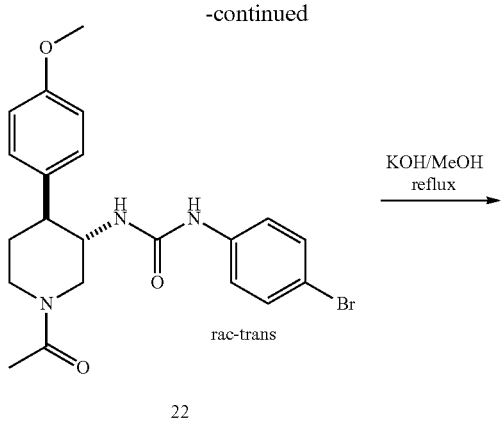

22 rac-trans

KOH/MeOH reflux →

62

Preparation of: rac-trans-1-(4-chlorophenyl)-3-(4-(4-methoxyphenyl)-1-methyl-6-oxopiperidin-3-yl)urea (Example 7)

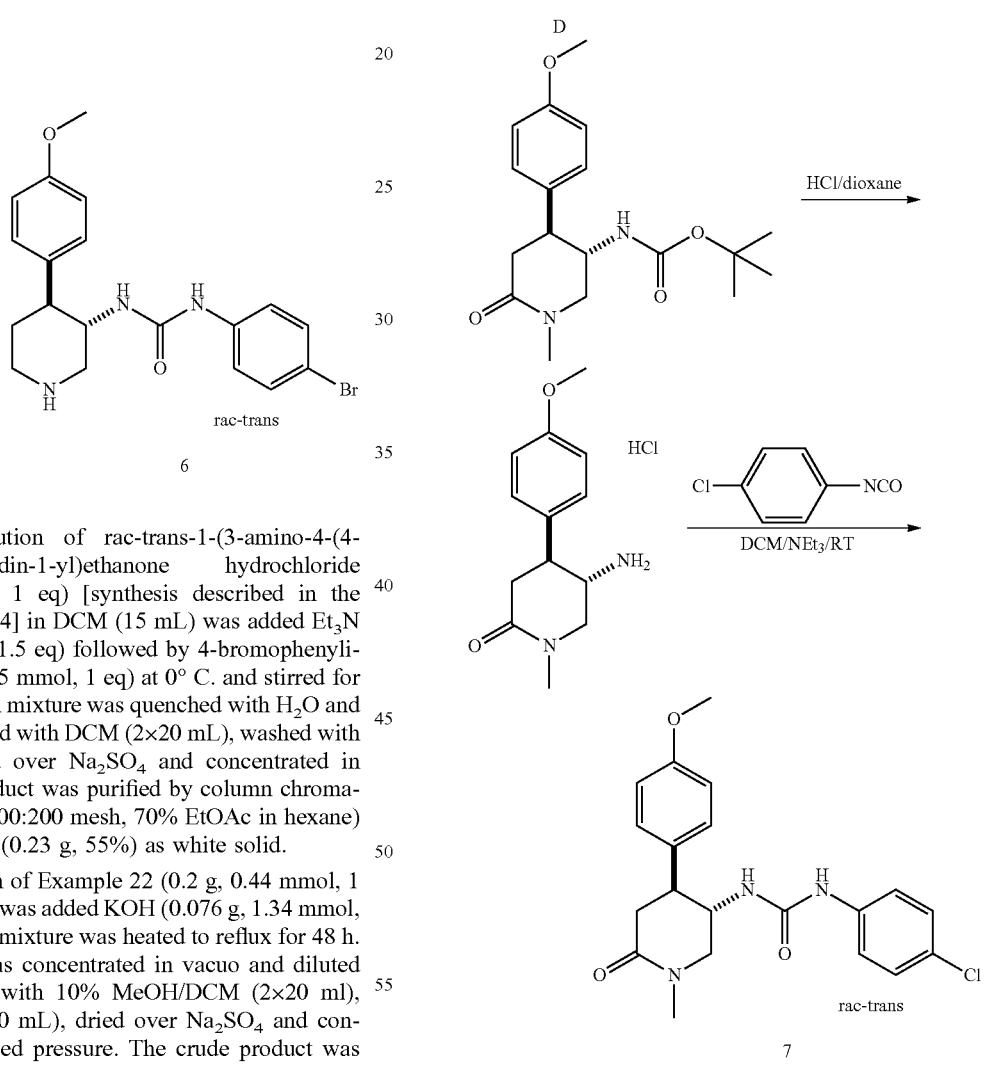

6 rac-trans

To a stirred solution of rac-trans-1-(3-amino-4-(4-methoxyphenyl)piperidin-1-yl)ethanone hydrochloride (0.27 g, 0.95 mmol, 1 eq) [synthesis described in the synthesis of Example 4] in DCM (15 mL) was added Et$_3$N (0.2 mL, 1.42 mmol, 1.5 eq) followed by 4-bromophenylisocyanate (0.19 g, 0.95 mmol, 1 eq) at 0° C. and stirred for 2 h at RT. The reaction mixture was quenched with H$_2$O and organics were extracted with DCM (2×20 mL), washed with brine (15 mL), dried over Na$_2$SO$_4$ and concentrated in vacuo. The crude product was purified by column chromatography (silica gel, 100:200 mesh, 70% EtOAc in hexane) to afford Example 22 (0.23 g, 55%) as white solid.

To a stirred solution of Example 22 (0.2 g, 0.44 mmol, 1 eq) in MeOH (12 mL) was added KOH (0.076 g, 1.34 mmol, 3 eq) and the reaction mixture was heated to reflux for 48 h. The reaction mass was concentrated in vacuo and diluted with H$_2$O, extracted with 10% MeOH/DCM (2×20 ml), washed with brine (10 mL), dried over Na$_2$SO$_4$ and concentrated under reduced pressure. The crude product was purified by column chromatography (Neutral alumina, 3% MeOH in DCM) followed by trituration with EtOAc to afford Example 6 (0.045 g, 25%) as an off white solid. LCMS: calculated for [M+H]$^+$: 404, found: 404 (Method 2).

$^1$H NMR (400 MHz, DMSO-d$_6$) δ 8.34 (s, 1H), 7.32 (d, J=9 Hz, 2H), 7.24 (d, J=9 Hz, 2H), 7.14 (d, J=8 Hz, 2H), 6.83 (d, J=8 Hz, 2H), 5.84 (d, J=8 Hz, 1H), 3.69 (m, 4H), 3.19-3.16 (m, 1H), 2.94-2.90 (m, 1H), 2.45 (m, 1H), 2.28-2.22 (m, 1H), 1.70-1.67 (m, 1H), 1.57-1.51 (m, 1H).

To a stirred solution of key intermediate D (0.2 g, 0.63 mmol, 1 eq) in DMF (5 mL) was added NaH (28 mg, 0.69 mmol, 1.1 eq) followed by MeI (0.06 mL, 0.94 mmol, 1.5 eq) at 0° C. and stirred for 2 h at RT. The reaction was quenched with ice-water, the organic components were extracted with EtOAc (2×15 mL), washed with brine (10 mL), dried over Na$_2$SO$_4$ and concentrated under reduced pressure. The crude material was purified by silica gel (100-200 mesh) column chromatography (70% EtOAc in hexane) to afford rac-trans-tert-butyl (4-(4-methoxyphenyl)-1-methyl-6-oxopiperidin-3-yl)carbamate (0.18 g, 87%) as yellow gum.

To a stirred solution of rac-trans-tert-butyl (4-(4-methoxyphenyl)-1-methyl-6-oxopiperidin-3-yl)carbamate (0.18 g, 0.54 mmol, 1 eq) in dioxane (10 mL) was added HCl (4M) in dioxane (4 mL) at 0° C. and stirred for 1 h at RT. The reaction mass was concentrated under reduced pressure and triturated with Et$_2$O to afford rac-trans-5-amino-4-(4-methoxyphenyl)-1-methylpiperidin-2-one (0.14 g, crude) as HCl salt.

To a stirred solution of 5-amino-4-(4-methoxy-phenyl)-1-methyl-piperidin-2-one hydrochloride (0.15 g, 0.55 mmol, 1 eq) in DCM (10 mL) was added Et$_3$N (0.12 mL, 0.83 mmol, 1.5 eq) followed by 4-chlorophenylisocyanate (0.085 g, 0.55 mmol, 1 eq) at 0° C. and stirred for 2 h at RT. The reaction was quenched with H$_2$O and the organic component was extracted with DCM (2×15 ml), washed with brine (10 mL), dried over Na$_2$SO$_4$ and concentrated under reduced pressure. The crude product was purified by preparative HPLC to afford Example 7 (0.068 g, 32%) as white solid. LCMS: calculated for [M+H]$^+$: 388, found: 388 (Method 2).

$^1$H NMR (400 MHz, DMSO-d$_6$) δ 8.46 (s, 1H), 7.33 (d, J=9 Hz, 2H), 7.22 (d, J=9 Hz, 2H), 7.18 (d, J=9 Hz, 2H), 6.87 (d, J=9 Hz, 2H), 6.18 (d, J=8 Hz, 1H), 4.22-4.13 (m, 1H), 3.71 (s, 3H), 3.50-3.44 (m, 1H), 3.20-3.10 (m, 2H), 2.83 (s, 3H), 2.50-2.42 (m, 2H).

Preparation of: rac-trans-1-(4-bromophenyl)-3-(4-(2,6-difluoro-4-methoxyphenyl)piperidin-3-yl)urea (Example 8) and rac-trans-1-(1-acetyl-4-(2,6-difluoro-4-methoxyphenyl)piperidin-3-yl)-3-(4-bromophenyl)urea (Example 34)

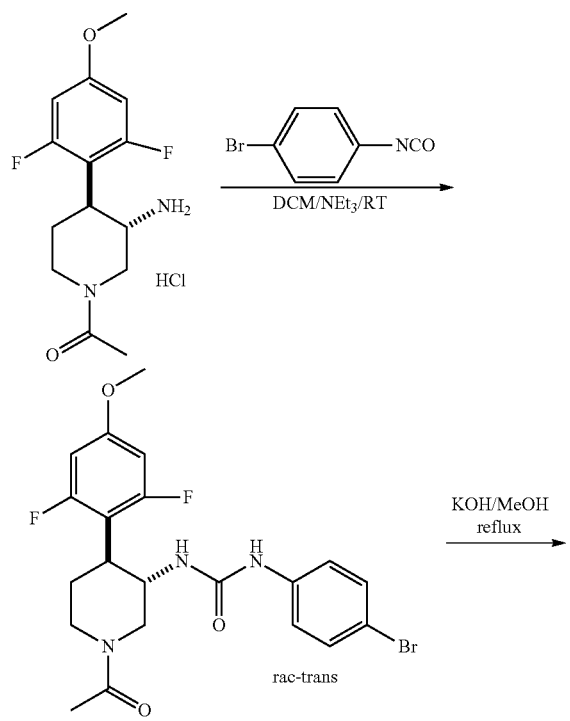

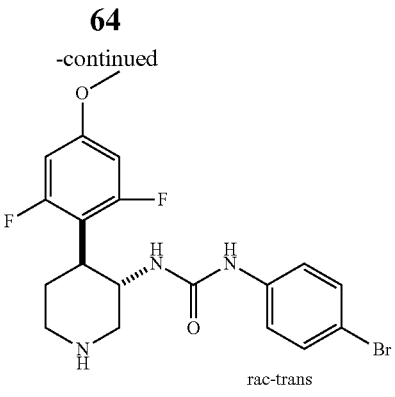

8

To a stirred solution of rac-trans-1-(3-amino-4-(2,6-difluoro-4-methoxyphenyl)piperidin-1-yl)ethanone hydrochloride (0.25 g, 0.78 mmol, 1 eq) [synthesis described in synthesis of Example 5] in DCM (15 mL) was added Et$_3$N (0.2 mL, 1.2 mmol, 1.5 eq) followed by 4-bromophenylisocyanate (0.15 g, 0.78 mmol, 1 eq) at 0° C. and stirred for 2 h at RT. The reaction was quenched with H$_2$O and organics were extracted with DCM (2×20 mL), washed with brine (15 mL), dried over Na$_2$SO$_4$ and concentrated in vacuo. The crude product was purified by column chromatography (Neutral alumina, 3% MeOH in DCM) to afford Example 34 (0.2 g, 53%) as white solid.

To a stirred solution of Example 34 (0.18 g, 0.38 mmol, 1 eq) in MeOH (10 mL) was added KOH (0.063 g, 1.14 mmol, 3 eq) and heated to reflux for 48 h. The reaction mass was concentrated in vacuo and diluted with H$_2$O, extracted with 10% MeOH/DCM (2×20 mL), washed with brine (10 mL), dried over Na$_2$SO$_4$ and concentrated under reduced pressure. The crude product was purified by column chromatography (Neutral alumina, 4% MeOH in DCM) followed by trituration with EtOAc to afford Example 8 (0.055 g, 34%) as an off white solid. LCMS: calculated for [M+H]$^+$: 440, found: 440 (Method 2).

$^1$H NMR (400 MHz, DMSO-d$_6$) δ 8.37 (s, 1H), 7.31 (d, J=8 Hz, 2H), 7.22 (d, J=7 Hz, 2H), 6.64 (d, J=11 Hz, 2H), 5.85 (d, J=8 Hz, 1H), 3.98 (m, 1H), 3.72 (s, 3H), 3.15-3.12 (m, 1H), 2.95-2.92 (m, 1H), 2.82-2.78 (m, 1H), 2.27-2.20 (m, 1H), 2.00-1.80 (m, 1H), 1.65-1.61 (m, 1H);

Preparation of: rac-trans-1-(4-chlorophenyl)-3-(4-(2,6-difluoro-4-methoxyphenyl)piperidin-3-yl)urea (Example 9)

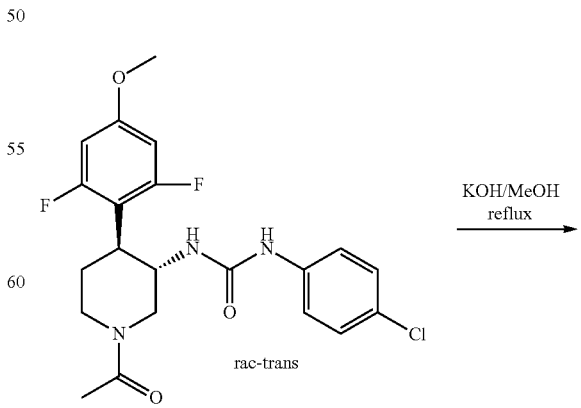

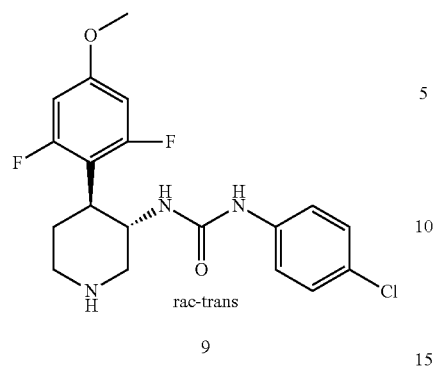

9

To a stirred solution of Example 5 (0.1 g, 0.228 mmol, 1 eq) in MeOH (10 mL) was added KOH (0.039 g, 0.686 mmol, 3 eq) and the reaction mixture was heated to reflux for 48 h. Then the reaction mass was concentrated in vacuo and diluted with H$_2$O, organic components were extracted with 10% MeOH/DCM (2×15 mL), washed with brine (10 mL), dried over Na$_2$SO$_4$ and concentrated under reduced pressure. The crude product was purified by column chromatography (Neutral alumina, 3% MeOH in DCM) followed by trituration with Et$_2$O to afford Example 9 (0.04 g, 45%) as white solid. LCMS: calculated for [M+H]$^+$: 396, found: 396 (Method 2).

$^1$H NMR (400 MHz, DMSO-d$_6$) δ 8.38 (s, 1H), 7.27 (d, J=9 Hz, 2H), 7.19 (d, J=9 Hz, 2H), 6.65 (d, J=11 Hz, 2H), 5.86 (d, J=9 Hz, 1H), 4.02-3.98 (m, 1H), 3.72 (s, 3H), 3.17-3.12 (m, 1H), 2.97-2.92 (m, 1H), 2.90-2.78 (m, 1H), 2.29-2.22 (m, 1H), 1.95-1.82 (m, 1H), 1.66-1.62 (m, 1H);

Preparation of: trans-ent1-(4-chlorophenyl)-3-(4-(4-methoxyphenyl)-1-methyl-6-oxopiperidin-3-yl)urea (Enantiomer 1) (Example 10) and trans-ent2-(4-chlorophenyl)-3-(4-(4-methoxyphenyl)-1-methyl-6-oxopiperidin-3-yl)urea (Enantiomer 2) (Example 11)

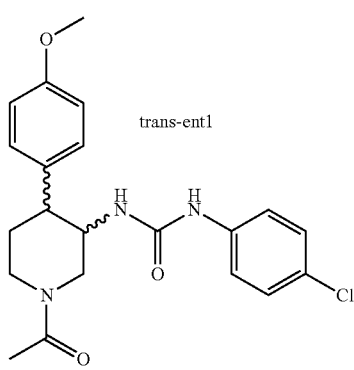

10

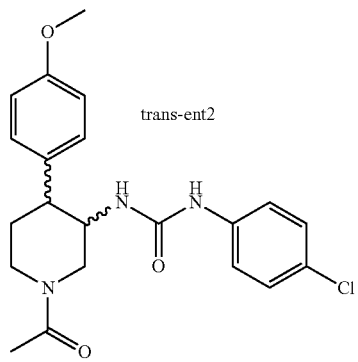

11

Example 4 was subjected to chiral SFC enantiomer separation using AD-H column and MeCN/MeOH as eluent to isolate enantiomerically pure isomers (Example 10 and Example 11).

(1$^{st}$ eluted peak): Example 10 (trans-ent1). LCMS: calculated for [M+H]$^+$: 402, found: 402 (Method 2).

(2$^{nd}$ eluted peak): Example 11 (trans-ent2). LCMS: calculated for [M+H]$^+$: 402, found: 402 (Method 2).

Preparation of: rac-trans-1-(4-chlorophenyl)-3-(1-(cyclopropanecarbonyl)-4-(4-methoxyphenyl)piperidin-3-yl)urea (Example 12)

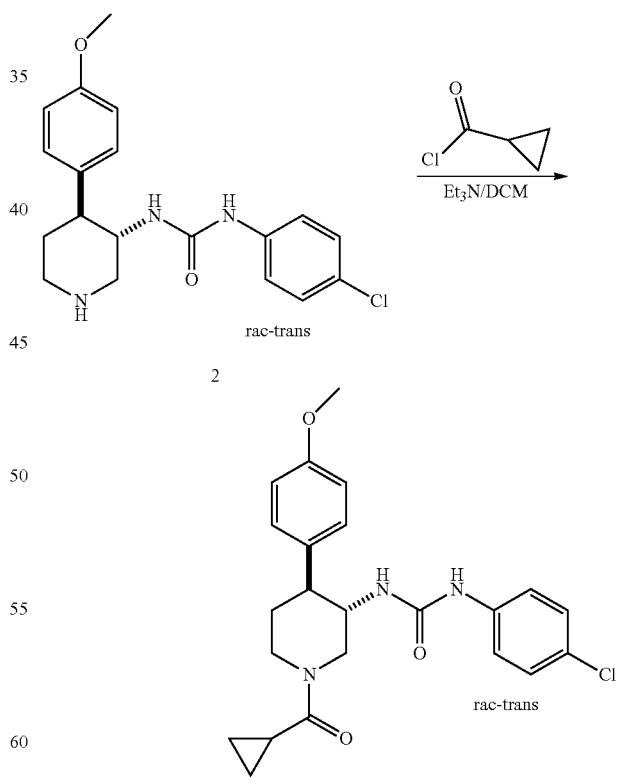

12

To a stirred solution of Example 2 (0.035 g, 0.09 mmol, 1 eq) in DCM (5 mL) was added Et$_3$N (0.024 mL, 0.18 mmol, 2 eq) followed by cyclopropylcarbonyl chloride (0.007 mL, 0.08 mmol, 0.9 eq) at 0° C. and stirred for 1 h. Then the reaction mass was diluted with DCM, washed with brine (10 mL), dried over Na₂SO₄ and concentrated. The crude product was purified by column chromatography (silica gel, 100-200 mesh, 50% EtOAc in hexane) to afford Example 12 (0.03 g, 81%) as white solid. LCMS: calculated for [M+H]⁺: 428, found: 428 (Method 2).

¹H NMR (100° C., 400 MHz, DMSO-d₆) δ 8.21 (s, 1H), 7.30 (d, J=8 Hz, 2H), 7.18 (d, J=8 Hz, 4H), 6.86 (d, J=8 Hz, 2H), 5.83 (d, J=8 Hz, 1H), 4.59 (d, J=9 Hz, 1H), 4.36 (d, J=11 Hz, 1H), 3.73 (m, 4H), 2.80-2.72 (m, 2H), 2.00-1.95 (m, 1H), 1.90-1.80 (m, 1H), 1.70-1.50 (m, 2H), 1.28 (m, 1H), 1.20 (m, 1H), 1.90-0.70 (m, 5H).

Preparation of: rac-trans-1-(4-chlorophenyl)-3-(1-(2-hydroxyacetyl)-4-(4-methoxyphenyl)piperidin-3-yl)urea (Example 13)

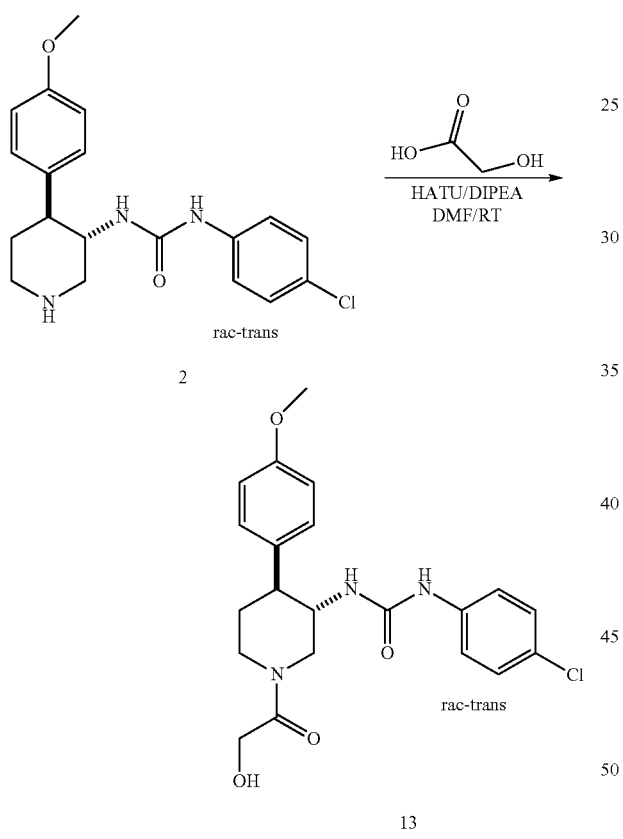

To a stirred solution of Example 2 (0.025 g, 0.06 mmol, 1 eq) in DMF (2 mL) was added hydroxyacetic acid (0.006 g, 0.08 mmol, 1.2 eq), HATU (0.03 g, 0.08 mmol, 1.2 eq) followed by DIPEA (0.03 mL, 1.45 mmoL, 2.3 eq) and stirred for 16 h at RT. Then the reaction mass was diluted with H₂O and extracted with EtOAc (2×10 mL), washed with brine (10 mL), dried over Na₂SO₄ and concentrated. The crude product was purified by column chromatography (silica gel, 100-200 mesh, 60% EtOAc in hexane) to afford Example 13 (0.02 g, 77%) as an off white solid. LCMS: calculated for [M+H]⁺: 418, found: 418 (Method 2).

¹H NMR (100° C., 400 MHz, DMSO-d₆) δ 8.20 (s, 1H), 7.30 (d, J=8 Hz, 2H), 7.18 (m, 4H), 6.85 (2, J=9 Hz, 2H), 5.82 (d, J=7 Hz, 1H), 4.21-4.15 (m, 4H), 3.73 (m, 4H), 2.90 (m, 1H), 2.76-2.65 (m, 2H), 1.85-1.80 (m, 1H), 1.70-1.60 (m, 1H).

Preparation of: rac-trans-1-(4-chlorophenyl)-3-(1-(2,2-difluoropropanoyl)-4-(4-methoxyphenyl)piperidin-3-yl)urea (Example 14)

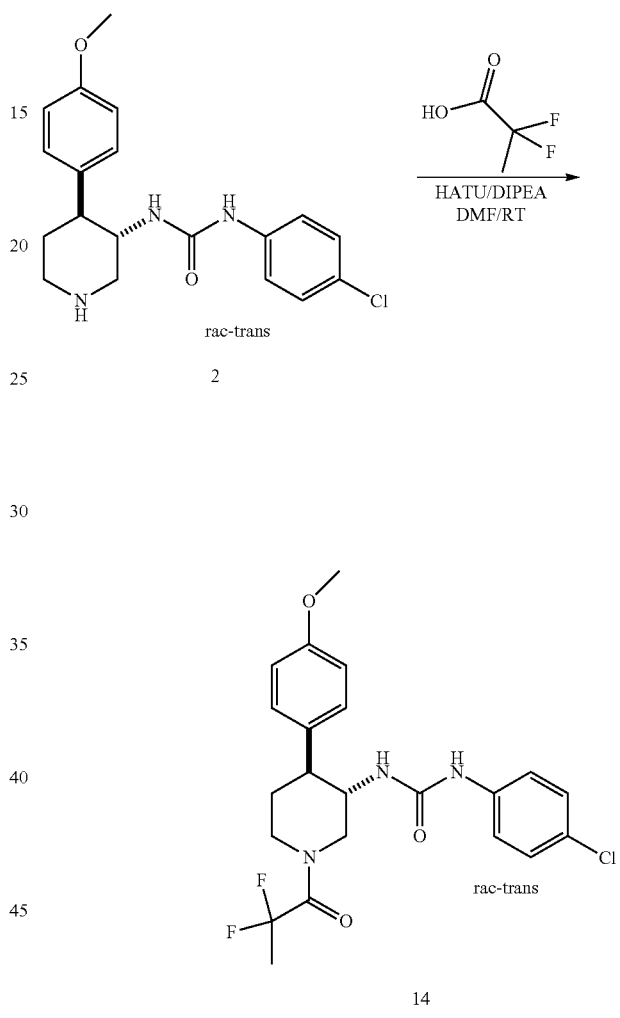

To a stirred solution of Example 2 (0.05 g, 0.13 mmol, 1 eq) in DMF (3 mL) was added 2,2-difluoro-propionic acid (0.017 g, 0.15 mmol, 1.2 eq), HATU (0.06 g, 0.15 mmol, 1.2 eq) followed by DIPEA (0.05 mL, 0.32 mmol, 2.5 eq) and stirred for 16 h at RT. Then the reaction mass was diluted with H₂O and extracted with EtOAc (2×15 mL), washed with brine (10 mL), dried over Na₂SO₄ and concentrated. The crude product was purified by column chromatography (silica gel, 100-200 mesh, 70% EtOAc in hexane) to afford Example 14 (0.035 g, 61%) as white solid. LCMS: calculated for [M+H]⁺: 452, found: 452 (Method 2).

¹H NMR (100° C., 400 MHz, DMSO-d₆) δ 8.20 (s, 1H), 7.29 (d, J=9 Hz, 2H), 7.19 (d, J=9 Hz, 4H), 6.86 (d, J=9 Hz, 2H), 5.87 (d, J=8 Hz, 1H), 4.54 (m, 1H), 4.29 (m, 1H), 3.80 (m, 1H), 3.73 (s, 3H), 3.10 (m, 1H), 2.82-2.78 (m, 2H), 1.88 (m, 4H), 1.68-1.62 (m, 1H).

Preparation of: rac-trans-1-(4-chlorophenyl)-3-(4-(4-methoxyphenyl)-1-(3-methoxypropanoyl)piperidin-3-yl)urea (Example 15)

Preparation of: rac-trans-1-(4-chlorophenyl)-3-(4-(4-methoxyphenyl)-1-(tetrahydro-2H-pyran-4-carbonyl)piperidin-3-yl)urea (Example 16)

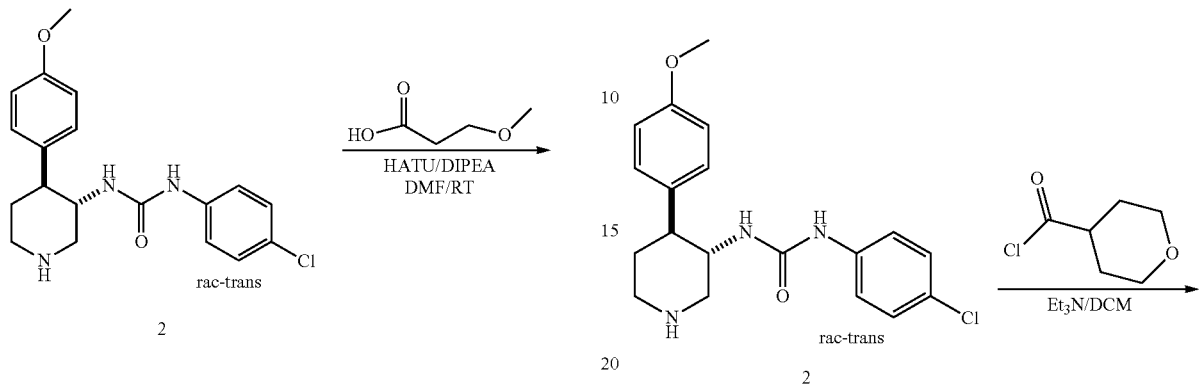

This compound was synthesized in analogy to Example 14.

LCMS: calculated for [M+H]$^+$: 446, found: 446 (Method 2).

$^1$H NMR (100° C., 400 MHz, DMSO-d$_6$) δ 8.20 (s, 1H), 7.30 (d, J=9 Hz, 2H), 7.20-7.15 (m, 4H), 6.85 (d, J=9 Hz, 2H), 5.81 (d, J=7 Hz, 1H), 4.50-4.00 (m, 2H), 3.73-3.63 (m, 6 H), 3.28 (s, 3H), 2.95-2.85 (m, 1H), 2.76-2.61 (m, 4H), 1.84-1.79 (m, 1H), 1.59-1.56 (m, 1H).

This compound was synthesized in analogy to Example 12.

LCMS: calculated for [M+H]$^+$: 472, found: 472 (Method 2).

$^1$H NMR (100° C., 400 MHz, DMSO-d$_6$) δ 8.20 (s, 1H), 7.30 (d, J=9 Hz, 2H), 7.20-7.15 (m, 4H), 6.85 (d, J=8 Hz, 2H), 5.82 (d, J=7 Hz, 1H), 4.46 (m, 1H), 4.29 (m, 1H), 3.92-3.85 (m, 2H), 3.73 (s, 3H), 3.70-3.60 (m, 1H), 3.47-3.37 (m, 2H), 2.90-2.80 (m, 2H), 2.76-2.65 (m, 2H), 1.90-1.80 (m, 1H), 1.82-1.65 (m, 3H), 1.60-1.50 (m, 2H).

71

Preparation of: rac-trans-1-(4-chlorophenyl)-3-(1-isobutyryl-4-(4-methoxyphenyl)piperidin-3-yl)urea (Example 17)

72

Preparation of: rac-trans-1-(4-chlorophenyl)-3-[4-(4-methoxyphenyl)-1-(3-methyl-butanoyl)-piperidin-3-yl]-urea (Example 18)

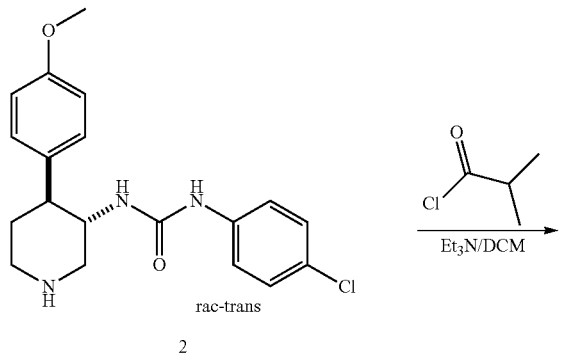

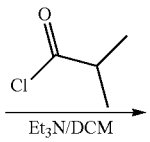

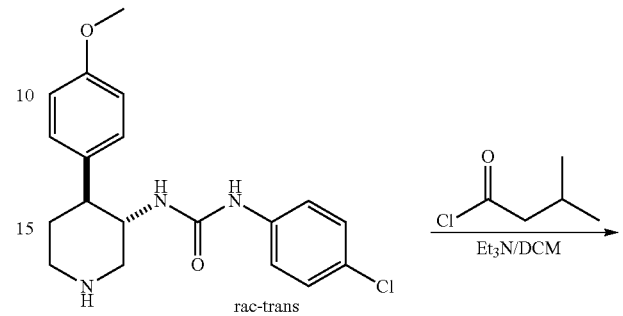

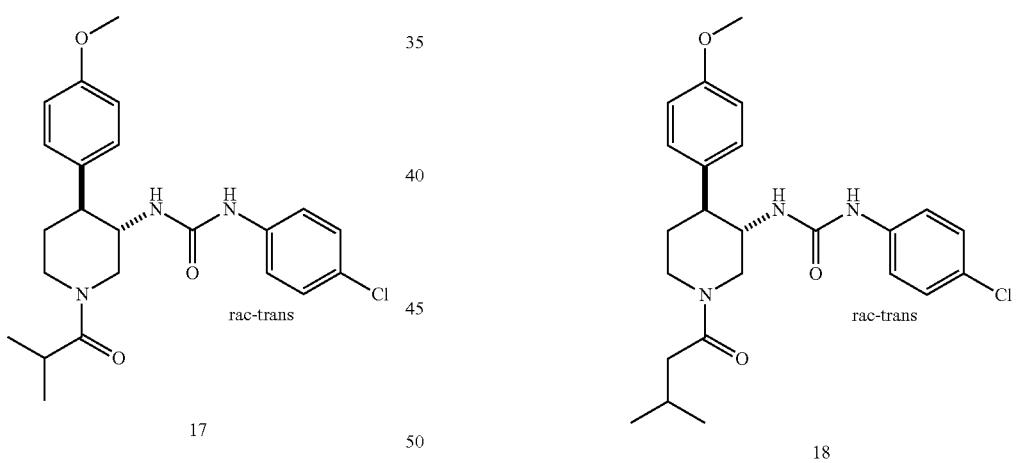

To a stirred solution of Example 2 (0.05 g, 0.126 mmol, 1 eq) in DCM (7 mL) was added Et$_3$N (0.03 mL, 0.19 mmol, 1.5 eq) followed by isobutyryl chloride (0.014 mL, 0.126 mmol, 1 eq) at 0° C. and stirred for 1 h. Then the reaction mass was diluted with DCM, washed with brine (10 mL), dried over Na$_2$SO$_4$ and concentrated. The crude product was purified preparative TLC to afford Example 17 (0.02 g, 37%) as white solid. LCMS: calculated for [M+H]$^+$: 430, found: 430 (Method 2).

$^1$H NMR (100° C., 400 MHz, DMSO-d$_6$) δ 8.20 (s, 1H), 7.30 (d, J=9 Hz, 2H), 7.20-7.15 (m, 4H), 6.85 (d, J=8 Hz, 2H), 5.81 (d, J=8 Hz, 1H), 4.44 (m, 1H), 4.28 (m, 1H), 3.72-3.60 (m, 4H), 2.91 (m, 2H), 2.75-2.65 (m, 2H), 1.85-1.82 (m, 1H), 1.60-1.50 (m, 1H), 1.11 (d, J=7 Hz, 3H), 1.06 (d, J=7 Hz, 3H).

To a stirred solution of Example 2 (0.05 g, 0.126 mmol, 1 eq) in DCM (7 mL) was added Et$_3$N (0.03 mL, 0.19 mmol, 1.5 eq) followed by 3-methyl-butyryl chloride (0.018 mL, 0.14 mmol, 1 eq) at 0° C. and stirred for 1 h. Then the reaction mass was diluted with DCM, washed with brine (10 mL), dried over Na$_2$SO$_4$ and concentrated. The crude product was purified preparative TLC to afford Example 18 (0.02 g, 36%) as white solid. LCMS: calculated for [M+H]$^+$: 444, found: 444 (Method 2).

$^1$H NMR (100° C., 400 MHz, DMSO-d$_6$) δ 8.20 (s, 1H), 7.30 (d, J=9 Hz, 2H), 7.20-7.15 (m, 4H), 6.85 (d, J=8 Hz, 2H), 5.81 (d, J=7 Hz, 1H), 4.50-4.20 (br m, 2H), 3.73 (s, 3H), 3.69 (m, 1H), 2.85-2.72 (m, 1H), 2.27-2.25 (m, 3H), 2.09 (m, 1H), 1.84-1.80 (m, 2H), 1.54 (m, 1H), 0.98-0.95 (m, 6H).

73

Preparation of: rac-trans-1-(1-acetyl-4-(4-methoxyphenyl)piperidin-3-yl)-3-(6-chloropyridin-3-yl)urea (Example 19)

74

Preparation of: rac-trans-2-(5-(3-(4-chlorophenyl)ureido)-4-(4-methoxyphenyl)-2-oxopiperidin-1-yl)acetamide (Example 20)

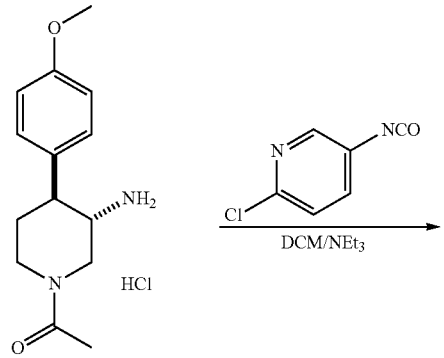

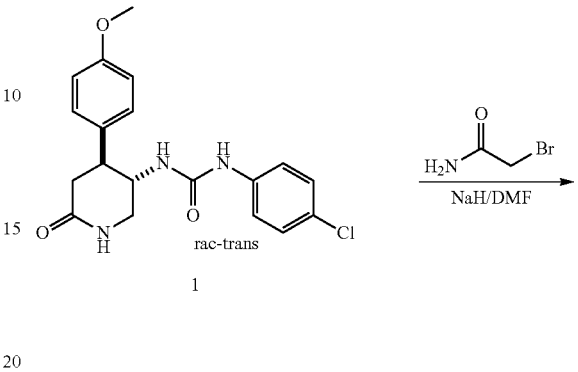

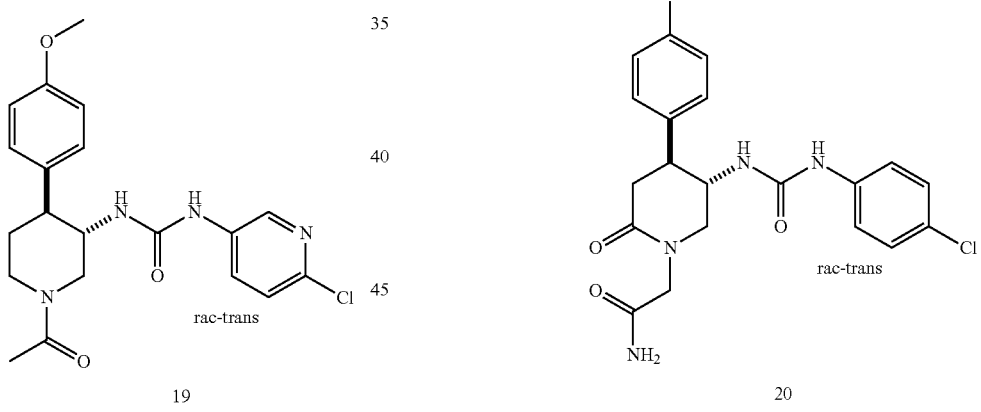

To a stirred solution of rac-trans-1-(3-amino-4-(4-methoxyphenyl)piperidin-1-yl)ethanone hydrochloride (0.04 g, 0.14 mmol, 1 eq) [synthesis described in the synthesis of Example 4] in DCM (10 mL) was added Et$_3$N (0.06 mL, 0.42 mmol, 3 eq) followed by 2-chloro-5-isocyanatopyridine (0.02 g, 0.14 mmol, 1 eq) at 0° C. and stirred for 2 h at RT. Then the reaction was quenched with sat. NaHCO$_3$ solution, the organic layer was separated, washed with brine (10 mL), dried over Na$_2$SO$_4$ and concentrated. The crude was purified by preparative TLC to afford Example 19 (0.03 g, 54%) as white solid. LCMS: calculated for [M+H]$^+$: 403, found: 403 (Method 2).

$^1$H NMR (100° C., 400 MHz, DMSO-d$_6$) δ 8.40 (m, 1H), 8.28 (s, 1H), 7.82-7.79 (m, 1H), 7.26 (d, J=8 Hz, 1H), 7.18 (d, J=9 Hz, 2H), 6.85 (d, J=8 Hz, 2H), 5.97 (d, J=8 Hz, 1H), 4.50-4.00 (br m, 3H), 3.72 (m, 4H), 2.77-2.72 (m, 2H), 2.06 (s, 3H), 1.83-1.79 (m, 1H), 1.63 (m, 1H).

To a stirred solution of Example 1 (0.05 g, 0.13 mmol, 1 eq) in DMF (3 mL) was added NaH (60% in mineral oil, 0.012 g, 0.26 mmol, 2 eq) at 0° C. and stirred for 15 min. To the reaction mixture was added 2-bromoacetamide (0.022 g, 0.2 mmol, 2 eq) and heated to 90° C. for 48 h. The reaction mass was quenched with ice and the organic components were extracted with EtOAc (2×20 mL), washed with H$_2$O (10 mL), brine (10 mL), dried over Na$_2$SO$_4$ and concentrated in vacuo. The crude product was purified by preparative TLC to afford Example 20 (0.022 g, 39%) as an off white solid. LCMS: calculated for [M+H]$^+$: 431, found: 431 (Method 2).

$^1$H NMR (400 MHz, DMSO-d$_6$) δ 8.42 (s, 1H), 7.35-7.18 (m, 5H), 7.06 (br s, 1H), 6.85 (d, J=8 Hz, 2H), 6.15 (d, J=8 Hz, 1H), 4.23 (m, 1H), 3.90-3.84 (m, 2H), 3.68 (s, 3H), 3.50-3.40 (m, 1H), 3.24-3.10 (m, 3H).

Preparation of: rac-trans-methyl 2-(5-(3-(4-chloro-phenyl)ureido)-4-(4-methoxyphenyl)-2-oxopiperi-din-1-yl)acetate (Example 21)

Preparation of: rac-trans-1-(4-chlorophenyl)-3-(4-(2,6-difluoro-4-methoxyphenyl)-6-oxopiperidin-3-yl)urea (Example 23)

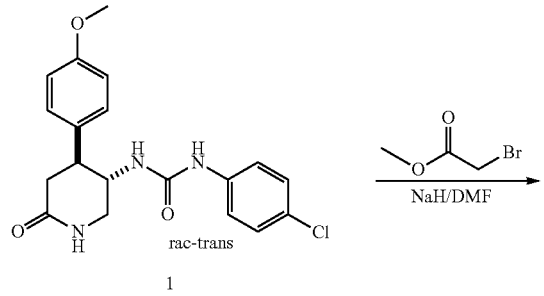

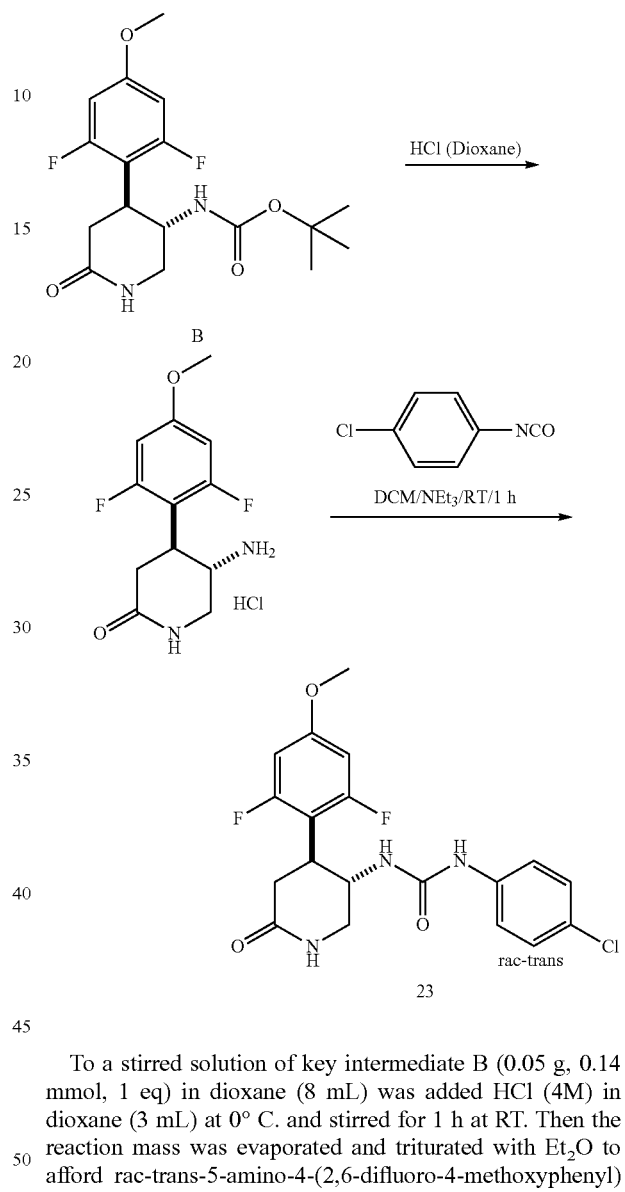

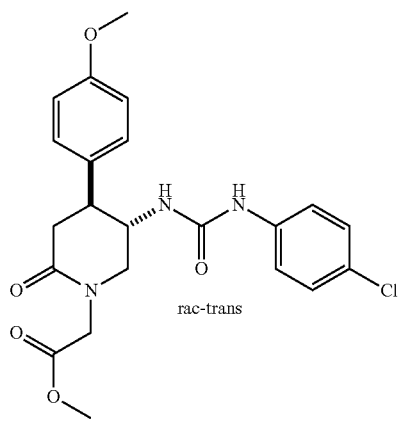

To a stirred solution of Example 1 (0.1 g, 0.27 mmol, 1 eq) in DMF (3 mL) was added NaH (60% in mineral oil, 0.012 g, 0.4 mmol, 1.5 eq) at 0° C. and stirred for 15 min. To the reaction mixture was added methyl 2-bromoacetate (0.04 g, 0.4 mmol, 1.5 eq) and heated to 90° C. for 48 h. The reaction mass was quenched with ice and extracted with EtOAc (2×20 mL), washed with H$_2$O (10 mL), brine (10 mL), dried over Na$_2$SO$_4$ and concentrated under reduced pressure. The crude product was purified by preparative TLC to afford Example 21 (0.03 g, 51%) as an off white solid. LCMS: calculated for [M+H]$^+$: 446, found: 446 (Method 2).

$^1$H NMR (400 MHz, DMSO-d$_6$) δ 8.48 (s, 1H), 7.34 (d, J=9 Hz, 2H), 7.22 (d, J=9 Hz, 4H), 6.88 (d, J=8 Hz, 2H), 6.26 (d, J=8 Hz, 1H), 4.25-4.10 (m, 3H), 3.72 (s, 3H), 3.66 (s, 3H), 3.56-3.50 (m, 1H), 3.27 (m, 1H), 3.18 (m, 1H), 2.56 (m, 2H);

To a stirred solution of key intermediate B (0.05 g, 0.14 mmol, 1 eq) in dioxane (8 mL) was added HCl (4M) in dioxane (3 mL) at 0° C. and stirred for 1 h at RT. Then the reaction mass was evaporated and triturated with Et$_2$O to afford rac-trans-5-amino-4-(2,6-difluoro-4-methoxyphenyl)piperidin-2-one (0.04 g, crude) as HCl salt.

To a stirred solution of rac-trans-5-amino-4-(2,6-difluoro-4-methoxyphenyl)piperidin-2-one hydrochloride (0.04 g, 0.14 mmol, 1 eq) in DCM (10 mL) was added Et$_3$N (0.04 mL, 0.28 mmol, 2 eq) followed by 1-chloro-4-isocyanato-benzene (0.021 g, 0.14 mmol, 1 eq) at 0° C. and stirred for 2 h at RT. Then the reaction mass was quenched with H$_2$O and the resulting solid was filtered and washed with EtOAc followed by trituration with pentane to afford Example 23 (0.035 g, 61%) as white solid. LCMS: calculated for [M+H]$^+$: 4410, found: 410 (Method 2).

$^1$H NMR (400 MHz, DMSO-d$_6$) δ 8.49 (s, 1H), 7.66 (br s, 1H), 7.30 (d, J=9 Hz, 2H), 7.21 (d, J=9 Hz, 2H), 6.70 (d, J=11 Hz, 2H), 6.16 (d, J=9 Hz, 1H), 4.25 (m, 1H), 3.74 (s, 3H), 3.50-3.40 (m, 1H), 3.09-3.01 (m, 1H).

Preparation of: rac-trans-1-(4-chlorophenyl)-3-(1-(cyclopropylmethyl)-4-(4-methoxyphenyl)-6-oxopiperidin-3-yl)urea (Example 24)

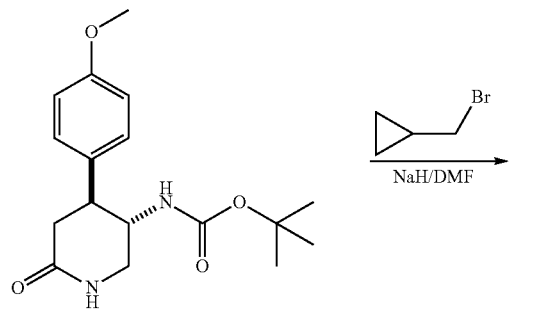

D

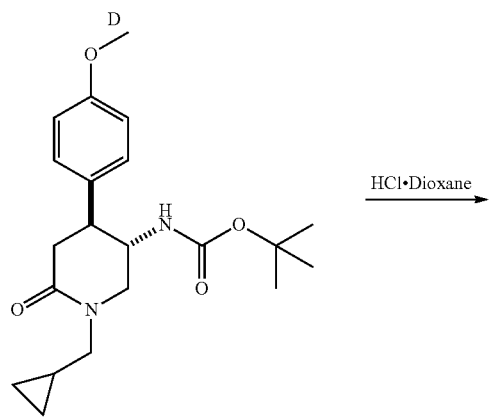

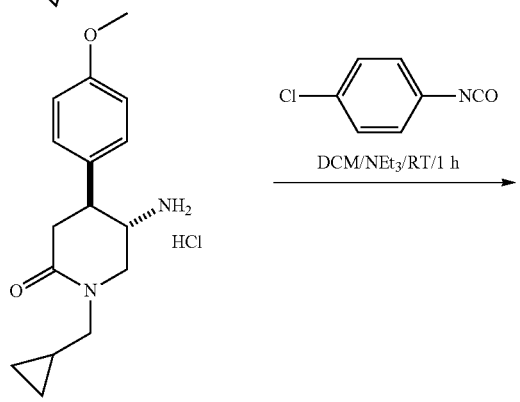

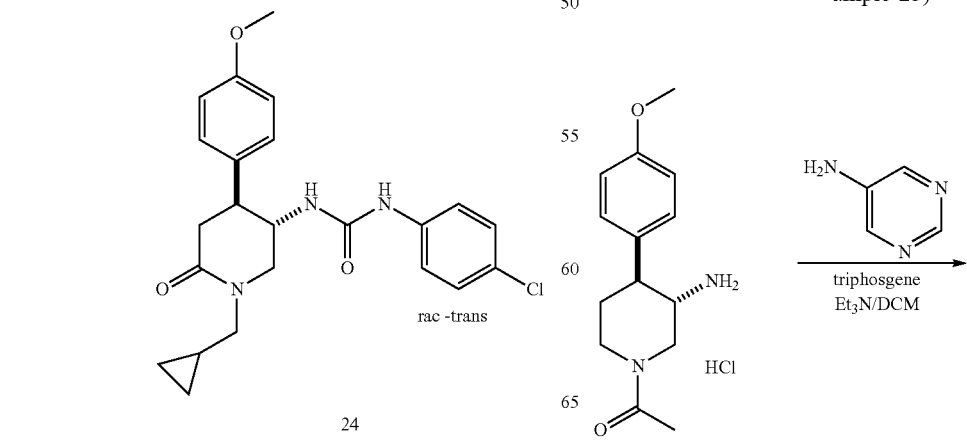

24 rac-trans

To a stirred solution of key intermediate D (0.05 g, 0.16 mmol, 1 eq) in DMF (3 mL) was added NaH (60% in mineral oil, 0.009 g, 0.23 mmol, 1.5 eq) at 0° C. and stirred for 15 min. To the reaction mixture was added (bromomethyl)cyclopropane (0.02 mL, 0.23 mmol, 1.5 eq) and stirred for 3 h at RT. The reaction mass was quenched with ice and the organics were extracted with EtOAc (2×15 mL), washed with $H_2O$ (10 mL), brine (10 mL), dried over $Na_2SO_4$ and concentrated under reduced pressure. The crude product was purified by column chromatography (silica gel, 100-200 mesh, 70% EtOAc in hexane) to afford rac-trans-tert-butyl (1-(cyclopropylmethyl)-4-(4-methoxyphenyl)-6-oxopiperidin-3-yl)carbamate (0.05 g, 78%) as yellow gum.

To a stirred solution of [rac-trans-tert-butyl (1-(cyclopropylmethyl)-4-(4-methoxyphenyl)-6-oxopiperidin-3-yl)carbamate (0.06 g, 0.16 mmol, 1 eq) in dioxane was added HCl (4M) in dioxane (3 mL) at 0° C. and stirred for 1 h at RT. The reaction mass was concentrated in vacuo and triturated with $Et_2O$ to afford rac-trans-5-amino-1-(cyclopropylmethyl)-4-(4-methoxyphenyl)piperidin-2-one hydrochloride (0.05 g, crude) as HCl salt.

To a stirred solution of rac-trans-5-amino-1-(cyclopropylmethyl)-4-(4-methoxyphenyl)piperidin-2-one hydrochloride (0.06 g, 0.19 mmol, 1 eq) in DCM (10 mL) was added $Et_3N$ (0.07 mL, 0.48 mmol, 2.5 eq) followed by 4-chlorophenylisocyanate (0.03 g, 0.19 mmol, 1 eq) at 0° C. and stirred for 2 h at RT. The reaction mass was quenched with $H_2O$ and extracted with DCM (2×15 mL), washed with $H_2O$ (10 mL), brine (10 mL), dried over $Na_2SO_4$ and concentrated. The crude product was purified by preparative TLC to afford Example 24 (0.035 g, 43%) as yellow gum. LCMS: calculated for $[M+H]^+$: 428, found: 428 (Method 2).

$^1$H NMR (400 MHz, DMSO-$d_6$) δ 8.48 (s, 1H), 7.33 (d, J=9 Hz, 2H), 7.24-7.19 (m, 4H), 6.87 (d, J=8 Hz, 2H), 6.21 (d, J=8 Hz, 1H), 4.16 (m, 1H), 3.71 (s, 3H), 3.57-3.55 (m, 1H), 3.25 (m, 2H), 3.16-3.14 (m, 2H), 0.96 (m, 1H), 0.46-0.42 (m, 2H), 0.22 (m, 2H).

Preparation of: rac-trans-1-(1-acetyl-4-(4-methoxyphenyl)piperidin-3-yl)-3-(pyrimidin-5-yl)urea (Example 25)

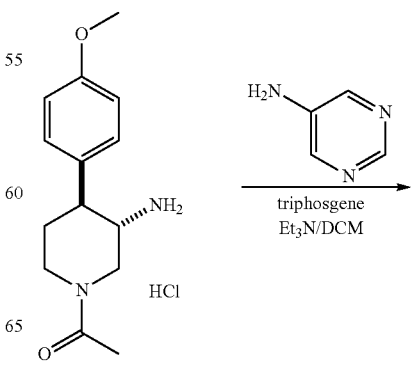

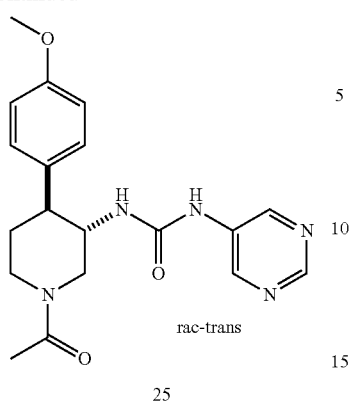

25 rac-trans

To a stirred solution of rac-trans-1-(3-amino-4-(4-methoxyphenyl)piperidin-1-yl)ethanone hydrochloride (0.051 g, 0.18 mmol, 1 eq) [synthesis described in the synthesis of Example 4] in DCM (10 mL) was added Et₃N (0.05 mL, 0.35 mmol, 2 eq) followed by triphosgene (0.022 g, 0.071 mmol, 0.4 eq) at 0° C. and stirred for 10 min. Pyrimidin-5-amine (0.05 g, 0.18 mmol, 1 eq) was then added and stirred for 2 h. The reaction mixture was diluted with DCM, washed with brine (10 mL), dried over Na₂SO₄ and concentrated. The crude product was purified by preparative TLC to afford Example 25 (0.025 g, 39%) as white solid. LCMS: calculated for [M+H]⁺: 370, found: 370 (Method 2).

¹H NMR (100° C., 400 MHz, DMSO-d₆) δ 8.71-8.68 (m, 3H), 8.42 (s, 1H), 7.19 (d, J=8 Hz, 2H), 6.86 (d, J=8 Hz, 2H), 6.10 (d, J=6 Hz, 1H), 4.50-4.00 (br m, 3H), 3.72 (m, 4H), 2.79-2.72 (m, 2H), 2.07 (s, 3H), 1.83-1.80 (m, 1H), 1.63-1.60 (m, 1H).

Preparation of: rac-trans-1-(1-acetyl-4-(4-methoxyphenyl)piperidin-3-yl)-3-(6-methylpyridin-3-yl)urea (Example 26)

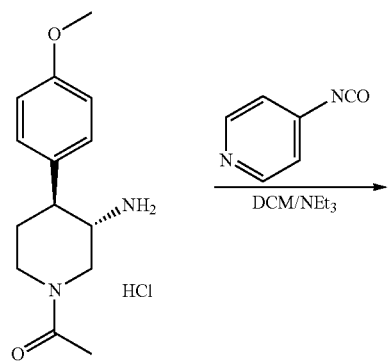

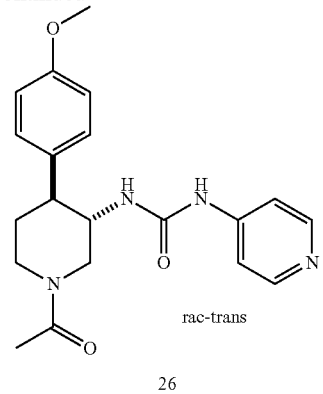

26 rac-trans

This compound was synthesized in analogy to Example 19.

LCMS: calculated for [M+H]⁺: 369, found: 369 (Method 2).

¹H NMR (100° C., 400 MHz, DMSO-d₆) δ 8.50 (m, 1H), 8.24 (d, J=5 Hz, 2H), 7.24 (d, J=5 Hz, 2H), 7.18 (d, J=8 Hz, 2H), 6.85 (d, J=9 Hz, 2H), 6.01 (m, 1H), 4.50-4.00 (br m, 2H), 3.72 (m, 4H), 3.13-3.06 (m, 1H), 2.76-2.71 (m, 1H), 2.07 (s, 3H), 1.83-1.79 (m, 1H), 1.62-1.57 (m, 1H).

Preparation of: rac-trans-1-(1-acetyl-4-(4-methoxyphenyl)piperidin-3-yl)-3-(6-(trifluoromethyl)pyridin-3-yl)urea (Example 27)

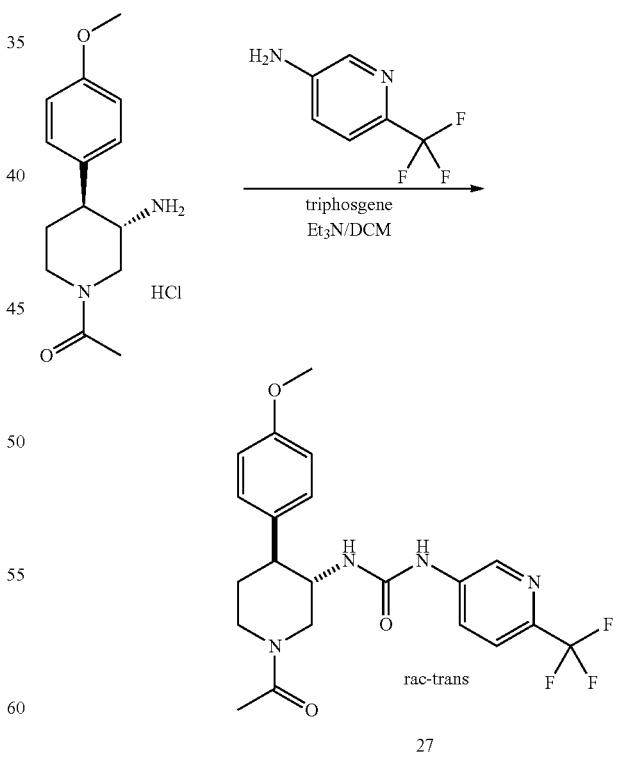

27 rac-trans

This compound was synthesized in analogy to Example 25.

LCMS: calculated for [M+H]⁺: 437, found: 437 (Method 2).

¹H NMR (100° C., 400 MHz, DMSO-d₆) δ 8.71 (m, 1H), 8.57 (s, 1H), 8.02-8.00 (m, 1H), 7.64 (d, J=9 Hz, 1H), 7.19 (d, J=8 Hz, 2H), 6.86 (d, J=9 Hz, 2H), 6.09 (d, J=8 Hz, 1H), 4.50-4.00 (br m, 2H), 3.74-3.72 (m, 4H), 2.95-2.85 (m, 1H), 2.79-2.73 (m, 2H), 2.07 (s, 3H), 1.84-1.80 (m, 1H), 1.63-1.58 (m, 1H).

Preparation of: rac-trans-1-(1-acetyl-4-(4-methoxyphenyl)piperidin-3-yl)-3-(6-methylpyridin-3-yl)urea (Example 28)

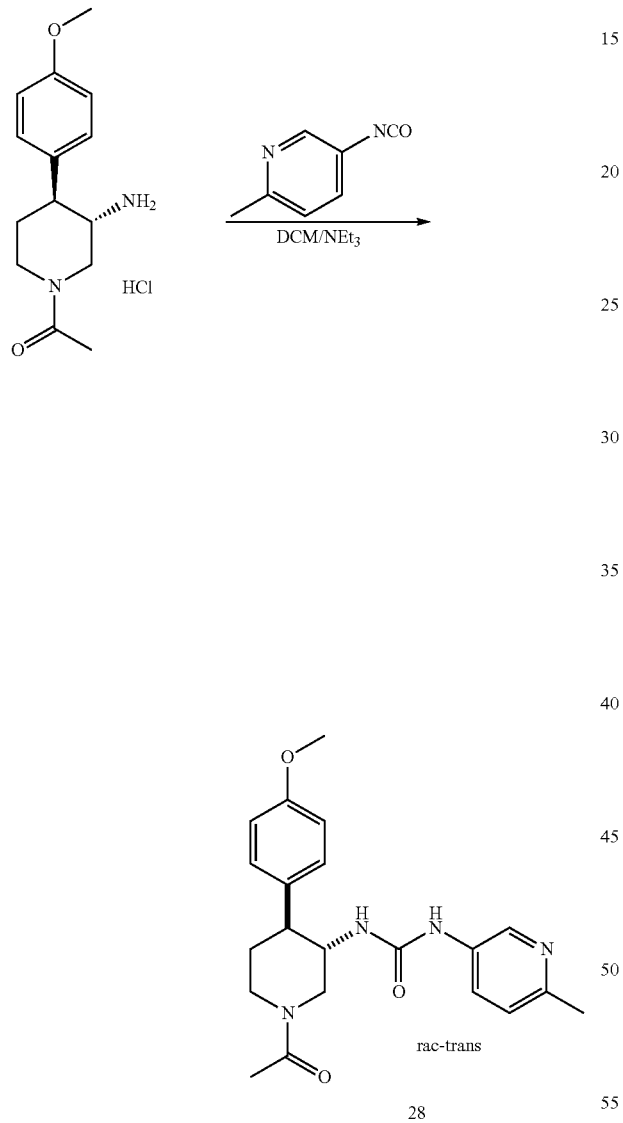

28

This compound was synthesized in analogy to Example 26.

LCMS: calculated for [M+H]⁺: 383, found: 383 (Method 2).

¹H NMR (100° C., 400 MHz, DMSO-d₆) δ 8.29 (s, 1H), 8.10 (bs, 1H), 7.62 (d, J=8 Hz, 1H), 7.18 (d, J=8 Hz, 2H), 7.03 (d, J=9 Hz, 1H), 6.85 (d, J=9 Hz, 2H), 5.83 (m, 1H), 4.50-4.00 (br m, 3H), 3.76-3.68 (m, 4H), 2.83-2.67 (m, 2H), 2.32 (s, 3H), 2.06 (s, 3H), 1.83-1.79 (m, 1H), 1.62-1.58 (m, 1H).

Preparation of: rac-trans-1-(4-chlorophenyl)-3-(1-(cyclopropylmethyl)-4-(2,6-difluoro-4-methoxyphenyl)-6-oxopiperidin-3-yl)urea (Example 29)

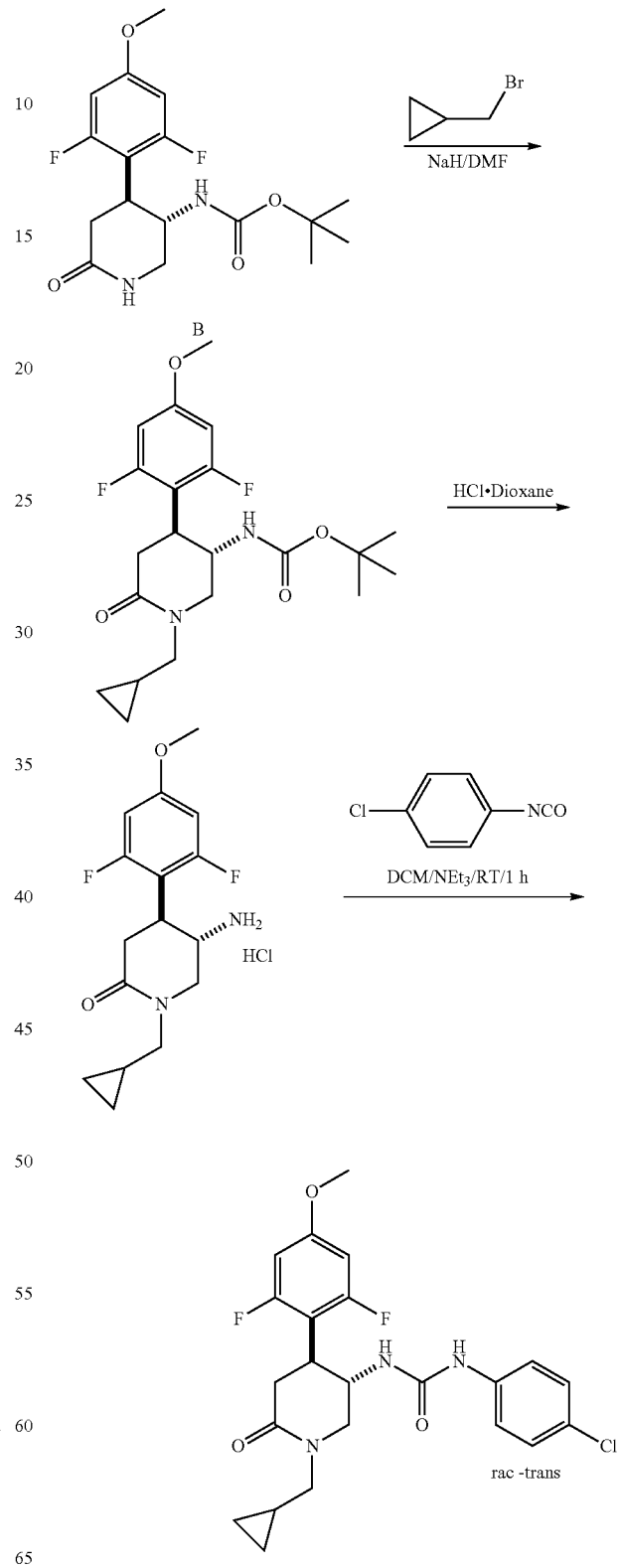

29

To a stirred solution of key intermediate B (0.05 g, 0.14 mmol, 1 eq) in DMF (3 mL) was added NaH (0.009 g, 0.21 mmol, 1.5 eq) at 0° C. and stirred for 15 min. Then added (bromomethyl)cyclopropane (0.02 mL, 0.21 mmol, 1.5 eq) and stirred for 3 h at RT. The reaction mass was quenched with ice and extracted with EtOAc (2×15 ml), washed with H$_2$O (10 ml), brine (10 mL), dried over Na$_2$SO$_4$ and concentrated. The crude product was purified by column chromatography (silica gel, 100-200 mesh, 50% EtOAc in hexane) to afford rac-trans-tert-butyl (1-(cyclopropylmethyl)-4-(2,6-difluoro-4-methoxyphenyl)-6-oxopiperidin-3-yl)carbamate (0.04 g, 70%) as yellow gum.

To a stirred solution of rac-trans-tert-butyl (1-(cyclopropylmethyl)-4-(2,6-difluoro-4-methoxyphenyl)-6-oxopiperidin-3-yl)carbamate (0.04 g, 0.09 mmol, 1 eq) in dioxane (6 mL) was added HCl (4M) in dioxane (2 mL) at 0° C. and stirred for 1 h at RT. Then the reaction mass was concentrated under reduced pressure and triturated with Et$_2$O to afford rac-trans-5-amino-1-(cyclo propylmethyl)-4-(2,6-difluoro-4-methoxyphenyl)piperidin-2-one (0.03 g, crude) as HCl salt.

To a stirred solution of rac-trans-5-amino-1-(cyclopropylmethyl)-4-(2,6-difluoro-4-methoxyphenyl)piperidin-2-one hydrochloride (0.03 g, 0.09 mmol, 1 eq) in DCM (10 mL) was added Et$_3$N (0.03 mL, 0.18 mmol, 2 eq) followed by 4 1-chloro-4-isocyanatobenzene (0.014 g, 0.09 mmol, 1 eq) at 0° C. and stirred for 2 h at RT. Then the reaction was quenched with H$_2$O and extracted with DCM (2×15 mL), washed with H$_2$O (10 mL), brine (10 mL), dried over Na$_2$SO$_4$ and concentrated. The crude product was purified by column chromatography (silica gel, 100-200 mesh, EtOAc) to afford Example 29 (0.025 g, 63%) as yellow gum. LCMS: calculated for [M+H]$^+$: 464, found: 464 (Method 2).

$^1$H NMR (400 MHz, DMSO-d$_6$) δ 8.52 (s, 1H), 7.32 (d, J=9 Hz, 2H), 7.22 (d, J=9 Hz, 2H), 6.71 (d, J=11 Hz, 2H), 6.24 (d, J=8 Hz, 1H), 4.35 (m, 1H), 3.74 (s, 3H), 3.60-3.40 (m, 2H), 3.32 (s, 2H), 3.12-3.07 (m, 1H), 2.56 (m, 2H), 0.97 (m, 1H), 0.48-0.44 (m, 2H), 0.22 (m, 2H).

Preparation of: rac-trans-1-(4-chlorophenyl)-3-(1-(3-hydroxypropanoyl)-4-(4-methoxyphenyl)piperidin-3-yl)urea (Example 30)

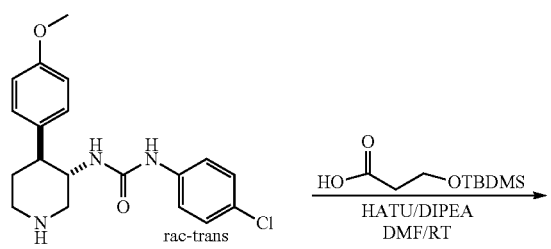

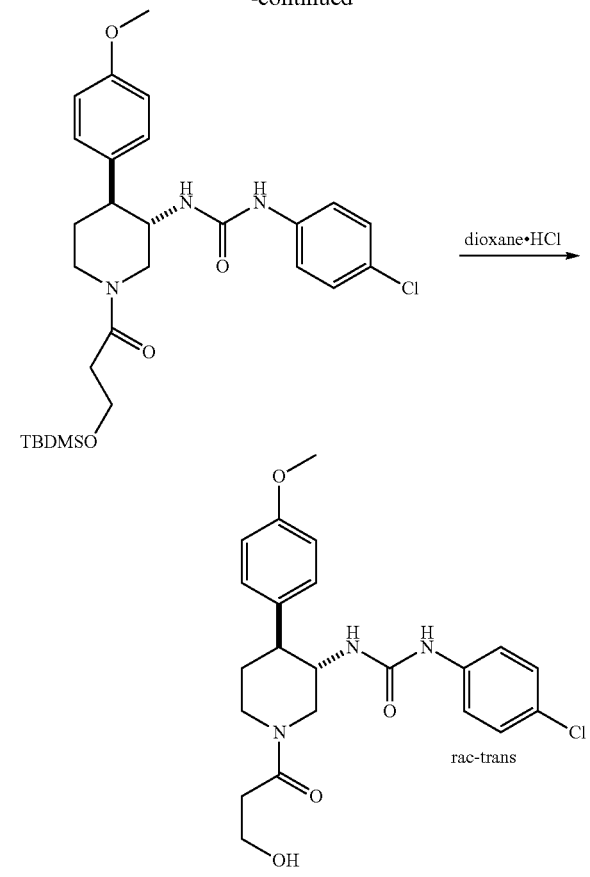

To a stirred solution of Example 2 (0.07 g, 0.18 mmol, 1 eq) in DMF (4 mL) was added 3-((tert-butyldimethylsilyl)oxy)propanoic acid (0.04 g, 0.2 mmol, 1.1 eq), HATU (0.08 g, 0.21 mmol, 1.2 eq) followed by DIPEA (0.08 mL, 0.44 mmol, 2.5 eq) and stirred for 16 h at RT. Then the reaction mass was diluted with H$_2$O and extracted with EtOAc (2×15 mL), washed with brine (10 mL), dried over Na$_2$SO$_4$ and concentrated. The crude was purified by column chromatography (silica gel, 100-200 mesh, 70% EtOAc in hexane) to afford rac-trans-1-(1-(3-((tert-butyldimethylsilyl)oxy)propanoyl)-4-(4-methoxyphenyl)piperidin-3-yl)-3-(4-chlorophenyl)urea (0.06 g, 63%) as an off white solid.

To a stirred solution of rac-trans-1-(1-(3-((tert-butyldimethylsilyl)oxy)propanoyl)-4-(4-methoxyphenyl)piperidin-3-yl)-3-(4-chlorophenyl)urea (0.08 g, 0.14 mmol, 1 eq) in dioxane (8 mL) was added HCl (4M) in dioxane (3 mL) at 0° C. and stirred for 1 h at RT. Then the reaction mass was evaporated, basified with sat. aqueous NaHCO$_3$ solution and the organic components were extracted with EtOAc (2×15 mL), washed with brine (10 mL), dried over Na$_2$SO$_4$ and concentrated under reduced pressure. The crude product was purified by preparative TLC to afford Example 30 (0.05 g, 79%) as white solid. LCMS: calculated for [M+H]$^+$: 432, found: 432 (Method 2).

$^1$H NMR (100° C., 400 MHz, DMSO-d$_6$) δ 8.20 (s, 1H), 7.30 (d, J=9 Hz, 2H), 7.20-7.16 (m, 4H), 6.85 (d, J=9 Hz, 2H), 5.81 (d, J=7 Hz, 1H), 4.50-4.00 (m, 2H), 4.17 (m, 1H), 3.72-3.69 (m, 6H), 2.75-2.70 (m, 2H), 2.58-2.54 (m, 2H), 1.83-1.80 (m, 1H), 1.58 (m, 1H).

Preparation of: rac-trans-1-(4-chlorophenyl)-3-(4-(2,6-difluoro-4-methoxyphenyl)-1-(2-hydroxyethyl)-6-oxopiperidin-3-yl)urea (Example 31) and rac-trans-methyl 2-(5-(3-(4-chlorophenyl)ureido)-4-(2,6-difluoro-4-methoxyphenyl)-2-oxopiperidin-1-yl)acetate (Example 35)

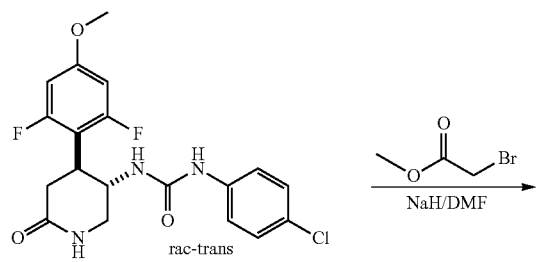

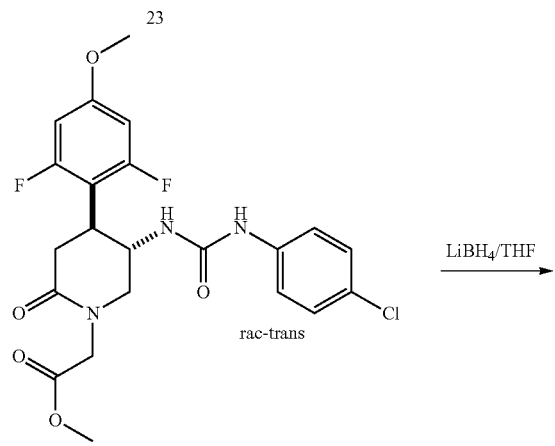

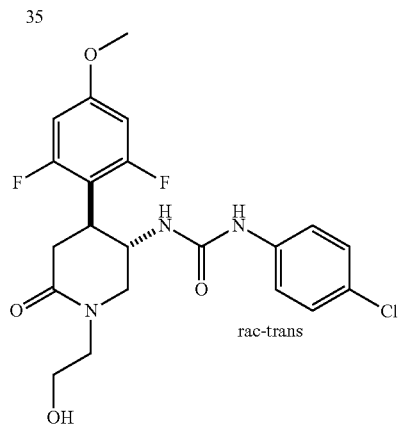

To a stirred solution of Example 23 (0.14 g, 0.34 mmol, 1 eq) in DMF (5 mL) was added NaH (60% in mineral oil, 0.03 g, 0.68 mmol, 2 eq) at 0° C. and stirred for 15 min. Then was added methyl 2-bromoacetate (0.07 mL, 0.68 mmol, 2 eq) and heated to 90° C. for 48 h. The reaction mass was quenched with ice and the organic components were extracted with EtOAc (2×20 mL), washed with H₂O (10 mL), brine (10 mL), dried over Na₂SO₄ and concentrated in vacuo. The crude product was purified by column chromatography (silica gel, 100-200 mesh, EtOAc) to afford Example 35 (0.065 g, 40%) as an off white solid.

To a stirred solution of Example 35 (0.065 g, 0.14 mmol, 1 eq) in THF (5 mL) was added LiBH₄ (2M in THF, 0.1 mL, 0.2 mmol, 1.5 eq) at 0° C. and stirred for 30 min. The reaction mass was quenched with H₂O and the organic components were extracted with EtOAc (2×15 ml), washed with brine (10 mL), dried over Na₂SO₄ and concentrated. The crude product was purified by preparative TLC to afford Example 31 (0.024 g, 39%) as white solid. LCMS: calculated for [M+H]⁺: 454, found: 454 (Method 2).

¹H NMR (400 MHz, DMSO-d₆) δ 8.48 (s, 1H), 7.31 (d, J=9 Hz, 2H), 7.22 (d, J=9 Hz, 2H), 6.70 (d, J=11 Hz, 2H), 6.20 (d, J=8 Hz, 1H), 4.72 (m, 1H), 4.35 (m, 1H), 3.74 (s, 3H), 3.60-3.40 (m, 5H), 3.30 (m, 1H), 2.67-2.50 (m, 2H).

Preparation of: rac-trans-1-(4-chlorophenyl)-3-(1-(2-hydroxyethyl)-4-(4-methoxyphenyl)-6-oxopiperidin-3-yl)urea (Example 32)

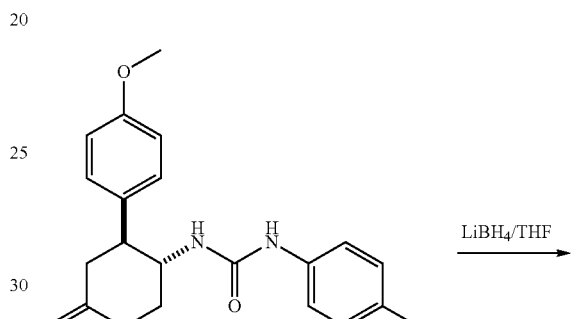

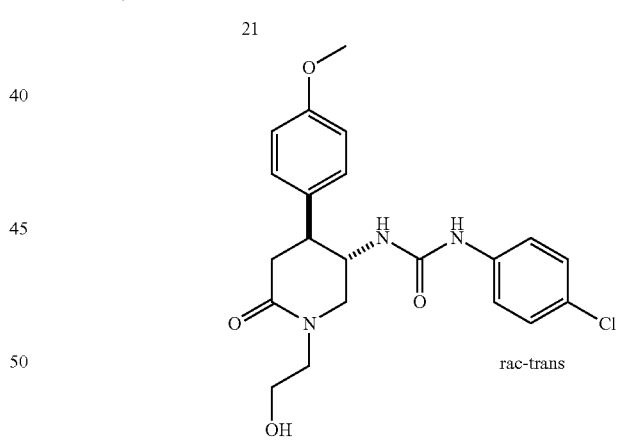

To a stirred solution of Example 21 (0.1 g, 0.22 mmol, 1 eq) in THF (7 mL) was added LiBH₄ (2M sol in THF, 0.17 mL, 0.33 mmol, 1.5 eq) at 0° C. and stirred for 30 min. The reaction mass was quenched with H₂O and the organics were extracted with EtOAc (2×15 mL), washed with brine (10 mL), dried over Na₂SO₄ and concentrated in vacuo. The crude product was purified by preparative TLC to afford Example 32 (0.024 g, 38%) as white solid. LCMS: calculated for [M+H]⁺: 418, found: 418 (Method 2).

¹H NMR (400 MHz, DMSO-d₆) δ 8.45 (s, 1H), 7.33 (d, J=9 Hz, 2H), 7.30-7.15 (m, 4H), 6.87 (d, J=9 Hz, 2H), 6.16

(d, J=8 Hz, 1H), 4.68 (m, 1H), 4.15 (m, 1H), 3.71 (s, 3H), 3.60-3.50 (m, 4H), 3.39 (m, 2H), 3.23 (m, 2H), 3.10 (m, 1H).

Preparation of: trans-ent1-1-(4-chlorophenyl)-3-(4-(2,6-difluoro-4-methoxyphenyl)piperidin-3-yl)urea (Example 36) and trans-ent2-1-(4-chlorophenyl)-3-(4-(2,6-difluoro-4-methoxyphenyl)piperidin-3-yl)urea (Example 37)

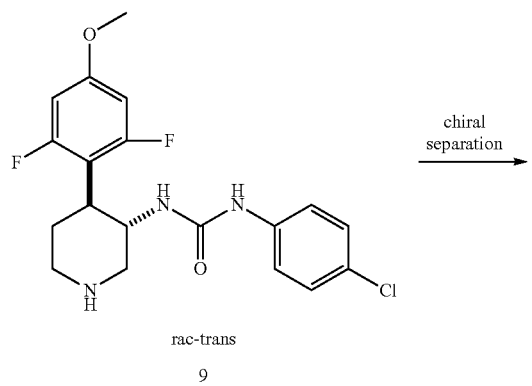

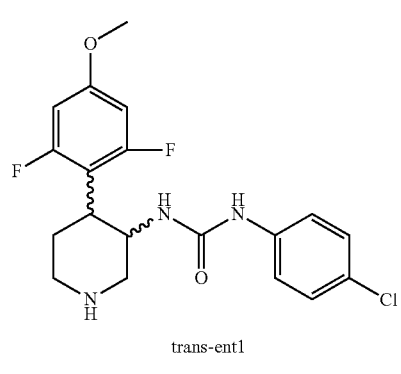

The racemic Example 9 was subjected to chiral separation by chiral SFC (Column: TE) to render both the enantiomers as Example 36 (first eluting enantiomer; specific rotation: [−10.44°; C=0.51% solution in CHCl$_3$] at ≅25° C.) and Example 37 (second eluting enantiomer; specific rotation: [+6.53°; C=0.52% solution in CHCl$_3$] at ≅25° C.).

Preparation of: rac-trans-1-(4-chlorophenyl)-3-(1-(cyclopropanecarbonyl)-4-(2,6-difluoro-4-methoxyphenyl)piperidin-3-yl)urea (Example 38), trans-ent1-1-(4-chlorophenyl)-3-(1-(cyclopropanecarbonyl)-4-(2,6-difluoro-4-methoxyphenyl)piperidin-3-yl)urea (Example 39) and trans-ent2-1-(4-chlorophenyl)-3-(1-(cyclopropanecarbonyl)-4-(2,6-difluoro-4-methoxyphenyl)piperidin-3-yl)urea (Example 40)

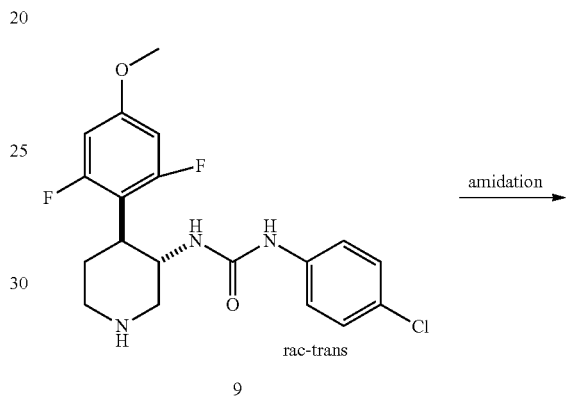

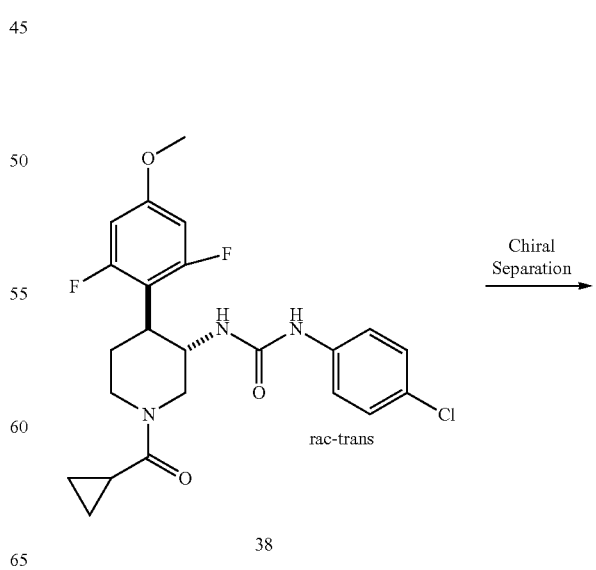

89

-continued

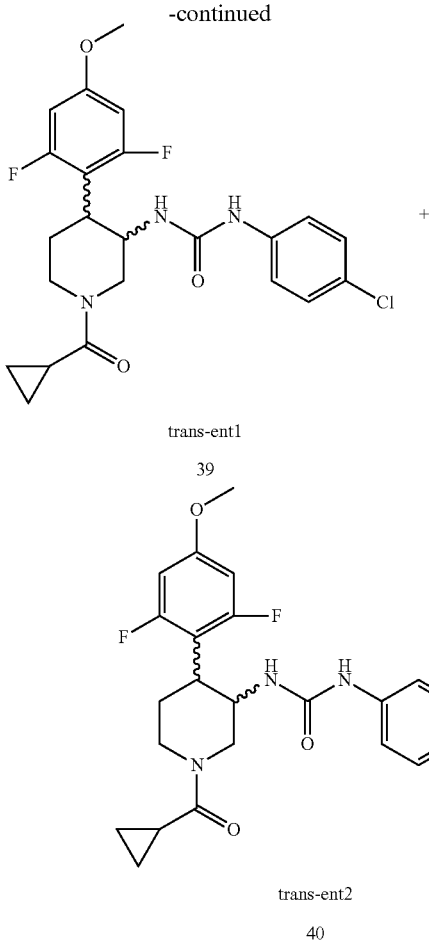

trans-ent1
39 trans-ent2
40

To a stirred solution of Example 9 (200 mg, 0.51 mmol, 1 eq) and TEA (170 µl, 1.27 mmol, 2.5 eq) in anhydrous DCM (30 mL) was added cyclopropylcarbonyl chloride (55 µl, 0.61, 1.2 eq) drop wise under ice cooled condition. The reaction mixture was stirred at RT for 3 h (until starting material was consumed). The mixture was diluted with DCM (50 mL) and the organic layer was washed successively with water (25 mL) and brine (25 mL). Collected organic phase was dried over sodium sulfate, filtered and evaporated under reduced pressure to furnish the crude as colorless gummy solid. It was purified over 100-200 mesh silica gel using 0 to 10% MeOH/DCM gradient to produce the rac-trans-1-(4-chlorophenyl)-3-(1-(cyclopropanecarbonyl)-4-(2,6-difluoro-4-methoxyphenyl)piperidin-3-yl)urea (180 mg, 76%) as off white solid.

$^1$H NMR (400 MHz, DMSO-d$_6$, 100° C.) δ 8.26 (s, 1H), 7.28 (d, J=8.8 Hz, 2H), 7.18 (d, J=8.8 Hz, 2H), 6.61 (d, J=10.8 Hz, 2H), 5.85 (d, J=8.0 Hz, 1H), 4.57 (d, J=13.6 Hz, 1H), 4.40 (d, J=11.6 Hz, 1H), 4.10-3.90 (m, 1H), 3.75 (s, 3H), 3.20-3.10 (m, 1H), 2.96-2.86 (m, 1H), 2.70-2.60 (m, 1H), 1.96-1.78 (m, 3H), 0.79-0.74 (m, 4H);

The racemic Example 38 was subjected to chiral separation by chiral SFC (Column: IB) to render both the enantiomers as Example 39 (first eluting enantiomer; specific rotation: [+42.08°; C=0.52% solution in CHCl$_3$] at ≅25° C.) and Example 40 (second eluting enantiomer; specific rotation: [−41.05°; C=0.51% solution in CHCl$_3$] at ≅25° C.).

90

Preparation of: rac-trans-1-(4-chlorophenyl)-3-(4-(2-fluoro-4-methoxyphenyl)-6-oxopiperidin-3-yl)urea (Example 41), trans-ent1-1-(4-chlorophenyl)-3-(4-(2-fluoro-4-methoxyphenyl)-6-oxopiperidin-3-yl) urea (Example 42) and trans-ent2-1-(4-chlorophenyl)-3-(4-(2-fluoro-4-methoxyphenyl)-6-oxopiperidin-3-yl)urea (Example 43)

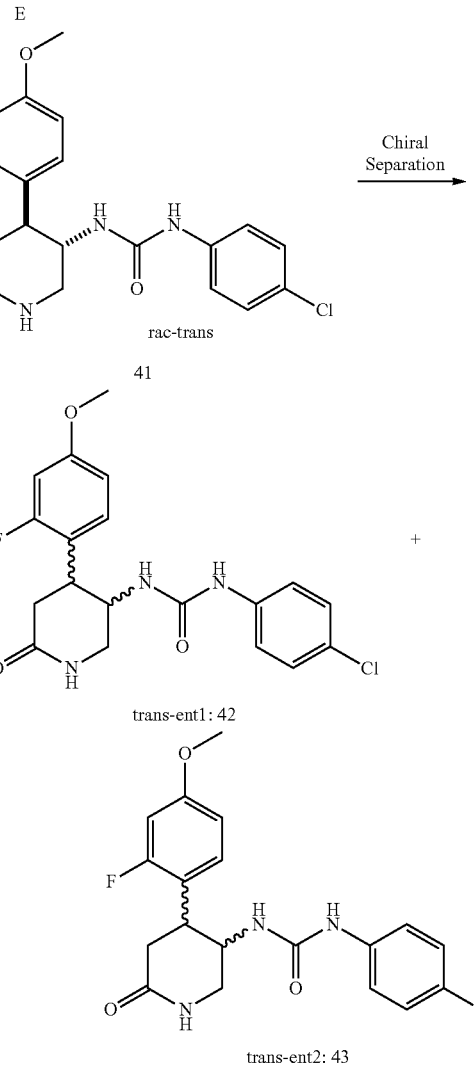

To a stirred solution of intermediate E (2.8 g, 10.48 mmol, 1 eq) in toluene-THF mixture (70 mL, 6:1) was added TEA (2.8 mL, 20.77 mmol, 2 eq) followed by DPPA (3.3 mL, 15.33 mmol, 1.5 eq) and the resulting mixture was allowed to reflux for 2 h. Reaction mixture was cooled back at RT and p-chloroanilne (6 g, 47.0 mmol, 4.5 eq) was added and the resulting mixture was again refluxed for another 4 h. Volatiles were then removed under reduced pressure to yield a reddish crude gum. It was then extracted with EtOAc (2×150 mL) and the combined organic phase was washed sequentially by water (100 mL) and brine (100 mL). The organic phase was then dried over sodium sulfate, filtered and evaporated under reduced pressure to furnish the crude as reddish gummy solid. It was then purified over 100-200 mesh silica gel using 0 to 10% MeOH/DCM gradient to produce rac-trans-1-(4-chlorophenyl)-3-(4-(2-fluoro-4-methoxyphenyl)-6-oxopiperidin-3-yl)urea (600 mg, 15%) as off white solid.

$^1$H NMR (400 MHz, DMSO-$d_6$) δ 8.48 (1H, s), 7.61 (1H, d, J=2.0 Hz), 7.34-7.32 (2H, m), 7.26-7.21 (3H, m), 6.80-6.75 (2H, m), 6.17 (1H, d, J=8.0 Hz), 4.18-4.14 (1H, m), 3.73 (3H, s), 3.40-3.36 (1H, m), 3.35-3.32 (1H, overlapped multiplet with DMSO), 3.06-3.01 (1H, m), 2.44-2.42 (2H, m).

The racemic Example 41 was subjected to chiral separation by chiral HPLC (Chiralcel OD-H (250×4.6 mm) 5µ) to render both the enantiomers as Example 42 (first eluting enantiomer; specific rotation: [−54.46°; C=0.36% solution in CHCl$_3$] at ≅25° C.) and Example 43 (second eluting enantiomer; specific rotation: [+55.35°; C=0.33% solution in CHCl$_3$] at ≅25° C.).

Preparation of: rac-trans-1-(4-chlorophenyl)-3-(4-(2-fluoro-4-methoxyphenyl)piperidin-3-yl)urea (Example 44), ent1-1-(4-chlorophenyl)-3-(4-(2-fluoro-4-methoxyphenyl)piperidin-3-yl)urea (Example 45) and ent2-1-(4-chlorophenyl)-3-(4-(2-fluoro-4-methoxyphenyl)piperidin-3-yl)urea (Example 46)

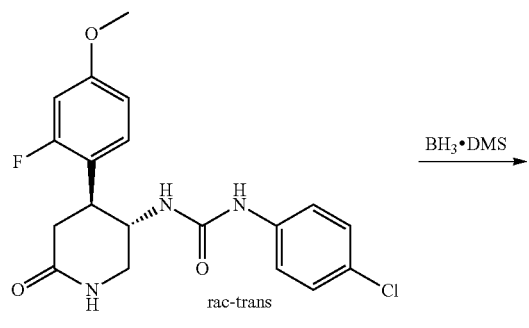

41

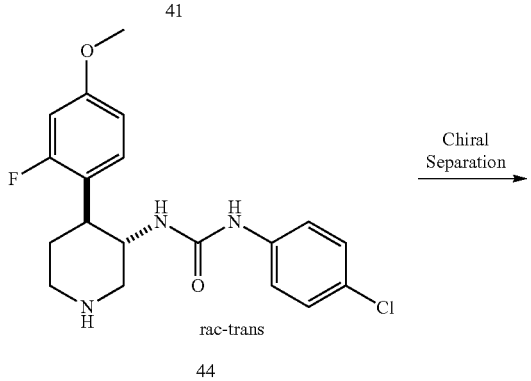

44

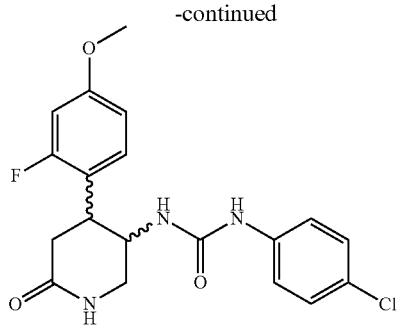

trans-ent1: 45

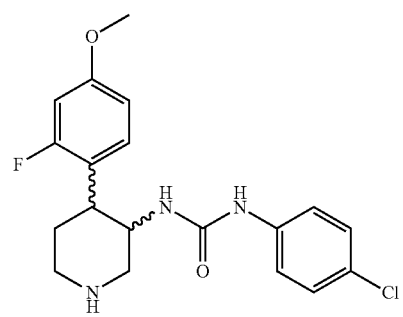

trans-ent2: 46

To a stirred solution of Example 41 (0.5 g, 1.28 mmol, 1 eq) in THF (10 mL) was added drop wise BH$_3$.DMS (10 mL, 105.3 mmol, 82 eq) under ice cooled condition. The reaction mixture was allowed to stir at RT for 3 h, solvent was evaporated under reduced pressure and the residue was quenched by 1N aq. HCl (10 mL). Extraction was done with MeOH/DCM (10%, 3×25 mL). Combined organic layer was dried over sodium sulfate, filtered and evaporated under reduced pressure to furnish the crude product as colorless gummy solid. Purification over 100-200 mesh silica gel using 0 to 10% MeOH/DCM gradient was done to produce rac-trans-1-(4-chlorophenyl)-3-(4-(2-fluoro-4-methoxyphenyl)piperidin-3-yl)urea (350 mg, 15%) as off white solid.

$^1$H NMR (400 MHz, DMSO-$d_6$) δ 8.40 (1H, s), 7.31-7.29 (2H, m), 7.21-7.18 (3H, m), 6.75-6.72 (2H, m), 5.90 (1H, d, J=8.4 Hz), 3.89-3.86 (1H, m), 3.71 (3H, s), 3.22-3.18 (1H, dd, J=11.6, 4.0 Hz), 2.99-2.96 (1H, m), 2.84-2.78 (1H, m), 2.61-2.56 (1H, m), 2.40-2.32 (1H, m), 1.73-1.71 (1H, m), 1.61-1.59 (1H, m).

The racemic Example 44 was subjected to chiral separation by chiral HPLC (Chiralpak ID (250×4.6 mm) to render both the enantiomers as Example 45 (first eluting enantiomer; specific rotation: [−20.89°; C=0.21% solution in CHCl$_3$] at ≅25° C.) and Example 46 (second eluting enantiomer; specific rotation: [+33.41°; C=0.25% solution in CHCl$_3$] at ≅25° C.).

Preparation of: rac-trans-1-(4-(2,6-difluoro-4-methoxyphenyl)-6-oxopiperidin-3-yl)-3-(pyridin-4-yl)urea, ent1-1-(4-(2,6-difluoro-4-methoxyphenyl)-6-oxopiperidin-3-yl)-3-(pyridin-4-yl)urea (Example 47) and ent2-1-(4-(2,6-difluoro-4-methoxyphenyl)-6-oxopiperidin-3-yl)-3-(pyridin-4-yl)urea (Example 48)

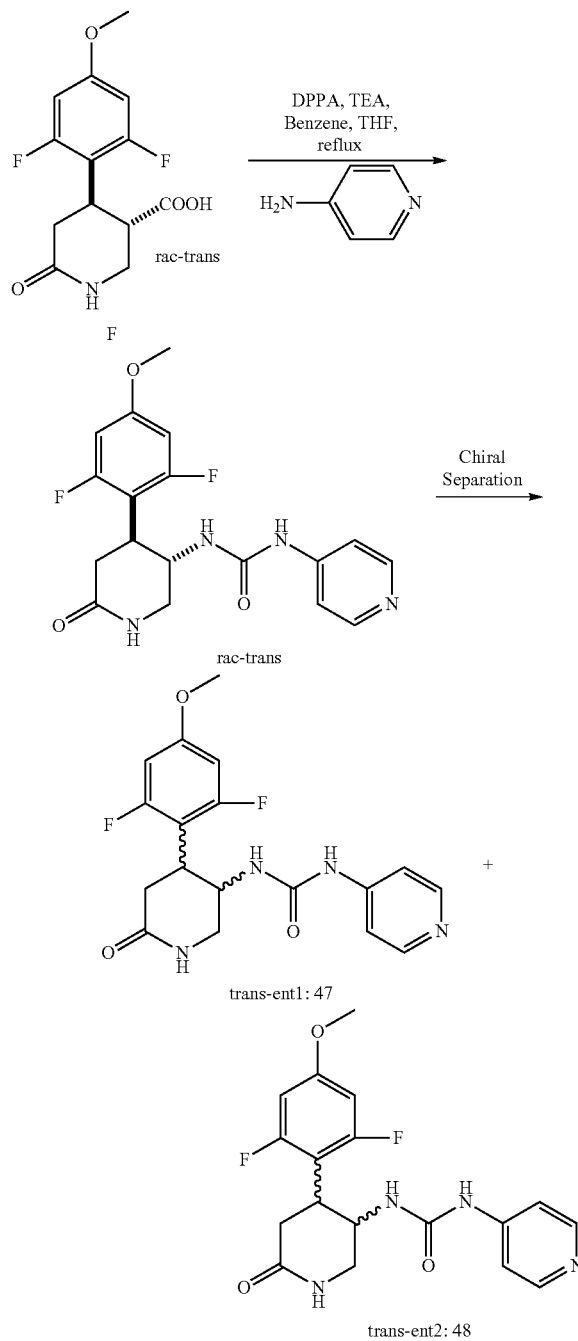

To a stirred solution of intermediate F (500 mg, 1.75 mmol, 1 eq) in benzene-THF mixture (20 mL, 3:1) was added TEA (0.5 mL, 3.5 mmol, 2.0 eq) followed by DPPA (0.5 mL, 2.27 mmol, 1.3 eq) at RT and the resulting mixture was allowed stir for 2 h at the same condition. Pyridin-4-amine (280 mg, 2.275 mmol, 1.3 eq) was then added and the resulting mixture was again stirred for another 16 h at 70° C. Volatiles were removed under reduced pressure to yield a reddish crude gum. It was then extracted with EtOAc (2×60 mL) and the combined organic phase was washed sequentially by water and brine. The organic phase was dried over sodium sulfate, filtered and evaporated under reduced pressure to furnish the crude product as yellowish gummy solid. It was purified over 100-200 silica gel using DCM to 10% MeOH/DCM gradient to produce rac-trans-1-(4-(2,6-difluoro-4-methoxyphenyl)-6-oxopiperidin-3-yl)-3-(pyridin-4-yl)urea (180 mg, 27% yield) as off white solid.

The racemic mixture was subjected to chiral separation by preparative HPLC (Column Name: Chiralpak IC; Mobile Phase: Hexane/EA/EtOH/DEA: 50/25/25/0.1; Flow Rate: 1.0 mL/min) to render both the enantiomers as Example 47 (first eluting enantiomer; $t_R$=6.4 min; specific rotation: [+1.6°; C=0.58% solution in $CHCl_3$] at ≅25° C.) and Example 48 (second eluting enantiomer; $t_R$=7.9 min; specific rotation: [+1.7°; C=0.53% solution in $CHCl_3$] at ≅25° C.).

$^1$H NMR (400 MHz, DMSO-$d_6$) δ 8.80 (1H, s), 8.24 (2H, d, J=6.0 Hz), 7.67 (1H, d, J=3.2 Hz), 7.25 (2H, d, J=6.4 Hz), 6.70 (2H, d, J=10.8 Hz), 6.40 (1H, d, J=8.4 Hz), 4.25-4.23 (1H, m), 3.74 (3H, s), 3.50-3.46 (1H, m), 3.36-3.32 (1H, m), 3.07 (1H, t, J=10.8 Hz), 2.50-2.45 (2H, overlapped multiplet with DMSO).

Preparation of: trans-ent1-1-(4-chlorophenyl)-3-(4-(2,6-difluoro-4-methoxyphenyl)-6-oxopiperidin-3-yl)urea (Example 49) and trans-ent2-1-(4-chlorophenyl)-3-(4-(2,6-difluoro-4-methoxyphenyl)-6-oxopiperidin-3-yl)urea (Example 50)

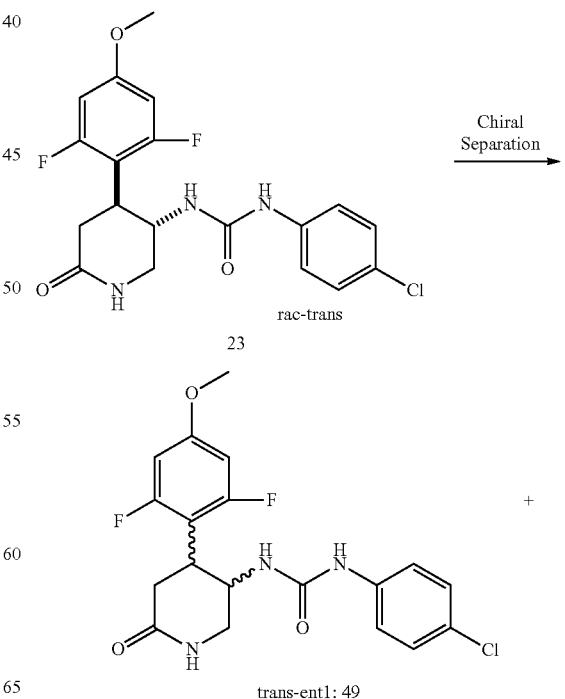

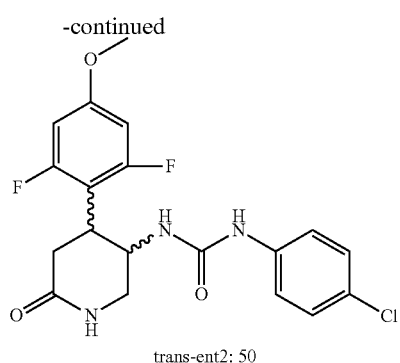

trans-ent2: 50

The racemic Example 23 was subjected to chiral separation by preparative HPLC (Column Name: Chiralpak ID; Mobile Phase: Hexane/EtOH/EA/DEA: 70/15/150/0.1; Flow Rate: 1.0 mL/min) to render both the enantiomers as Example 49 (first eluting enantiomer; $t_R$=11.7 min; specific rotation: [+73.6°; C=0.58% solution in CHCl$_3$] at ≅25° C.) and Example 50 (second eluting enantiomer; $t_R$=13.5 min; specific rotation: [−66.1°; C=0.41% solution in CHCl$_3$] at ≅25° C.).

Preparation of: rac-trans-1-(5-chlorothiophen-2-yl)-3-(4-(2,6-difluoro-4-methoxyphenyl)-6-oxopiperidin-3-yl)urea (Example 51)

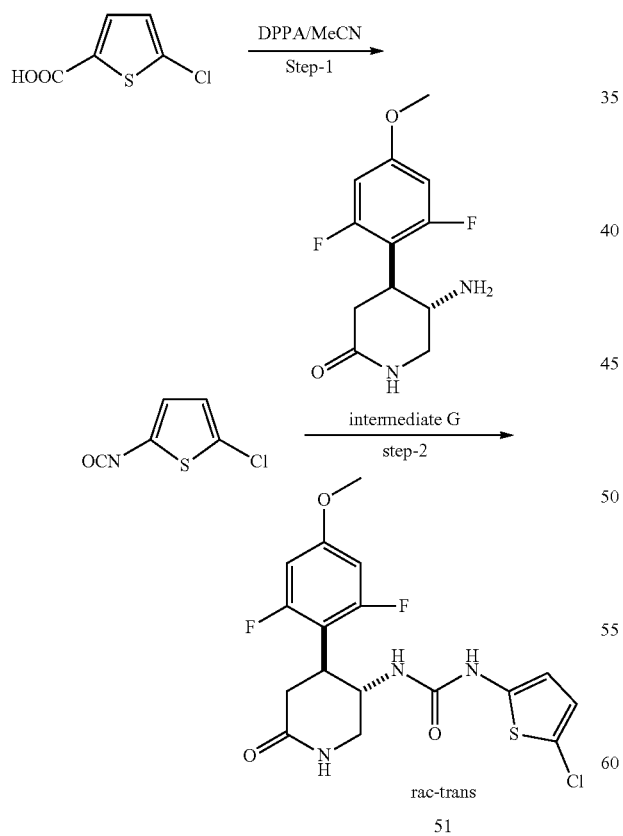

Step1:
To a stirred solution of 5-chlorothiophene-2-carboxylic acid (500 mg, 3.08 mmol, 1 eq) in benzene-THF mixture (20 mL, 7:1) was added Et$_3$N (0.83 mL, 6.16 mmol, 2.0 eq) followed by DPPA (0.86 mL, 4.01 mmol, 1.3 eq) at RT and the resulting mixture was allowed to stir for 2 h at the same condition to get crude 2-chloro-5-isocyanatothiophene. Next step was done with this reaction mixture.

Step2:
Yellowish crude (380 mg) intermediate G was dissolved in benzene-THF (20 mL, 7:1) and was added to the reaction mixture of 2-chloro-5-isocyanatothiophene which was obtained as described in step1. Resulting mixture was allowed to stir for another 16 h at 70° C. Volatiles were removed under reduced pressure to yield a reddish crude gum. It was extracted with EtOAc (2×60 mL) and the combined organic phase was washed sequentially by water and brine. The organic phase was dried over sodium sulfate, filtered and evaporated under reduced pressure to furnish the crude as yellowish gummy solid. It was purified over 100-200 silica gel using DCM to 10% MeOH/DCM gradient to produce the desired product. Finally purification by prep HPLC rendered rac-trans-1-(5-chlorothiophen-2-yl)-3-(4-(2,6-difluoro-4-methoxyphenyl)-6-oxopiperidin-3-yl)urea (54 mg, 12% over two steps) as off white solid.

$^1$H NMR (400 MHz, DMSO-d$_6$) δ 9.52 (s, 1H), 7.66 (d, J=3.2 Hz, 1H), 6.71-6.68 (m, 3H), 6.35 (d, J=8.4 Hz, 1H), 6.15 (d, J=4.0 Hz, 1H), 4.23-4.20 (m, 1H), 3.74 (s, 3H), 3.49-3.45 (m, 1H), 3.30-3.28 (m, 1H), 3.11-3.05 (m, 1H), 2.45-2.47 (m, 2H).

Preparation of: rac-trans-1-(4-chlorophenyl)-3-(4-(4-ethyl-2,6-difluorophenyl)-6-oxopiperidin-3-yl)urea (Example 69)

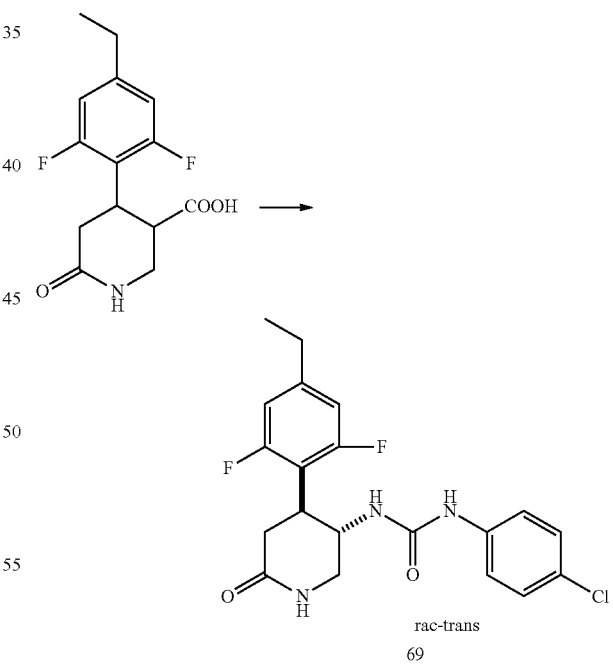

Starting from 4-ethyl-2,6-difluorobenzaldehyde, rac-trans-4-(4-ethyl-2,6-difluorophenyl)-6-oxopiperidine-3-carboxylic acid was synthesized in analogy to synthesis described for intermediate F. Example 69 was synthesized following synthetic procedure as described in as described in the General procedure for the Synthesis of different Urea Analogous (GM; see below) (8% yield, off white powder).

¹H NMR (400 MHz, DMSO-d₆) δ 8.49 (s, 1H), 7.68-7.67 (m, 1H), 7.29 (d, J=9 Hz, 2H), 7.21 (d, J=9 Hz, 2H), 6.93 (d, J=10 Hz, 2H), 6.18 (d, J=8 Hz, 1H), 4.27-4.26 (m, 1H), 3.53-3.4.8 (m, 1H), 3.36-3.32 (m, 1H), 3.09-3.04 (m, 1H), 2.59-2.54 (m, 2H), 1.15-1.11 (m, 3H).

Preparation of: rac-trans-1-(4-chlorophenyl)-3-(4-(4-(difluoromethoxy)-2,6-difluorophenyl)-6-oxopiperidin-3-yl)urea (Example 70)

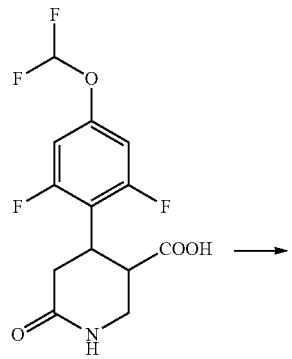

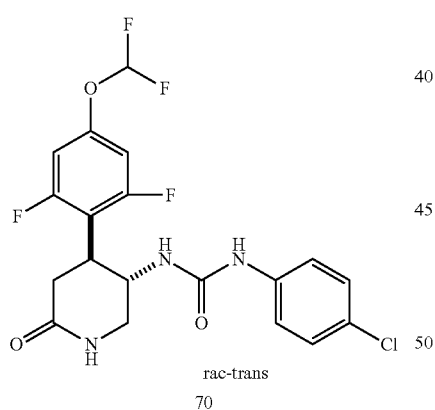
rac-trans
70

Starting from 4-(difluoromethoxy)-2,6-difluorobenzaldehyde, rac-trans-4-(4-(difluoromethoxy)-2,6-difluorophenyl)-6-oxopiperidine-3-carboxylic acid was synthesized in analogy to synthesis described for intermediate F. Example 70 was synthesized following synthetic procedure as described in as described in the General procedure for the Synthesis of different Urea Analogous (GM; see below) (38% yield, off white solid).

¹H NMR (400 MHz, DMSO-d₆) δ 8.48 (s, 1H), 7.68 (d, J=3 Hz, 1H), 7.49-7.12 (m, 5H), 7.03 (d, J=10 Hz, 2H), 6.23 (d, J=9 Hz, 1H), 4.29-4.26 (m, 1H), 3.58-3.50 (m, 1H), 3.35-3.31 (m, 1H), 3.12-3.06 (m, 1H), 2.52-2.49 (m, 2H).

Preparation of: rac-trans-1-(4-chlorophenyl)-3-(4-(4-(methylthio)phenyl)-6-oxopiperidin-3-yl)urea (Example 72)

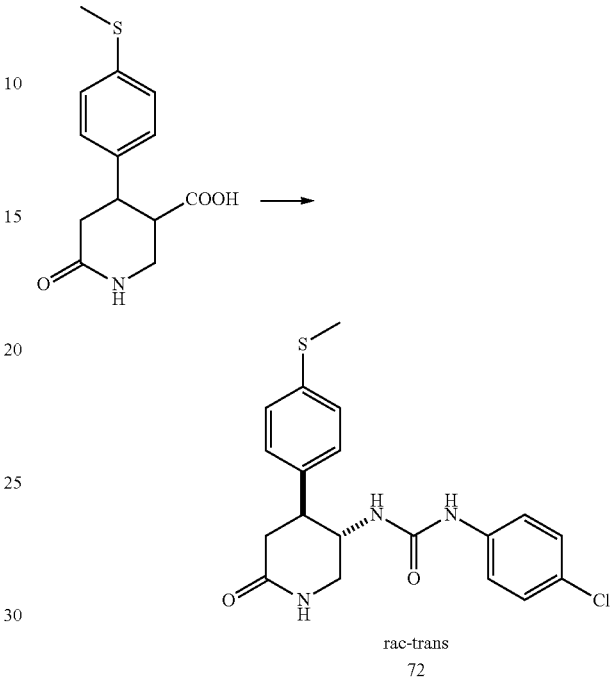
rac-trans
72

Starting from 4-(methylthio)benzaldehyde, 4-(4-(methylthio)phenyl)-6-oxopiperidine-3-carboxylic acid was synthesized in analogy to synthesis described for intermediate F. Example 72 was synthesized following synthetic procedure as described in as described in the General procedure for the Synthesis of different Urea Analogous (GP1; see below) (48% yield, off white solid).

¹H NMR (400 MHz, DMSO-d₆) δ 8.46 (1H, s), 7.59 (1H, s), 7.34-7.31 (2H, m), 7.23-7.19 (6H, m), 6.18 (1H, d, J=7.6 Hz), 4.10-4.07 (1H, m), 3.34-3.32 (1H, m), 3.17-3.14 (1H, m), 3.03-2.98 (1H, m), 2.43 (3H, s), 2.42-2.44 (2H, m).

Preparation of: rac-trans-1-(4-chlorophenyl)-3-(4-(4-ethylphenyl)-6-oxopiperidin-3-yl)urea (Example 73)

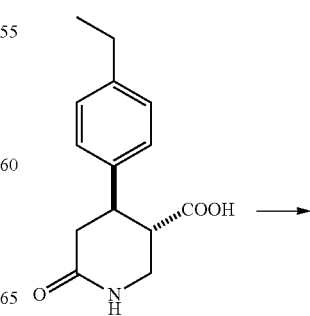

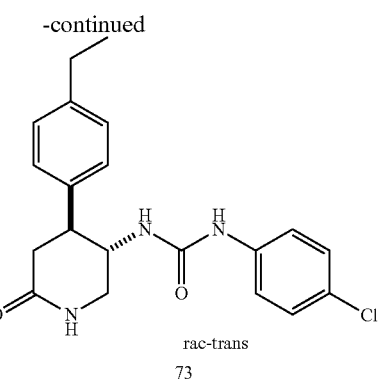

rac-trans
73

Starting from 4-ethylbenzaldehyde, 4-(4-ethylphenyl)-6-oxopiperidine-3-carboxylic acid was synthesized in analogy to synthesis described for intermediate F. Example 73 was synthesized following synthetic procedure as described in as described in the General procedure for the Synthesis of different Urea Analogous (GP1; see below) (53% yield, off white solid).

$^1$H NMR (400 MHz, DMSO-d$_6$) δ 8.44 (1H, s), 7.55 (1H, s), 7.29 (2H, d, J=8.0 Hz), 7.19 (1H, d, J=8.0 Hz), 7.16-7.11 (4H, m), 6.15 (1H, d, J=8.0 Hz), 4.04-4.03 (1H, m), 3.30-3.28 (1H, m), 3.13-3.11 (1H, m), 3.00-2.95 (1H, m), 2.52 (2H, q, J=7.6 Hz), 2.46-2.37 (2H, m), 1.12 (3H, t, J=7.6 Hz).

Preparation of: rac-trans-1-(4-chlorophenyl)-3-(4-(4-(difluoromethoxy)phenyl)-6-oxopiperidin-3-yl)urea
(Example 74)

acid was synthesized in analogy to synthesis described for intermediate F. Example 74 was synthesized following synthetic procedure as described in as described in the General procedure for the Synthesis of different Urea Analogous (GP1; see below) (22% yield, off white solid).

$^1$H NMR (400 MHz, DMSO-d$_6$) δ 8.45 (1H, s), 7.61 (1H, s), 7.37-7.00 (9H, m), 6.18 (1H, d, J=8.0 Hz), 4.13-4.10 (1H, m), 3.35-3.32 (1H, m), 3.24-3.18 (1H, m), 3.05-2.99 (1H, m), 2.45-2.43 (2H, m).

Preparation of: rac-trans-1-(4-chlorophenyl)-3-(4-(4-(methylsulfonyl)phenyl)-6-oxopiperidin-3-yl)urea
(Example 75)

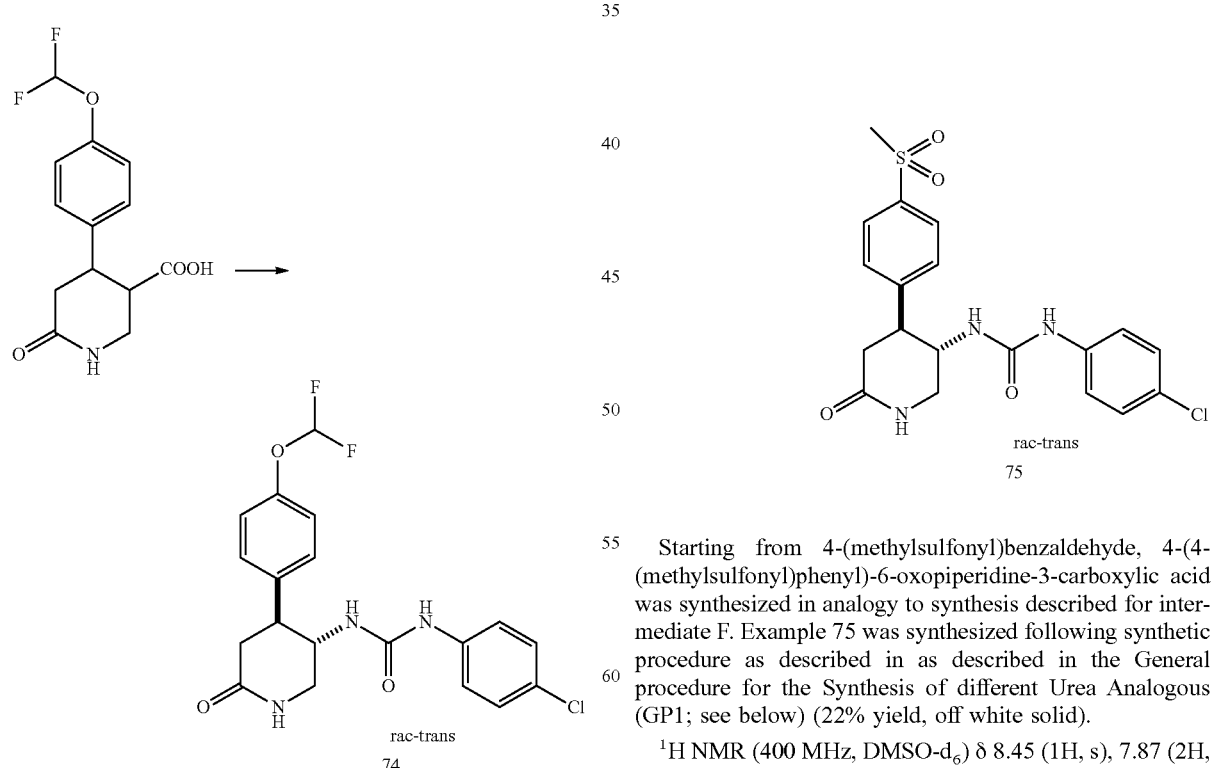

rac-trans
74

Starting from 4-(difluoromethoxy)benzaldehyde, 4-(4-(difluoromethoxy)phenyl)-6-oxopiperidine-3-carboxylic rac-trans
75

Starting from 4-(methylsulfonyl)benzaldehyde, 4-(4-(methylsulfonyl)phenyl)-6-oxopiperidine-3-carboxylic acid was synthesized in analogy to synthesis described for intermediate F. Example 75 was synthesized following synthetic procedure as described in as described in the General procedure for the Synthesis of different Urea Analogous (GP1; see below) (22% yield, off white solid).

$^1$H NMR (400 MHz, DMSO-d$_6$) δ 8.45 (1H, s), 7.87 (2H, d, J=8.4 Hz), 7.64 (1H, d, J=2.0 Hz), 7.57 (2H, d, J=8.4 Hz), 7.30 (2H, d, J=9.2 Hz), 7.21 (2H, d, J=9.2 Hz), 6.24 (1H, d, J=8.4 Hz), 4.23-4.20 (1H, m), 3.39-3.35 (2H, m), 3.18 (3H, s), 3.08-3.03 (1H, m), 2.54-2.50 (1H, m), 2.49-2.44 (1H, m).

101

Preparation of: trans-ent1-1-(4-chlorophenyl)-3-(4-(4-methoxyphenyl)-6-oxopiperidin-3-yl)urea (Example 76) and trans-ent2-1-(4-chlorophenyl)-3-(4-(4-methoxyphenyl)-6-oxopiperidin-3-yl)urea (Example 77)

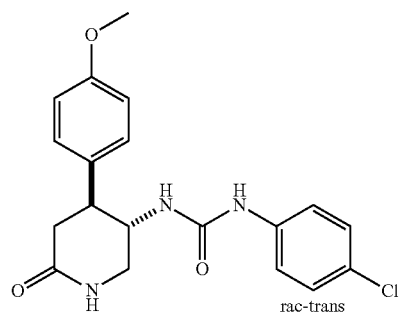
rac-trans
1 chiral separation

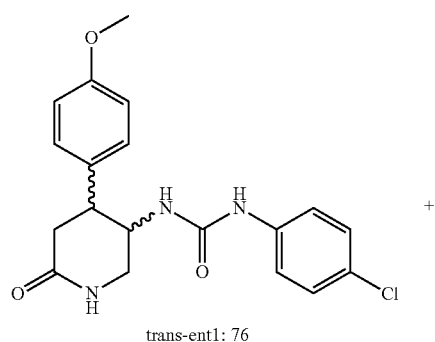
trans-ent1: 76

+

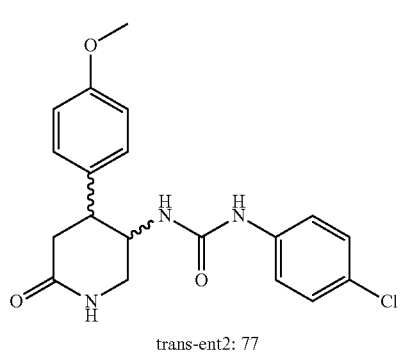
trans-ent2: 77

The racemic Example 1 was subjected to chiral separation by chiral HPLC (Chiralcel-OD-H, Hexane/EtOH/DEA/=80/20/0.1) to render both the enantiomers as Example 76 (first eluting enantiomer; specific rotation: [−47.3°; C=0.44% solution in CHCl₃] at ≅25° C.) and Example 77 (second eluting enantiomer; specific rotation: [+39.8°; C=0.19% solution in CHCl₃] at ≅25° C.).

102

Preparation of: rac-trans-1-(4-chlorophenyl)-3-(6-oxo-4-phenylpiperidin-3-yl)urea (Example 78a)

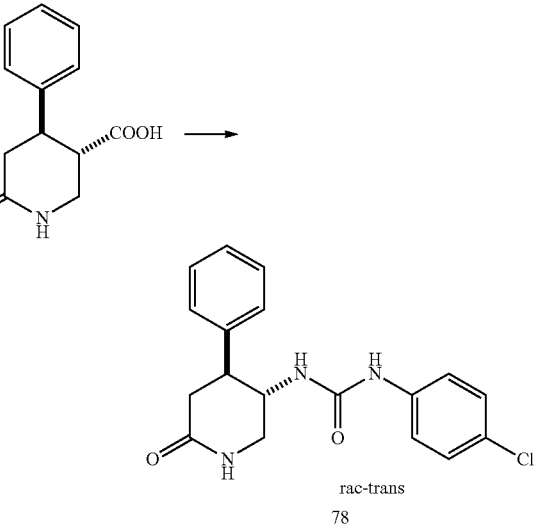
rac-trans
78

Starting from benzaldehyde, 6-oxo-4-phenylpiperidine-3-carboxylic acid was synthesized in analogy to synthesis described for intermediate F. Example 78 was synthesized following the synthetic procedure as described in the General procedure for the Synthesis of different Urea Analogous (GP1; see below) (16% yield, off white solid).

$^1$H NMR (400 MHz, DMSO-$d_6$, 100° C.) δ 8.45 (1H, s), 7.60 (1H, s), 7.34-7.27 (6H, m), 7.23-7.21 (3H, m), 6.19 (1H, d, J=8.0 Hz), 4.13-4.10 (1H, m), 3.31-3.30 (1H, m), 3.20-3.18 (1H, m), 3.04-2.99 (1H, m), 2.49-2.44 (2H, m).

Preparation of: rac-trans-1-(4-chlorophenyl)-3-(4-phenylpiperidin-3-yl)urea (Example 79), trans-ent1-1-(4-chlorophenyl)-3-(4-phenylpiperidin-3-yl)urea (Example 80) and trans-ent2-1-(4-chlorophenyl)-3-(4-phenylpiperidin-3-yl)urea (Example 81)

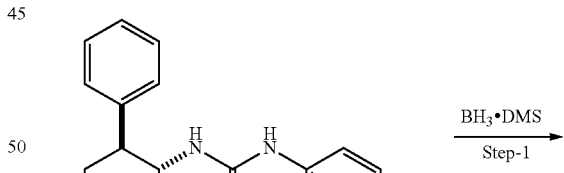
rac-trans
78

BH₃•DMS
Step-1

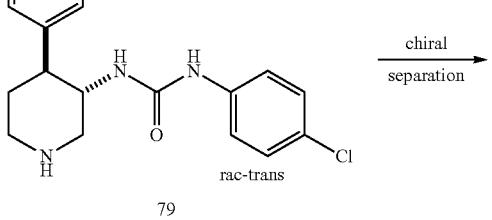
rac-trans
79 chiral separation

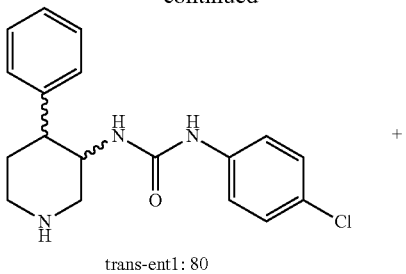

trans-ent1: 80

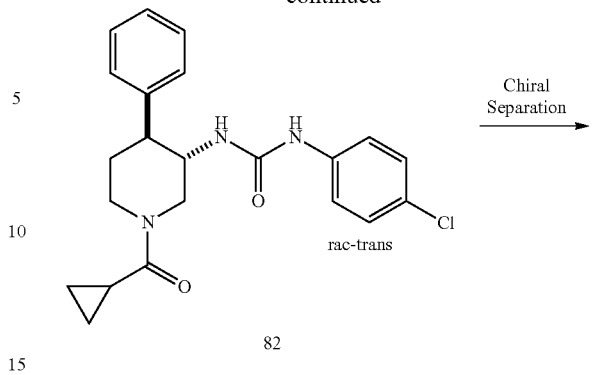

rac-trans 82

Example 79 was synthesized in analogy to synthesis described for Example 44 using Example 78 as starting material (yield: 44%, off white solid).

$^1$H NMR (400 MHz, DMSO-$d_6$) δ 8.31 (s, 1H), 7.30-7.23 (m, 6H), 7.20-7.14 (m, 3H), 5.86 (d, J=8.0 Hz, 1H), 3.78-3.75 (m, 1H), 3.17 (dd, J=12.0, 4.0 Hz, 1H), 2.92 (d, J=12.0 Hz, 1H), 2.56-2.49 (overlapped multiplet with DMSO, 2H), 2.29-2.24 (m, 1H), 1.73-1.69 (m, 1H), 1.60-1.53 (m, 1H).

The racemic Example 79 was subjected to chiral separation by chiral SFC (AD-H column) to render both the enantiomers as Example 80 (first eluting enantiomer; specific rotation: [+7.8°; C=0.19% solution in CHCl$_3$] at ≅25° C.) and Example 81 (second eluting enantiomer; specific rotation: [−5.9°; C=0.98% solution in CHCl$_3$] at ≅25° C.).

Preparation of: rac-trans-1-(4-chlorophenyl)-3-(1-(cyclopropanecarbonyl)-4-phenylpiperidin-3-yl)urea (Example 82), trans-ent1-1-(4-chlorophenyl)-3-(1-(cyclopropanecarbonyl)-4-phenylpiperidin-3-yl)urea (Example 83) and trans-ent2-1-(4-chlorophenyl)-3-(1-(cyclopropanecarbonyl)-4-phenylpiperidin-3-yl)urea (Example 84)

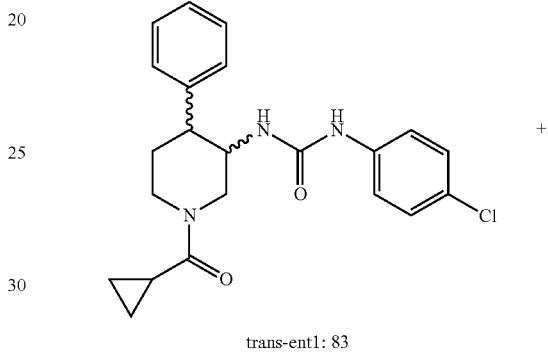

trans-ent1: 83

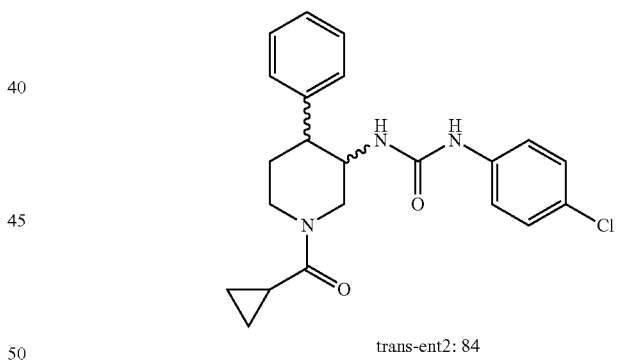

trans-ent2: 84

Example 82 was synthesized in analogy to synthesis described for Example 38 (yield: 50%, off white solid).

$^1$H NMR (400 MHz, DMSO-$d_6$, 100° C.) δ 8.20 (s, 1H), 7.30-7.28 (m, 6H), 7.19-7.17 (m, 3H), 5.87 (d, J=6.8 Hz, 2H), 4.60 (d, J=12.0 Hz, 1H), 4.38 (d, J=12.0 Hz, 1H), 3.82-3.79 (m, 1H), 2.97 (overlapped multiplet with DMSO, 1H), 2.84-2.79 (m, 2H), 1.96-1.95 (m, 1H), 1.89-1.85 (m, 1H), 1.63-1.61 (m, 1H), 0.80-0.74 (m, 4H).

The racemic Example 82 was subjected to chiral separation by chiral HPLC (Chiralpak IC (250×4.6 mm) 5μ; Mobile Phase: Hexane/DCM/EtOH/DEA: 80/10/10/0.1) to render both the enantiomers as Example 83 (first eluting enantiomer; specific rotation: [−27.8°; C=0.54% solution in CHCl$_3$] at ≅25° C.) and Example 84 (second eluting enantiomer; specific rotation: [+26.1°; C=0.34% solution in CHCl$_3$] at ≅25° C.).

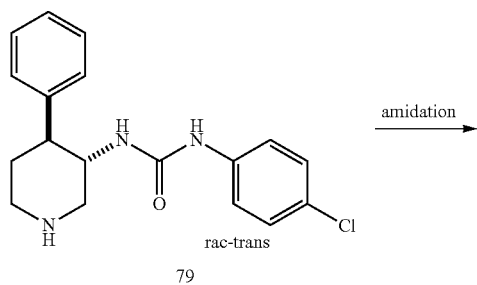

rac-trans
79

Preparation of: rac-trans-1-(4-chlorophenyl)-3-(1-(cyclopropanecarbonyl)-4-(2-fluoro-4-methoxyphenyl)piperidin-3-yl)urea (Example 85), trans-ent1-1-(4-chlorophenyl)-3-(1-(cyclopropanecarbonyl)-4-(2-fluoro-4-methoxyphenyl)piperidin-3-yl)urea (Example 86) and trans-ent2-1-(4-chlorophenyl)-3-(1-(cyclopropanecarbonyl)-4-(2-fluoro-4-methoxyphenyl)piperidin-3-yl)urea (Example 71)

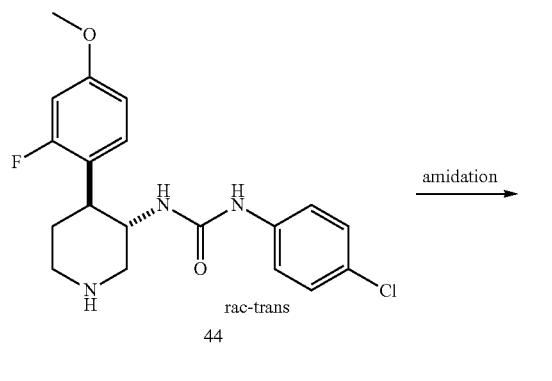
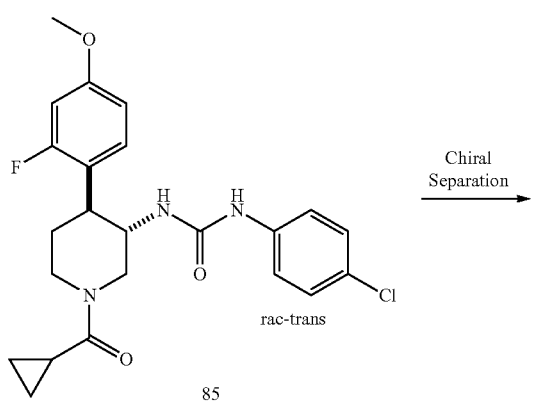
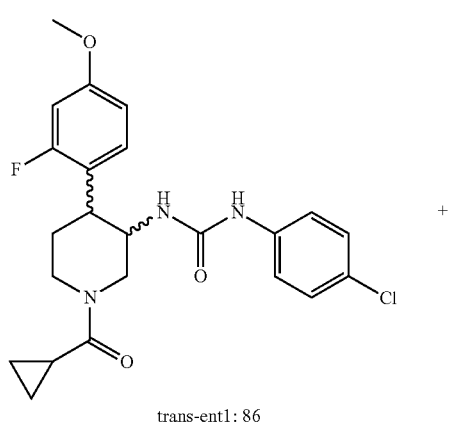
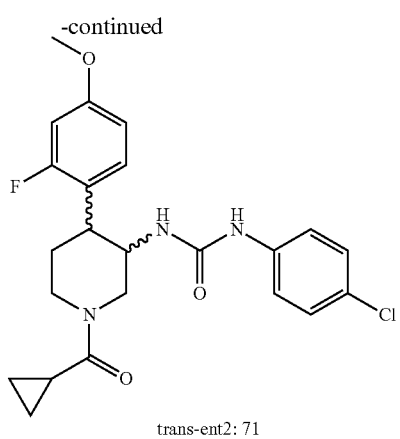

Example 85 was synthesized in analogy to synthesis described for Example 38 (yield: 15%, off white solid).

$^1$H NMR (400 MHz, DMSO-$d_6$, 100° C.) δ 8.23 (1H, s), 7.31-7.29 (2H, m), 7.26-7.18 (3H, m), 6.73-6.69 (2H, m), 5.85 (1H, d, J=8.4 Hz), 4.59 (1H, d, J=13.2 Hz), 4.38 (1H, d, J=12.4 Hz), 3.89-3.86 (1H, m), 3.75 (3H, s), 3.05-2.99 (1H, m), 2.90 (1H, overlapped multiplet with DMSO), 2.80-2.70 (1H, m), 1.98-1.92 (1H, m), 1.85-1.82 (1H, m), 1.68-1.62 (1H, m), 0.81-0.74 (4H, m).

The racemic Example 85 was subjected to chiral separation by chiral SFC (IE column) to render both the enantiomers as Example 86 (first eluting enantiomer; specific rotation: [+21.6°; C=0.27% solution in CHCl$_3$] at ≅25° C.) and Example 71 (second eluting enantiomer; specific rotation: [−22-0.2°; C=0.21% solution in CHCl$_3$] at ≅25° C.).

General Procedure for the Synthesis of Different Urea Analogous (GP1)

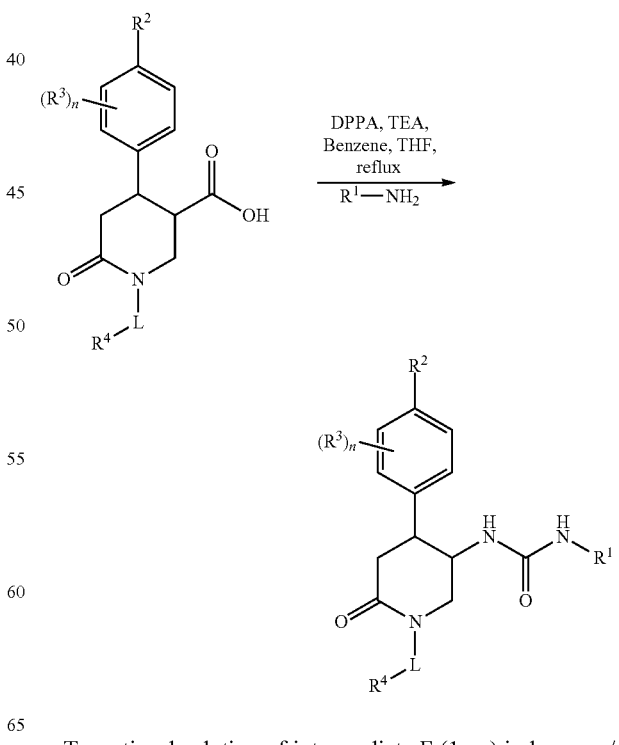

To a stirred solution of intermediate F (1 eq) in benzene/THF (4:1) was added Et$_3$N (2 eq) followed by DPPA (1.3 eq)

at RT and the resulting mixture was allowed stir for 2 h at the same condition. Required amine Ar—NH$_2$ (1.3 eq) was then added and the resulting mixture was again stirred for another 16 h at 70° C. Volatiles were then removed under reduced pressure to yield a reddish crude gum. It was then extracted with EtOAc (two times) and the combined organic phase was washed sequentially by water and brine. The organic phase was then dried over sodium sulfate, filtered and evaporated under reduced pressure to furnish the crude as yellowish gummy solid. It was then purified over 100-200 silica gel using DCM to 10% MeOH/DCM gradient to produce different urea derivatives as off white solid. Examples 52 to 58 were synthesized in analogy to GP1 (see Table 1 below).

TABLE 1

| Ex. # | Intermediates | Structure | Yield (%) | chemical name | $^1$H NMR |
|---|---|---|---|---|---|
| 52 | Intermediate F + 5-chlorothiophen-3-amine | rac-trans | 23 | rac-trans-1-(5-Chloro-thiophen-3-yl)-3-[4-(2,6-difluoro-4-methoxy-phenyl)-6-oxo-piperidin-3-yl]-urea | $^1$H NMR (400 MHz, DMSO-d$_6$) δ 8.62 (1H, s), 7.65 (1H, d, J = 3.6 Hz), 6.92-6.90 (2H, m), 6.70 (2H, d, J = 10.8 Hz), 6.17 (1H, d, J = 8.4 Hz), 4.23-4.21 (1H, m), 3.74 (3H, s), 3.46-3.43 (1H, m), 3.32-3.29 (1H, m), 3.07-3.02 (1H, m), 2.50-2.46 (2H, m). |
| 53 | Intermediate F + benzo[b]thiophen-2-amine | rac-trans | 35 | rac-trans-1-(Benzo[b]thiophen-2-yl)-3-(4-(2,6-difluoro-4-methoxy-phenyl)-6-oxo-piperidin-3-yl]-urea | $^1$H NMR (400 MHz, DMSO-d$_6$) δ 9.63 (1H, s), 7.68-7.64 (2H, m), 7.49-7.47 (1H, d, J = 8.0 Hz), 7.18 (1H, t, J = 7.6 Hz), 7.06 (1H, d, J = 7.6 Hz), 6.68 (2H, d, J = 7.2 Hz), 6,58 (1H, s), 6.40 (1H, d, J = 8.0 Hz), 4.28-4.20 (1H, m), 3.70 (3H, s), 3.51-3.44 (1H, m), 3.35-3.28 (1H, m), 3.10-3.05 (1H, m), 2.50-2.45 (2H, overlapped multiplet with DMSO). |
| 54 | Intermediate F + 4-phenoxyaniline | rac-trans | 20 | rac-trans-1-[4-(2,6-Difluoro-4-methoxy-phenyl)-6-oxo-piperidin-3-yl]-3-(4-phenoxy-phenyl)-urea | $^1$H NMR (400 MHz, DMSO-d$_6$) δ 8.37 (1H, s), 7.65 (1H, d, J = 3.2 Hz), 7.35-7.28 (4H, m), 7.06 (1H, t, J = 7.6 Hz), 6.91-6.87 (4H, m), 6.71 (2H, d, J = 11.2 Hz), 6.08 (1H, d, J = 8.4 Hz), 4.28-4.20 (1H, m), 3.75 (3H, s), 3.47-3.45 (1H, m), 3.36-3.31 (1H, m), 3.08-3.03 (1H, m), 2.50-2.45 (2H, overlapped multiplet with DMSO). |

TABLE 1-continued

| Ex. # | Intermediates | Structure | Yield (%) | chemical name | $^1$H NMR |
|---|---|---|---|---|---|
| 55 | Intermediate F + 3-methylisothiazol-5-amine | rac-trans | 34 | rac-trans-1-[4-(2,6-Difluoro-4-methoxy-phenyl)-6-oxo-piperidin-3-yl]-3-(3-methyl-isothiazol-5-yl)-urea | $^1$H NMR (400 MHz, DMSO-d$_6$) δ 10.07 (1H, s), 7.67 (1H, s), 6.69 (3H, d, J = 10.8 Hz), 6.42 (1H, s), 4.26-4.22 (1H, m), 3.73 (3H, S), 3.53-3.46 (1H, m), 3.35-3.28 (1H, overlapped multiplet with DMSO), 3.13-3.08 (1H, m), 2.50-2.47 (2H, m). |
| 56 | Intermediate F + 5-chlorothiazol-2-amine | rac-trans | 20 | rac-trans-1-(5-Chloro-thiazol-2-yl)-3-(4-(2,6-difluoro-4-methoxy-phenyl)-6-oxo-piperidin-3-yl]-urea | $^1$H NMR (400 MHz, DMSO-d$_6$) δ 10.49 (1H, brs), 7.68 (1H, d, J = 3.2 Hz), 7.28 (1H, s), 6.71 (2H, d. J = 11.2 Hz), 6.60 (1H, brs), 4.28-4.21 (1H, m), 3.74 (3H, s), 3.54-3.47 (1H, m), 3.35-3.32 (1H, m), 3.13-3.08 (1H, m), 2.49-2.45 (2H, m). |
| 57 | Intermediate F + 5-amino-2-chlorophenol | rac-trans | 16 | rac-trans-1-(4-Chloro-3-hydroxy-phenyl)-3-[4-(2,6-difluoro-4-methoxy-phenyl)-6-oxo-piperidin-3-yl]-urea | $^1$H NMR (400 MHz, DMSO-d$_6$) δ 9.97 (1H, s), 8.38 (1H, s), 7.66 (1H, d, J = 2.8 Hz), 7.16 (1H, d, J = 2 Hz), 7.07 (1H, d, J = 8.8 Hz), 6.70 (2H, d, J = 10.8), 6.62 (1H, dd, J = 8.8, 2.0 Hz), 6.08 (1H, dd, J = 8.4 Hz), 4.30-4.20 (1H, m), 3.74 (3H, s), 3.49-3.42 (1H, m), 3.35-3.32 (1H, m), 3.04 (1H, t, J = 10.4 Hz), 2.50-2.45 (2H, m). |
| 58 | Intermediate F + 4-chloro-3-fluoroaniline | rac-trans | 21 | rac-trans-1-(4-Chloro-3-fluoro-phenyl)-3-[4-(2,6-difluoro-4-methoxy-phenyl)-6-oxo-piperidin-3-yl]-urea | $^1$H NMR (400 MHz, DMSO-d$_6$) δ 8.71 (1H, s), 7.66 (1H, d, J = 3.2 Hz), 7.51 (1H, dd, J = 12.4, 2.4 Hz), 7.37-7.33 (1H, m), 6.99-6.97 (1H, m), 6.70 (2H, d, J = 10.8 Hz), 6.29 (1H, d, J = 8.4 Hz), 4.25-4.23 (1H, m), 3.74 (3H, s), 3.50-3.43 (1H, m), 3.36-3.32 (1H, m), 3.07 (1H, t, J = 10.8 Hz), 2.50-2.45 (2H, overlapped multiplet with DMSO). |

General Procedure for N-alkylation Followed by Deprotection and Urea Formation (GP2)

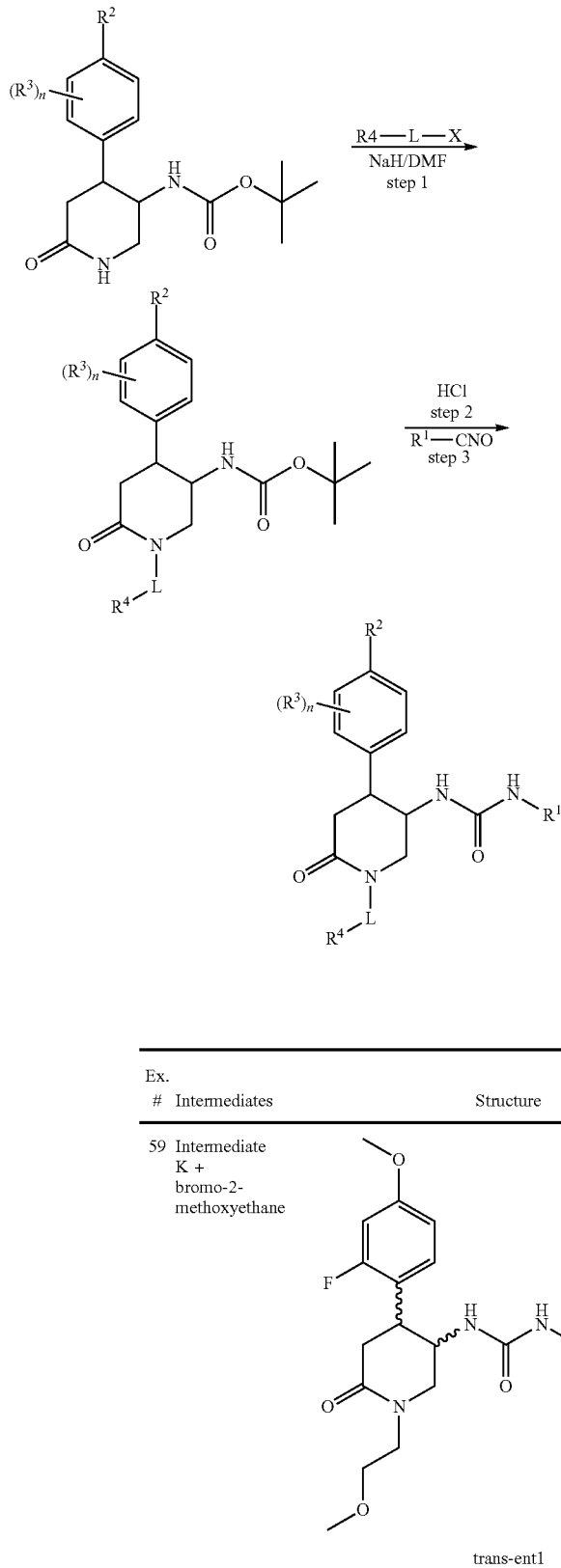

Step1:

To the stirred solution of key intermediate like intermediate B, D, H, I, J, K, L, M, N or O (1 eq) in dry DMF (6.0 mL/mmol) were added NaH (60%) (1.0 eq) followed by the addition of corresponding ester or bromide (1.0 eq) and stirred the reaction mixture at RT for 16 h. After completion of the reaction, it was quenched with ice water and extracted with EtOAc. The organic layer was dried over anhyd. $Na_2SO_4$ and concentrated under reduced pressure to obtain crude product which was purified by silica gel (100-200 mesh) column chromatography (20-25% EtOAc/Hexane) to afford corresponding N-alkylated desired compound.

Step2:

To the stirred solution of step1 product (N-alkylated intermediate B, D, H, I, J, K, L, M, N or O) (1 eq) in 1,4-dioxane was added 4M HCl in 1,4-dioxane (2.0 mL/mmol) followed by stirring at RT for a period of 2 h. After completion of the reaction (monitor by TLC and LC MS), the reaction mixture was evaporated under reduced pressure to get the crude material which was purified by triturating with pentane and ether to get the corresponding HCl salt as off white solid.

Step3:

To a stirred solution of step2 product (corresponding HCl salt of amine derived from intermediate B, D, H, I, J, K, L, M, N or O) (1 eq) in DCM (10.0 mL/mmol) was added $Et_3N$ (5 eq) followed by the addition of 1-chloro-4-isocyanato-benzene (1 eq) stirring at RT for a period of 1 h. After completion of the reaction, the reaction mixture was diluted with water and extracted with 5% MeOH in DCM and washed with ice-cold water and brine. The organic layer was dried over anhyd. $Na_2SO_4$ and concentrated under reduced pressure to obtain crude product which was purified by silica gel (100-200 mesh) column chromatography (2% MeOH/DCM) to afford desired compound.

Examples 59 to 68, 91 and 92 were synthesized in analogy to GP2, whereas in case of Examples 67, 68, 91 and 92 step 1 of GP2 was omitted (see Table 2 below).

TABLE 2

| Ex. # | Intermediates | Structure | chemical name | $^1$H NMR; specific rotation |
|---|---|---|---|---|
| 59 | Intermediate K + bromo-2-methoxyethane | trans-ent1 | trans-ent1-1-(4-Chlorophenyl)-3-[4-(2-fluoro-4-methoxy-phenyl)-1-(2-methoxy-ethyl)-6-oxo-piperidin-3-yl]-urea | $^1$H NMR (400 MHz, DMSO-$d_6$) δ 8.49 (s, 1 H), 7.34 (d, J = 8 Hz, 2 H), 7.26-7.22 (m, 3 H), 6.80-6.74 (m, 2 H), 6.23 (d, J = 8 Hz, 1 H), 4.30-4.21 (m, 1 H), 3.73 (s, 3 H), 3.62-3.55 (m, 2 H), 3.44 (s, 4 H), 3.41-3.36 (m, 2 H), 3.32-3.23 (m, 4 H); specific relation: [−42°; C = 0.22% solution in CHCl$_3$] at ≃ 25° C. |

TABLE 2-continued

| Ex. # | Intermediates | Structure | chemical name | ¹H NMR; specific rotation |
|---|---|---|---|---|
| 60 | Intermediate L + bromo-2-methoxyethane | trans-ent2 | trans-ent2-1-(4-Chlorophenyl)-3-[4-(2-fluoro-4-methoxy-phenyl)-1-(2-methoxy-ethyl)-6-oxo-piperidin-3-yl]-urea | ¹H NMR (400 MHz, DMSO-$d_6$) δ 8.49 (s, 1 H), 7.34 (d, J = 8 Hz, 2 H), 7.26-7.21 (m, 3 H), 6.80-6.74 (m, 2 H), 6.23 (d, J = 8 Hz, 1 H), 4.28-4.22 (m, 1 H), 3.73 (s, 3 H), 3.55-3.46 (m, 5 H), 3.40-3.31 (m, 1 H), 3.21 (s, 4 H), 2.52-2.48 (m, 2 H); specific rotation: [+45°; C = 0.27% solution m CHCl$_3$ at ≅ 25° C. |
| 61 | Intermediate K + 2,2-difluoroethyl trifluoromethane-sulfonate | trans-ent1 | trans-ent1-1-(4-Chlorophenyl)-3-[1-(2,2-difluoro-ethyl)-4-(2-fluoro-4-methoxy-phenyl)-6-oxo-piperidin-3-yl]-urea | ¹H NMR (400 MHz, DMSO-$d_6$) δ 8.50 (s, 1 H), 7.33 (d, J = 6 Hz, 2 H), 7.28-7.21 (m, 3H), 6.80-6.74 (m, 2 H), 6.24-6.16 (m, 3 H), 4.38-23 (m, 1 H), 3.82-3.71 (m, 5 H), 3.68-3.57 (m, 2 H), 3.48-3.38 (m, 2 H), 2.62-2.52 (m, 2 H); specific rotation: [−32°; C = 0.27% solution m CHCl$_3$ at ≅ 25°C. |
| 62 | Intermediate L + 2,2-difluoroethyl trifluoromethane-sulfonate | trans-ent2 | trans-ent2-1-(4-Chlorophenyl)-3-[1-(2,2-difluoro-ethyl)-4-(2-fluoro-4-methoxy-phenyl)-6-oxo-piperidin-3-yl]-urea | ¹H NMR (400 MHz, DMSO-$d_6$) δ 8.50 (s, 1 H), 7.33 (d, J = 6 Hz, 2 H), 7.28-7.21 (m, 3 H), 6.80-6.74 (m, 2 H), 6.24-6.16 (m, 3 H), 4.38-23 (m, 1 H), 3.82-3.71 (m, 5 H), 3.68-3.57 (m, 2 H), 3.48-3.38 (m, 2 H), 2.62-2.52 (m, 2 H); specific rotation: [+48°; C = 0.25% solution m CHCl$_3$ at ≅ 25° C. |

TABLE 2-continued

| Ex. # | Intermediates | Structure | chemical name | ¹H NMR; specific rotation |
|---|---|---|---|---|
| 63 | Intermediate M + 1-bromo-2-methoxyethane | trans-ent1 | trans-ent1-1-(4-Chlorophenyl)-3-[4-(2,4-difluoro-phenyl)-1-(2-methoxy-ethyl)-6-oxo-piperidin-3-yl]-urea | ¹H NMR (400 MHz, DMSO-d₆) δ 8.48 (s, 1 H), 7.42-7.38 (m, 1 H), 7.33 (d, J = 8 Hz, 2 H), 7.23-7.16 (m, 3 H), 7.08-7.06 (m, 1 H), 6.26 (d, J = 8 Hz, 1 H), 4.35-4.24 (m, 1 H), 3.55-3.42 (m, 6 H), 3.32-3.29 (m, 1 H), 3.25 (s, 3 H), 2.55-2.53 (m, 2 H); specific rotation: [−31°; C = 0.34% solution in CHCl₃] at ≈ 25° C. |
| 64 | Intermediate N + 1-bromo-2-methoxyethane | trans-ent2 | trans-ent2-1-(4-Chlorophenyl)-3-[4-(2,4-difluoro-phenyl)-1-(2-methoxy-ethyl)-6-oxo-piperidin-3-yl]-urea | ¹H NMR (400 MHz, DMSO-d₆) δ 8.48 (s, 1 H), 7.42-7.38 (m, 1 H), 7.33 (d, J = 8 Hz, 2 H), 7.23-7.16 (m, 3 H), 7.08-7.06 (m, 1 H), 6.26 (d, J = 8 Hz, 1 H), 4.35-4.24 (m, 1 H), 3.55-3.42 (m, 6 H), 3.32-3.29 (m, 1 H), 3.25 (s, 3 H), 2.55-2.53 (m, 2 H); specific rotation: (+34°; C = 0.24% solution in CHCl₃] at ≈ 25° C. |
| 65 | Intermediate M + 2,2-difluoroethyl trifluoromethane-sulfonate | trans-ent1 | trans-ent1-1-(4-Chlorophenyl)-3-[1-(2,2-difluoro-ethyl)-4-(2,4-difluoro-phenyl)-6-oxo-piperidin-3-yl]-urea | ¹H NMR (400 MHz, DMSO-d₆) δ 8.49 (s, 1 H), 7.47-7.40 (m, 1 H), 7.33 (d, J = 8 Hz, 2 H), 7.23-7.17 (m, 3 H), 7.09-7.05 (m, 1 H), 6.30-6.02 (m, 1 H), 6.26 (d, J = 9 Hz, 1 H), 4.37-4.33 (m, 1 H), 3.83-3.72 (m, 2 H), 3.61-3.57 (m, 1 H), 3.54-3.47 (m, 1 H), 3.32-3.31 (m, 1 H), 2.67-2.58 (m, 2 H); specific rotation: [−17°; C = 0.25% solution in CHCl₃] at ≈ 25° C. |

TABLE 2-continued

| Ex. # | Intermediates | Structure | chemical name | ¹H NMR; specific rotation |
|---|---|---|---|---|
| 66 | Intermediate N + 2,2-difluoroethyl trifluoromethane-sulfonate | trans-ent2 | trans-ent2-1-(4-Chlorophenyl)-3-[1-(2,2-difluoro-ethyl)-4-(2,4-difluoro-phenyl)-6-oxo-piperidin-3-yl]-urea | ¹H NMR (400 MHz, DMSO-d₆) δ 8.49 (s, 1 H), 7.47-7.40 (m, 1 H), 7.33 (d, J = 8 Hz, 2 H), 7.23-7.17 (m, 3 H), 7.09-7.05 (m, 1 H), 6.30-6.02 (m, 1 H), 6.26 (d, J = 9 Hz, 1 H), 4.37-4.33 (m, 1 H), 3.83-3.72 (m, 2 H), 3.61-3.57 (m, 1 H), 3.54-3.47 (m, 1 H), 3.32-3.31 (m. 1 H), 2.67-2.58 (m, 2 H); specific rotation: (+19°; C = 0.28% solution in CHCl₃] at ≅ 25° C. |
| 67 | Intermediate M | trans-ent1 | trans-ent1-1-(4-Chlorophenyl)-3-[4-(2,4-difluoro-phenyl)-6-oxo-piperidin-3-yl]-urea | ¹H NMR (400 MHz, DMSO-d₆) δ 8.46 (s, 1 H), 7.64 (s, 1 H), 7.42-7.38 (m, 1 H), 7.31 (d, J = 8 Hz, 2 H), 7.23-7.16 (m, 3 H), 7.09-7.05 (m. 1 H), 6.19 (d, J = 8 Hz, 1 H), 4.21-4.19 (m, 1 H), 3.46-3.43 (m, 1 H), 3.36-3.31 (m, 2 H), 3.09-3.04 (m, 1 H), 2.50-2.44 (m, 2 H); [−13°; C = 0.25% solution in CHCl₃] at ≅ 25° C. |
| 68 | Intermediate N | trans-ent2 | trans-ent2-1-(4-Chlorophenyl)-3-[4-(2,4-difluoro-phenyl)-6-oxo-piperidin-3-yl]-urea | ¹H NMR (400 MHz, DMSO-d₆) δ 8.46 (s, 1 H), 7.64 (s, 1 H), 7.42-7.38 (m, 1 H), 7.31 (d, J = 8 Hz, 2 H), 7.23-7.16 (m, 3 H), 7.09-7.05 (m, 1 H), 6.19 (d, J = 8 Hz, 1 H), 4.21-4.19 (m, 1 H), 3.46-3.43 (m, 1 H), 3.36-3.31 (m, 2 H), 3.09-3.04 (m, 1 H), 2.50-2.44 (m, 2 H); specific rotation: [−13°; C = 0.24% solution in CHCl₃] at ≅ 25° C. |
| 91 | Intermediate O | trans-ent1 | trans-ent1-1-(4-chlorophenyl)-3-(4-(4-chlorophenyl)-6-oxopiperidin-3-yl)urea | ¹H NMR (400 MHz, DMSO-d₆) δ 8.44 (s, 1 H), 7.61 (s, 1H), 7.38 (d, J = 8 Hz, 2 H), 7.32-7.30 (m, 4 H), 7.22 (d, J = 8 Hz, 2 H), 6.18 (d, J = 8 Hz, 1 H), 4.13-4.10 (m, 1 H), 3.34-3.30 (m, 1 H), 3.22-3.20 (m, 1 H), 3.05-3.00 (m, 1 H), 2.45-2.43 (m, 2 H); specific rotation: [+5°; C = 0.23% solution in CHCl₃] at ≅ 25° C. |

TABLE 2-continued

| Ex. # | Intermediates | Structure | chemical name | $^1$H NMR; specific rotation |
|---|---|---|---|---|
| 92 | Intermediate O | trans-ent2 | trans-ent2-1-(4-chlorophenyl)-3-(4-(4-chlorophenyl)-6-oxopiperidin-3-yl)urea | $^1$H NMR (400 MHz, DMSO-d$_6$) δ 8.44 (s, 1 H), 7.61 (s, 1 H), 7.38 (d, J = 8 Hz, 2 H), 7.32-7.30 (m, 4 H), 7.22 (d, J = 8 Hz, 2 H), 6.18 (d, J = 8 Hz, 1 H), 4.13-4.10 (m, 1 H), 3.34-3.30 (m 1 H), 3.22-3.20 (m, 1 H), 3.05-3.00 (m, 1 H), 2.45-2.43 (m, 2 H); specific rotation: [−3°; C = 0.23% solution in CHCl$_3$] at ≅ 25° C. |

General Procedure for N-methylation Followed by Deprotection and Urea Formation (GP3)

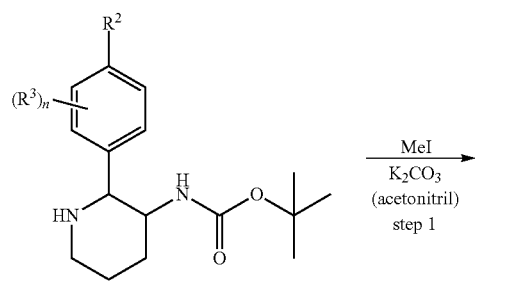

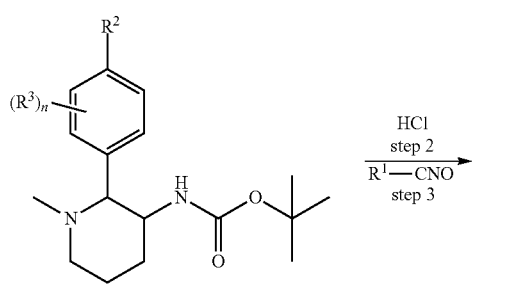

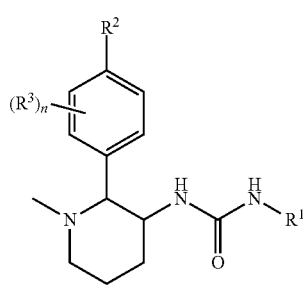

Step 1:

To a stirred solution of intermediate Q, R, S or T (1 eq) in ACN (5 mL/mmol) at ice cooled condition was added K$_2$CO$_3$ (3 eq) followed by the addition of MeI (1 eq) and the reaction mixture was stirred at RT for 16 h. After completion of the reaction, it was concentrated under reduced pressure, diluted with water and extracted with 5% MeOH in DCM; the combined organic layer was dried over anh. Na$_2$SO$_4$, filtered and concentrated to get the crude product which was purified by silica gel (100-200 mesh) column chromatography (2% MeOH/DCM) to afford desired N-methylated derivative of intermediate Q, R, S or T.

Step 2:

To a stirred solution of step1 product (N-methylated derivative of intermediate Q, R, S or T) (1 eq) in 1,4-dioxane (4 mL/mmol) was added 4M HCl in dioxane (10 mL/mmol) followed by stirring at RT for a period of 2 h. After completion of the reaction (monitored by TLC and LC MS), the reaction mixture was evaporated under reduced pressure to get the crude material which was purified by triturating with pentane and ether to get the desired HCl salt of amine derived from intermediate Q, R, S or T.

Step 3:

To a stirred of step2 product (HCl salt of amine derived from intermediate Q, R, S or T) (1 eq) in DCM (5 mL) was added Et$_3$N (5.0 eq) followed by the addition of 4-chloro phenyl isocyanate (1 eq) stirring at RT for a period of 24 h. After completion of the reaction, it was diluted with DCM, given washed with water and brine. The combined organic layer was dried over anh. Na$_2$SO$_4$, filtered and Rota evaporated to get the crude product which was purified by silica gel (100-200 mesh) column chromatography to afford corresponding final compound.

Examples 87 to 90 were synthesized in analogy to GP3 (see Table 3 below).

TABLE 3

| Ex. # | Intermediates | Structure | Yield (%) | chemical name | 1H NMR |
|---|---|---|---|---|---|
| 87 | Intermediate S + 4-chloro phenyl isocyanate | diastereoisomer1 | 57 (step3) | dia1-1-(4-chlorophenyl)-3-(2-(2,6-difluoro-4-methoxyphenyl)-1-methylpiperidin-3-yl)urea | 1H NMR (400 MHz, DMSO-$d_6$) δ 8.88 (s, 1 H), 7.28 (d, J = 9 Hz, 2 H), 7.19 (d, J = 9 Hz, 2 H), 6.71-6.68 (m, 1 H), 6.62-6.59 (m, 1 H), 6.47 (d, J = 10 Hz, 1 H), 3.87-3.82 (m, 1 H), 3.72 (s, 3 H), 3.48 (s, 1 H), 2.99-2.94 (m, 1 H), 2.02 (s. 4 H). 1.81-1.75 (m, 1 H), 1.68-1.63 (m, 1 H), 1.59-1.52 (m, 2 H). |
| 88 | Intermediate T + 4-chloro phenyl isocyanate | diastereoisomer2 | 65 (step3) | dia2-1-(4-chlorophenyl)-3-(2-(2,6-difluoro-4-methoxyphenyl)-1-methylpiperidin-3-yl)urea | 1H NMR (400 MHz, DMSO-$d_6$) δ 8.28 (s, 1 H), 7.23-7.16 (m, 4 H), 6.60 (d, J = 11 Hz, 2 H), 5.90 (d, J = 9 Hz, 1 H), 4.10-4.06 (m, 1 H), 3.71 (s, 3 H), 3.02 (d, J = 10 Hz, 1 H), 2.88 (d, J = 11 Hz, 1 H), 1.98-1.93 (m, 5 H), 1.68-1.52 (m, 2 H), 1.24-1.20 (m, 1 H). |
| 89 | Intermediate Q + 4-chloro phenyl isocyanate | diastereoisomer1 | 11.5 (step3) | dia1-1-(4-chlorophenyl)-3-(2-(4-methoxyphenyl)-1-methylpiperidin-3-yl)urea | 1H NMR (400 MHz, DMSO-$d_6$) δ 8.20 (s, 1 H), 7.23-7.15 (m, 6 H), 6.82 (d, J = 9 Hz, 2 H), 5.84 (d, J = 9 Hz, 1 H), 3.69 (s, 3 H), 3.68-3.54 (m, 1 H), 2.91-2.85 (m, 1 H), 2.58-2.51 (m, 1 H), 2.20-1.94 (m, 2 H), 1.84 (s. 3 H), 1.68-1.61 (m, 2 H), 1.28-1.21 (m, 1 H). |
| 90 | Intermediate R + 4-chloro phenyl isocyanate | diastereoisomer2 | 41 (step3) | dia2-1-(4-chlorophenyl)-3-(2-(4-methoxyphenyl)-1-methylpiperidin-3-yl)urea | 1H NMR (400 MHz, DMSO-$d_6$) δ 8.75 (s, 1 H), 7.28-7.14 (m, 6 H), 6.81 (d, J = 8 Hz, 2 H), 6.57 (d, J = 9 Hz, 1 H), 3.71-3.62 (m, 4 H), 3.05 (s, 1 H), 3.00-2.95 (m, 1 H), 2.98-2.15 (m, 1 H), 1.93 (s, 3 H), 1.82-1.68 (2, 2 H), 1.61-1.51 (m, 2 H). |

Biological Activity of the Compounds According to the Invention:

Assay Method for Measuring Agonistic Activity of Compounds in hFPR1-Gα15-CHO and hFPR2-Aq-CHO Cell Cryo-vial containing 6×10$^6$ cells (hFPR1-Gα15-CHO or hFPR2-Aq-CHO) was thawed in a 37° C. water bath. Cells were suspended in 10 ml of respective complete growth media (F12(1×) HAM media (Gibco; Cat#11765); 10% HI-FBS (Gibco; Cat#10082); 0.1 mg/ml Hygromycin B (Invitrogen; Cat#10687-010) [for hFPR1 only]; 0.2 mg/ml Zeocin (Invitrogen; Cat#R25001) [for hFPR1 only]; 0.4 mg/ml Geneticin (Gibco; Cat#10131) [for hFPR2-Aq only]; 0.25 mg/ml Zeocin (Invitrogen; Cat#R25001) [for hFPR2-Aq only]) in a 15 ml centrifuge tube. The cell viability was checked with the help of Trypan Blue dye. Upon washing the cells, those were plated in a 384-well sterile clear bottom black plate (Greiner Bioone Cat#781091) so that, each well contained 10,000 cells in 40 µl complete growth media. The plate was incubated in a 5% $CO_2$ incubator at 37° C. for 18 hours.

Before assay on the next day, the cell plating media was removed from each well of the plate by decanting and gentle tapping. 30 µl, 0.11 of 0.5× Calcium 5 dye solution (0.5× FLIPR Calcium 5 dye (Molecular devices Cat# R8186); HBSS (Invitrogen; Cat#14025); 20 mM HEPES (Sigma; Cat#H0887); 2.5 mM Probenecid (Sigma; Cat#P8761); 0.025% Pluronic F-127 (Sigma; Cat#P2443); pH adjusted to 7.4) was added to each well. The plate was then incubated at 37° C. for 30 minutes. Following which the plate was equilibrated at room temperature for 10 minutes before placing it in a 384 well FLIPR for assay. Compounds were dissolved in DMSO and serially diluted following 11 point half log (3.16 fold) dilution with a starting concentration of 2 mM (Final assay concentration 10 µM). Aliquots of above mentioned each dilution was mixed with assay buffer (HBSS (Invitrogen; Cat#14025); 20 mM HEPES (Sigma; Cat#H0887); 2.5 mM Probenecid (Sigma; Cat#P8761); 0.05% gelatin (Sigma; Cat#G1890); 0.1% BSA (Sigma; Cat#A3059); pH adjusted to 7.4) just before performing the assay. Compounds were added to the respective wells of the assay ready cell plate with the help of the FLIPR (FLIPR Tetra) and fluorescence readings were captured for 5 minutes to measure any agonistic response of the compounds. The increase in fluorescence readings from the basal reading in presence of the compounds were compared with that of the control wells (wells having no compound) to calculate the agonistic activity of the compounds. The $EC_{50}$ values of the compounds were determined using the Graph pad Prism software. The results are summarized in Table 4 below.

TABLE 4

| Ex. # | EC50 on FPR2 (A < 1 nM, B = 1-1000 nM) | EC50 on FPR1 (A < 1 nM, B = 1-1000 nM) |
|---|---|---|
| 1 | A | B |
| 2 | A | A |
| 3 | A | B |
| 4 | A | B |
| 5 | A | B |
| 6 | A | B |
| 7 | A | A |
| 8 | A | B |
| 9 | A | B |
| 10 | A | A |
| 11 | B | B |
| 12 | A | A |
| 13 | A | A |
| 14 | A | A |
| 15 | A | A |
| 16 | A | A |
| 17 | A | A |
| 18 | A | A |
| 19 | B | B |
| 20 | A | B |
| 21 | A | A |
| 23 | A | B |
| 24 | A | B |
| 25 | B | B |
| 26 | B | B |
| 27 | B | B |
| 28 | B | B |
| 29 | A | B |
| 30 | A | A |
| 31 | A | B |
| 32 | A | B |
| 36 | A | B |
| 37 | B | B |

TABLE 4-continued

| Ex. # | EC50 on FPR2 (A < 1 nM, B = 1-1000 nM) | EC50 on FPR1 (A < 1 nM, B = 1-1000 nM) |
|---|---|---|
| 39 | A | B |
| 40 | B | B |
| 42 | A | B |
| 43 | B | B |
| 45 | A | B |
| 46 | B | B |
| 47 | B | B |
| 48 | B | B |
| 49 | B | B |
| 50 | A | B |
| 51 | B | B |
| 52 | A | B |
| 53 | B | B |
| 54 | A | B |
| 55 | B | B |
| 56 | B | B |
| 57 | A | B |
| 58 | B | B |
| 59 | A | B |
| 60 | B | B |
| 61 | A | A |
| 62 | B | B |
| 63 | B | B |
| 64 | B | B |
| 65 | B | B |
| 66 | B | B |
| 67 | B | B |
| 68 | B | B |
| 69 | B | B |
| 70 | B | B |
| 72 | A | B |
| 72 | B | B |
| 73 | B | B |
| 74 | B | B |
| 75 | B | B |
| 76 | A | B |
| 77 | B | B |
| 80 | B | B |
| 81 | B | B |
| 83 | B | B |
| 84 | B | B |
| 86 | A | A |
| 88 | B | B |
| 89 | B | B |
| 90 | B | B |
| 91 | B | B |

The invention claimed is:

1. A compound according to general formula (I):

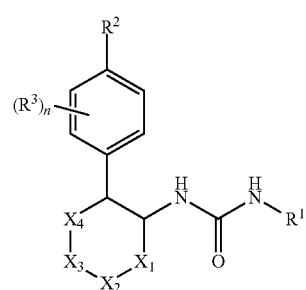

wherein
$X_2$ represents $N(L-R^4)$ and $X_1$, $X_3$ and $X_4$ represent $CH_2$; or
$X_2$ represents $N(L-R^4)$ and $X_3$ represents $C(O)$ and $X_1$ and $X_4$ represent $CH_2$; or
$X_4$ represents $N(L-R^4)$, and $X_3$ represents $CH_2$ or $C(O)$ and $X_1$ and $X_2$ represent $CH_2$;

and n represents 0, 1 or 2

$R^1$ represents phenyl or 5 or 6-membered heteroaryl, $R^2$ represents F, Br, CN, $C_{1-6}$-alkyl, $C_{3-6}$-cycloalkyl, $CHF_2$, $CH_2F$, $CF_3$, OH, $OCHF_2$, $OCH_2F$, $OCF_3$, O—$C_{1-6}$-alkyl, S—$C_{1-6}$-alkyl, S(O)—$C_{1-6}$-alkyl, $S(O)_2$—$C_{1-6}$-alkyl, O—$C_{3-6}$-cycloalkyl, S—$C_{3-6}$-cycloalkyl, S(O)—$C_{3-6}$-cycloalkyl, $S(O)_2$—$C_{3-6}$-cycloalkyl, $NH_2$, $N(H)(C_{1-6}$-alkyl), $N(C_{1-6}$-alkyl)$_2$, $N(H)(C_{3-6}$-cycloalkyl), $N(C_{1-6}$-alkyl)($C_{3-6}$-cycloalkyl), $NC(O)(C_{1-6}$-alkyl), $NC(O)(C_{3-6}$-cycloalkyl), NC(O)(3 to 6-membered heterocycloalkyl);

$R^3$ represents F, Cl, Br, $CHF_2$, $CH_2F$, $CF_3$, $C_{1-6}$-alkyl, $C_{3-6}$-cycloalkyl, O—$C_{1-6}$-alkyl, $OCHF_2$, $OCH_2F$, $OCF_3$, S(O)—$C_{1-6}$-alkyl, S(O)—$C_{3-6}$-cycloalkyl, $S(O)_2$—$C_{1-6}$-alkyl, $S(O)_2$—$C_{3-6}$-cycloalkyl;

L represents bond, $C_{1-6}$-alkylene, C(O), $S(O)_2$, $C(CH_3)_2$; and $R^4$ represents H, $C_{1-6}$-alkyl, $C_{3-6}$-cycloalkyl, 3 to 6-membered heterocycloalkyl, aryl, 5 or 6-membered heteroaryl, $C(O)NH_2$, $C(O)N(H)(C_{1-6}$-alkyl), $C(O)N(C_{1-6}$-alkyl)$_2$, $C(O)N(H)(C_{3-6}$-cycloalkyl), $C(O)N(H)(3$ to 6-membered heterocycloalkyl), C(O)N(H)(aryl), C(O)N(H)(5 or 6-membered heteroaryl), $C(O)N(C_{1-6}$-alkyl)($C_{3-6}$-cycloalkyl), $C(O)N(C_{1-6}$-alkyl)(3 to 6-membered heterocycloalkyl), $C(O)N(C_{1-6}$-alkyl)(aryl), $C(O)N(C_{1-6}$-alkyl)(5 or 6-membered heteroaryl), $C(O)N(C_{3-6}$-cycloalkyl)($C_{3-6}$-cycloalkyl), $C(O)N(C_{3-6}$-cycloalkyl)(3 to 6-membered heterocycloalkyl), $C(O)N(C_{3-6}$-cycloalkyl)(aryl), $C(O)N(C_{3-6}$-cycloalkyl)(5 or 6-membered heteroaryl), C(O)O—($C_{1-6}$-alkyl), C(O)O—($C_{3-6}$-cycloalkyl), C(O)O-(3 to 6-membered heterocycloalkyl), C(O)O-(aryl), C(O)O-(5 or 6-membered heteroaryl), S(O)—$C_{1-6}$-alkyl, $S(O)_2$—$C_{1-6}$-alkyl, S(O)—$C_{3-6}$-cycloalkyl, $S(O)_2$—$C_{3-6}$-cycloalkyl, $C_{1-6}$-alkylene-OH, $C_{1-6}$-alkylene-O—$C_{1-6}$-alkyl, $C_{1-6}$-alkylene-$C_{3-6}$-cycloalkyl, $C_{1-6}$-alkylene-3 to 6-membered heterocycloalkyl, $C_{1-6}$-alkylene-aryl, $C_{1-6}$-alkylene-5 or 6-membered heteroaryl;

wherein $C_{1-6}$-alkyl in each case independently from one another is linear or branched, saturated or unsaturated;

wherein $C_{1-6}$-alkylene is linear and saturated or unsaturated;

wherein $C_{1-6}$-alkyl, $C_{1-6}$-alkylene, $C_{3-6}$-cycloalkyl and 3 to 6-membered heterocycloalkyl in each case independently from one another are unsubstituted or mono- or polysubstituted with one or more substituents selected from F, Cl, CN, $C_{1-6}$-alkyl, $CF_3$, $CF_2H$, $CFH_2$, $CF_2Cl$, $CFCl_2$, C(O)—$C_{1-6}$-alkyl, C(O)—OH, C(O)—$OC_{1-6}$-alkyl, C(O)—$NH_2$, C(O)—$N(H)(C_{1-6}$-alkyl), C(O)—$N(C_{1-6}$-alkyl)$_2$, OH, =O, $OCF_3$, $OCF_2H$, $OCFH_2$, $OCF_2Cl$, $OCFCl_2$, O—$C_{1-6}$-alkyl, O—C(O)—$C_{1-6}$-alkyl, O—C(O)—O—$C_{1-6}$-alkyl, O—(CO)—$N(H)(C_{1-6}$-alkyl), O—C(O)—$N(C_{1-6}$-alkyl)$_2$, O—$S(O)_2$—$NH_2$, O—$S(O)_2$—$N(H)(C_{1-6}$-alkyl), O—$S(O)_2$—$N(C_{1-6}$-alkyl)$_2$, $NH_2$, $N(H)(C_{1-6}$-alkyl), $N(C_{1-6}$-alkyl)$_2$, N(H)—C(O)—$C_{1-6}$-alkyl, N(H)—C(O)—O—$C_{1-6}$-alkyl, N(H)—C(O)—$NH_2$, N(H)—C(O)—$N(H)(C_{1-6}$-alkyl), N(H)—C(O)—$N(C_{1-6}$-alkyl)$_2$, $N(C_{1-6}$-alkyl)-C(O)—$C_{1-6}$-alkyl, $N(C_{1-6}$-alkyl)-C(O)—O—$C_{1-6}$-alkyl, $N(C_{1-6}$-alkyl)-C(O)—$NH_2$, $N(C_{1-6}$-alkyl)-C(O)—$N(H)(C_{1-6}$-alkyl), $N(C_{1-6}$-alkyl)-C(O)—$N(C_{1-6}$-alkyl)$_2$, N(H)—$S(O)_2$OH, N(H)—$S(O)_2$—$C_{1-6}$-alkyl, N(H)—S(O)$_2$—O—$C_{1-6}$-alkyl, N(H)—$S(O)_2$—$NH_2$, N(H)—S(O)$_2$—$N(H)(C_{1-6}$-alkyl), N(H)—$S(O)_2N(C_{1-6}$-alkyl)$_2$, $N(C_{1-6}$-alkyl)-$S(O)_2$—OH, $N(C_{1-6}$-alkyl)-$S(O)_2$—$C_{1-6}$-alkyl, $N(C_{1-6}$-alkyl)-$S(O)_2$—O—$C_{1-6}$-alkyl, $N(C_{1-6}$-alkyl)-$S(O)_2$—$NH_2$, $N(C_{1-6}$-alkyl)-$S(O)_2$—$N(H)(C_{1-6}$-alkyl), $N(C_{1-6}$-alkyl)-$S(O)_2$—$N(C_{1-6}$-alkyl)$_2$, $SCF_3$, $SCF_2H$, $SCFH_2$, S—$C_{1-6}$-alkyl, S(O)—$C_{1-6}$-alkyl, $S(O)_2$—$C_{1-6}$-alkyl, $S(O)_2$—OH, $S(O)_2$—O—$C_{1-6}$-alkyl, $S(O)_2$—$NH_2$, $S(O)_2$—$N(H)(C_{1-6}$-alkyl), $S(O)_2$—$N(C_{1-6}$-alkyl)$_2$, $C_{3-6}$-cycloalkyl, 3 to 6-membered heterocycloalkyl, phenyl, 5 or 6-membered heteroaryl, O—$C_{3-6}$-cycloalkyl, O-(3 to 6-membered heterocycloalkyl), O-phenyl, O-(5 or 6-membered heteroaryl), C(O)—$C_{3-6}$-cycloalkyl, C(O)-(3 to 6-membered heterocycloalkyl), C(O)-phenyl, C(O)-(5 or 6-membered heteroaryl), $S(O)_2$—($C_{3-6}$-cycloalkyl), $S(O)_2$-(3 to 6-membered heterocycloalkyl), $S(O)_2$-phenyl or $S(O)_2$-(5 or 6-membered heteroaryl);

wherein aryl, phenyl and 5 or 6-membered heteroaryl in each case independently from one another are unsubstituted or mono- or disubstituted with one or two substituents selected from F, Cl, Br, CN, $C_{1-6}$-alkyl, $CF_3$, $CF_2H$, $CFH_2$, $C_{1-4}$-alkylene-$CF_3$, $C_{1-4}$-alkylene-$CF_2H$, $C_{1-4}$-alkylene-$CFH_2$, C(O)—$C_{1-6}$-alkyl, C(O)—OH, C(O)—$OC_{1-6}$-alkyl, C(O)—N(H)(OH), C(O)—$NH_2$, C(O)—$N(H)(C_{1-6}$-alkyl), C(O)—$N(C_{1-6}$-alkyl)$_2$, OH, $OCF_3$, $OCF_2H$, $OCFH_2$, $OCF_2Cl$, $OCFCl_2$, O—$C_{1-6}$-alkyl, O—$C_{3-6}$-cycloalkyl, O-(3 to 6-membered heterocycloalkyl), O-phenyl, O-(5 to 6-membered heteroaryl), $NH_2$, $N(H)(C_{1-6}$-alkyl), $N(C_{1-6}$-alkyl)$_2$, N(H)—C(O)—$C_{1-6}$-alkyl, $N(C_{1-6}$-alkyl)-C(O)—$C_{1-6}$-alkyl, N(H)—C(O)—$NH_2$, N(H)—C(O)—$N(H)(C_{1-6}$-alkyl), N(H)—C(O)—$N(C_{1-6}$-alkyl)$_2$, $N(C_{1-6}$-alkyl)-C(O)—$N(H)(C_{1-6}$-alkyl), $N(C_{1-6}$-alkyl)-C(O)—$N(C_{1-6}$-alkyl)$_2$, N(H)—$S(O)_2$—$C_{1-6}$-alkyl, $SCF_3$, S—$C_{1-6}$-alkyl, S(O)—$C_{1-6}$-alkyl, $S(O)_2$—$C_{1-6}$-alkyl, $S(O)_2$—$NH_2$, $S(O)_2$—$N(H)(C_{1-6}$-alkyl), $S(O)_2$—$N(C_{1-6}$-alkyl)$_2$, $C_{3-6}$-cycloalkyl, $C_{1-4}$-alkylene-$C_{3-6}$-cycloalkyl, 3 to 6-membered heterocycloalkyl, $C_{1-4}$-alkylene-(3 to 6-membered heterocycloalkyl), phenyl or 5 or 6-membered heteroaryl;

in the form of the free compound or a physiologically acceptable salt thereof.

2. The compound according to claim 1, which has general formula (Ia) or (Ib):

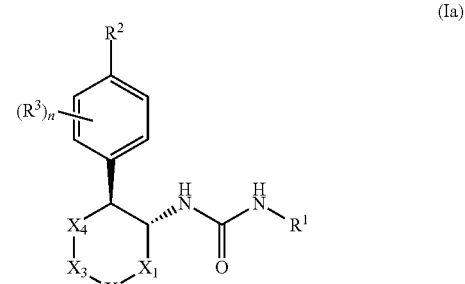

(Ia)

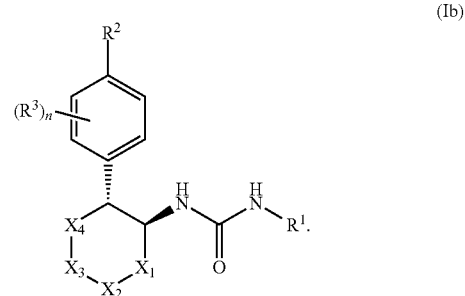

(Ib)

3. The compound according to claim 1, which has general formula (II):

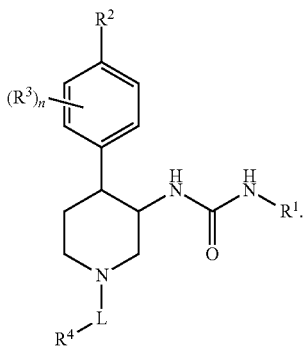

4. The compound according to claim 1, which has general formula (III):

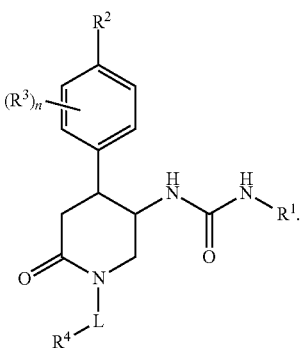

5. The compound according to claim 1, which has general formula (IV) or (V):

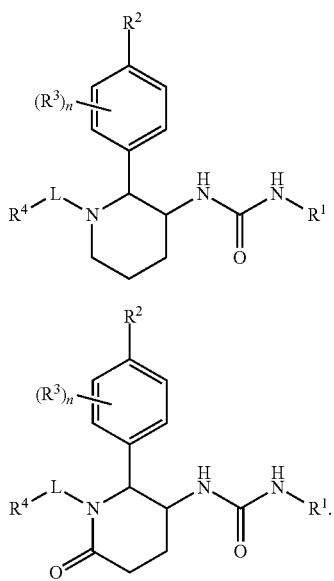

6. The compound according to claim 1, wherein $R^1$ represents phenyl or 5 or 6-membered heteroaryl, wherein the 5 or 6-membered heteroaryl is selected from the group consisting of pyridyl, pyrimidinyl, pyridazinyl, pyrazinyl, pyrrolyl, imidazolyl, pyrazolyl, oxazolyl, isoxazolyl, thiazolyl, isothiazolyl, furanyl, thienyl (thiophenyl), triazolyl, thiadiazolyl, 4,5,6,7-tetrahydro-2H-indazolyl, 2,4,5,6-tetrahydrocyclopenta[c]pyrazolyl, benzofuranyl, benzoimidazolyl, benzothienyl, benzothiadiazolyl, benzothiazolyl, benzotriazolyl, benzooxazolyl, benzooxadiazolyl, quinazolinyl, quinoxalinyl, carbazolyl, quinolinyl, dibenzofuranyl, dibenzothienyl, imidazothiazolyl, indazolyl, indolizinyl, indolyl, isoquinolinyl, naphthyridinyl, oxazolyl, oxadiazolyl, phenazinyl, phenothiazinyl, phthalazinyl, purinyl, phenazinyl, tetrazolyl and triazinyl.

7. The compound according to claim 1, wherein $R^2$ represents F, Br, $CH_3$, $CH_2CH_3$, OH, O—$CH_3$, O—$CH_2CH_3$, O—$(CH_2)_2CH_3$, O—$CH(CH_3)_2$, $OCH_2F$, $OCHF_2$, $OCF_3$, S—$CH_3$, S—$CH_2CH_3$, S(O)—$CH_3$, S(O)—$CH_2CH_3$, $S(O)_2$—$CH_3$ or $S(O)_2$—$CH_2CH_3$.

8. The compound according to claim 1, wherein $R^3$ represents F and/or n represents 2.

9. The compound according to claim 1, wherein
L represents bond, $CH_2$ or C(O); and/or
$R^4$ represents H, $C_{1-6}$-alkyl, $C_{1-6}$-alkylene-OH, $C_{1-6}$-alkylene-O—$C_{1-6}$-alkyl, 3 to 6-membered cycloalkyl, 3 to 6-membered heterocycloalkyl, $C(O)NH_2$, C(O)N(H)($C_{1-6}$-alkyl), $C(O)N(C_{1-6}$-alkyl$)_2$, C(O)O—($C_{1-6}$-alkyl); S(O)—$C_{1-6}$-alkyl, $S(O)_2$—$C_{1-6}$-alkyl, S(O)—$C_{3-6}$-cycloalkyl, $S(O)_2$—$C_{3-6}$-cycloalkyl, or aryl.

10. The compound according to claim 1, wherein
$X_2$ represents N(L-$R^4$) and $X_3$ represents $CH_2$ or C(O) and $X_1$ and $X_4$ represent $CH_2$;
or
$X_4$ represents N(L-$R^4$) and $X_1$, $X_2$ and $X_3$ represent $CH_2$; and
n represents 0, 1 or 2
$R^1$ represents phenyl, pyridyl, pyrimidinyl, thiazolyl, isothiazolyl, thienyl or benzothienyl
wherein phenyl, pyridyl, pyrimidinyl, thiazolyl, isothiazolyl, thienyl and benzothienyl independently from one another are unsubstituted or monosubstituted with one or more substituents selected from F, Cl, Br, unsubstituted $C_{1-6}$-alkyl, $CF_3$; OH and O-(unsubstituted phenyl);
$R^2$ represents O—$CH_3$, F, $CH_3$, $CH_2CH_3$, O—$CH_2F$, O—$CHF_2$, O—$CF_3$, S—$CH_2CH_3$, $S(O)_2$—$CH_3$ or $S(O)_2$—$CH_2CH_3$;
$R^3$ represents F;
L represents bond, $CH_2$ or C(O); and
$R^4$ represents
H;
$C_{1-6}$-alkyl selected from the group consisting of methyl, ethyl, n-propyl, 2-propyl, n-butyl, isobutyl, sec-butyl, tert-butyl, n-pentyl, 2-pentyl, 3-pentyl, 2-methylbutyl, 3-methylbutyl, 3-methylbut-2-yl, 2-methylbut-2-yl, 2,2-dimethylpropyl and n-hexyl;
wherein $C_{1-6}$-alkyl is unsubstituted or mono- or polysubstituted with one or more substituents selected from F, Cl, Br, CN, OH, O—$CH_3$, O—$CH_2CH_3$, O—$(CH_2)_2CH_3$ and O—$CH(CH_3)_2$;
$C_{1-6}$-alkylene-OH selected from the group consisting of $CH_2OH$, $CH_2CH_2OH$, $(CH_2)_3OH$, $(CH_2)_4OH$, C(H)(OH)—$CH_3$, $CH_2C(H)(OH)$—$CH_3$, $C(CH_3)_2$—OH, C(H)(OH)—$C(CH_3)_2$, $CH_2C(CH_3)_2$—OH, C$_{1-6}$-alkylene-O—C$_{1-6}$-alkyl selected from the group consisting of CH$_2$OCH$_3$, CH$_2$CH$_2$OCH$_3$, (CH$_2$)$_3$OCH$_3$, (CH$_2$)$_4$OCH$_3$, (CH$_2$)$_5$OCH$_3$, (CH$_2$)$_6$OCH$_3$, 3 to 6-membered cycloalkyl selected from the group consisting of cyclopropyl, cyclobutyl, cyclopentyl and cyclohexyl;

3 to 6-membered heterocycloalkyl selected from the group consisting of tetrahydropyranyl, morpholinyl, pyrrolidinyl, 4-methylpiperazinyl, morpholinonyl, azetidinyl, aziridinyl, dithiolanyl, dihydropyrrolyl, dioxanyl, dioxolanyl, dihydropyridinyl, dihydrofuranyl, dihydroisoxazolyl, dihydrooxazolyl, imidazolidinyl, isoxazolidinyl, oxazolidinyl, oxiranyl, oxetanyl, piperazinyl, piperidinyl, pyrazolidinyl, pyranyl and tetrahydropyrrolyl;

C(O)NH$_2$,

C(O)N(H)(C$_{1-6}$-alkyl) selected from the group consisting of C(O)N(H)(CH$_3$) and C(O)N(H)(CH$_2$CH$_3$);

C(O)N(C$_{1-6}$-alkyl)$_2$ selected from the group consisting of C(O)N(CH$_3$)$_2$ and C(O)N(CH$_2$CH$_3$)$_2$;

C(O)O—(C$_{1-6}$-alkyl) selected from the group consisting of C(O)O—CH$_3$, C(O)O—CH$_2$CH$_3$, C(O)O—(CH$_2$)$_2$CH$_3$, C(O)O—CH(CH$_3$)$_2$;

S(O)—C$_{1-6}$-alkyl selected from the group consisting of S(O)—CH$_3$, S(O)—CH$_2$CH$_3$, S(O)—(CH$_2$)$_2$CH$_3$, S(O)—CH(CH$_3$)$_2$;

S(O)$_2$—C$_{1-6}$-alkyl selected from the group consisting of S(O)$_2$—CH$_3$, S(O)$_2$—CH$_2$CH$_3$, S(O)$_2$—(CH$_2$)$_2$CH$_3$, S(O)$_2$—CH(CH$_3$)$_2$;

S(O)—C$_{3-6}$-cycloalkyl selected from the group consisting of S(O)-cyclopropyl, S(O)-cyclobutyl, S(O)-cyclopentyl, S(O)-cyclohexyl;

S(O)$_2$—C$_{3-6}$-cycloalkyl selected from the group consisting of S(O)$_2$-cyclopropyl, S(O)$_2$-cyclobutyl, S(O)$_2$-cyclopentyl, S(O)$_2$-cyclohexyl; or phenyl;

in the form of the free compound or a physiologically acceptable salt thereof.

11. The compound according to claim 1 which has general formula (X):

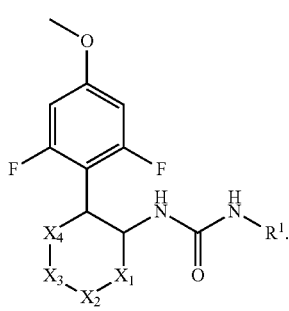

(X)

12. The compound according to claim 1, which is selected from the group consisting of:

1 rac-trans-1-(4-chlorophenyl)-3-(-4-(4-methoxyphenyl)-6-oxopiperidin-3-yl)urea
2 rac-trans-1-(1-acetyl-4-(4-methoxyphenyl)piperidin-3-yl)-3-(4-chlorophenyl)urea
3 rac-trans-1-(4-bromophenyl)-3-(4-(4-methoxyphenyl)-6-oxopiperidin-3-yl)urea
4 rac-trans-1-(4-chlorophenyl)-3-(4-(4-methoxyphenyl)piperidin-3-yl)urea
5 rac-trans-1-(1-acetyl-4-(2,6-difluoro-4-methoxyphenyl)piperidin-3-yl)-3-(4-chlorophenyl)urea
6 rac-trans-1-(4-bromophenyl)-3-(4-(4-methoxyphenyl)piperidin-3-yl)urea
7 rac-trans-1-(4-chlorophenyl)-3-(4-(4-methoxyphenyl)-1-methyl-6-oxopiperidin-3-yl)urea
8 rac-trans-1-(4-bromophenyl)-3-(4-(2,6-difluoro-4-methoxyphenyl)piperidin-3-yl)urea
9 rac-trans-1-(4-chlorophenyl)-3-(4-(2,6-difluoro-4-methoxyphenyl)piperidin-3-yl)urea
10 trans-ent1-(4-chlorophenyl)-3-(4-(4-methoxyphenyl)-1-methyl-6-oxopiperidin-3-yl)urea
11 trans-ent2-(4-chlorophenyl)-3-(4-(4-methoxyphenyl)-1-methyl-6-oxopiperidin-3-yl)urea
12 rac-trans-1-(4-chlorophenyl)-3-(1-(cyclopropanecarbonyl)-4-(4-methoxyphenyl)piperidin-3-yl)urea
13 rac-trans-1-(4-chlorophenyl)-3-(1-(2-hydroxyacetyl)-4-(4-methoxyphenyl)piperidin-3-yl)urea
14 rac-trans-1-(4-chlorophenyl)-3-(1-(2,2-difluoropropanoyl)-4-(4-methoxyphenyl)piperidin-3-yl)urea
15 rac-trans-1-(4-chlorophenyl)-3-(4-(4-methoxyphenyl)-1-(3-methoxypropanoyl)piperidin-3-yl)urea
16 rac-trans-1-(4-chlorophenyl)-3-(4-(4-methoxyphenyl)-1-(tetrahydro-2H-pyran-4-carbonyl)-piperidin-3-yl)urea
17 rac-trans-1-(4-chlorophenyl)-3-(1-isobutyryl-4-(4-methoxyphenyl)piperidin-3-yl)urea
18 rac-trans-1-(4-chlorophenyl)-3-[4-(4-methoxyphenyl)-1-(3-methyl-butanoyl)-piperidin-3-yl]-urea
19 rac-trans-1-(1-acetyl-4-(4-methoxyphenyl)piperidin-3-yl)-3-(6-chloropyridin-3-yl)urea
20 rac-trans-2-(5-(3-(4-chlorophenyl)ureido)-4-(4-methoxyphenyl)-2-oxopiperidin-1-yl)acetamide
21 rac-trans-methyl 2-(5-(3-(4-chlorophenyl)ureido)-4-(4-methoxyphenyl)-2-oxopiperidin-1-yl)acetate
22 rac-trans-1-(1-acetyl-4-(4-methoxyphenyl)piperidin-3-yl)-3-(4-bromophenyl)urea
23 rac-trans-1-(4-chlorophenyl)-3-(4-(2,6-difluoro-4-methoxyphenyl)-6-oxopiperidin-3-yl)urea
24 rac-trans-1-(4-chlorophenyl)-3-(1-(cyclopropylmethyl)-4-(4-methoxyphenyl)-6-oxopiperidin-3-yl)urea
25 rac-trans-1-(1-acetyl-4-(4-methoxyphenyl)piperidin-3-yl)-3-(pyrimidin-5-yl)urea
26 rac-trans-1-(1-acetyl-4-(4-methoxyphenyl)piperidin-3-yl)-3-(6-methylpyridin-3-yl)urea
27 rac-trans-1-(1-acetyl-4-(4-methoxyphenyl)piperidin-3-yl)-3-(6-(trifluoromethyl)pyridin-3-yl)urea
28 rac-trans-1-(1-acetyl-4-(4-methoxyphenyl)piperidin-3-yl)-3-(6-methylpyridin-3-yl)urea
29 rac-trans-1-(4-chlorophenyl)-3-(1-(cyclopropylmethyl)-4-(2,6-difluoro-4-methoxyphenyl)-6-oxopiperidin-3-yl)urea
30 rac-trans-1-(4-chlorophenyl)-3-(1-(3-hydroxypropanoyl)-4-(4-methoxyphenyl)piperidin-3-yl)urea
31 rac-trans-1-(4-chlorophenyl)-3-(4-(2,6-difluoro-4-methoxyphenyl)-1-(2-hydroxyethyl)-6-oxopiperidin-3-yl)urea
32 rac-trans-1-(4-chlorophenyl)-3-(1-(2-hydroxyethyl)-4-(4-methoxyphenyl)-6-oxopiperidin-3-yl)urea
34 rac-trans-1-(1-acetyl-4-(2,6-difluoro-4-methoxyphenyl)piperidin-3-yl)-3-(4-bromophenyl)urea
35 rac-trans-methyl 2-(5-(3-(4-chlorophenyl)ureido)-4-(2,6-difluoro-4-methoxyphenyl)-2-oxopiperidin-1-yl)acetate
36 trans-ent1-1-(4-chlorophenyl)-3-(4-(2,6-difluoro-4-methoxyphenyl)piperidin-3-yl)urea 37 trans-ent2-1-(4-chlorophenyl)-3-(4-(2,6-difluoro-4-methoxyphenyl)piperidin-3-yl)urea
38 rac-trans-1-(4-chlorophenyl)-3-(1-(cyclopropanecarbonyl)-4-(2,6-difluoro-4-methoxyphenyl)piperidin-3-yl)urea
39 trans-ent1-1-(4-chlorophenyl)-3-(1-(cyclopropanecarbonyl)-4-(2,6-difluoro-4-methoxyphenyl)piperidin-3-yl)urea
40 trans-ent2-1-(4-chlorophenyl)-3-(1-(cyclopropanecarbonyl)-4-(2,6-difluoro-4-methoxyphenyl)piperidin-3-yl)urea
41 rac-trans-1-(4-chlorophenyl)-3-(4-(2-fluoro-4-methoxyphenyl)-6-oxopiperidin-3-yl)urea
42 trans-ent1-1-(4-chlorophenyl)-3-(4-(2-fluoro-4-methoxyphenyl)-6-oxopiperidin-3-yl)urea
43 trans-ent2-1-(4-chlorophenyl)-3-(4-(2-fluoro-4-methoxyphenyl)-6-oxopiperidin-3-yl)urea
44 rac-trans-1-(4-chlorophenyl)-3-(4-(2-fluoro-4-methoxyphenyl)piperidin-3-yl)urea
45 trans-ent1-1-(4-chlorophenyl)-3-(4-(2-fluoro-4-methoxyphenyl)piperidin-3-yl)urea
46 trans-ent2-1-(4-chlorophenyl)-3-(4-(2-fluoro-4-methoxyphenyl)piperidin-3-yl)urea
47 trans-ent1-1-(4-(2,6-difluoro-4-methoxyphenyl)-6-oxopiperidin-3-yl)-3-(pyridin-4-yl)urea
48 trans-ent2-1-(4-(2,6-difluoro-4-methoxyphenyl)-6-oxopiperidin-3-yl)-3-(pyridin-4-yl)urea
49 trans-ent1-1-(4-chlorophenyl)-3-(4-(2,6-difluoro-4-methoxyphenyl)-6-oxopiperidin-3-yl)urea
50 trans-ent2-1-(4-chlorophenyl)-3-(4-(2,6-difluoro-4-methoxyphenyl)-6-oxopiperidin-3-yl)urea
51 rac-trans-1-(5-chlorothiophen-2-yl)-3-(4-(2,6-difluoro-4-methoxyphenyl)-6-oxopiperidin-3-yl)urea
52 rac-trans-1-(5-Chloro-thiophen-3-yl)-3-[4-(2,6-difluoro-4-methoxy-phenyl)-6-oxo-piperidin-3-yl]-urea
53 rac-trans-1-(Benzo[b]thiophen-2-yl)-3-[4-(2,6-difluoro-4-methoxy-phenyl)-6-oxo-piperidin-3-yl]-urea
54 rac-trans-1-[4-(2,6-Difluoro-4-methoxy-phenyl)-6-oxo-piperidin-3-yl]-3-(4-phenoxy-phenyl)-urea
55 rac-trans-1-[4-(2,6-Difluoro-4-methoxy-phenyl)-6-oxo-piperidin-3-yl]-3-(3-methyl-isothiazol-5-yl)-urea
56 rac-trans-1-(5-Chloro-thiazol-2-yl)-3-[4-(2,6-difluoro-4-methoxy-phenyl)-6-oxo-piperidin-3-yl]-urea
57 rac-trans-1-(4-Chloro-3-hydroxy-phenyl)-3-[4-(2,6-difluoro-4-methoxy-phenyl)-6-oxo-piperidin-3-yl]-urea
58 rac-trans-1-(4-Chloro-3-fluoro-phenyl)-3-[4-(2,6-difluoro-4-methoxy-phenyl)-6-oxo-piperidin-3-yl]-urea
59 trans-ent1-1-(4-Chlorophenyl)-3-[4-(2-fluoro-4-methoxy-phenyl)-1-(2-methoxy-ethyl)-6-oxo-piperidin-3-yl]-urea
60 trans-ent2-1-(4-Chlorophenyl)-3-[4-(2-fluoro-4-methoxy-phenyl)-1-(2-methoxy-ethyl)-6-oxo-piperidin-3-yl]-urea
61 trans-ent1-1-(4-Chlorophenyl)-3-[1-(2,2-difluoro-ethyl)-4-(2-fluoro-4-methoxy-phenyl)-6-oxo-piperidin-3-yl]-urea
62 trans-ent2-1-(4-Chlorophenyl)-3-[1-(2,2-difluoro-ethyl)-4-(2-fluoro-4-methoxy-phenyl)-6-oxo-piperidin-3-yl]-urea
63 trans-ent1-1-(4-Chlorophenyl)-3-[4-(2,4-difluoro-phenyl)-1-(2-methoxy-ethyl)-6-oxo-piperidin-3-yl]-urea
64 trans-ent2-1-(4-Chlorophenyl)-3-[4-(2,4-difluoro-phenyl)-1-(2-methoxy-ethyl)-6-oxo-piperidin-3-yl]-urea
65 trans-ent1-1-(4-Chlorophenyl)-3-[1-(2,2-difluoro-ethyl)-4-(2,4-difluoro-phenyl)-6-oxo-piperidin-3-yl]-urea
66 trans-ent2-1-(4-Chlorophenyl)-3-[1-(2,2-difluoro-ethyl)-4-(2,4-difluoro-phenyl)-6-oxo-piperidin-3-yl]-urea
67 trans-ent1-1-(4-Chlorophenyl)-3-[4-(2,4-difluoro-phenyl)-6-oxo-piperidin-3-yl]-urea
68 trans-ent2-1-(4-Chlorophenyl)-3-[4-(2,4-difluoro-phenyl)-6-oxo-piperidin-3-yl]-urea
69 rac-trans-1-(4-chlorophenyl)-3-(4-(4-ethyl-2,6-difluorophenyl)-6-oxopiperidin-3-yl)urea
70 rac-trans-1-(4-chlorophenyl)-3-(4-(4-(difluoromethoxy)-2,6-difluorophenyl)-6-oxopiperidin-3-yl)urea
71 trans-ent2-1-(4-chlorophenyl)-3-(1-(cyclopropanecarbonyl)-4-(2-fluoro-4-methoxyphenyl)piperidin-3-yl)urea
72 rac-trans-1-(4-chlorophenyl)-3-(4-(4-(methylthio)phenyl)-6-oxopiperidin-3-yl)urea
73 rac-trans-1-(4-chlorophenyl)-3-(4-(4-ethylphenyl)-6-oxopiperidin-3-yl)urea
74 rac-trans-1-(4-chlorophenyl)-3-(4-(4-(difluoromethoxy)phenyl)-6-oxopiperidin-3-yl)urea
75 rac-trans-1-(4-chlorophenyl)-3-(4-(4-(methylsulfonyl)phenyl)-6-oxopiperidin-3-yl)urea
76 trans-ent1-1-(4-chlorophenyl)-3-(4-(4-methoxyphenyl)-6-oxopiperidin-3-yl)urea
77 trans-ent2-1-(4-chlorophenyl)-3-(4-(4-methoxyphenyl)-6-oxopiperidin-3-yl)urea
78 rac-trans-1-(4-chlorophenyl)-3-(6-oxo-4-phenylpiperidin-3-yl)urea
79 rac-trans-1-(4-chlorophenyl)-3-(4-phenylpiperidin-3-yl)urea, 1-(4-chlorophenyl)-3-((3S,4S)-4-phenylpiperidin-3-yl)urea
80 trans-ent1-1-(4-chlorophenyl)-3-(4-phenylpiperidin-3-yl)urea, 1-(4-chlorophenyl)-3-((3S,4S)-4-phenylpiperidin-3-yl)urea
81 trans-ent2-1-(4-chlorophenyl)-3-(4-phenylpiperidin-3-yl)urea, 1-(4-chlorophenyl)-3-((3S,4S)-4-phenylpiperidin-3-yl)urea
82 rac-trans-1-(4-chlorophenyl)-3-(1-(cyclopropanecarbonyl)-4-phenylpiperidin-3-yl)urea
83 trans-ent1-1-(4-chlorophenyl)-3-(1-(cyclopropanecarbonyl)-4-phenylpiperidin-3-yl)urea
84 trans-ent2-1-(4-chlorophenyl)-3-(1-(cyclopropanecarbonyl)-4-phenylpiperidin-3-yl)urea
85 rac-trans-1-(4-chlorophenyl)-3-(1-(cyclopropanecarbonyl)-4-(2-fluoro-4-methoxyphenyl)piperidin-3-yl)urea
86 trans-ent1-1-(4-chlorophenyl)-3-(1-(cyclopropanecarbonyl)-4-(2-fluoro-4-methoxyphenyl)piperidin-3-yl)urea
87 dia1-1-(4-chlorophenyl)-3-(2-(2,6-difluoro-4-methoxyphenyl)-1-methylpiperidin-3-yl)urea
88 dia2-1-(4-chlorophenyl)-3-(2-(2,6-difluoro-4-methoxyphenyl)-1-methylpiperidin-3-yl)urea
89 dia1-1-(4-chlorophenyl)-3-(2-(4-methoxyphenyl)-1-methylpiperidin-3-yl)urea
90 dia2-1-(4-chlorophenyl)-3-(2-(4-methoxyphenyl)-1-methylpiperidin-3-yl)urea
91 trans-ent1-1-(4-chlorophenyl)-3-(4-(4-chlorophenyl)-6-oxopiperidin-3-yl)urea
92 trans-ent2-1-(4-chlorophenyl)-3-(4-(4-chlorophenyl)-6-oxopiperidin-3-yl)urea
in the form of the free compound or a physiologically acceptable salt thereof.

13. A pharmaceutical dosage form comprising a compound according to claim 1.

14. A method for the treatment of a disorder which is mediated at least in part by FPR2, said method comprising administering to a patient in need thereof an effective amount therefor of at least one compound according to claim 1.

15. The method according to claim 14, wherein the disorder is selected from the group consisting of inflammatory diseases, diabetes, obstructive airway diseases, autoimmune diseases, allergic conditions, rheumatological disorders, HIV-mediated retroviral infections, infectious diseases, sepsis, cardiovascular disorders, fibrotic disorders, neuroinflammation, neurological disorders, pain, prion-mediated diseases, amyloid-mediated disorders and Graft versus Host Disease (GvHD).

\* \* \* \* \*